(12) United States Patent
Dai et al.

(10) Patent No.: US 9,493,461 B2
(45) Date of Patent: Nov. 15, 2016

(54) TETRACYCLIC HETEROCYCLE COMPOUNDS AND METHODS OF USE THEREOF FOR THE TREATMENT OF HEPATITIS C

(71) Applicant: Merck Sharp & Dohme Corp., Rahway, NJ (US)

(72) Inventors: Xing Dai, Cranford, NJ (US); Hong Liu, Hillsborough, NJ (US); Anandan Palani, Bridgewater, NJ (US); Shuwen He, Fanwood, NJ (US); Zhong Lai, East Brunswick, NJ (US); Ravi Nargund, East Brunswick, NJ (US); Karen Marcantonio, New York, NY (US); Dong Xiao, Warren, NJ (US); Linda L. Brockunier, Orange, NJ (US); Nicolas Zorn, Durmenach (FR); Qun Dang, Westfield, NJ (US); Xuanjia Peng, Shanghai (CN); Peng Li, Shanghai (CN)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 14/766,487

(22) PCT Filed: Feb. 3, 2014

(86) PCT No.: PCT/US2014/014363
§ 371 (c)(1),
(2) Date: Aug. 7, 2015

(87) PCT Pub. No.: WO2014/123794
PCT Pub. Date: Aug. 14, 2014

(65) Prior Publication Data
US 2015/0368246 A1    Dec. 24, 2015

(30) Foreign Application Priority Data

Feb. 7, 2013    (WO) ................ PCT/CN2013/000129

(51) Int. Cl.

| C07D 471/14 | (2006.01) |
| C07D 471/04 | (2006.01) |
| C07F 9/6512 | (2006.01) |
| A61K 31/5377 | (2006.01) |
| A61K 31/675 | (2006.01) |
| C07D 471/20 | (2006.01) |
| A61K 31/519 | (2006.01) |
| A61K 45/06 | (2006.01) |
| C07D 519/00 | (2006.01) |
| C07D 487/14 | (2006.01) |

(52) U.S. Cl.
CPC ........... *C07D 471/14* (2013.01); *A61K 31/519* (2013.01); *A61K 31/5377* (2013.01); *A61K 31/675* (2013.01); *A61K 45/06* (2013.01); *C07D 471/04* (2013.01); *C07D 471/20* (2013.01); *C07D 487/14* (2013.01); *C07D 519/00* (2013.01); *C07F 9/65128* (2013.01)

(58) Field of Classification Search
None
See application file for complete search history.

(56) References Cited

U.S. PATENT DOCUMENTS

| 6,777,392 B2 | 8/2004 | Maurya et al. |
| 7,105,499 B2 | 9/2006 | Carroll et al. |
| 7,112,600 B1 | 9/2006 | Hashimoto et al. |
| 7,125,855 B2 | 10/2006 | Bhat et al. |
| 7,202,224 B2 | 4/2007 | Eldrup et al. |
| 2003/0203948 A1 | 10/2003 | Fujishita et al. |
| 2004/0067901 A1 | 4/2004 | Bhat et al. |
| 2004/0110717 A1 | 6/2004 | Carroll et al. |
| 2006/0100262 A1 | 5/2006 | Conte et al. |
| 2009/0048239 A1 | 2/2009 | Conte et al. |
| 2012/0083483 A1 | 4/2012 | Coburn et al. |
| 2012/0328569 A1 | 12/2012 | McComas et al. |

FOREIGN PATENT DOCUMENTS

| WO | WO0147883 | 7/2001 |
| WO | WO0177091 | 10/2001 |
| WO | WO0204425 | 1/2002 |

(Continued)

OTHER PUBLICATIONS

Carroll et al., Inhibition of Hepatitis C Virus RNA Replication by 2'—Modified Nucleoside Analogs, J. Biol. Chem., 2003, 11979-11984, 278(14).

*Primary Examiner* — Brian J Davis
(74) *Attorney, Agent, or Firm* — Alysia A. Finnegan; Gloria M. Fuentes

(57) ABSTRACT

The present invention relates to compounds of formula I that are useful as hepatitis C virus (HCV) NS5B polymerase inhibitors, the synthesis of such compounds, and the use of such compounds for inhibiting HCV NS5B polymerase activity, for treating or preventing HCV infections and for inhibiting HCV viral replication and/or viral production in a cell-based system.

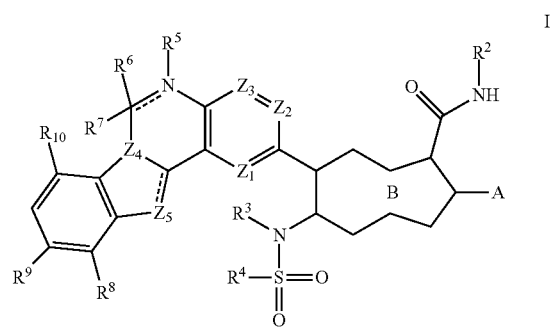

18 Claims, No Drawings

(56) References Cited

FOREIGN PATENT DOCUMENTS

| | | |
|---|---|---|
| WO | WO0206246 | 1/2002 |
| WO | WO0220497 | 3/2002 |
| WO | WO02057287 | 7/2002 |
| WO | WO02057425 | 7/2002 |
| WO | WO03068244 | 8/2003 |
| WO | WO2004000858 | 12/2003 |
| WO | WO2004003138 | 1/2004 |
| WO | WO2004007512 | 1/2004 |
| WO | WO2004041201 | 5/2004 |
| WO | WO2005003147 | 1/2005 |
| WO | WO2005016927 | 2/2005 |
| WO | WO2006020082 | 2/2006 |
| WO | WO2006066079 | 6/2006 |
| WO | WO2006066080 | 6/2006 |
| WO | WO2008075103 | 6/2008 |
| WO | WO2009010783 | 1/2009 |
| WO | WO2009010785 | 1/2009 |
| WO | WO2011106992 | 9/2011 |
| WO | WO2012041014 | 4/2012 |
| WO | WO2013033900 | 3/2013 |
| WO | WO2013033971 | 3/2013 |
| WO | WO2014123793 | 8/2014 |
| WO | WO2014123795 | 8/2014 |

TETRACYCLIC HETEROCYCLE COMPOUNDS AND METHODS OF USE THEREOF FOR THE TREATMENT OF HEPATITIS C

CROSS-REFERENCE TO RELATED APPLICATIONS

This application is a §371 National Stage Application of PCT/US2014/014363, international filing date of Feb. 3, 2014, which claims the benefit of International Application No. PCT/CN2013/000129, filed Feb. 7, 2013, now expired.

FIELD OF THE INVENTION

The present disclosure relates to antiviral compounds that are useful as inhibitors of the hepatitis C virus (HCV) NS5B (non-structural protein 5B) polymerase, compositions comprising such compounds, the use of such compounds for treating HCV infection and/or reducing the likelihood or severity of symptoms of HCV infection, methods for inhibiting the function of the NS5B polymerase, and methods for inhibiting HCV viral replication and/or viral production.

BACKGROUND OF THE INVENTION

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside analog ribavirin.

Several virally-encoded enzymes are putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

HCV NS5B polymerase is described, for example, in Behrens et al., *EMBO J.* 15(1) 12-22 (1996). Antagonists of NS5B activity are known to be inhibitors of HCV replication. See Carroll et al., *J. Biol. Chem.* 278(14) 11979-84 (2003).

There is a clear and long-felt need to develop effective therapeutics for treatment of HCV infection. Specifically, there is a need to develop compounds that selectively inhibit HCV viral replication and that would be useful for treating HCV-infected patients.

SUMMARY OF THE INVENTION

The present disclosure relates to novel compounds of formula I and/or pharmaceutically acceptable salts thereof. These compounds are useful, either as compounds or their pharmaceutically acceptable salts (when appropriate), in the inhibition of HCV (hepatitis C virus) NS5B (non-structural 5B) polymerase, the prevention or treatment of one or more of the symptoms of HCV infection, the inhibition of HCV viral replication and/or HCV viral production, and/or as pharmaceutical composition ingredients. As pharmaceutical composition ingredients, these compounds and their salts may be the primary active therapeutic agent, and, when appropriate, may be combined with other therapeutic agents including but not limited to other HCV antivirals, anti-infectives, immunomodulators, antibiotics or vaccines, as well as the present Standard of Care treatment options for HCV.

In one aspect, the present invention relates to a compound of formula I:

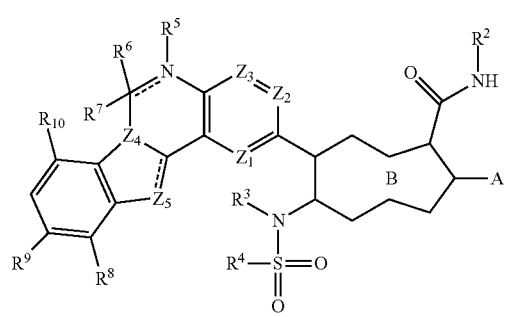

or a pharmaceutically acceptable salt thereof,
wherein:
A is $C_3$-$C_6$ cycloalkyl,

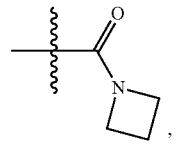 [SMILES: *C(=O)N1CCC1]

wherein the azetinidyl is substituted with 1 or 2 substituents selected from halo and $C_1$-$C_6$ alkyl;

or a 5-6 membered aromatic monocyclic ring with 0, 1, 2 or 3 heteroatom ring atoms selected from N and S, optionally substituted with 1 or 2 substituents independently selected from $C_1$-$C_6$ alkyl, $C_1$-$C_6$ alkoxy, $C_1$-$C_6$ haloalkyl, oxo, halo, and —O—$C_1$-$C_6$ haloalkyl;

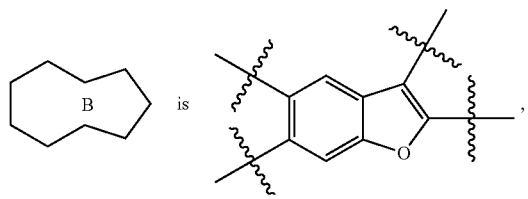

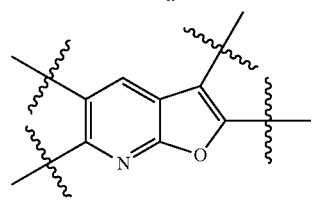

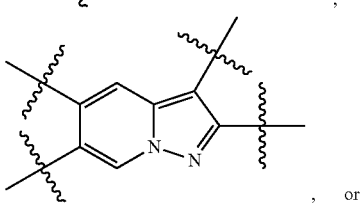

, or

-continued

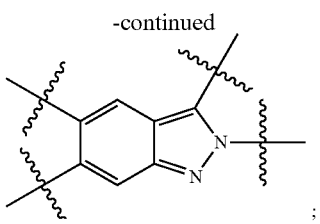
;

$Z_1$, $Z_2$, and $Z_3$ are independently CH or N wherein no more than one of $Z_1$, $Z_2$, and $Z_3$ is N;

$Z_4$ is N, $Z_5$ is CH, and the ----- attached to $Z_5$ is a double bond, or $Z_4$ is C, $Z_5$ is NH, and the ----- attached to $Z_5$ is a single bond;

$R^2$ is hydrogen, $C_1$-$C_6$ alkyl or —O—$C_1$-$C_6$ alkyl;

$R^3$ is hydrogen or $C_1$-$C_6$ alkyl;

$R^4$ is $C_1$-$C_6$ alkyl or —O—$C_1$-$C_6$ alkyl;

$R^5$ is hydrogen, $C_1$-$C_6$ alkyl, or —$CH_2COOR^a$, —$SO_2CH_3$;

$R^a$ is hydrogen or $C_1$-$C_6$ alkyl;

$R^6$ is hydrogen, $C_1$-$C_6$ alkyl, $C_1$-$C_6$ haloalkyl, $C_1$-$C_6$ hydroxyalkyl, —$C_0$-$C_6$ alkyl-$COOR^a$, —$CH_2SO_2CH_3$, —$CH_2NH_2$, —$CH_2N(CH_3)CH_2CON(CH_3)_2$, —$C_0$-$C_6$ alkyl-(4- to 7-membered monocyclic heterocycloalkyl), —$C_1$-$C_6$ alkyl-(6- to 9-membered bicyclic heterocycloalkyl) [will include spirocyclic rings in definition], —$CH_2$-triazole, —$CH_2PO(OCH_2CH_3)_2$, or —$NH_2$;

wherein the 4- to 7-membered monocyclic heterocycloalkyl is optionally substituted with one or two substituents independently selected from oxo, F, $C_1$-$C_6$ alkyl, $C_1$-$C_6$ haloalkyl, $C_1$-$C_6$ hydroxyalkyl, $C_1$-$C_6$ alkoxy, —$COCH_3$, —$OR^a$, $C_3$-$C_6$ cycloalkyl, cyano and —$SO_2CH_3$;

$R^7$ is hydrogen or $C_1$-$C_6$ alkyl;

or $R^6$ and $R^7$ together form oxo or together with the C to which they are attached form a $C_3$-$C_4$ cycloalkyl; and $R^8$ is hydrogen, halo, or cyano;

$R^9$ and $R^{10}$ are independently hydrogen or halogen;

wherein when the ----- adjacent to $NR_5$ is a double bond, $R^5$ and $R^7$ are absent.

The present invention also includes pharmaceutical compositions containing a compound of the present invention and methods of preparing such pharmaceutical compositions. The present invention further includes methods of treating or reducing the likelihood or severity of HCV infection, methods for inhibiting the activity of the NS5B polymerase, and methods for inhibiting HCV viral replication and/or viral production.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts thereof. The compounds of formula I are HCV NS5B polymerase inhibitors.

In a first embodiment of the invention, $R^2$ and $R^4$ are independently $C_1$-$C_6$ alkyl. In this embodiment, all other groups are as provided in the general formula above.

In a second embodiment of the invention, $R^2$, $R^3$ and $R^4$ are methyl. In this embodiment, all other groups are as provided in the general formula above and/or in the first embodiment.

In a third embodiment of the invention, two or three of $R^8$, $R^9$ and $R^{10}$ are hydrogen. In all aspects of this embodiment, all other groups are as provided in the general formula above and/or in the first or second embodiments.

In a fourth embodiment of the invention, when $R^8$, $R^9$ or $R^{10}$ are halo, the halo is F. In this embodiment, all other groups are as provided in the general formula above and/or in the first through third embodiments.

In a fifth embodiment of the invention, the compound of the invention has the formula:

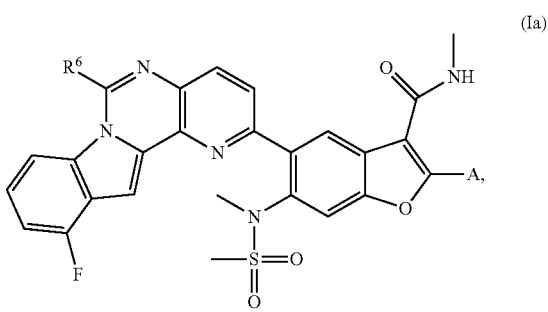
(Ia)

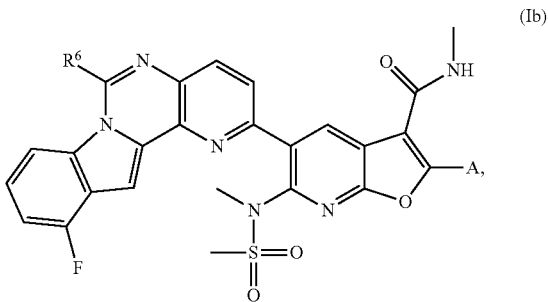
(Ib)

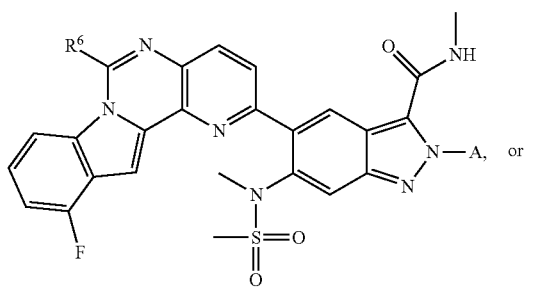
(Ic)

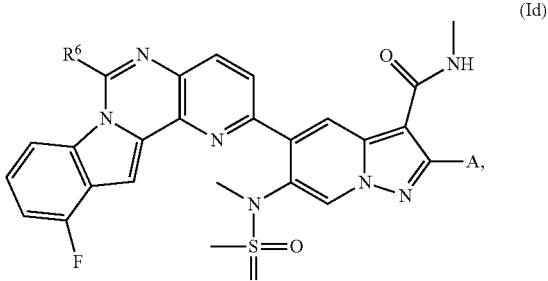
(Id)

or a pharmaceutically acceptable salt thereof. In this embodiment, all other groups are as provided in the general formula above and/or in the first through fourth embodiments.

In a sixth embodiment of the invention, A is $C_3$-$C_6$ cycloalkyl, or a 5-6 membered aromatic monocyclic ring with 0, 1, 2 or 3 heteroatom ring atoms selected from N and S, optionally substituted with 1 or 2 substituents independently selected from $C_1$-$C_6$ alkyl, $C_1$-$C_6$ alkoxy, $C_1$-$C_6$ haloalkyl, oxo, halo, and —O—$C_1$-$C_6$ haloalkyl. In one aspect of this embodiment, A is cyclopropyl,

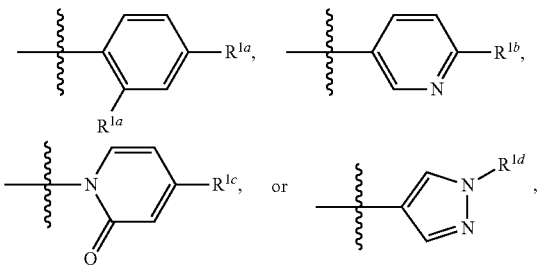

wherein each $R^{1a}$ is independently selected from hydrogen, F, methyl, ethyl, and —OCHF$_2$; $R^{1b}$ is independently selected from hydrogen, F, methyl, ethyl, —CHF$_2$, —CF$_3$, —OCH$_3$, —OCHF$_2$, —OCH$_2$CF$_3$, and —OCHF$_2$; $R^{1c}$ is independently selected from hydrogen, and methyl; $R^{1d}$ is independently selected from hydrogen, methyl, and ethyl. In another aspect of this embodiment, A is cyclopropyl,

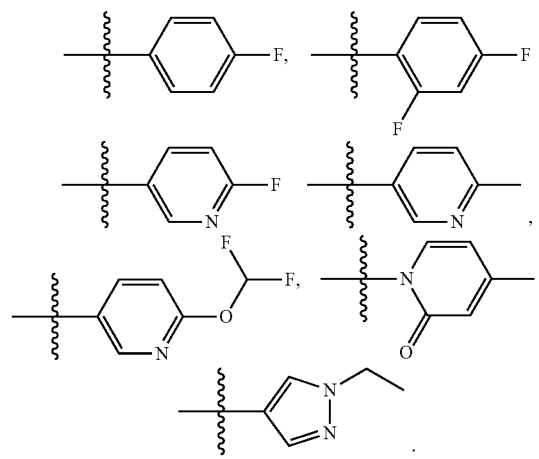

In this embodiment, all other groups are as provided in the general formula above and/or in the first through fifth embodiments.

In a seventh embodiment of the invention, $R^6$ is hydrogen, —CH$_2$SO$_2$CH$_3$, —CH$_2$PO(OCH$_2$CH$_3$)$_2$,

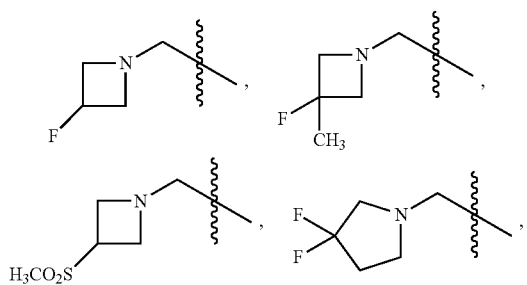

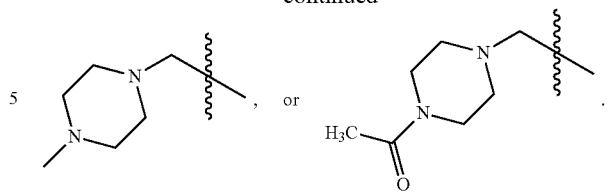

In all aspects of this embodiment, all other groups are as provided in the general formula above and/or in the first through sixth embodiments.

In an eighth embodiment of the invention, $R^6$ is

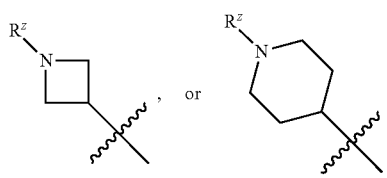

wherein $R^z$ is hydrogen, $C_1$-$C_6$ alkyl, $C_1$-$C_6$ haloalkyl, $C_1$-$C_6$ hydroxyalkyl, —$C_1$-$C_6$ alkyl-COOH, —$C_0$-$C_6$ alkyl-(3- to 7-membered monocyclic cycloalkyl). In all aspects of this embodiment, all other groups are as provided in the general formula above and/or in the first through seventh embodiments.

In another embodiment of the invention, the compound of the invention is selected from the exemplary species depicted in Examples 1 through 151 shown below, and pharmaceutically acceptable salts thereof.

In another embodiment of the invention, the compound of the invention is selected from the exemplary species depicted in Examples 2, 5, 10, 14, 15, 16, 23, 28, 30, 31, 32, 33, 39, 49, 76, 81, 82, 147, 148, and 151 shown below, and pharmaceutically acceptable salts thereof.

Other embodiments of the present invention include the following:

(a) A pharmaceutical composition comprising an effective amount of a compound of formula I and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(d) A pharmaceutical combination that is (i) a compound of formula I and (ii) a second therapeutic agent selected from the group consisting of HCV antiviral agents, immunomodulators, and anti-infective agents; wherein the compound of formula I and the second therapeutic agent are each employed in an amount that renders the combination effective for inhibiting HCV NS5B activity, or for inhibiting HCV viral replication, or for treating HCV infection and/or reducing the likelihood or severity of symptoms of HCV infection.

(e) The combination of (d), wherein the HCV antiviral agents are one or more antiviral agents selected from the group consisting of direct inhibitors of HCV, including but not limited to NS3 and NS3/4A protease inhibitors, NS5A inhibitors and HCV NS5B polymerase inhibitors.

(f) A use of a compound of formula I in the preparation of a medicament for inhibiting HCV NS5B activity in a subject in need thereof.

(g) A use of a compound of formula I in the preparation of a medicament for preventing and/or treating infection by HCV in a subject in need thereof.

(h) A method of treating HCV infection and/or reducing the likelihood or severity of symptoms of HCV infection in a subject in need thereof, which comprises administering to the subject an effective amount of a compound of formula I.

(i) The method of (h), wherein the compound of formula I is administered in combination with an effective amount of at least one second therapeutic agent selected from the group consisting of HCV antiviral agents, immunomodulators, and anti-infective agents.

(j) The method of (i), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(k) A method of inhibiting HCV viral replication and/or HCV viral production in a cell-based system, which comprises administering to the subject an effective amount of a compound of formula I in combination with an effective amount of at least one second therapeutic agent selected from the group consisting of HCV antiviral agents, immunomodulators, and anti-infective agents.

(l) The method of (k), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(m) A method of inhibiting HCV NS5B activity in a subject in need thereof, which comprises administering to the subject the pharmaceutical composition of (a), (b), or (c) or the combination of (d) or (e).

(n) A method of treating HCV infection and/or reducing the likelihood or severity of symptoms of HCV infection in a subject in need thereof, which comprises administering to the subject the pharmaceutical composition of (a), (b), or (c) or the combination of (d) or (e).

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (n) above are understood to include all embodiments of the compounds and/or salts, including such embodiments as result from combinations of embodiments.

Additional embodiments of the invention include the pharmaceutical compositions, combinations, uses and methods set forth in (a) through (n) above, wherein the compound of the present invention employed therein is a compound of one of the embodiments, or aspects of the compounds described above. In all of these embodiments, the compound may optionally be used in the form of a pharmaceutically acceptable salt or hydrate as appropriate.

The present invention also includes a compound of the present invention for use (i) in, (ii) as a medicament for, or (iii) in the preparation of a medicament for: (a) inhibiting HCV NS5B activity, or (b) inhibiting HCV viral replication, or (c) treating HCV infection and/or reducing the likelihood or severity of symptoms of HCV infection, or (d) use in medicine. In these uses, the compounds of the present invention can optionally be employed in combination with one or more second therapeutic agents selected from HCV antiviral agents, anti-infective agents, and immunomodulators.

As used herein, all ranges are inclusive, and all sub-ranges are included within such ranges, although not necessarily explicitly set forth. In addition, the term "or," as used herein, denotes alternatives that may, where appropriate, be combined; that is, the term "or" includes each listed alternative separately as well as their combination.

Chemical names, common names, and chemical structures may be used interchangeably to describe the same structure. If a chemical compound is referred to using both a chemical structure and a chemical name and an ambiguity exists between the structure and the name, the structure is understood to predominate.

As used herein, the term "administration" and variants thereof (e.g., "administering" a compound) in reference to a compound of the invention mean providing the compound to the individual in need of treatment. When a compound of the invention is provided in combination with one or more other active agents (e.g., antiviral agents useful for treating HCV infection), "administration" and its variants are each understood to include concurrent and sequential provision of the compound or salt and other agents.

The term "alkoxy" refers to an "alkyl-O—" group. Alkoxy groups may be substituted as indicated.

The term "alkyl" refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "aryl" (or "aryl ring system") refers to aromatic mono- and poly-carbocyclic ring systems wherein the individual carbocyclic rings in the polyring systems are fused or attached to each other via a single bond. As used herein, the term aryl includes aromatic mono- and poly-carbocyclic ring systems that include from 0 to 4 heteroatoms (non-carbon atoms) that are independently chosen from N, O and S. Suitable aryl groups include phenyl, naphthyl, biphenylenyl, pyridinyl, pyrimidinyl and pyrrolyl, as well as those discussed below. Aryl groups may be substituted as indicated. Aryl ring systems may include, where appropriate, an indication of the variable to which a particular ring atom is attached. Unless otherwise indicated, substituents to the aryl ring systems can be attached to any ring atom, provided that such attachment results in formation of a stable ring system.

The term "carbocycle" (and variations thereof such as "carbocyclic") as used herein, unless otherwise indicated, refers to (i) a $C_5$ to $C_7$ monocyclic, saturated or unsaturated ring, or (ii) a $C_8$ to $C_{10}$ bicyclic saturated or unsaturated ring system. Each ring in (ii) is either independent of, or fused to, the other ring, and each ring is saturated or unsaturated. Carbocycle groups may be substituted as indicated. When the carbocycles contain one or more heteroatoms independently chosen from N, O and S, the carbocycles may also be referred to as "heterocycles," as defined below. The carbocycle may be attached to the rest of the molecule at any carbon or nitrogen atom that results in a stable compound. The fused bicyclic carbocycles are a subset of the carbocycles; i.e., the term "fused bicyclic carbocycle" generally refers to a $C_8$ to $C_{10}$ bicyclic ring system in which each ring is saturated or unsaturated and two adjacent carbon atoms are shared by each of the rings in the ring system. A fused bicyclic carbocycle in which both rings are saturated is a saturated bicyclic ring system. Saturated carbocyclic rings are also referred to as cycloalkyl rings, e.g., cyclopropyl, cyclobutyl, etc. A fused bicyclic carbocycle in which one or both rings are unsaturated is an unsaturated bicyclic ring system. Carbocycle ring systems may include, where appropriate, an indication of the variable to which a particular ring atom is attached. Unless otherwise indicated, substituents to the ring systems can be attached to any ring atom, provided that such attachment results in formation of a stable ring system.

The term "composition" is intended to encompass a product comprising the specified ingredients, as well as any product which results, directly or indirectly, from combining the specified ingredients.

The term "compound" is intended to encompass chemical agents described by generic formula I in all forms, including hydrates and solvates of such chemical agents.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

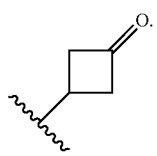 [SMILES: *C1CC(=O)C1]

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. In another embodiment, the effective amount is a "therapeutically effective amount" for inhibition of HCV viral replication and/or HCV viral production. The term also includes herein the amount of active compound sufficient to inhibit HCV NS5B activity and thereby elicit the response being sought (i.e., an "inhibition effective amount"). When the active compound (i.e., active ingredient) is administered as the salt, references to the amount of active ingredient are to the free acid or free base form of the compound.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "halogen" (or "halo") refers to atoms of fluorine, chlorine, bromine and iodine (alternatively referred to as fluoro, chloro, bromo, and iodo).

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and has 9 or 10 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. The term "heteroaryl" also encompasses any fused polycyclic ring system containing at least one ring heteroatom selected from N, O and S, wherein at least one ring of the fused polycyclic ring system is aromatic. For example, the term "9 to 10-membered bicyclic heteroaryl" encompasses a non-aromatic 5 membered heterocyclic ring that is fused to a benzene or pyridyl ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

As used herein, the term "heterocycle" (and variations thereof such as "heterocyclic" or "heterocyclyl") broadly refers to (i) a stable 5- to 7-membered, saturated or unsaturated monocyclic ring, or (ii) a stable 8- to 10-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) independently selected from N, O and S and a balance of carbon atoms (the monocyclic ring typically contains at least one carbon atom and the bicyclic ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Heterocycle groups may be substituted as indicated, and unless otherwise specified, the substituents may be attached to any atom in the ring, whether a heteroatom or a carbon atom, provided that a stable chemical structure results. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

The term "heterocycloalkyl," as used herein, refers to a non-aromatic saturated monocyclic or multicyclic ring system comprising 3 to about 11 ring atoms, wherein from 1 to 4 of the ring atoms are independently O, S, or N, and the remainder of the ring atoms are carbon atoms. A heterocycloalkyl group can be joined via a ring carbon or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is monocyclic has from about 5 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. The bicylic heterocycoalkyl group encompasses spirocyclic groups. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, and the like, and all isomers thereof.

A ring carbon atom of a heterocycloalkyl group may be functionalized as a carbonyl group. Illustrative example of such heterocycloalkyl groups, include:

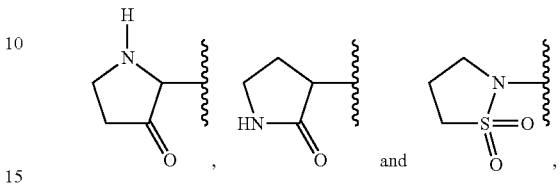

In one embodiment, a heterocycloalkyl group is a 5-membered monocyclic heterocycloalkyl. In another embodiment, a heterocycloalkyl group is a 6-membered monocyclic heterocycloalkyl. The term "3 to 7-membered monocyclic cycloalkyl" refers to a monocyclic heterocycloalkyl group having from 3 to 7 ring atoms. The term "4 to 7-membered monocyclic cycloalkyl" refers to a monocyclic heterocycloalkyl group having from 4 to 7 ring atoms. The term "5 to 7-membered monocyclic cycloalkyl" refers to a monocyclic heterocycloalkyl group having from 5 to 7 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

As used herein, the term "oxo" or "=O" forms a carbonyl moiety with the carbon atom to which it is attached.

By "pharmaceutically acceptable" is meant that the ingredients of the pharmaceutical composition must be compatible with each other and not deleterious to the recipient thereof.

The term "preventing," as used herein with respect to an HCV viral infection or HCV-virus related disorder, refers to reducing the likelihood of HCV infection.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

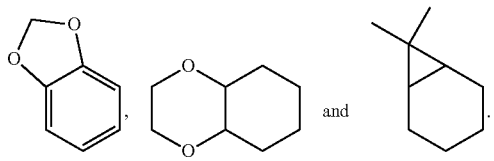

The term "subject" (alternatively referred to herein as "patient"), as used herein, refers to an animal, preferably a mammal, most preferably a human.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of formula I. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within formula I can be prepared without undue experimentation by conventional techniques well known to those skilled in the art or by processes analogous to those described in the Schemes and Examples herein using appropriate isotopically-enriched reagents and/or intermediates.

Unless expressly stated to the contrary, all ranges cited herein are inclusive. For example, a heteroaryl ring described as containing from "0 to 3 heteroatoms" means the ring can contain 0, 1, 2, or 3 heteroatoms. It is also to be understood that any range cited herein includes within its scope all of the sub-ranges within that range. The oxidized forms of the heteroatoms N and S are also included within the scope of the present invention.

When any variable (for example, R$^1$ or R$^3$) occurs more than one time in any constituent or in formula I or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom provided such substitution is chemically allowed and results in a stable compound. A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers. For the purposes of the present invention a reference to a compound of formula I is a reference to the compound per se, or to any one of its tautomers per se, or to mixtures of two or more tautomers.

The compounds of the present inventions are useful in the inhibition of HCV replication (e.g., HCV NS5B activity), the treatment of HCV infection and/or reduction of the likelihood or severity of symptoms of HCV infection. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for identifying resistant HCV replicon cell lines harboring mutations within NS5B, which are excellent screening tools for more powerful antiviral compounds. Furthermore, the compounds of this invention are useful in establishing or determining the binding site of other antivirals to the HCV replicase.

The compounds of the present invention may be administered in the form of pharmaceutically acceptable salts. The term "pharmaceutically acceptable salt" refers to a salt that possesses the effectiveness of the parent compound and that is not biologically or otherwise undesirable (e.g., is neither toxic nor otherwise deleterious to the recipient thereof). Suitable salts include acid addition salts that may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

For the purposes of inhibiting HCV NS5B polymerase, treating HCV infection and/or reducing the likelihood or severity of symptoms of HCV infection and inhibiting HCV viral replication and/or HCV viral production, the compounds of the present invention, optionally in the form of a salt, can be administered by any means that produces contact of the active agent with the agent's site of action. They can be administered by one or more conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following: orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, HCV viral genotype, viral resistance, and the host undergoing therapy.

As noted above, the present invention also relates to a method of inhibiting HCV NS5B activity, inhibiting HCV viral replication and/or HCV viral production, treating HCV infection and/or reducing the likelihood or severity of symptoms of HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, R7025 (an enhanced interferon (Roche)), interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as ROFERON interferon available from Hoffmann-LaRoche, Nutley, N.J.), pegylated interferon-α2a (PEGASYS), interferon-α2b (such as INTRON-A interferon available from Schering Corp., Kenilworth, N.J.), pegylated interferon-α2b (PEGINTRON), a recombinant consensus interferon (such as interferon alphacon-1), albuferon (interferon-α bound to human serum albumin (Human Genome Sciences)), and a purified interferon-α product. Amgen's recombinant consensus interferon has the brand name INFERGEN. Levovirin is the L-enantiomer of ribavirin which has shown immunomodulatory activity similar to ribavirin. Viramidine represents an analog of ribavirin disclosed in International Patent Application Publication WO 01/60379. In accordance with the method of the present invention, the individual components of the combination can be administered separately at different times during the course of therapy or concurrently in divided or single combination forms.

For the treatment of HCV infection, the compounds of the invention may also be administered in combination with the antiviral agent NS5B polymerase inhibitor R7128 (Roche). The compounds of the present invention also may be combined for the treatment of HCV infection with antiviral 2'-C-branched ribonucleosides disclosed in Rogers E.

Harry-O'Kuru et al., *A Short, Flexible Route toward 2'-C-Branched Ribonucleosides*, 62 J. ORG. CHEM. 1754-59 (1997); Michael S. Wolfe & Rogers E. Harry-O'Kuru, *A Concise Synthesis of 2'-C-Methylribonucleosides*, 36(42) TETRAHEDRON LETTERS 7611-14 (1995); U.S. Pat. No. 3,480,613; and International Patent Application Publications WO 01/90121, WO 01/92282, WO 02/32920, WO 04/002999, WO 04/003000 and WO 04/002422; the entire contents of each of which are incorporated by reference. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Exemplary substrate and non-substrate based inhibitors of HCV NS3 protease inhibitors are disclosed in International Patent Application Publications WO 98/22496, WO 98/46630, WO 99/07733, WO 99/07734, WO 99/38888, WO 99/50230, WO 99/64442, WO 00/09543, WO 00/59929, WO 02/48116, WO 02/48172, WO 2008/057208 and WO 2008/057209, in British Patent No. GB 2 337 262, and in U.S. Pat. Nos. 6,323,180 and 7,470,664.

The compounds of the present invention may also be combined for the treatment of HCV infection with nucleosides having anti-HCV properties, such as those disclosed in International Patent Application Publications WO 02/51425, WO 01/79246, WO 02/32920, WO 02/48165 and WO 2005/003147 (including R1656, (2'R)-2'-deoxy-2'-fluoro-2'-C-methylcytidine, shown as compounds 3-6 on page 77); WO 01/68663; WO 99/43691; WO 02/18404 and WO 2006/021341, and U.S. Patent Application Publication US 2005/0038240, including 4'-azido nucleosides such as R1626, 4'-azidocytidine; U.S. Patent Application Publications US 2002/0019363, US 2003/0236216, US 2004/0006007, US 2004/0063658 and US 2004/0110717; U.S. Pat. Nos. 7,105,499, 7,125,855, 7,202,224; and International Patent Application Publications WO 02/100415, WO 03/026589, WO 03/026675, WO 03/093290, WO 04/011478, WO 04/013300 and WO 04/028481; the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in International Patent Application Publications WO 02/057287, WO 02/057425, WO 03/068244, WO 2004/000858, WO 04/003138 and WO 2004/007512; U.S. Pat. Nos. 6,777,392, 7,105,499, 7,125,855, 7,202,224 and U.S. Patent Application Publications US 2004/0067901 and US 2004/0110717; the content of each is incorporated herein by reference in its entirety. Other such HCV polymerase inhibitors include, but are not limited to, valopicitabine (NM-283; Idenix) and 2'-F-2'-beta-methylcytidine (see also WO 2005/003147).

In one embodiment, additional nucleoside HCV NS5B polymerase inhibitors that are used in combination with the present HCV NS5B inhibitors are selected from the following compounds: 4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C,2-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C,2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as those disclosed in U.S. Patent Application Publications US 2006/0100262 and US 2009/0048239; International Patent Application Publications WO 01/77091, WO 01/47883, WO 02/04425, WO 02/06246, WO 02/20497, WO 2005/016927 (in particular JTK003), WO 2004/041201, WO 2006/066079, WO 2006/066080, WO 2008/075103, WO 2009/010783 and WO 2009/010785; the content of each is incorporated herein by reference in its entirety.

In one embodiment, additional non-nucleoside HCV NS5B polymerase inhibitors that are used in combination with the present HCV NS5B inhibitors are selected from the following compounds: 14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl] amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 4-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis (trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-a][2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

In another embodiment, the present HCV NS5B polymerase inhibitors are used in combination with non-nucleoside HCV NS5A inhibitors and pharmaceutically acceptable salts thereof.

The HCV NS5B inhibitory activity of the present compounds may be tested using assays known in the art. The HCV NS5B polymerase inhibitors described herein have activities in a genotype 1b replicon assay as described in the Examples. The assay is performed by incubating a replicon harboring cell-line in the presence of inhibitor for a set period of time and measuring the effect of the inhibitor on HCV replicon replication either directly by quantifying replicon RNA level, or indirectly by measuring enzymatic activity of a co-encoded reporter enzyme such as luciferase or β-lactamase. By performing a series of such measurements at different inhibitor concentrations, the effective inhibitory concentration of the inhibitor ($EC_{50}$ or $EC_{90}$) is determined See Jan M. Vrolijk et al., *A replicons-based bioassay for the measurement of interferons in patients with chronic hepatitis C*, 110 J. VIROLOGICAL METHODS 201 (2003). Such assays may also be run in an automated format for high through-put screening. See Paul Zuck et al., *A cell-based β-lactamase reporter gene assay for the identification of inhibitors of hepatitis C virus replication*, 334 ANALYTICAL BIOCHEMISTRY 344 (2004).

The present invention also includes processes for making compounds of formula I. The following reaction schemes and examples serve only to illustrate the invention and its practice.

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-5 below. Alternative synthetic pathways and analogous structures will be apparent to those skilled in the art of organic synthesis. All stereoisomers and tautomeric forms of the compounds are contemplated.

Some commercially available starting materials and intermediates used for the synthesis of the Compounds of Formula (I) are available. These starting materials and intermediates are available from commercial suppliers such as Sigma-Aldrich (St. Louis, Mo.) and Acros Organics Co. (Fair Lawn, N.J.). Such starting materials and intermediates compounds are used as received.

Scheme 1 shows methods useful for making the intermediates of formula A and B, which can be converted to intermediate C.

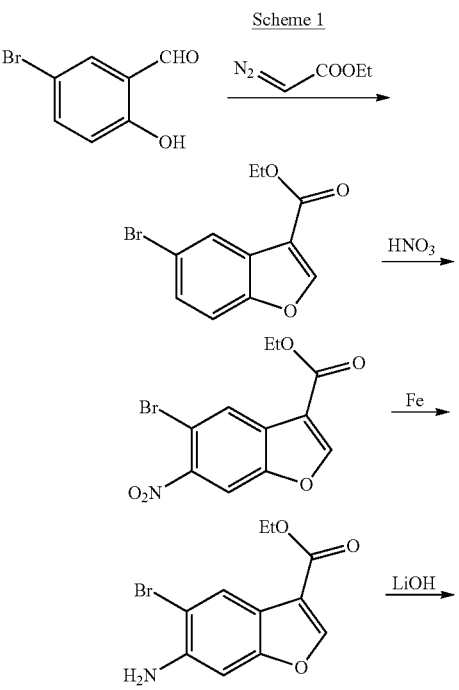

Scheme 1

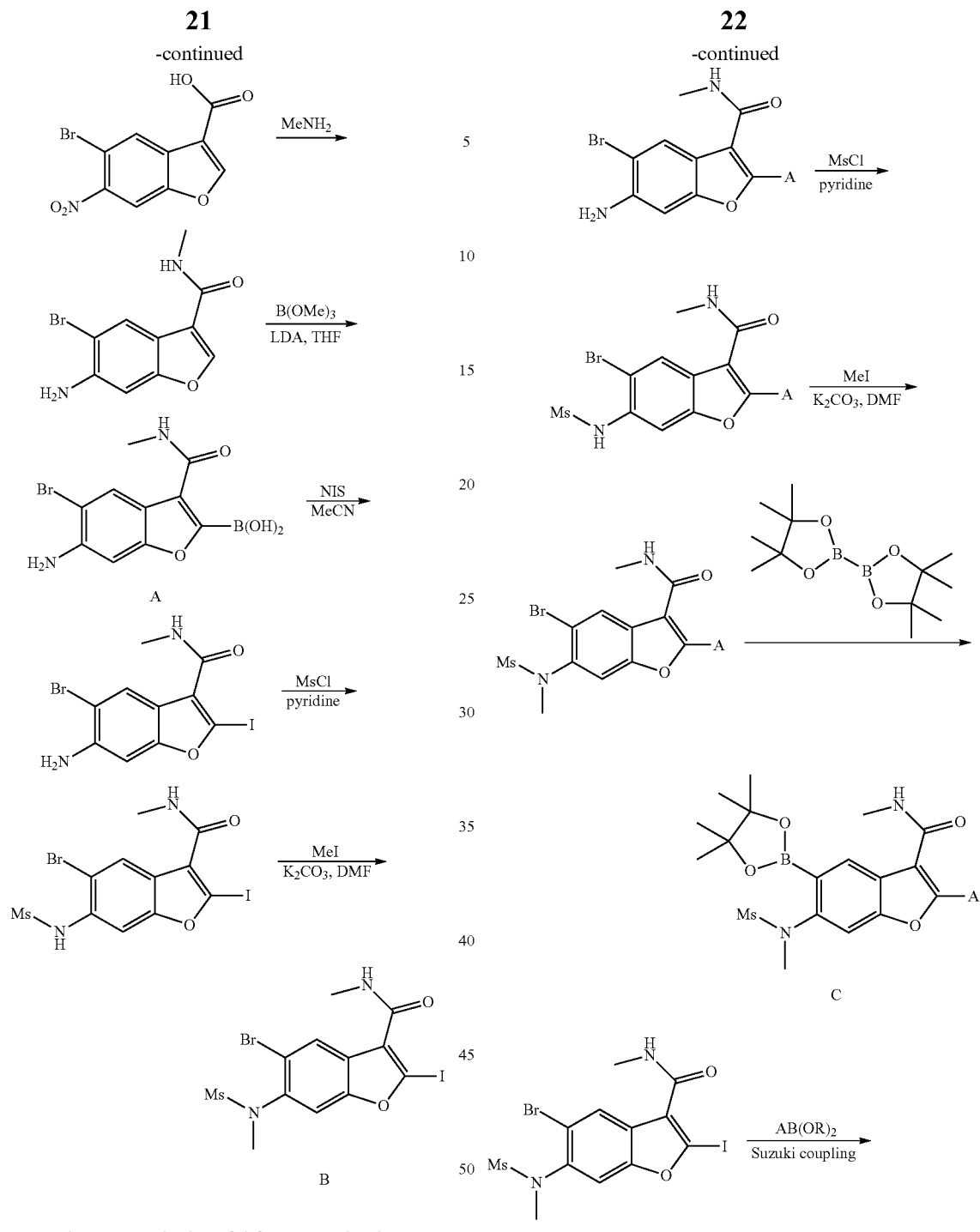
Scheme 2 shows a method useful for converting intermediate of formula A or B to intermediate C, which can be converted to Compounds of Formula (I).
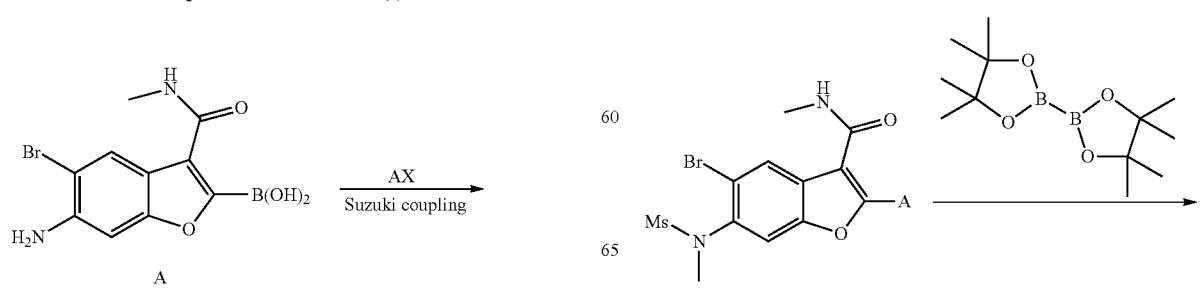

-continued

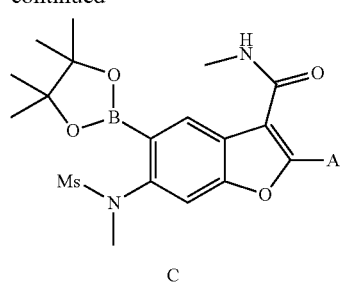

C

Scheme 3 shows methods useful for making the intermediates of formula D and E, which can be converted to Compounds of Formula (I).

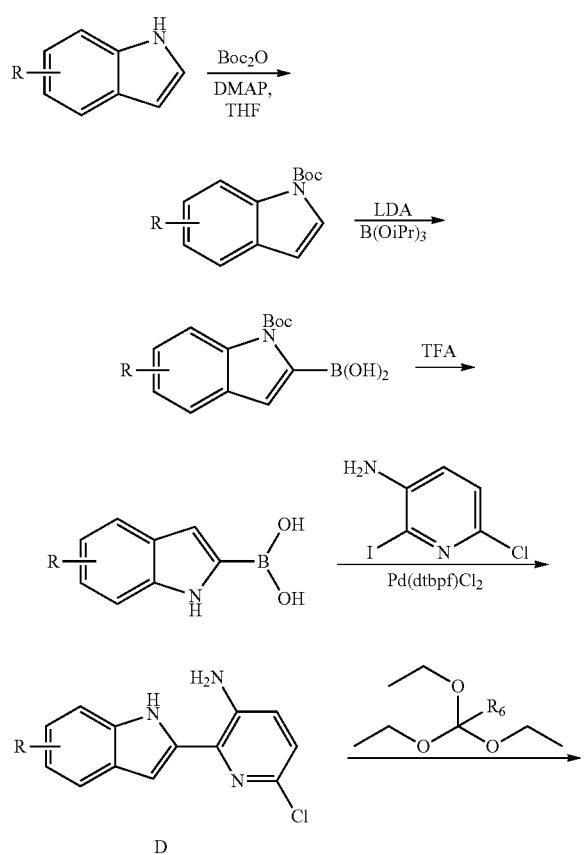

D

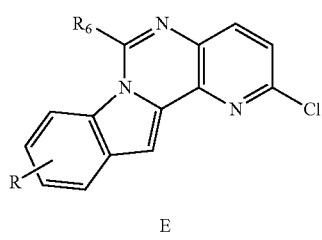

E

Scheme 4 shows a method useful for converting intermediates of formula C, D and E to Compounds of formula (Ia).

Scheme 4

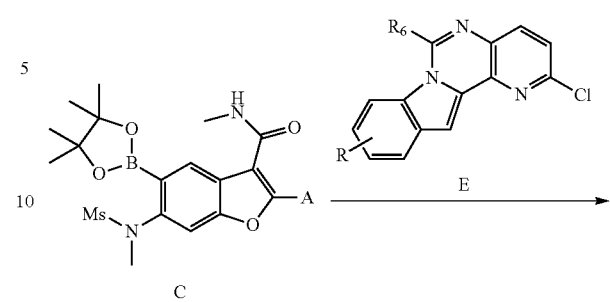

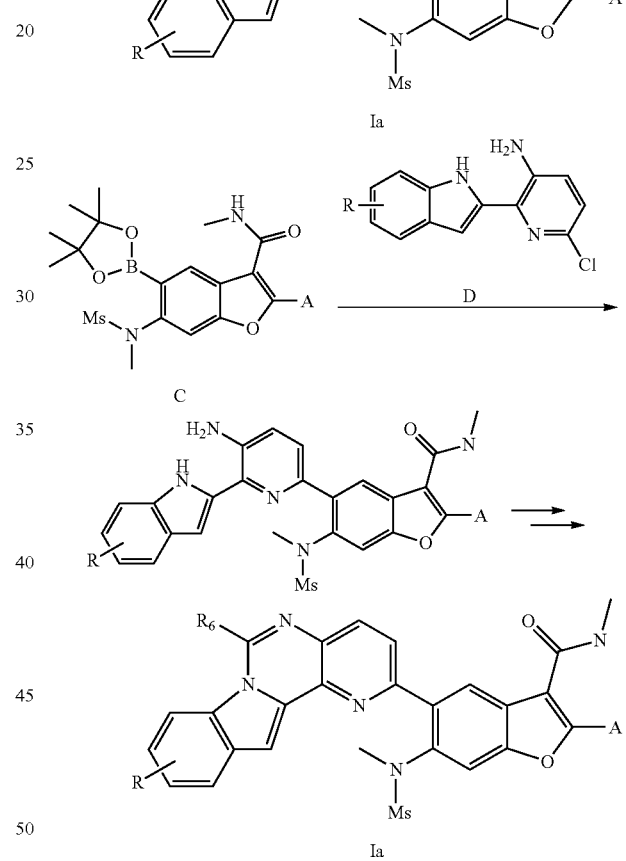

Scheme 5 shows a method useful for converting intermediate a of formula E to Compounds of formula (Ib, Ic, and Id).

Scheme 5

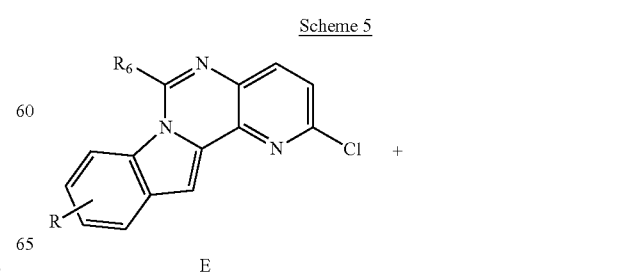

E

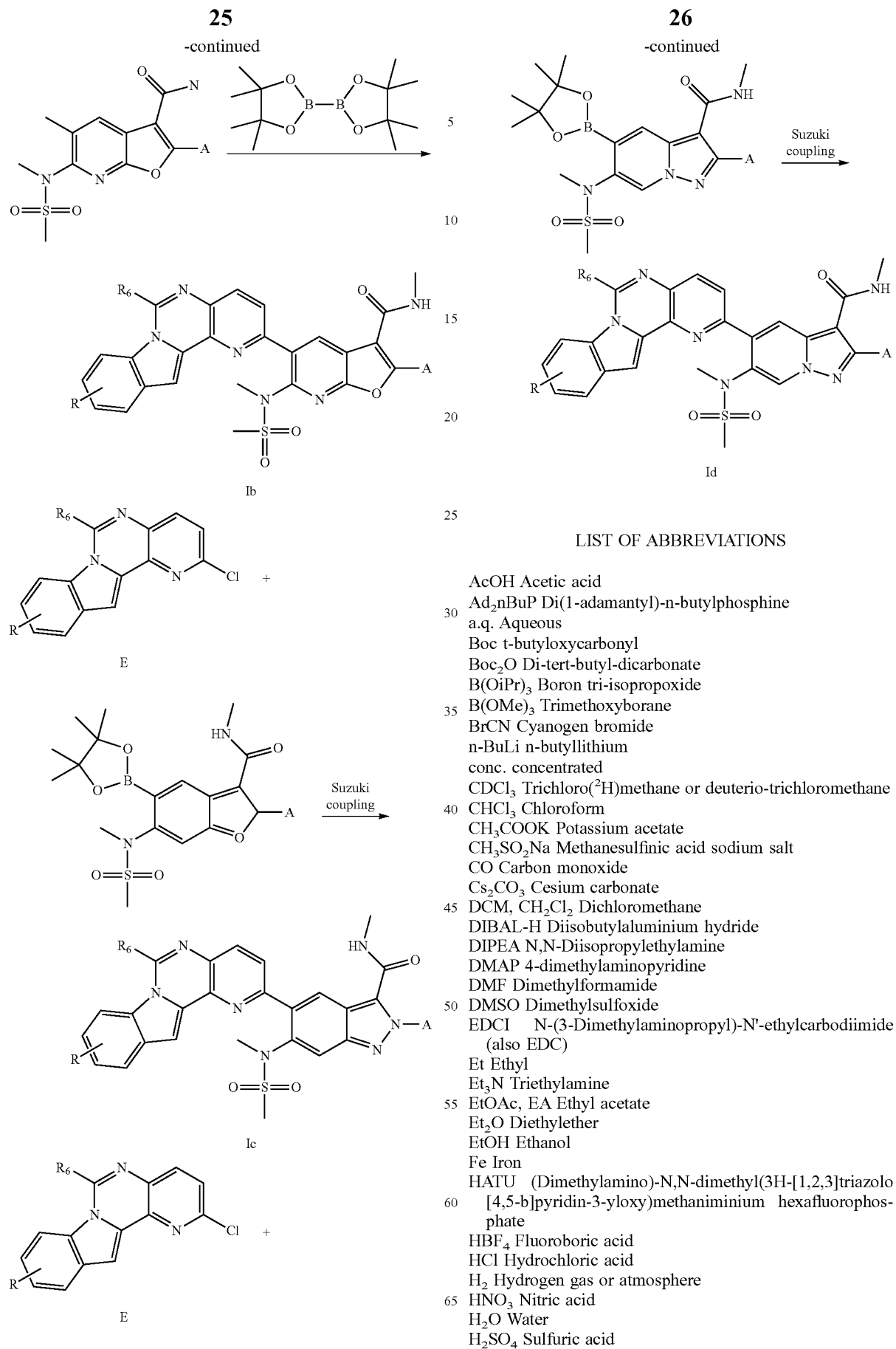

LIST OF ABBREVIATIONS

AcOH Acetic acid
$Ad_2nBuP$ Di(1-adamantyl)-n-butylphosphine
a.q. Aqueous
Boc t-butyloxycarbonyl
$Boc_2O$ Di-tert-butyl-dicarbonate
$B(OiPr)_3$ Boron tri-isopropoxide
$B(OMe)_3$ Trimethoxyborane
BrCN Cyanogen bromide
n-BuLi n-butyllithium
conc. concentrated
$CDCl_3$ Trichloro($^2$H)methane or deuterio-trichloromethane
$CHCl_3$ Chloroform
$CH_3COOK$ Potassium acetate
$CH_3SO_2Na$ Methanesulfinic acid sodium salt
CO Carbon monoxide
$Cs_2CO_3$ Cesium carbonate
DCM, $CH_2Cl_2$ Dichloromethane
DIBAL-H Diisobutylaluminium hydride
DIPEA N,N-Diisopropylethylamine
DMAP 4-dimethylaminopyridine
DMF Dimethylformamide
DMSO Dimethylsulfoxide
EDCI N-(3-Dimethylaminopropyl)-N'-ethylcarbodiimide (also EDC)
Et Ethyl
$Et_3N$ Triethylamine
EtOAc, EA Ethyl acetate
$Et_2O$ Diethylether
EtOH Ethanol
Fe Iron
HATU (Dimethylamino)-N,N-dimethyl(3H-[1,2,3]triazolo[4,5-b]pyridin-3-yloxy)methaniminium hexafluorophosphate
$HBF_4$ Fluoroboric acid
HCl Hydrochloric acid
$H_2$ Hydrogen gas or atmosphere
$HNO_3$ Nitric acid
$H_2O$ Water
$H_2SO_4$ Sulfuric acid HOBT 1-Hydroxy benzotriazole
1H-NMR Proton Nuclear Magnetic Resonance
HPLC High Performance Liquid Chromatography
IPA Isopropyl alcohol
$K_2CO_3$ Potassium carbonate
KOAc Potassium acetate
$K_2HPO_4$ Dipotassium phosphate
$K_3PO_4$ Potassium Phosphate
LDA Lithium diisopropylamide
LiOH Lithium hydroxide
$MeNH_2$, $CH_3NH_2$ Methylamine
MeCN, $CH_3CN$ Acetonitrile
MeI, $CH_3I$ Methyl iodide
MeOD Methan($^2$H)ol
MeOH, $CH_3OH$ Methanol
MS Mass spectroscopy
Ms Methanesulfonyl (or mesyl) group
MsCl Methanesulfonyl chloride
$N_2$ Nitrogen gas or atmosphere
$NaBH_4$ Sodium borohydride
$Na_2CO_3$ Sodium carbonate
$NaHCO_3$ Sodium bicarbonate
$Na_2SO_4$ Sodium sulfate (anhydrous)
NaH Sodium hydride
$NH_4Cl$ Ammonium chloride
NIS N-iodosuccinimide
$OPPh_3$ Triphenyl phosphine
Pd Palladium
$Pd_2(dba)_3$ Tris(dibenzylideneacetone)dipalladium(0)
$Pd(dppf)Cl_2$ 1,1'-bis(diphenylphosphino)ferrocene-palladium(II)dichloride
$Pd(dtbpf)Cl_2$ 1,1'-bis(di-tert-butylphosphino)ferrocene-dichloropalladium(II)
$Pd(OAc)_2$ Palladium(II)acetate
$Pd(PPh_3)_2Cl_2$ 1,1'-bis(tetrakis(triphenylphosphine))palladium(II)dichloride
PE Petroleum ether
Ph Phenyl
$POCl_3$ Phosphoryl chloride
$P(OC_2H_5)_3$ Triethoxyphosphorus
RT Room temperature, approximately 25° C.
sat saturated
SFC Supercritical fluid chromatography
TEA Triethnolamine
Tf Triflate
Tf2O Trifluoromethanesulfonic anhydride
TFA Trifluoroacetic acid
THF Tetrahydrofuran
TLC Thin layer chromatography

EXAMPLES

Example 1

5-(11-fluoropyrido[3',2':4,5]pyrimido[1,6-a]indol-2-yl)-N-methyl-6-(N-methylmethylsulfonamido)-2-(6-(trifluoromethyl)pyridin-3-yl)benzofuran-3-carboxamide

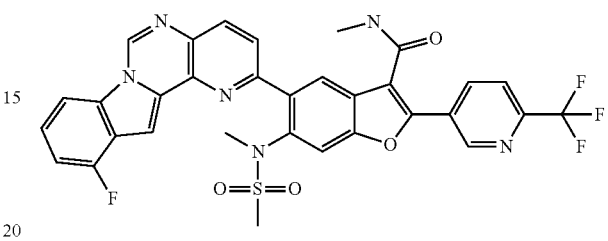

Step 1—Synthesis of ethyl 5-bromobenzofuran-3-carboxylate

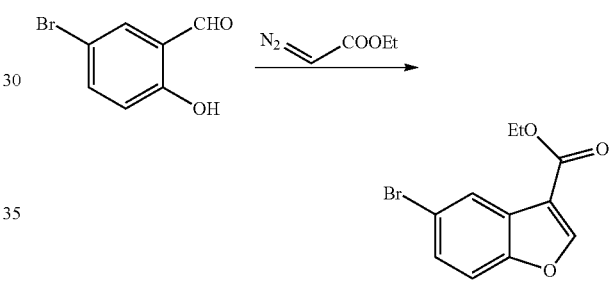

HBF$_4$·Et$_2$O (16.2 g, 99.5 mmol) was added to a solution of 5-bromo-2-hydroxybenzaldehyde (200 g, 995 mmol) in CH$_2$Cl$_2$ (500 mL), and then a solution of ethyl diazoacetate (180 g, 1.42 mol) in CH$_2$Cl$_2$ (500 mL) was introduced as evolution of N$_2$ gas while the reaction was not allowed over 38° C. Once gas evolution ceased, the reaction mixture was concentrated by rotary evaporator and conc. H$_2$SO$_4$ (129 g, 1.29 mol, 98%) was added to the mixture while stirring. After 20 minutes, the acidic mixture was neutralized with Na$_2$CO$_3$ (a.q.). After the mixture was stored and crystallized overnight, ethyl 5-bromobenzofuran-3-carboxylate (100 g, yield: 75%) was obtained by filtration. $^1$H-NMR (CDCl$_3$, 400 MHz) δ 8.25 (s, 1H), 8.15~8.21 (m, 1H), 7.44~7.50 (m, 1H), 7.37~7.42 (m, 1H), 4.41 (q, J=7.2 Hz, 2H), 1.43 (t, J=7.2 Hz, 3H). MS (M+H)$^+$: 269/271.

Step 2—Synthesis of ethyl 5-bromo-6-nitrobenzofuran-3-carboxylate

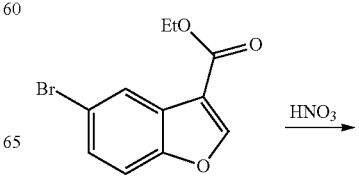

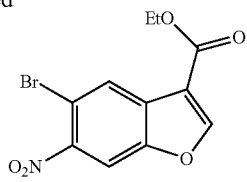

To a solution of ethyl 5-bromobenzofuran-3-carboxylate (95 g, 353 mmol) in CHCl$_3$ (1000 mL), fuming HNO$_3$ (192 mL, 95%) was added dropwise at −20° C. over 90 min and stirred at 0° C. for 1 hour. The reaction mixture was added to ice water and extracted with CH$_2$Cl$_2$. The organic layer was washed with NaHCO$_3$ and brine. The solvent was removed by distillation to provide the crude product of ethyl 5-bromo-6-nitrobenzofuran-3-carboxylate (95 g, yield: 85%). It was used for the next step without further purification.

Step 3—Synthesis of ethyl 6-amino-5-bromobenzofuran-3-carboxylate

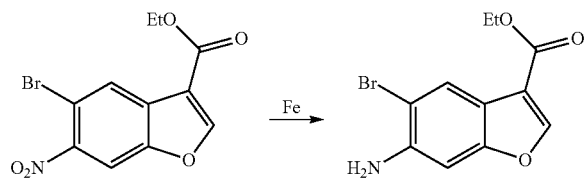

A mixture of crude ethyl 5-bromo-6-nitrobenzofuran-3-carboxylate (95 g, 302 mmol), iron filings (50.67 g, 907 mmol) and NH$_4$Cl (97 g, 1.82 mol) in MeOH-THF-H$_2$O (2:2:1, 1000 mL) were stirred at reflux for 3 hours. After filtered and concentrated in vacuum, the residue was purified by column chromatography (eluted with PE:EA from 20:1 to 10:1) to furnish the pure product of ethyl 6-amino-5-bromobenzofuran-3-carboxylate (58.0 g, yield: 68%). $^1$H-NMR (DMSO-d$_6$, 400 MHz) δ 8.46 (s, 1H), 7.85 (s, 1H), 7.03 (s, 1H), 5.55 (br s, 2H), 4.31 (q, J=7.2 Hz, 2H), 1.32 (t, J=7.2 Hz, 3H). MS (M+H)$^+$: 284/286.

Step 4—Synthesis of 6-amino-5-bromobenzofuran-3-carboxylic acid

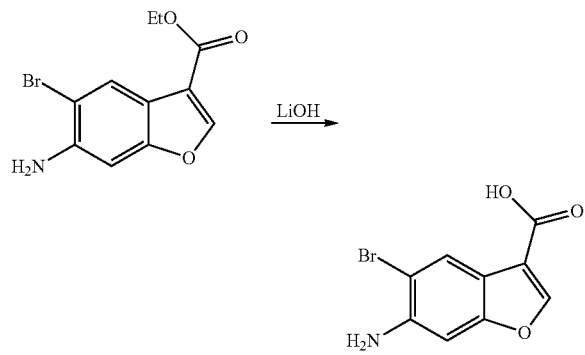

To a solution of ethyl 6-amino-5-bromobenzofuran-3-carboxylate (58 g, 204 mmol) in 1,4-dioxane and H$_2$O (850 mL and 150 mL) was add LiOH.H$_2$O (42.8 g, 1.02 mol). The reaction mixture was refluxed for 2 hours, and then 400 mL H$_2$O was added to the reaction mixture. After acidified to pH 4~5 with a.q. HCl, the resulting solid was filtered to give the product of 6-amino-5-bromobenzofuran-3-carboxylic acid (51 g, yield: 97%). $^1$H-NMR (DMSO-d$_6$, 400 MHz) δ 8.36 (s, 1H), 7.87 (s, 1H), 7.02 (s, 1H), 5.51 (br s, 2H). MS (M+H)$^+$: 256/258.

Step 5—Synthesis of 6-amino-5-bromo-N-methylbenzofuran-3-carboxamide

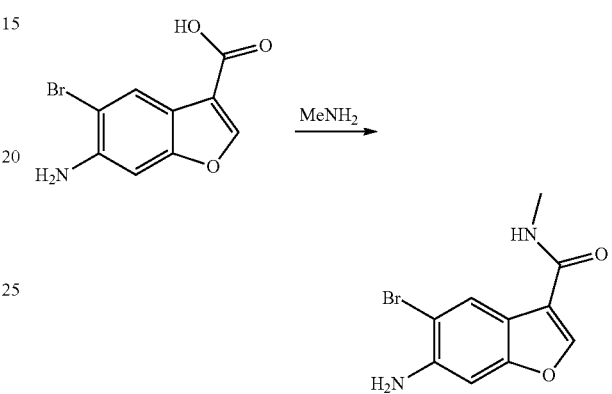

To a solution of 6-amino-5-bromobenzofuran-3-carboxylic acid (51 g, 199 mmol) in dry DMF (500 mL) were add EDCI (53.1 g, 298.77 mmol) and HOBT (40.4 g, 299 mmol). The reaction mixture was stirred at room temperature for 2 h, and then Et$_3$N (60.5 g, 598 mmol) and MeNH$_2$.HCl (40.3 g, 598 mmol) were added to the reaction mixture. After stirred for another 2 hours, the reaction mixture was concentrated in vacuum and then 300 mL Na$_2$CO$_3$ (sat., a.q.) was added to the mixture. The resulting solid was filtered to give the crude product, which was purified by column chromatography (DCM:MeOH=30:1) to give the product 6-amino-5-bromo-N-methylbenzofuran-3-carboxamide (38 g, yield: 71%). $^1$H-NMR (DMSO-d$_6$, 400 MHz) δ 8.19~8.21 (m, 2H), 7.98 (s, 1H), 6.97 (s, 1H), 5.46 (br s, 2H), 2.75 (d, J=4.4 Hz, 3H). MS (M+H)$^+$: 269/271.

Step 6—Synthesis of (6-amino-5-bromo-3-(methylcarbamoyl)benzofuran-2-yl)boronic acid

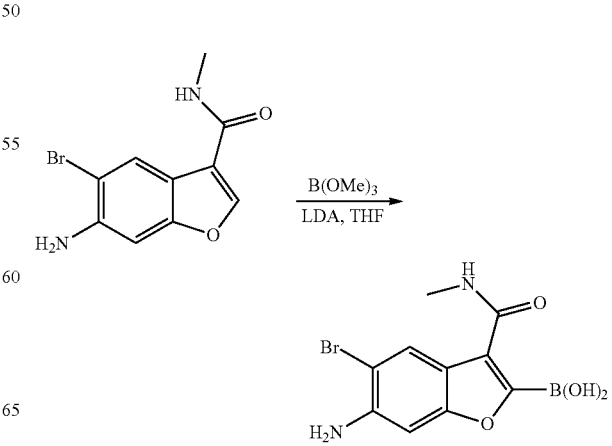

To a solution of LDA in THF (62.5 mmol, 70 mL, freshly prepared), 6-amino-5-bromo-N-methylbenzofuran-3-carboxamide (4 g, 14.86 mmol) in THF (60 mL) was added dropwise at −78° C. under N₂. After the mixture was stirred for 1 hour, trimethyl borate (6.18 g, 59.5 mmol) was added dropwise at −78° C. After the mixture was stirred for 1 hour, NH₄Cl (a.q.) was added, and the mixture was extracted with EtOAc (100 mL×3), dried over Na₂SO₄, filtrated and concentrated to give (6-amino-5-bromo-3-(methylcarbamoyl)benzofuran-2-yl)boronic acid (3.3 g, yield: 70%). ¹H-NMR (DMSO-d₆, 400 MHz) δ 9.56 (s, 2H), 8.46 (d, J=4.8 Hz, 1H), 8.00 (s, 1H), 6.95 (s, 1H), 5.20~5.82 (br s, 2H), 2.87 (d, J=4.8 Hz, 3H). MS (M+H)⁺: 313/315.

Step 7—Synthesis of 6-amino-5-bromo-2-iodo-N-methylbenzofuran-3-carboxamide

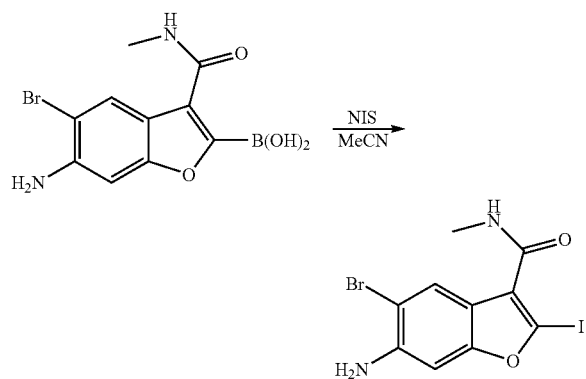

To a solution of (6-amino-5-bromo-3-(methylcarbamoyl)benzofuran-2-yl)boronic acid (2 g, 6.4 mmol) in MeCN (20 mL) was added NIS (1.44 g, 6.4 mmol) at 0° C., and then the mixture was stirred at 25° C. overnight. After concentrated in vacuum, the residue was purified by column chromatography (DCM:EtOAc=10:1) to give to give pure 6-amino-5-bromo-2-iodo-N-methylbenzofuran-3-carboxamide (2 g, yield: 80%). ¹H-NMR (CDCl₃, 400 MHz) δ 7.84 (s, 1H), 6.80 (s, 1H), 6.45 (s, 1H), 2.92 (s, 3H). MS (M+H)⁺: 395/397.

Step 8—Synthesis of 5-bromo-2-iodo-N-methyl-6-(methylsulfonamido)benzofuran-3-carboxamide

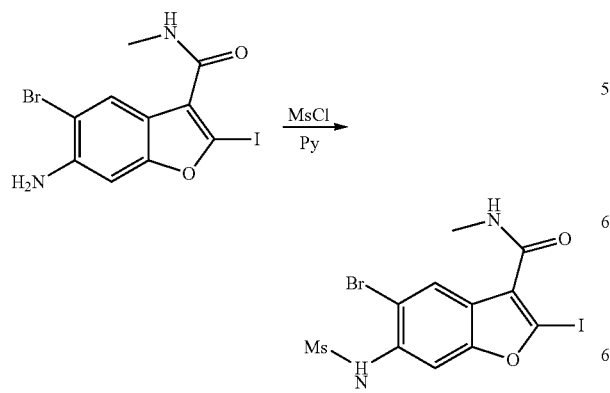

To a solution of 6-amino-5-bromo-2-iodo-N-methylbenzofuran-3-carboxamide (1 g, 2.53 mmol) in pyridine, MsCl (580 mg, 5.06 mmol) was added dropwise at 0° C. The mixture was allowed to warm to room temperature and stirred for 1.5 h. After the solvent was removed in vacuo, the reaction mixture was adjusted to pH=5-6 with 1 N HCl aq. After filtration, the solid was dissolved in THF:H₂O=5:1 (15 mL) and then LiOH.H₂O (800 mg, 20 mmol) was added. The mixture was stirred for 30 minutes at room temperature. After the solvent was removed in vacuo, the reaction mixture was adjusted to pH=5-6 with 1 N HCl aq. Finally the precipitate was collected to give 5-bromo-2-iodo-N-methyl-6-(methylsulfonamido)benzofuran-3-carboxamide (800 mg, 90% purity by HPLC, yield: 60%), which was used for the next step without further purification. ¹H-NMR (CDCl₃, 400 MHz) δ 8.37 (s, 1H), 7.84 (s, 1H), 6.86 (s, 1H), 6.29 (s, 1H), 3.07 (d, J=4.8 Hz, 3H), 2.99 (s, 3H). MS (M+H)⁺: 473/475.

Step 9—Synthesis of 5-bromo-2-iodo-N-methyl-6-(N-methylmethylsulfonamido)benzofuran-3-carboxamide

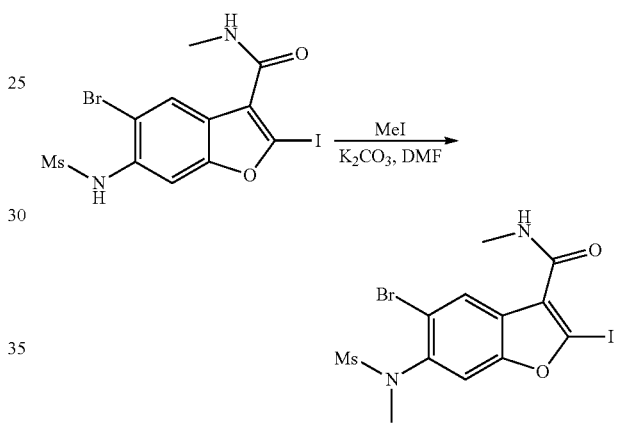

To a suspension of 5-bromo-2-iodo-N-methyl-6-(methylsulfonamido)benzofuran-3-carboxamide (177 mg, 90% purity, 0.34 mmol) and K₂CO₃ (140 mg, 1.01 mmol) in DMF (3 mL) was added dropwise CH₃I (79 mg, 0.68 mol) at 0° C. under N₂, and then the mixture was stirred at 80° C. for 1 hour. After concentrated in vacuum, the residue was suspended in H₂O and extracted with DCM. The residue was purified by column chromatography (eluted with DCM:EtOAc from 10:1 to 2:1) to give 5-bromo-2-iodo-N-methyl-6-(N-methylmethylsulfonamido)benzofuran-3-carboxamide (150 mg, yield: 90%). ¹H-NMR (CDCl₃, 400 MHz) δ 8.38 (s, 1H), 7.66 (s, 1H), 6.27 (s, 1H), 3.32 (s, 3H), 3.08 (d, J=4.8 Hz, 3H), 2.89 (s, 3H). MS (M+H)⁺: 487/489.

Step 10—Synthesis of 5-bromo-N-methyl-6-(N-methylmethylsulfonamido)-2-(6-(trifluoromethyl)pyridin-3-yl)benzofuran-3-carboxamide

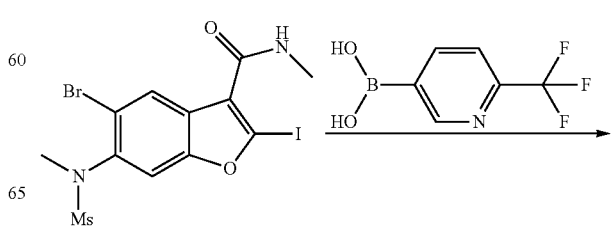

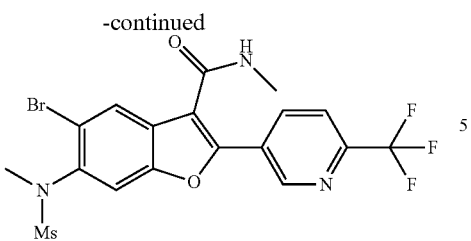

A mixture of 5-bromo-2-iodo-N-methyl-6-(N-methylmethylsulfonamido)benzofuran-3-carboxamide (1.5 g, 3.1 mmol), (6-(trifluoromethyl)pyridin-3-yl)boronic acid (705 mg, 3.7 mmol), Pd(dppf)Cl$_2$ (245 mg, 0.3 mmol) and Na$_2$CO$_3$ (985 mg, 9.3 mmol) in dioxane/H$_2$O (20 mL/4 mL) was stirred at 80° C. for 6 h. Water was added and the mixture was extracted with EtOAc. The organic phase was dried over Na$_2$SO$_4$ and concentrated in vacuum. The residue was purified by column chromatography (PE:EA=1:1) to give the product of 5-bromo-N-methyl-6-(N-methylmethylsulfonamido)-2-(6-(trifluoromethyl)pyridin-3-yl)benzofuran-3-carboxamide (1.4 g, yield: 90%). $^1$H-NMR (DMSO-d$_6$, 400 MHz) δ 9.24 (s, 1H), 8.65 (d, J=4.4 Hz, 1H), 8.56 (d, J=8.0 Hz, 1H), 8.17 (s, 1H), 8.12 (d, J=8.0 Hz, 1H), 8.08 (s, 1H), 3.23 (s, 3H), 3.22 (s, 3H), 2.85 (d, J=4.4 Hz, 3H). MS (M+H)$^+$: 506/508.

Step 11—Synthesis of N-methyl-6-(N-methylmethylsulfonamido)-5-(4,4,5,5-tetramethyl-1,3,2-dioxaborolan-2-yl)-2-(6-(trifluoromethyl)pyridin-3-yl)benzofuran-3-carboxamide

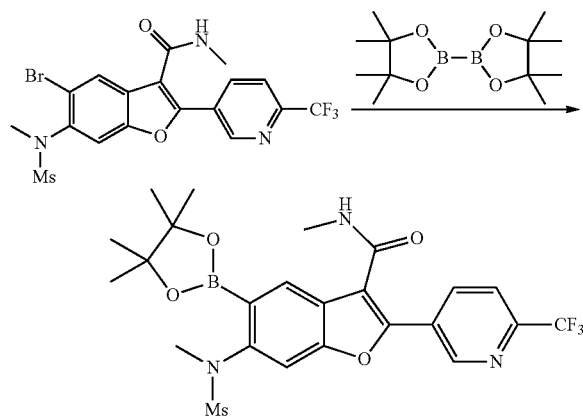

A mixture of 5-bromo-N-methyl-6-(N-methylmethylsulfonamido)-2-(6-(trifluoromethyl)pyridin-3-yl)benzofuran-3-carboxamide (1.4 g, 2.7 mmol), bis(pinacolato)diboron (3.5 g, 13.8 mmol), Pd(dppf)Cl$_2$ (226 mg, 0.27 mmol) and KOAc (814 mg, 8.3 mmol) in dioxane/H$_2$O (10 mL/1 mL) was stirred at 120° C. for 5 h. Water was added and the mixture was extracted with EtOAc. The organic phase was dried over Na$_2$SO$_4$ and concentrated in vacuum. The residue was purified by column chromatography (PE:EA=1:1) to give the product of N-methyl-6-(N-methylmethylsulfonamido)-5-(4,4,5,5-tetramethyl-1,3,2-dioxaborolan-2-yl)-2-(6-(trifluoromethyl)pyridin-3-yl)benzofuran-3-carboxamide (1.3 g, yield: 87%). $^1$H-NMR (MeOD, 400 MHz) δ 9.22 (s, 1H), 8.54 (d, J=8.4 Hz, 1H), 8.11 (s, 1H), 7.97 (d, J=8.4 Hz, 1H), 7.79 (s, 1H), 3.38 (s, 3H), 3.01 (s, 3H), 3.00 (s, 3H), 1.39 (s, 12H). MS (M+H)$^+$: 554.

Step 12—Synthesis of ten-butyl 4-fluoro-1H-indole-1-carboxylate

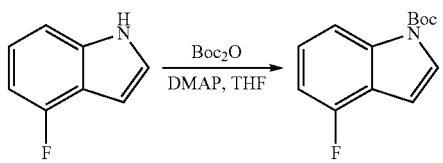 [SMILES: "Boc2O" ; Fc1cccc2[nH]ccc12 ; CC(C)(C)OC(=O)n1ccc2c(F)cccc21]

To a solution of 4-fluoro-1H-indole (150 g, 1.11 mol) and DMAP (4.5 g, 3% Wt) in THF (2.5 L) was added (Boc)$_2$O (255 g, 1.16 mol) dropwise. The mixture was stirred at room temperature overnight. The organic solvent was removed in vacuum, and the residue was purified by column chromatography (PE) to give tert-butyl 4-fluoro-1H-indole-1-carboxylate (250 g, yield: 96%). $^1$H-NMR (CDCl$_3$, 400 MHz) δ 7.92 (d, J=8.4 Hz, 1H), 7.55 (d, J=3.6 Hz, 1H), 7.23 (m, 1H), 6.90 (m, 1H), 6.66 (d, J=3.6 Hz, 1H), 1.67 (s, 9H). MS (M+H)$^+$: 236.

Step 13—Synthesis of (1-(tert-butoxycarbonyl)-4-fluoro-1H-indol-2-yl)boronic acid

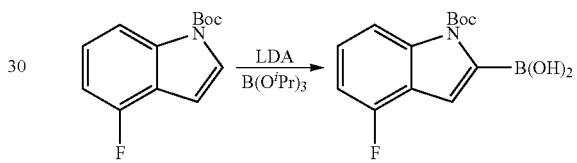

To a solution of diisopropylamine (175 mL, 1.25 mol) in THF (800 mL) at 0° C. was added n-BuLi (500 mL, 1.25 mol) dropwise. The mixture was stirred at 0° C. for 40 min. Then the mixture was cooled to −78° C. Tert-butyl 4-fluoro-1H-indole-1-carboxylate (118 g, 0.50 mol) in THF (300 mL) was added dropwise slowly, followed by triisopropyl borate (231 mL, 1.00 mol). The mixture was stirred at −78° C. for another 40 min. The reaction was monitored by HPLC. When the reaction was completed, the reaction was quenched with NH$_4$Cl (sat. 500 mL). Then the mixture was adjusted to pH=6 with 1 N HCl. Extracted with EtOAc (2000 mL) and the combined organic layers were washed with brine (500 mL), dried over Na$_2$SO$_4$, filtered and concentrated. The obtained solid was recrystallized with EtOAc and PE to give (1-(tert-butoxycarbonyl)-4-fluoro-1H-indol-2-yl)boronic acid (93 g, yield: 64%, which might be unstable at high temp. work up, store in fridge). $^1$H-NMR (CDCl$_3$, 400 MHz) δ 7.77 (d, J=8.4 Hz, 1H), 7.57 (s, 1H), 7.44 (s, 2H), 7.24 (m, 1H), 6.90 (m, 1H), 1.66 (s, 9H). MS (M+H)$^+$: 280.

Step 14—Synthesis of 4-fluoro-1H-indol-2-ylboronic acid

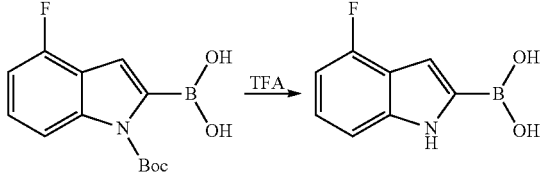 [SMILES: CC(C)(C)OC(=O)n1c(B(O)O)cc2c(F)cccc21 ; OB(O)c1cc2c(F)cccc2[nH]1 ; "TFA"]

TFA (60 mL) was added to 1-(tert-butoxycarbonyl)-4-fluoro-1H-indol-2-ylboronic acid (10 g, 35.83 mmol) in portions at 0° C. and then the mixture was stirred at room temperature for 3 hours. The mixture was poured into ice water, stirred for 10 minutes and filtered through a pad to give the crude 4-fluoro-1H-indol-2-ylboronic acid (6.0 g, yield: 94%) without further purification. $^1$H-NMR (DMSO-$d_6$, 400 MHz) δ 11.09 (s, 1H), 8.35 (br s, 2H), 7.22 (d, J=8.00 Hz, 1H), 7.02~7.07 (m, 2H), 6.68~6.72 (m, 1H). MS (M+H)$^+$: 180.

Step 15—Synthesis of 6-chloro-2-(4-fluoro-1H-indol-2-yl)pyridin-3-amine

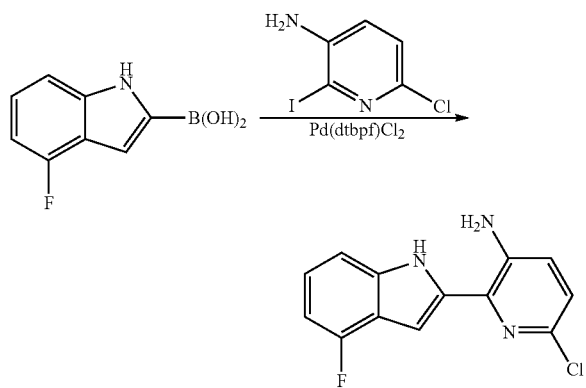

A mixture of 4-fluoro-1H-indol-2-ylboronic acid (2.32 g, 12.96 mmol), 6-chloro-2-iodopyridin-3-amine (3.0 g, 11.79 mmol), cesium carbonate (7.68 g, 23.57 mmol) and Pd(dtbpf)Cl$_2$ (200 mg) in 1,4-dioxane (30 mL) was stirred at 70° C. for 16 hours under nitrogen atmosphere. After filtered through celite and concentrated, the residue was suspended in water and EtOAc. After extracted with EtOAc, the combined organic phase was washed with brine, dried over sodium sulfate and concentrated to afford 6-chloro-2-(4-fluoro-1H-indol-2-yl)pyridin-3-amine (2.8 g, yield: 90%) through the column chromatography (PE:DCM=5:1).

$^1$H-NMR (DMSO-$d_6$, 400 MHz) δ 11.57 (s, 1H), 7.31~7.35 (m, 2H), 7.16 (d, J=8.40 Hz, 1H), 7.06~7.11 (m, 2H), 6.75~6.77 (m, 1H), 5.73 (s, 2H). MS (M+H)$^+$: 262.

Step 16—Synthesis of 2-chloro-11-fluoropyrido[3',2':4,5]pyrimido[1,6-a]indole

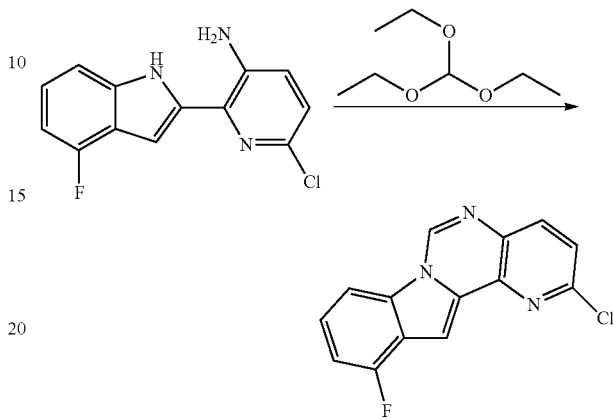

To a solution of 6-chloro-2-(4-fluoro-1H-indol-2-yl)pyridin-3-amine (1 g, 3.82 mmol) and triethoxymethane (811 mg, 7.64 mmol) in 1,4-dioxane (10 mL) was added 4 M HCl/1,4-dioxane (0.05 mL) at RT under N$_2$. Then the mixture was stirred in sealed tube overnight, concentrated and purified by column chromatography (PE:EA=5:1) to give 2-chloro-11-fluoropyrido[3',2':4,5]pyrimido[1,6-a]indole (650 mg, yield: 62%). $^1$H-NMR (DMSO-$d_6$, 400 MHz) δ 9.58 (s, 1H), 8.21 (d, J=8.4 Hz, 1H), 8.16 (d, J=8.4 Hz, 1H), 7.66 (d, J=8.4 Hz, 1H), 7.45~7.49 (m, 2H), 7.25 (dd, J=10.0 Hz, 8.0 Hz, 1H). MS (M+H)$^+$: 272.

Step 17—Synthesis of 5-(11-fluoropyrido[3',2':4,5]pyrimido[1,6-a]indol-2-yl)-N-methyl-6-(N-methylmethylsulfonamido)-2-(6-(trifluoromethyl)pyridin-3-yl)benzofuran-3-carboxamide

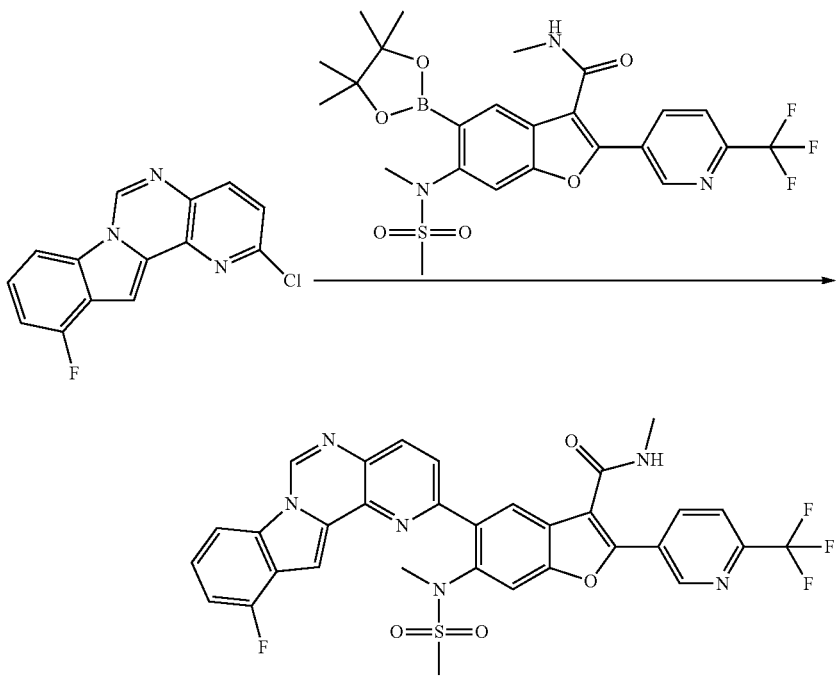

To a degassed solution of 2-chloro-11-fluoropyrido[3',2':4,5]pyrimido[1,6-a]indole (194 mg, 0.72 mmol), N-methyl-6-(N-methylmethylsulfonamido)-5-(4,4,5,5-tetramethyl-1,3,2-dioxaborolan-2-yl)-2-(6-(trifluoromethyl)pyridin-3-yl)benzofuran-3-carboxamide (300 mg, 0.6 mmol) and Na₂CO₃ (127 mg, 1.2 mmol) in 1,4-dioxane (10 mL) and H₂O (0.5 mL) were added Pd₂(dba)₃ (30 mg) and X-Phos (30 mg) under nitrogen atmosphere. The reaction mixture was stirred at 100° C. for 16 h, concentrated in vacuo to remove 1,4-dioxane. The residue was diluted with H₂O and extracted with DCM. The combined organic layers were washed with brine (20 mL), dried over Na₂SO₄, filtered, concentrated and purified to give the product of 5-(11-fluoropyrido[3',2':4,5]pyrimido[1,6-a]indol-2-yl)-N-methyl-6-(N-methylmethylsulfonamido)-2-(6-(trifluoromethyl)pyridin-3-yl)benzofuran-3-carboxamide (100 mg, yield: 27%) through the prep-HPLC. ¹H-NMR (CDCl₃, 400 MHz) δ 9.03 (s, 1H), 8.15 (d, J=8.0 Hz, 1H), 8.10 (s, 1H), 7.93~7.96 (m, 2H), 7.77 (d, J=8.4 Hz, 2H), 7.67 (s, 1H), 7.55 (s, 1H), 7.37~7.42 (m, 1H), 7.12~7.21 (m, 3H), 6.01 (br s, 1H), 3.40 (s, 3H), 2.98 (d, J=4.8 Hz, 3H), 2.68 (s, 3H). MS (M+H)⁺: 663.

Examples 2-8

Examples 2-8, depicted in the table below, were prepared in accordance with the methods described in Example 1.

| Example | Structure | NMR | MS (M + H)⁺ |
|---|---|---|---|
| 2 | 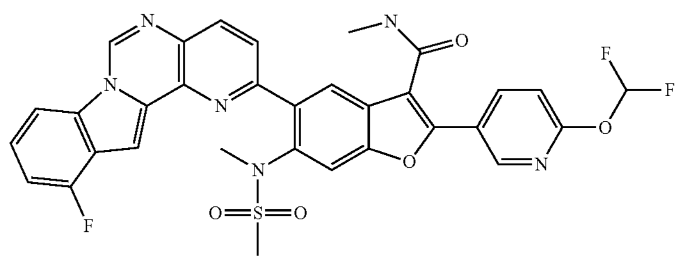 [SMILES: CNC(=O)c1c(-c2ccc(OC(F)F)nc2)oc2cc(N(C)S(C)(=O)=O)c(-c3ccc4ncn5c6cccc(F)c6cc5c4n3)cc12] | ¹H-NMR (CDCl₃, 400 MHz) δ 9.05 (s, 1H), 8.81 (d, J = 8.8 Hz, 1H), 8.38~8.41 (dd, J = 8.8, 2.0 Hz, 1H), 8.13 (d, J = 8.4 Hz, 1H), 8.00 (s, 1H), 7.73~7.77 (m, 2H), 7.68 (s, 1H), 7.53 (s, 1H), 7.49 (t, J = 72.4 Hz, 1H), 7.34~7.38 (m, 1H), 7.09~7.14 (m, 1H), 6.98 (d, J = 8.8 Hz, 1H), 5.94~5.98 (m, 1H), 3.35 (s, 3H), 2.99 (d, J = 4.4 Hz, 3H), 2.67 (s, 3H). | 661 |
| 3 | 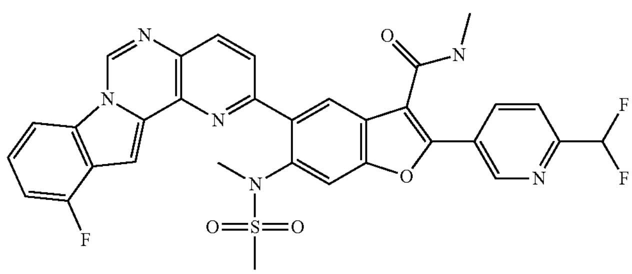 [SMILES: CNC(=O)c1c(-c2ccc(C(F)F)nc2)oc2cc(N(C)S(C)(=O)=O)c(-c3ccc4ncn5c6cccc(F)c6cc5c4n3)cc12] | ¹H-NMR (CDCl₃, 400 MHz) δ 9.27 (s, 1H), 9.08 (s, 1H), 8.59 (d, J = 8.8 Hz, 1H), 8.21 (d, J = 8.0 Hz, 1H), 8.10 (s, 1H), 7.80~7.84 (m, 3H), 7.78 (s, 2H), 7.60 (s, 1H), 7.18 (d, J = 8.8 Hz, 1H), 6.58~6.86 (m, 1H), 6.12 (s, 1H), 3.43 (s, 3H), 3.08 (d, J = 4.8 Hz, 3H), 2.76 (s, 3H). | 645 |
| 4 | 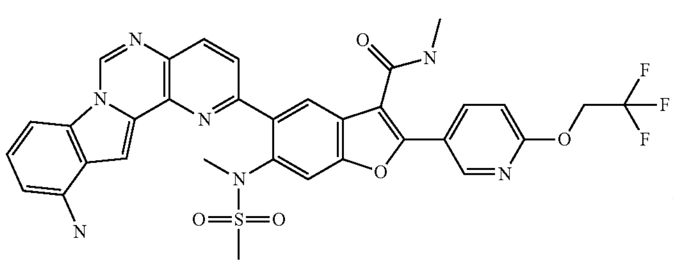 [SMILES: CNC(=O)c1c(-c2ccc(OCC(F)(F)F)nc2)oc2cc(N(C)S(C)(=O)=O)c(-c3ccc4ncn5c6cccc(N)c6cc5c4n3)cc12] | ¹H-NMR (CDCl₃, 400 MHz) δ 9.07 (s, 1H), 8.80 (d, J = 1.6 Hz, 1H), 8.33 (dd, J = 2.4, 8.8 Hz, 1H), 8.20 (d, J = 8.0 Hz, 1H), 8.09 (s, 1H), 7.81 (dd, J = 2.8, 8.0 Hz, 2H), 7.73 (s, 1H), 7.59 (s, 1H), 7.41~7.47 (m, 1H), 7.18 (t, J = 8.8 Hz, 1H), 7.02 (d, J = 8.8 Hz, 1H), 6.05 (s, 1H), 4.84~4.91 (m, 2H), 3.43 (s, 3H), 3.05 (d, J = 4.8 Hz, 3H), 2.74 (s, 3H). | 693 |
| 5 | 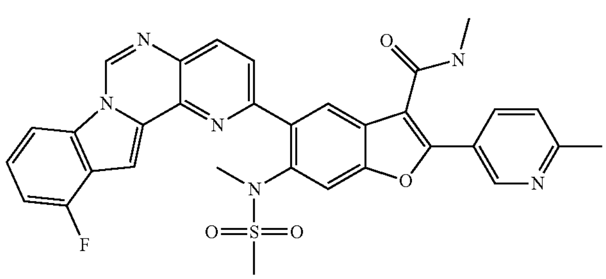 [SMILES: CNC(=O)c1c(-c2ccc(C)nc2)oc2cc(N(C)S(C)(=O)=O)c(-c3ccc4ncn5c6cccc(F)c6cc5c4n3)cc12] | ¹H-NMR (CDCl₃, 400 MHz) δ 9.00 (s, 2H), 8.11~8.18 (m, 2H), 8.06 (s, 1H), 7.72~7.76 (m, 2H), 7.67 (s, 1H), 7.52 (s, 1H), 7.26 (d, J = 8.4 Hz, 1H), 7.10 (s, 1H), 7.08 (s, 1H), 5.19 (s, 1H), 3.36 (s, 3H), 3.99 (d, J = 4.8 Hz, 3H), 3.66 (s, 3H), 2.59 (s, 3H). | 609 |

| Example | Structure | NMR | MS (M + H)+ |
|---|---|---|---|
| 6 | 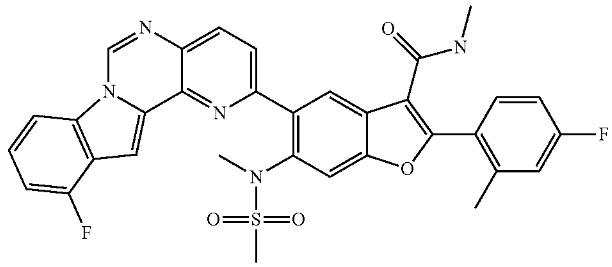 | ¹H-NMR (CDCl₃, 400 MHz) δ 9.01 (s, 1H), 8.42 (s, 1H), 8.12 (d, J = 8.0 Hz, 1H), 7.73~7.78 (m, 2H), 7.63 (s, 1H), 7.50 (s, 1H), 7.47 (d, J = 2.4 Hz, 1H), 7.30~7.41 (m, 1H), 7.03~7.10 (m, 3H), 5.43 (d, J = 3.6 Hz, 1H), 3.39 (s, 3H), 2.78 (d, J = 4.8 Hz, 3H), 2.59 (s, 3H), 2.30 (s, 3H). | 626 |
| 7 | 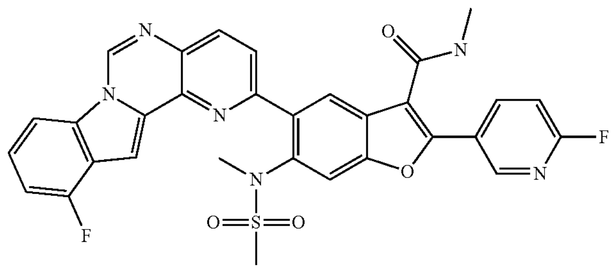 [SMILES: CNC(=O)c1c(-c2ccc(F)nc2)oc2cc(N(C)S(C)(=O)=O)c(-c3ccc4ncn5c6cccc(F)c6cc5c4n3)cc12] | ¹H-NMR (DMSO-d₆, 400 MHz) δ 9.68 (s, 1H), 8.81 (s, 1H), 8.52~8.59 (m, 2H), 8.23~8.30 (m, 2H), 8.14 (s, 1H), 8.01 (s, 1H), 7.89 (d, J = 8.4 Hz, 1H), 7.40~7.46 (m, 3H), 7.20~7.30 (m, 1H), 3.35 (s, 3H), 3.91 (s, 3H), 2.81 (d, J = 4.8 Hz, 3H). | 613 |
| 8 | 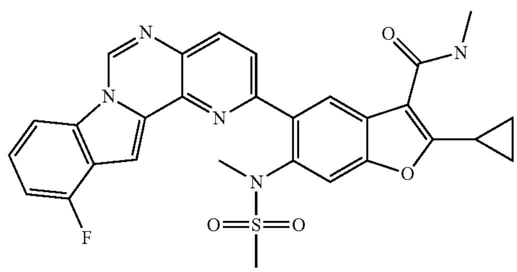 [SMILES: CNC(=O)c1c(C2CC2)oc2cc(N(C)S(C)(=O)=O)c(-c3ccc4ncn5c6cccc(F)c6cc5c4n3)cc12] | ¹H-NMR (CDCl₃, 400 MHz) δ 9.03 (s, 1H), 8.13 (d, J = 8.4 Hz, 1H), 7.98 (s, 1H), 7.77 (d, J = 7.6 Hz, 2H), 7.54 (d, J = 8.4 Hz, 2H), 7.36~7.45 (m, 1H), 7.14 (t, J = 8.8 Hz, 1H), 6.15 (d, J = 3.6 Hz, 1H), 3.37 (s, 3H), 3.05 (d, J = 4.8 Hz, 3H), 2.80~2.89 (m, 1H), 2.69 (s, 3H), 1.25~1.28 (m, 2H), 1.18~1.23 (m, 2H). | 558 |

Example 9

2-(2,4-difluorophenyl)-5-(11-fluoropyrido[3',2':4,5]pyrimido[1,6-a]indol-2-yl)-N-methyl-6-(N-methylmethylsulfonamido)benzofuran-3-carboxamide

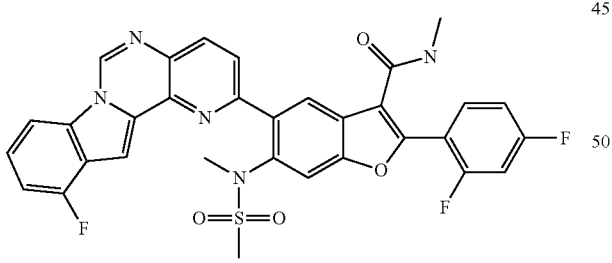

Step 1—Synthesis of 6-amino-5-bromo-2-(2,4-difluorophenyl)-N-methylbenzofuran-3-carboxamide

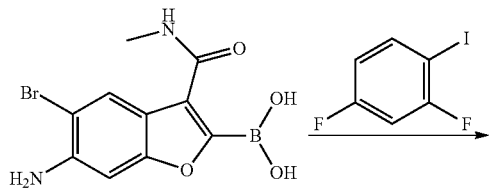

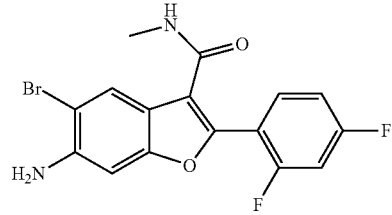

To a mixture of (6-amino-5-bromo-3-(methylcarbamoyl)benzofuran-2-yl)boronic acid (4.78 g, 11.46 mmol), K₃PO₄·3H₂O (8.32 g, 31.25 mmol) and 2,4-difluoro-1-iodobenzene (2.50 g, 10.42 mmol) in DMF (25 mL) was added Pd(dppf)Cl₂ (380 mg, 0.52 mmol) under N₂, and then the mixture was stirred at 15° C. for 3 hours. After the solvent was removed, EtOAc/H₂O (10 mL/20 mL) was added to the mixture. After stirring 15 minutes, the resulting solid was filtered to give the product of 6-amino-5-bromo-2-(2,4-difluorophenyl)-N-methylbenzofuran-3-carboxamide (2.80 g, yield: 70%). ¹H-NMR (DMSO-d₆, 400 MHz) δ 8.06 (d, J=1.6 Hz, 1H), 7.74 (d, J=10.4 Hz, 1H), 7.70 (s, 1H), 7.41 (s, 1H), 7.24 (s, 1H), 7.00 (s, 1H), 5.58 (br s, 2H), 2.76 (s, 3H). MS (M+H)⁺: 281/283

Step 2—Synthesis of 5-bromo-2-(2,4-difluorophenyl)-N-methyl-6-(methylsulfonamido)benzofuran-3-carboxamide

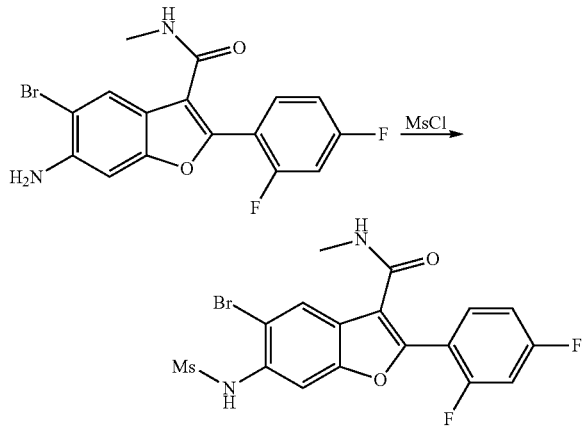

To a mixture of (6-amino-5-bromo-3-(methylcarbamoyl)benzofuran-2-yl)boronic acid (400 mg, 1.01 mmol) and pyridine (830 mg, 10.49 mmol) in DCM (15 mL), MsCl (601 mg, 5.25 mmol) was added dropwise at 0° C. The mixture was allowed to room temperature and stirred overnight. The reaction mixture was quenched with NaHCO$_3$ and extracted with DCM. The organic phase was washed with brine, dried over Na$_2$SO$_4$, and concentrated. The residue was dissolved in THF:H$_2$O=5:1 (15 mL) and LiOH.H$_2$O (800 mg, 0.02 mmol) was added. The mixture was stirred for 1 hour at room temperature. EtOAc (300 mL) was added, and the organic phase washed with NH$_4$Cl (a.q.), brine, dried over Na$_2$SO$_4$, filtrated and concentrated in vacuo. The residue was purified by column chromatography (eluted with DCM/EtOAc=10/1 to 2/1) to give 5-bromo-2-(2,4-difluorophenyl)-N-methyl-6-(methylsulfonamido)benzofuran-3-carboxamide (210 mg, yield: 43%). $^1$H-NMR (CDCl$_3$, 400 MHz) δ 8.32 (s, 1H), 7.91 (s, 1H), 7.6~47.90 (m, 1H), 7.06 (d, J=3.0 Hz, 1H), 7.03 (d, J=3.0 Hz, 1H), 6.88 (s, 1H), 3.02 (s, 3H), 2.97 (d, J=4.8 Hz, 3H). MS (M+H)$^+$: 459/461

Step 3—Synthesis of 5-bromo-2-(2,4-difluorophenyl)-N-methyl-6-(N-methylmethylsulfonamido)benzofuran-3-carboxamide

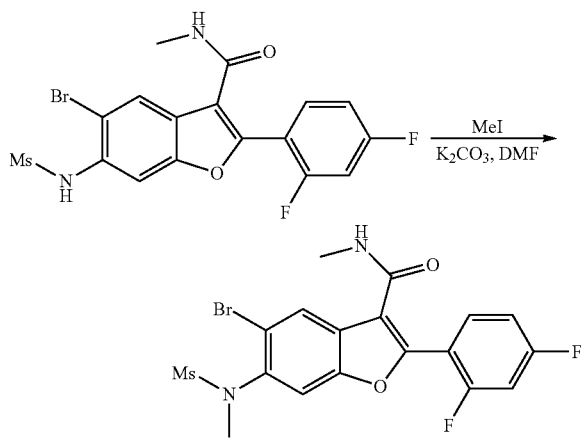

To a mixture of 5-bromo-2-(2,4-difluorophenyl)-N-methyl-6-(methylsulfonamido)benzofuran-3-carboxamide (653 mg, 1.38 mmol), K$_2$CO$_3$ (406 mg, 2.94 mmol) in DMF (10 mL) was added MeI (519 mg, 3.66 mmol), then the mixture was stirred at 80° C. After 3 hours, the solvent was removed by vacuum, the mixture was washed with H$_2$O (20 mL) and extract with DCM (50 mL×3), dried over Na$_2$SO$_4$ and concentrated to give the desired product of 5-bromo-2-(2,4-difluorophenyl)-N-methyl-6-(N-methylmethylsulfonamido)benzofuran-3-carboxamide (600 mg, yield: 89%). $^1$H-NMR (CDCl$_3$, 400 MHz) δ 8.24 (s, 1H), 7.69~7.75 (m, 2H), 7.05~7.10 (m, 1H), 6.98~7.03 (m, 1H), 5.64 (d, J=3.0 Hz, 1H), 3.09 (s, 3H), 2.97 (s, 3H), 2.95 (d, J=3.6 Hz, 3H). MS (M+H)$^+$: 473/475.

Step 4—Synthesis of 2-(2,4-difluorophenyl)-N-methyl-6-(N-methylmethylsulfonamido)-5-(4,4,5,5-tetramethyl-1,3,2-dioxaborolan-2-yl)benzofuran-3-carboxamide

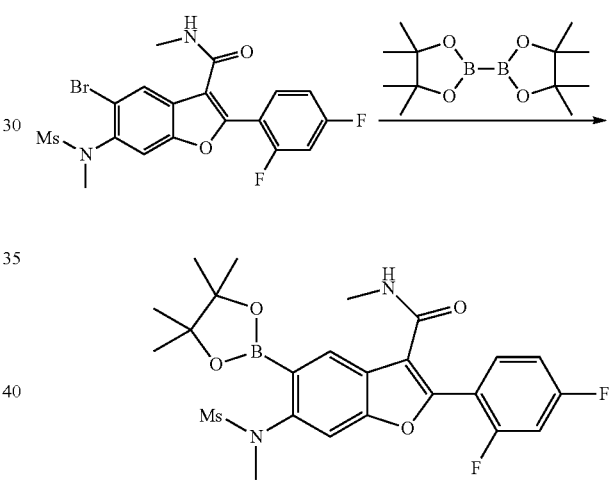

To a degassed mixture of 5-bromo-2-(2,4-difluorophenyl)-N-methyl-6-(N-methylmethylsulfonamido)benzofuran-3-carboxamide (400 mg, 0.85 mmol), bis(pinacolato)diboron (1 g, 4.23 mmol), KOAc (249 mg, 2.54 mmol) in 1,4-Dioxane (5 mL) and H$_2$O (1 mL) was added Pd(dppf)Cl$_2$ (5 mg), then the mixture was stirred at 130° C. After 3 hours, the solvent was removed by vacuum, and the mixture was washed with H$_2$O (20 mL), extract with DCM (50 mL×3), dried over Na$_2$SO$_4$. After concentrated, the residue was purified by column chromatography (PE/EtOAc=2/1) to give the product of 2-(2,4-difluorophenyl)-N-methyl-6-(N-methylmethylsulfonamido)-5-(4,4,5,5-tetramethyl-1,3,2-dioxaborolan-2-yl)benzofuran-3-carboxamide (240 mg, yield: 54%). $^1$H-NMR (CDCl$_3$, 400 MHz) δ 8.26 (s, 1H), 7.73 (d, J=6.8 Hz, 1H), 7.56 (s, 1H), 7.05 (t, J=6.8 Hz, 1H), 6.96 (q, J=6.8 Hz, 1H), 5.96 (s, 1H), 3.33 (s, 3H), 2.97 (s, 3H), 2.93 (d, J=4.8 Hz, 3H), 1.20 (s, 12H). MS (M+H)$^+$: 521.

Step 5—Synthesis of 2-(2,4-difluorophenyl)-5-(11-fluoropyrido[3',2':4,5]pyrimido[1,6-a]indol-2-yl)-N-methyl-6-(N-methylmethylsulfonamido)benzofuran-3-carboxamide

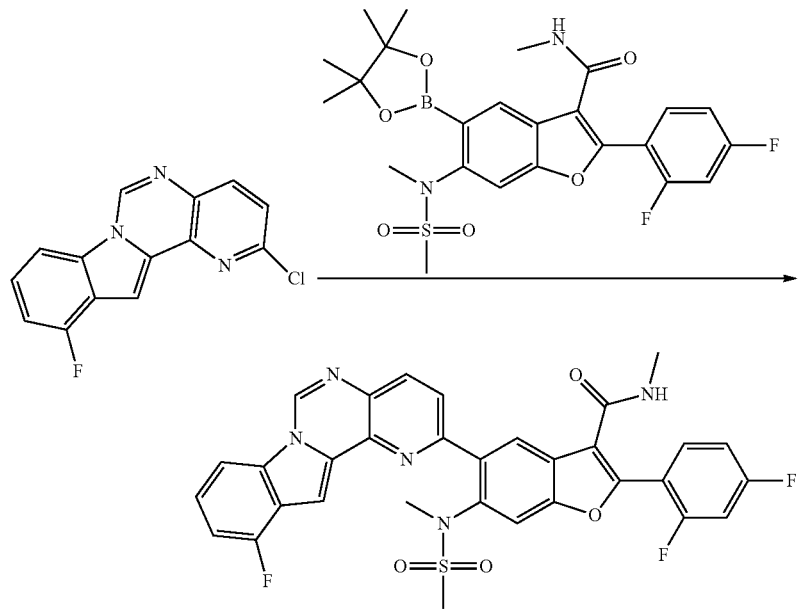

To a degassed solution of 2-(2,4-difluorophenyl)-N-methyl-6-(N-methylmethylsulfonamido)-5-(4,4,5,5-tetramethyl-1,3,2-dioxaborolan-2-yl)benzofuran-3-carboxamide (100 mg, 0.19 mmol), 2-chloro-11-fluoropyrido[3',2':4,5]pyrimido[1,6-a]indole (46 mg, 0.17 mmol) and $Cs_2CO_3$ (125 mg, 0.38 mmol) in 1,4-dioxane (2 mL) and $H_2O$ (5 drops) was added $Pd(dtbpf)Cl_2$ (10 mg) under nitrogen atmosphere. The reaction mixture was stirred at 100° C. for 3 h, concentrated in vacuo to remove 1,4-dioxane. The residue was diluted with $H_2O$ and extracted with DCM. The combined organic layers were washed with brine (30 mL), dried over $Na_2SO_4$, filtered and concentrated and purified (PE:EA=1:2) to give the product of 2-(2,4-difluorophenyl)-5-(11-fluoropyrido[3',2':4,5]pyrimido[1,6-a]indol-2-yl)-N-methyl-6-(N-methylmethylsulfonamido)benzofuran-3-carboxamide (60 mg, yield: 50%) through the prep-TLC. $^1$H-NMR (DMSO-$d_6$, 400 MHz) δ 9.70 (s, 1H), 8.22~8.29 (m, 3H), 8.11 (s, 1H), 8.04 (s, 1H), 7.83~7.88 (m, 2H), 7.43~7.51 (m, 3H), 7.25~7.33 (m, 2H), 3.34 (s, 3H), 2.90 (s, 3H), 2.73 (d, J=4.8 Hz, 3H). MS (M+H)$^+$: 630.

Example 10

2-(4-fluorophenyl)-5-(11-fluoropyrido[3',2':4,5]pyrimido[1,6-a]indol-2-yl)-N-methyl-6-(N-methylmethylsulfonamido)benzofuran-3-carboxamide

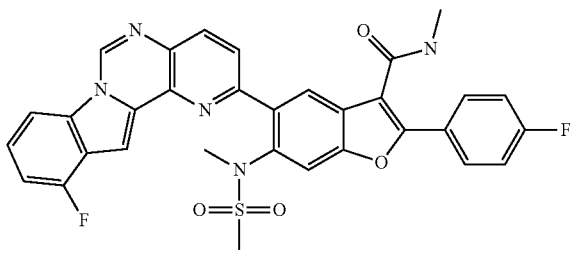 [SMILES: CNC(=O)c1c(-c2ccc(F)cc2)oc2cc(N(C)S(C)(=O)=O)c(-c3ccc4ncn5c6cccc(F)c6cc5c4n3)cc12]

Step 1—Synthesis of 2-(4-fluorophenyl)-5-(11-fluoropyrido[3',2':4,5]pyrimido[1,6-a]indol-2-yl)-N-methyl-6-(N-methylmethylsulfonamido)benzofuran-3-carboxamide

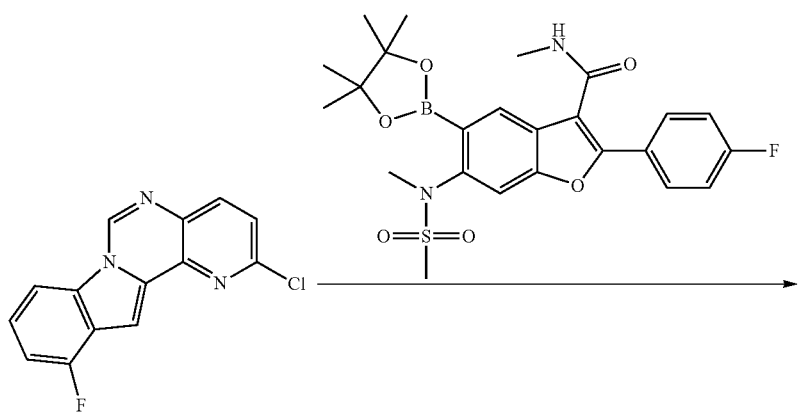

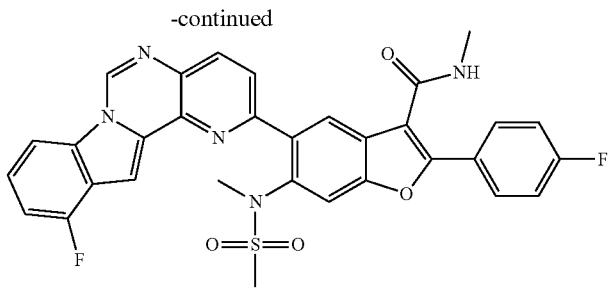

To a degassed solution of 2-chloro-11-fluoropyrido[3',2':4,5]pyrimido[1,6-a]indole (194 mg, 0.72 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (described in previous patent, 300 mg, 0.6 mmol) and Na$_2$CO$_3$ (127 mg, 1.2 mmol) in 1,4-dioxane (10 mL) and H$_2$O (0.5 mL) were added Pd$_2$(dba)$_3$ (30 mg) and X-Phos (30 mg) under nitrogen atmosphere. The reaction mixture was stirred at 100° C. for 16 h, concentrated in vacuo to remove 1,4-dioxane. The residue was diluted with H$_2$O and extracted with DCM. The combined organic layers were washed with brine (20 mL), dried over Na$_2$SO$_4$, filtered, concentrated and purified to give the product of 2-(4-fluorophenyl)-5-(11-fluoropyrido[3',2':4,5]pyrimido[1,6-a]indol-2-yl)-N-methyl-6-(N-methylmethylsulfonamido)benzofuran-3-carboxamide (100 mg, yield: 27%) through the prep-HPLC. $^1$H-NMR (CDCl$_3$, 400 MHz) δ 9.03 (s, 1H), 8.15 (d, J=8.0 Hz, 1H), 8.10 (s, 1H), 7.93~7.96 (m, 2H), 7.77 (d, J=8.4 Hz, 2H), 7.67 (s, 1H), 7.55 (s, 1H), 7.37~7.42 (m, 1H), 7.12~7.21 (m, 3H), 6.01 (br s, 1H), 3.40 (s, 3H), 2.98 (d, J=4.8 Hz, 3H), 2.68 (s, 3H). MS (M+H)$^+$: 612.

Example 11

5-(11-fluoropyrido[3',2':4,5]pyrimido[1,6-a]indol-2-yl)-N-methyl-6-(N-methylmethylsulfonamido)-2-(2-oxopyridin-1(2H)-yl)benzofuran-3-carboxamide

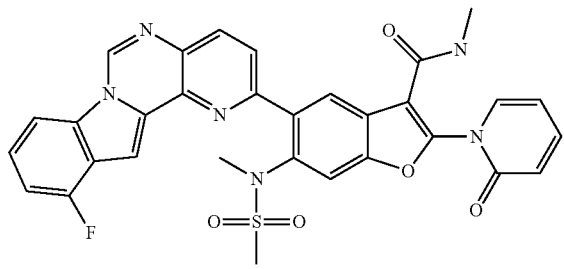 [SMILES: CNC(=O)c1c(-n2ccccc2=O)oc2cc(N(C)S(C)(=O)=O)c(-c3ccc4ncn5c6cccc(F)c6cc5c4n3)cc12]

Step 1—Synthesis of 5-bromo-N-methyl-6-(N-methylmethylsulfonamido)-2-(2-oxopyridin-1(2H)-yl)benzofuran-3-carboxamide

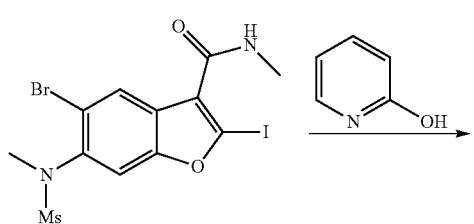

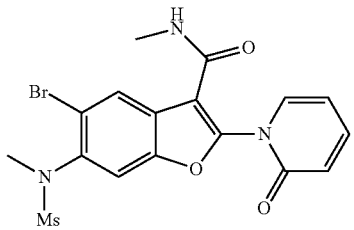

A mixture of 5-bromo-2-iodo-N-methyl-6-(N-methylmethylsulfonamido)benzofuran-3-carboxamide (1 mg, 2.05 mmol), pyridin-2-ol (293 mg, 3.08 mmol) and K$_2$CO$_3$ (567 mg, 4.11 mmol) in DMF (20 mL) was stirred at 90° C. for 3 hours. The mixture was then diluted with water and extracted with EtOAc. The organic layer was washed with brine, dried over Na$_2$SO$_4$ and concentrated. The residue was purified by column chromatography (PE:EtOAc=1:1) to afford the product of 5-bromo-N-methyl-6-(N-methylmethylsulfonamido)-2-(2-oxopyridin-1(2H)-yl)benzofuran-3-carboxamide (500 mg, yield: 50%). $^1$H-NMR (CDCl$_3$, 400 MHz) δ 8.32 (s, 1H), 7.72 (d, J=4.0 Hz, 1H), 7.68 (s, 1H), 7.53~7.59 (m, 1H), 7.34 (d, J=5.6 Hz, 1H), 6.74 (d, J=9.2 Hz, 1H), 6.45 (t, J=6.4 Hz, 1H), 3.33 (s, 3H), 3.08 (s, 3H), 2.91 (d, J=5.2 Hz, 3H). MS (M+H)$^+$: 454/456.

Step 2—Synthesis of N-methyl-6-(N-methylmethylsulfonamido)-2-(2-oxopyridin-1(2H)-yl)-5-(4,4,5,5-tetramethyl-1,3,2-dioxaborolan-2-yl)benzofuran-3-carboxamide

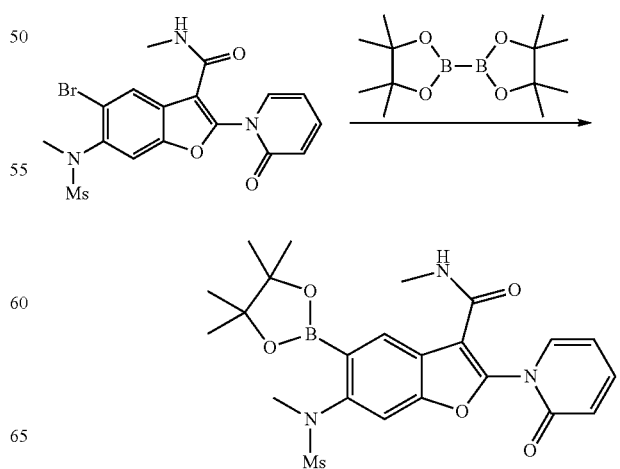

To a mixture of 5-bromo-N-methyl-6-(N-methylmethyl-sulfonamido)-2-(2-oxopyridin-1(2H)-yl)benzofuran-3-carboxamide (500 mg, 1.10 mmol), bis(pinacolato)diboron (838 mg, 3.30 mmol) and KOAc (216 mg, 2.20 mmol) in 1,4-dioxane (10 mL) was added Pd(dppf)Cl$_2$ (20 mg) under N$_2$. The mixture was stirred at 100° C. for 2 hours. The mixture was then filtered through Celite pad and concentrated. The residue was purified by column chromatography (DCM:EtOAc=2:1) to afford the product of N-methyl-6-(N-methylmethylsulfonamido)-2-(2-oxopyridin-1(2H)-yl)-5-(4,4,5,5-tetramethyl-1,3,2-dioxaborolan-2-yl)benzofuran-3-carboxamide (250 mg, yield: 45%). $^1$H-NMR (CDCl$_3$, 400 MHz) δ 8.41 (s, 1H), 7.58 (br s, 1H), 7.49~7.56 (m, 2H), 7.35 (d, J=6.0 Hz, 1H), 6.70 (d, J=9.2 Hz, 1H), 6.40 (t, J=6.4 Hz, 1H), 3.32 (s, 3H), 2.94 (s, 3H), 2.90 (d, J=4.4 Hz, 3H), 1.34 (s, 12H). MS (M+H)$^+$: 502.

Step 3—Synthesis of 5-(11-fluoropyrido[3',2':4,5]pyrimido[1,6-a]indol-2-yl)-N-methyl-6-(N-methylethylsulfonamido)-2-(2-oxopyridin-1(2H)-yl)benzofuran-3-carboxamide

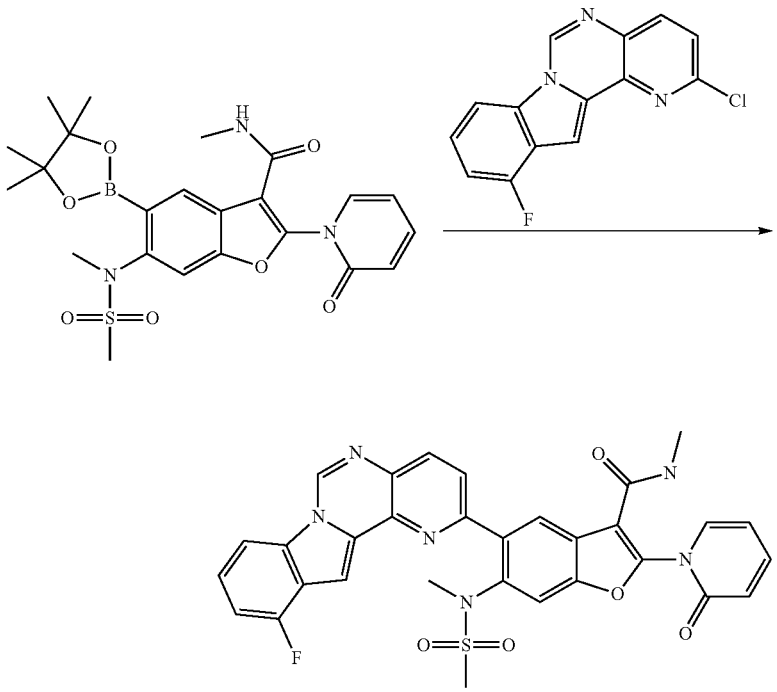 [SMILES: CNC(=O)c1c(-n2ccccc2=O)oc2cc(N(C)S(C)(=O)=O)c(B3OC(C)(C)C(C)(C)O3)cc12 ; Fc1cccc2c1cc1c3nc(Cl)ccc3ncn21 ; CNC(=O)c1c(-n2ccccc2=O)oc2cc(N(C)S(C)(=O)=O)c(-c3ccc4ncn5c6cccc(F)c6cc5c4n3)cc12]

To a mixture of N-methyl-6-(N-methylmethylsulfonamido)-2-(2-oxopyridin-1(2H)-yl)-5-(4,4,5,5-tetramethyl-1,3,2-dioxaborolan-2-yl)benzofuran-3-carboxamide (200 mg, 0.40 mmol), 2-chloro-11-fluoropyrido[3',2':4,5]pyrimido[1,6-a]indole (140 mg, 0.48 mmol) and K$_2$CO$_3$ (260 mg, 0.80 mmol) in 1,4-dioxane (3 mL) was added Pd(dtbpf)Cl$_2$ (20 mg) under N$_2$. The mixture was stirred at 100° C. for 16 hours. The mixture was then concentrated in vacuo, and the residue was purified by prep-HPLC to afford the product of 5-(11-fluoropyrido[3',2':4,5]pyrimido[1,6-a]indol-2-yl)-N-methyl-6-(N-methylmethylsulfonamido)-2-(2-oxopyridin-1(2H)-yl)benzofuran-3-carboxamide (30 mg, yield: 12%). $^1$H-NMR (CDCl$_3$, 400 MHz) δ 8.98 (s, 1H), 8.19 (s, 1H), 8.09 (d, J=8.8 Hz, 1H), 7.72 (dd, J=2.8, 8.4 Hz, 2H), 7.67 (d, J=4.4 Hz, 1H), 7.61 (s, 1H), 7.45~7.54 (m, 2H), 7.30~7.40 (m, 2H), 7.06~7.12 (m, 1H), 6.69 (d, J=9.6 Hz, 1H), 6.39 (t, J=6.8 Hz, 1H), 3.35 (s, 3H), 2.86 (d, J=4.8 Hz, 3H), 2.57 (s, 3H). MS (M+H)$^+$: 611.

Examples 12-13

Examples 12 and 13, depicted in the table below, were prepared in accordance with the method described in Example 11.

| Compound ID | Structure | NMR | MS (M + H)+ |
|---|---|---|---|
| 12 | 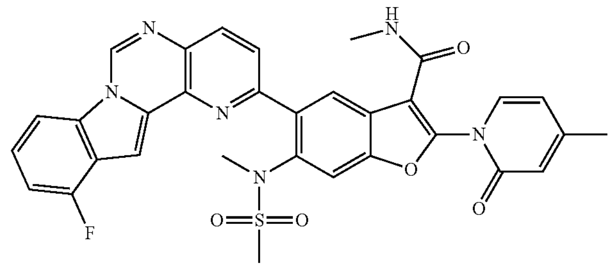 [SMILES: CNC(=O)c1c(-n2ccc(C)cc2=O)oc2cc(N(C)S(C)(=O)=O)c(-c3ccc4ncn5c6cccc(F)c6cc5c4n3)cc12] | ¹H-NMR (CDCl₃, 400 MHz) δ 9.07 (s, 1H), 8.29 (s, 1H), 8.18 (d, J = 8.4 Hz, 1H), 7.84 (br s, 1 H), 7.80 (d, J = 8.4 Hz, 2 H), 7.69 (s, 1H), 7.55 (s, 1H), 7.40~7.45 (m, 1H), 7.30 (d, J = 7.2 Hz, 1H), 7.17 (t, J = 8.4 Hz, 1H), 6.55 (s, 1H), 6.31 (d, J = 6.4 Hz, 1H), 3.43 (s, 3H), 2.91 (d, J = 4.8 Hz, 3H), 2.63 (s, 3H), 2.34 (s, 3H). | 625 |
| 13 | 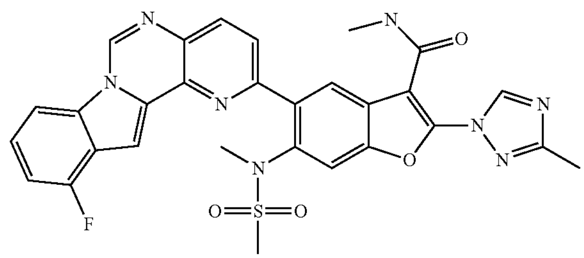 [SMILES: CNC(=O)c1c(-n2cnc(C)n2)oc2cc(N(C)S(C)(=O)=O)c(-c3ccc4ncn5c6cccc(F)c6cc5c4n3)cc12] | ¹H-NMR (CDCl₃, 400 MHz) δ 9.02 (s, 1H), 8.52 (s, 1H), 8.07~8.15 (m, 3H), 7.74~7.77 (m, 2H), 7.68 (s, 1H), 7.49 (s, 1H), 7.37 (d, J = 4.8 Hz, 1H), 7.10 (d, J = 8.8 Hz, 1H), 3.39 (s, 3H), 2.88 (d, J = 4.8 Hz, 3H), 2.67 (s, 3H), 2.57 (s, 3H). | 599 |

Example 14

2-(4-fluorophenyl)-5-(11-fluoropyrido[3',2':4,5]pyrimido[1,6-a]indol-2-yl)-N-methyl-6-(N-methylmethylsulfonamido)furo[2,3-b]pyridine-3-carboxamide Step 1—Synthesis of 2-(4-fluorophenyl)-5-(11-fluoropyrido[3',2':4,5]pyrimido[1,6-a]indol-2-yl)-N-methyl-6-(N-methylmethylsulfonamido)furo[2,3-b]pyridine-3-carboxamide

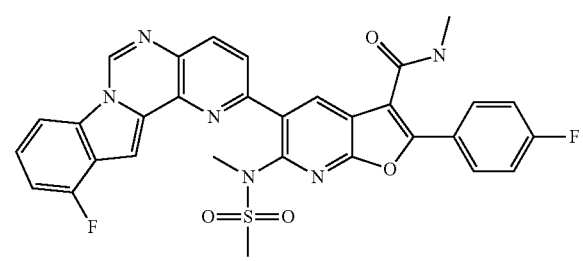

A mixture of 2-chloro-11-fluoropyrido[3',2':4,5]pyrimido[1,6-a]indole (216 mg, 0.795 mmol), 2-(4-fluorophenyl)-5-iodo-6-(N-methylmethylsulfonamido)furo[2,3-b]pyridine-3-carboxamide (200 mg, 0.398 mmol), bis(pinacolato)diboron (505 mg, 1.99 mmol), KOAc (78 mg, 0.795 mmol), sodium carbonate (84 mg, 0.795 mmol), Pd$_2$(dba)$_3$ (20 mg) and X-Phos (20 mg) in 1,4-dioxane/H$_2$O (5/0.5 mL) was stirred 100° C. for 16 hours under nitrogen atmosphere. After filtered through celite and concentrated, the residue was suspended in water. After extracted with EtOAc, the combined organic phase was washed with brine, dried over sodium sulfate and concentrated to afford the product of 2-(4-fluorophenyl)-5-(11-fluoropyrido[3',2':4,5]pyrimido[1,6-a]indol-2-yl)-N-methyl-6-(N-methylmethylsulfonamido)furo[2,3-b]pyridine-3-carboxamide (40 mg, yield: 16%) through the prep-HPLC. $^1$H-NMR (DMSO-d$_6$, 400 MHz) δ 9.72 (s, 1H), 8.66 (d, J=4.0 Hz, 1H), 8.55 (s, 1H), 8.32 (d, J=8.8 Hz, 2H), 8.12 (d, J=8.0 Hz, 2H), 8.04~8.09 (m, 1H), 7.53 (s, 2H), 7.42~7.47 (m, 2H), 7.30~7.32 (m, 1H), 3.27 (s, 3H), 3.18 (s, 3H), 2.85 (d, J=4.4 Hz, 3H). MS (M+H)$^+$: 613.

Example 15

2-(4-fluorophenyl)-5-(11-fluoropyrido[3',2':4,5]pyrimido[1,6-a]indol-2-yl)-N-methyl-6-(N-methylmethylsulfonamido)-2H-indazole-3-carboxamide

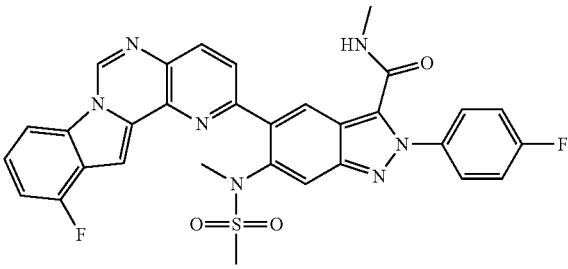 [SMILES: CNC(=O)c1c2cc(-c3ccc4ncn5c6cccc(F)c6cc5c4n3)c(N(C)S(C)(=O)=O)cc2nn1-c1ccc(F)cc1]

Step 1—Synthesis of 2-(4-fluorophenyl)-5-(11-fluoropyrido[3',2':4,5]pyrimido[1,6-a]indol-2-yl)-N-methyl-6-(N-methylmethylsulfonamido)-2H-indazole-3-carboxamide

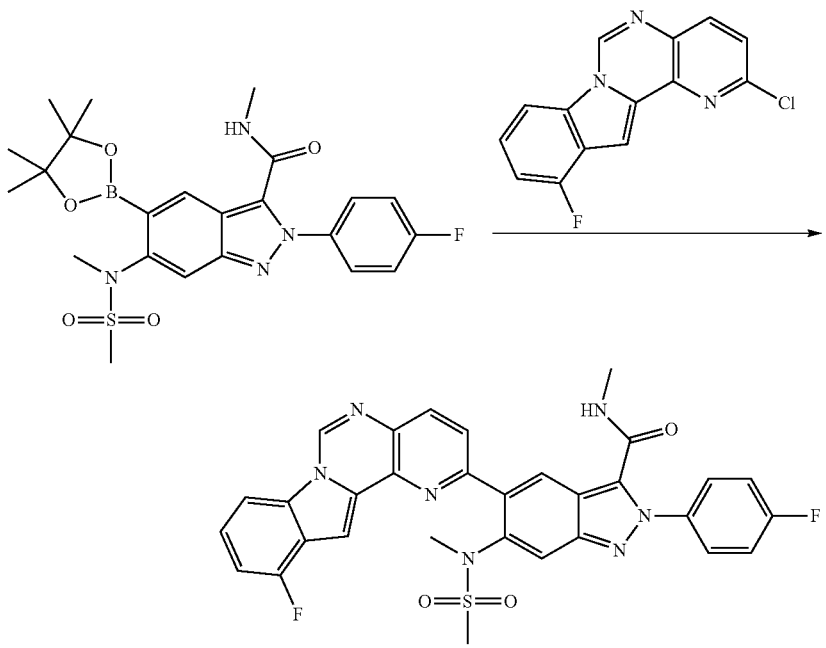

To a degassed solution of 2-(4-fluorophenyl)-N-methyl-6-(N-methylmethylsulfonamido)-5-(4,4,5,5-tetramethyl-1,3,2-dioxaborolan-2-yl)-2H-indazole-3-carboxamide (30 mg, 0.06 mmol), 2-chloro-11-fluoropyrido[3',2':4,5]pyrimido[1,6-a]indole (20 mg, 0.07 mmol) and K$_3$PO$_4$.3H$_2$O (48 mg, 0.18 mmol) in 1,4-dioxane (1 mL) were added Pd$_2$(dba)$_3$ (7 mg) and X-Phos (7 mg) under N$_2$ protection. The reaction mixture was heated to 100° C. and stirred for 2 hours, and then filtered through a Celite pad. The filtrate was concentrated in vacuo, and the residue was purified by prep-HPLC to give 2-(4-fluorophenyl)-5-(11-fluoropyrido[3',2':4,5]pyrimido[1,6-a]indol-2-yl)-N-methyl-6-(N-methylmethylsulfonamido)-2H-indazole-3-carboxamide (10 mg, yield: 32%). $^1$H-NMR (CDCl$_3$, 400 MHz) δ 9.08 (s, 1H), 8.19~8.23 (m, 2H), 7.95 (s, 1H), 7.80~7.38 (m, 2H), 7.54~7.61 (m, 3H), 7.43~7.45 (m, 1H), 7.26~7.29 (m, 2H), 7.25 (s, 1H), 7.18~7.25 (m, 1H), 3.47 (s, 3H), 3.03 (d, J=4.8 Hz, 3H), 2.83 (s, 3H). MS (M+H)$^+$: 612.

Example 16

2-(4-fluorophenyl)-5-(11-fluoropyrido[3',2':4,5]pyrimido[1,6-a]indol-2-yl)-N-methyl-6-(N-methylmethylsulfonamido)pyrazolo[1,5-a]pyridine-3-carboxamide

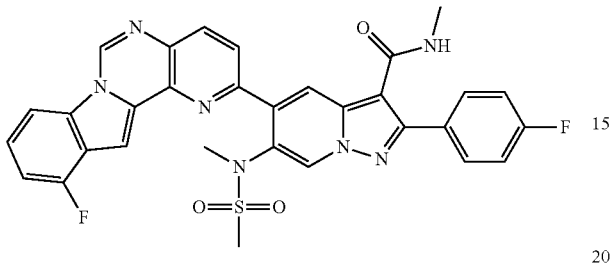

Step 1—Synthesis of 2-(4-fluorophenyl)-5-(11-fluoropyrido[3',2':4,5]pyrimido[1,6-a]indol-2-yl)-N-methyl-6-(N-methylmethylsulfonamido)pyrazolo[1,5-a]pyridine-3-carboxamide

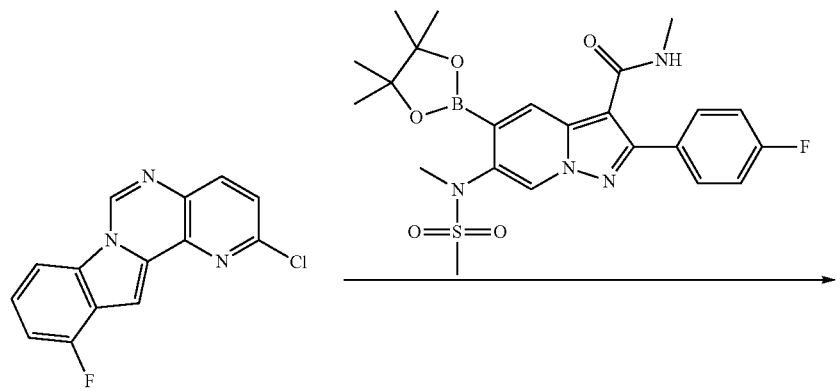

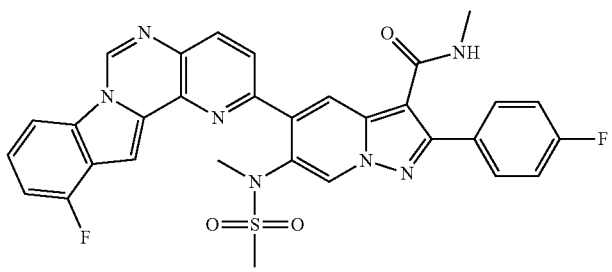 [SMILES: CNC(=O)c1c(-c2ccc(F)cc2)nn2cc(N(C)S(C)(=O)=O)c(-c3ccc4ncn5c6cccc(F)c6cc5c4n3)cc12]

To a mixture of 2-chloro-11-fluoropyrido[3',2':4,5]pyrimido[1,6-a]indole (50 mg, 0.184 mmol), 2-(4-fluorophenyl)-N-methyl-6-(N-methylmethylsulfonamido)-5-(4,4,5,5-tetramethyl-1,3,2-dioxaborolan-2-yl)pyrazolo[1,5-a]pyridine-3-carboxamide (100 mg, 0.202 mmol) and $Na_2CO_3$ (39. mg, 0.368 mmol) in dioxane (2 mL) was added X-Phos (10 mg) and $Pd_2(dba)_3$ (10 mg) under $N_2$. The reaction mixture was stirred at 100° C. for 5 hours and concentrated in vacuo to remove dioxane. The reaction mixture was extracted with EtOAc, washed with brine, dried over $Na_2SO_4$, filtered and concentrated in vacuo. The residue was purified by prep-HPLC to give the product of 2-(4-fluorophenyl)-5-(11-fluoropyrido[3',2':4,5]pyrimido[1,6-a]indol-2-yl)-N-methyl-6-(N-methylmethylsulfonamido)pyrazolo[1,5-a]pyridine-3-carboxamide (30 mg, yield: 26%). $^1$H-NMR (CDCl$_3$, 400 MHz) δ 9.69 (s, 1H), 9.37 (s, 1H), 8.29 (d, J=8.4 Hz, 2H), 8.10 (d, J=8.0 Hz, 2H), 7.96 (d, J=8.4 Hz, 1H), 7.94~7.90 (m, 2H), 7.48 (t, J=5.6 Hz, 2H), 7.35~7.27 (m, 3H), 3.44 (s, 3H), 2.97 (s, 3H), 2.77 (d, J=4.8 Hz, 3H). MS (M+H)$^+$: 612.

Example 17

5-(11-fluoropyrido[3',4':4,5]pyrimido[1,6-a]indol-2-yl)-N-methyl-6-(N-methylmethylsulfonamido)-2-(6-(trifluoromethyl)pyridin-3-yl)benzofuran-3-carboxamide

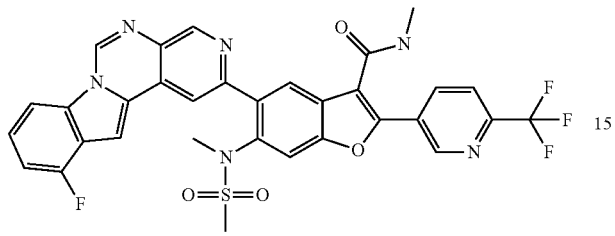

Step 1—Synthesis of 5-(11-fluoropyrido[3',4':4,5]pyrimido[1,6-a]indol-2-yl)-N-methyl-6-(N-methylmethylsulfonamido)-2-(6-(trifluoromethyl)pyridin-3-yl)benzofuran-3-carboxamide

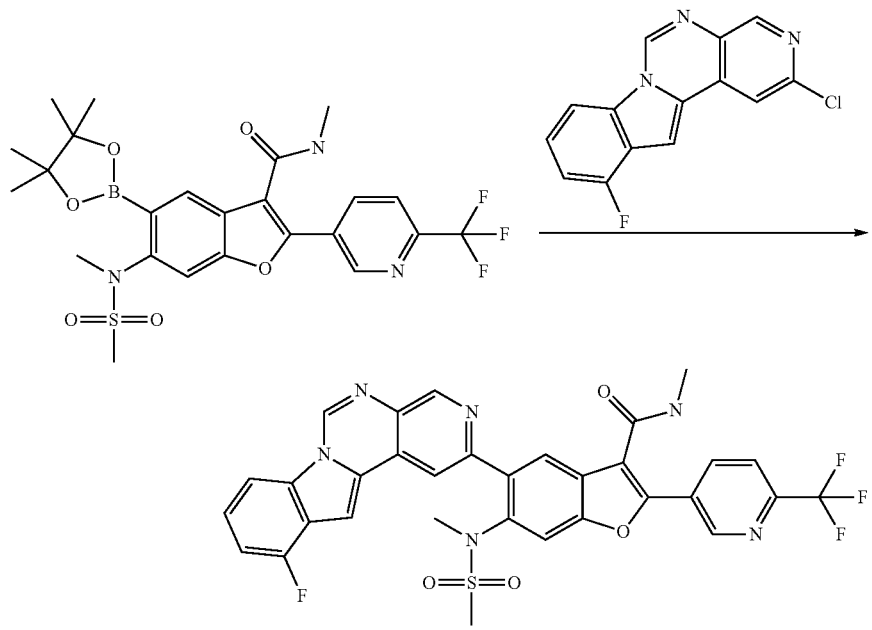

To a mixture of N-methyl-6-(N-methylmethylsulfonamido)-5-(4,4,5,5-tetramethyl-1,3,2-dioxaborolan-2-yl)-2-(6-(trifluoromethyl)pyridin-3-yl)benzofuran-3-carboxamide (80 mg, 0.145 mmol), 2-chloro-11-fluoropyrido[3',4':4,5]pyrimido[1,6-a]indole (prepared using the similar method described in Example 1, 39 mg, 0.145 mmol) and $K_2CO_3$ (60 mg, 0.435 mmol) in dioxane/$H_2O$ (3 mL/0.3 mL) under $N_2$ were added $Pd_2(dba)_3$ (7 mg, 0.007 mmol) and X-Phos (7 mg, 0.0146 mmol). The reaction mixture was stirred at 85° C. for 2 h. The mixture was diluted with water, and then extracted with EA, washed with brine, dried over $Na_2SO_4$, concentrated. It was purified by prep-TLC (DCM/MeOH=30:1, DCM/EA=1:1) to obtain 5-(11-fluoropyrido[3',4':4,5]pyrimido[1,6-a]indol-2-yl)-N-methyl-6-(N-methylmethylsulfonamido)-2-(6-(trifluoromethyl)pyridin-3-yl)benzofuran-3-carboxamide (55 mg, yield: 57%). $^1$H-NMR (CDCl$_3$, 400 MHz) δ 9.32 (s, 1H), 9.17 (s, 1H), 9.06 (s, 1H), 8.69 (d, J=7.6 Hz, 1H), 8.38 (s, 1H), 8.12 (s, 1H), 7.80 (dd, J=5.4, 8.0 Hz, 2H), 7.74 (s, 1H), 7.48~7.42 (m, 2H), 7.18 (t, J=8.8 Hz, 1H), 6.35 (br s, 1H), 3.20 (s, 3H), 3.07 (d, J=4.8 Hz, 3H), 2.98 (s, 3H). MS (M+H)$^+$: 663.

Examples 18 and 19

Examples 18 and 19, depicted in the table below, were prepared in accordance with the method described in Example 17.

| Example | Structure | NMR | MS (M + H)+ |
|---|---|---|---|
| 18 | 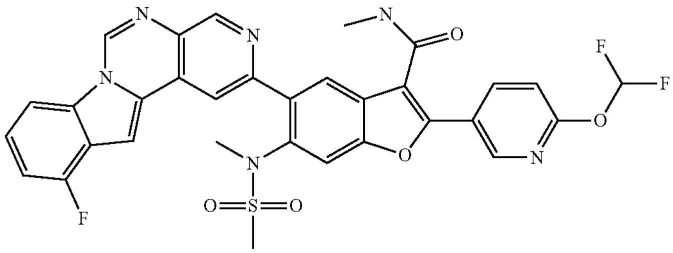 [SMILES: CNC(=O)c1c(-c2ccc(OC(F)F)nc2)oc2cc(N(C)S(C)(=O)=O)c(-c3cc4c(cn3)ncn3c5cccc(F)c5cc43)cc12] | ¹H-NMR (CDCl₃, 400 MHz) δ 9.12 (s, 1H), 8.96 (s, 1H), 8.79 (s, 1H), 8.42 (dd, J = 2.0, 8.4 Hz, 1H), 8.31 (s, 1H), 8.06 (s, 1H), 7.75~7.70 (m, 1H), 7.66 (s, 1H), 7.53~7.34 (m, 3H), 7.15 (t, J = 8.8 Hz, 1H), 6.98 (d, J = 8.4 Hz, 1H), 6.41 (d, J = 4.0 Hz, 1H), 3.18 (s, 3H), 3.05 (d, J = 5.2 Hz, 3H), 2.98 (s, 3H). | 661 |
| 19 | 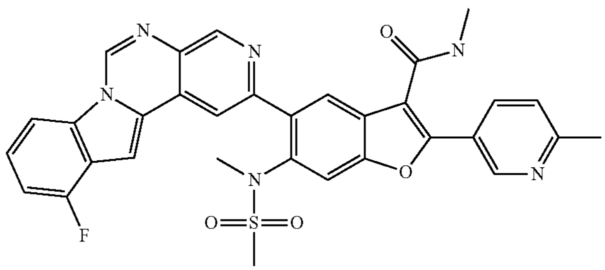 [SMILES: CNC(=O)c1c(-c2ccc(C)nc2)oc2cc(N(C)S(C)(=O)=O)c(-c3cc4c(cn3)ncn3c5cccc(F)c5cc43)cc12] | ¹H-NMR (CDCl₃, 400 MHz) δ 9.11 (s, 1H), 9.90 (d, J = 6.4 Hz, 2H), 8.29 (s, 1H), 8.21 (d, J = 8.0 Hz, 1H), 8.08 (s, 1H), 7.73 (d, J = 8.4 Hz, 1H), 7.64 (s, 1H), 7.38~7.41 (m, 2H), 7.24 (d, J = 8.4 Hz, 1H), 7.12 (t, J = 8.8 Hz, 1H), 6.05 (s, 1H), 3.15 (s, 3H), 2.97 (d, J = 4.4 Hz, 3H), 2.87 (s, 3H), 2.59 (s, 3H). | 609 |

Example 20

2-(4-fluorophenyl)-5-(10-fluoropyrido[3',2':4,5]pyrimido[1,6-a]indol-2-yl)-N-methyl-6-(N-methylmethylsulfonamido)benzofuran-3-carboxamide

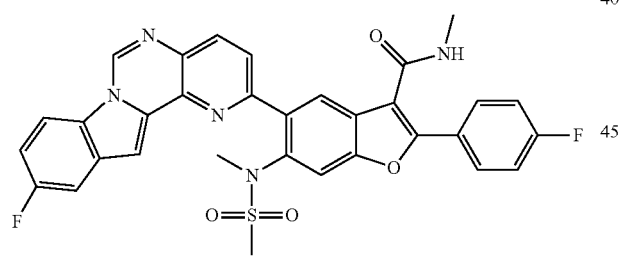

Step 1—Synthesis of tert-butyl (6-chloro-2-iodopyridin-3-yl)carbamate

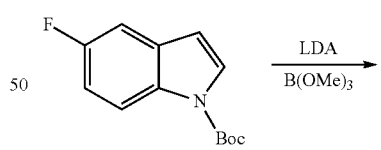

(Boc)₂O (3.24 g, 14.85 mmol) was added slowly to a mixture of 6-chloro-2-iodopyridin-3-amine (3.4 g, 13.36 mmol), DMAP (122 mg, 1.00 mmol) and TEA (2.63 g, 26.00 mmol) in CH₂Cl₂ (40 mL). The mixture was stirred at room temperature for 1 hour and then concentrated. The residue was purified by prep-TLC (PE:EA=80:1) to afford the desired product of tert-butyl (6-chloro-2-iodopyridin-3-yl) carbamate (1.63 g, yield: 34.4%). ¹H-NMR (CDCl₃, 400 MHz) δ 8.29 (d, J=8.4 Hz, 1H), 7.23 (d, J=8.4 Hz, 1H), 6.86 (br s, 1H), 1.53 (s, 9H). MS (M+H)⁺: 355.

Step 2—Synthesis of (1-(tert-butoxycarbonyl)-5-fluoro-1H-indol-2-yl)boronic acid

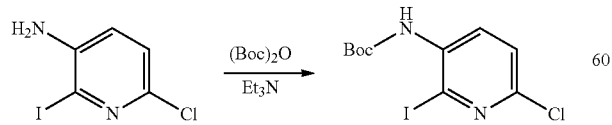

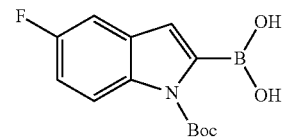

To a solution of LDA (42.5 mL, 0.085 mol) in THF (60 mL) at −78° C. was added tert-butyl 5-fluoro-1H-indole-1-carboxylate (10 g, 0.042 mol) dropwise under N₂. The mixture was stirred at −78° C. for 1 hour. Then trimethyl borate (5.68 g, 0.055 mol) was added to the mixture. The mixture was stirred at −78° C. for another 40 min. The reaction was monitored by TLC. When the reaction was completed, the reaction was quenched with NH₄Cl (sat. 50 mL). Then the pH of mixture was adjusted to 6 with 1 N HCl and extracted with EtOAc (50 mL*3). The combined organic layers were washed with brine (100 mL), dried over Na₂SO₄, filtered and concentrated. The obtained solid was recrystallized with EtOAc and PE to give (1-(tert-butoxycarbonyl)-5-fluoro-1H-indol-2-yl)boronic acid (10 g, yield: 84.5%, which might be unstable at high temp. work up, store in fridge). ¹H-NMR (CDCl₃, 400 MHz) δ 7.95 (dd, J=4.0, 9.2 Hz, 1H), 7.43 (s, 1H), 7.21~7.26 (m, 1H), 7.13 (br s, 2H), 7.07 (dt, J=2.4, 9.2 Hz, 1H), 1.74 (s, 9H). MS (M+H)⁺: 280.

Step 3—Synthesis of tert-butyl 2-(3-((tert-butoxycarbonyl)amino)-6-chloropyridin-2-yl)-5-fluoro-1H-indole-1-carboxylate

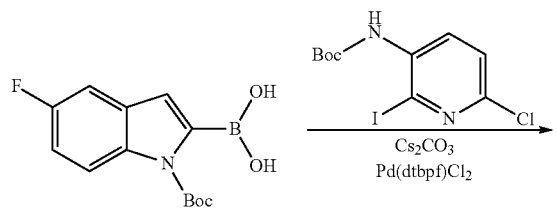

A mixture of (1-(tert-butoxycarbonyl)-5-fluoro-1H-indol-2-yl)boronic acid (1.41 g, 5.06 mmol), tert-butyl (6-chloro-2-iodopyridin-3-yl)carbamate (1.63 g, 4.60 mmol), Pd(dtbpf)Cl₂ (300 mg, 0.46 mmol) and Cs₂CO₃ (2.99 g, 9.20 mmol) in dioxane (15 mL) was stirred at 70° C. for 1.5 hours under N₂ atmosphere. The mixture was then diluted with water (150 mL) and extracted with EtOAc (50 mL*3). The organic layer was washed with brine (100 mL), dried over Na₂SO₄ and concentrated. The residue was purified by column chromatography (PE:EA=80:1) to afford the desired product of tert-butyl 2-(3-((tert-butoxycarbonyl)amino)-6-chloropyridin-2-yl)-5-fluoro-1H-indole-1-carboxylate (1.6 g, yield: 75.4%). ¹H-NMR (CDCl₃, 400 MHz) δ 8.52 (d, J=8.8 Hz, 1H), 8.24 (dd, J=4.4, 9.2 Hz, 1H), 7.31 (d, J=8.4 Hz, 1H), 7.27 (d, J=2.0 Hz, 1H), 7.12 (dt, J=2.4, 9.2 Hz, 1H), 6.72 (s, 1H), 6.65 (br s, 1H), 1.46 (s, 9H), 1.23~1.32 (m, 9H). MS (M+H)⁺: 462.

Step 4—Synthesis of 6-chloro-2-(5-fluoro-1H-indol-2-yl)pyridin-3-amine

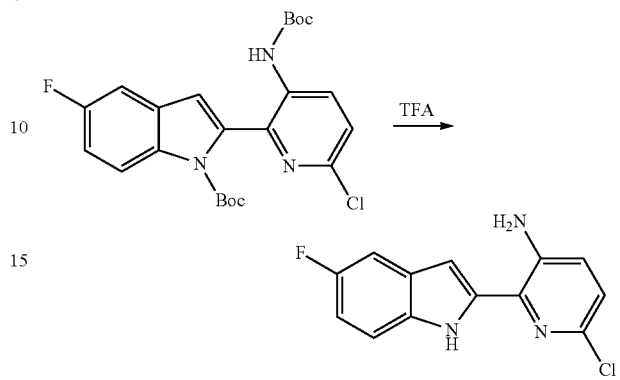

A mixture of tert-butyl 2-(3-((tert-butoxycarbonyl)amino)-6-chloropyridin-2-yl)-5-fluoro-1H-indole-1-carboxylate (800 mg, 1.735 mmol) and TFA/CH₂Cl₂ (5 mL/10 mL) was stirred at room temperature for 1 hour. The mixture was then adjusted to pH 7 with 1N NaOH and extracted with EtOAc (30 mL*3). The organic layer was washed with brine (60 mL), dried over Na₂SO₄ and concentrated. The residue was purified by column chromatography (PE:EA=25:1) to afford the desired product of 6-chloro-2-(5-fluoro-1H-indol-2-yl)pyridin-3-amine (200 mg, yield: 43.8%). ¹H-NMR (CDCl₃, 400 MHz) δ 9.47 (br s, 1H), 7.36 (dd, J=4.4, 8.8 Hz, 1H), 7.29 (dd, J=2.4, 9.2 Hz, 1H), 7.09~7.14 (m, 1H), 7.04~7.09 (m, 1H), 7.00 (dt, J=2.4, 9.2 Hz, 1H), 6.94 (d, J=1.2 Hz, 1H), 4.24 (br s, 2H). MS (M+H)⁺: 262.

Step 5—Synthesis of 2-chloro-10-fluoropyrido[3',2':4,5]pyrimido[1,6-a]indole

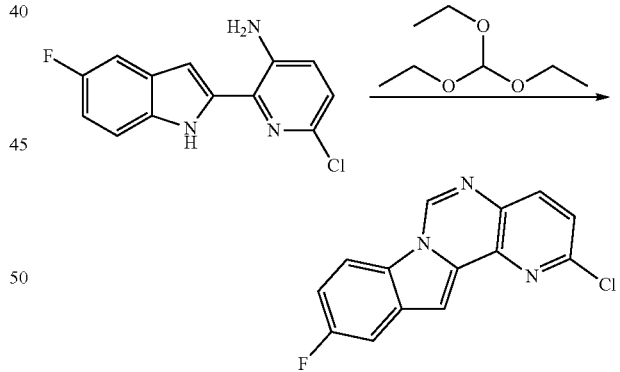

A mixture of 6-chloro-2-(5-fluoro-1H-indol-2-yl)pyridin-3-amine (100 mg, 0.383 mmol), triethoxymethane (2 mL) and HCl/CH₃OH (5 mL) was stirred at 80° C. overnight. The mixture was then diluted with water (30 mL) and extracted with EtOAc (20 mL*3). The organic layer was washed with brine (30 mL), dried over Na₂SO₄ and concentrated. The residue was purified by column chromatography (PE:EA=5:1) to afford the desired product of 2-chloro-10-fluoropyrido[3',2':4,5]pyrimido[1,6-a]indole (90 mg, yield: 86.5%). ¹H-NMR (CDCl₃, 400 MHz) δ 9.01 (s, 1H), 8.03 (d, J=8.4 Hz, 1H), 7.94 (dd, J=4.4, 9.2 Hz, 1H), 7.51~7.57 (m, 2H), 7.48 (d, J=8.4 Hz, 1H), 7.21~7.25 (m, 1H). MS (M+H)⁺: 272.

Step 6—Synthesis of 2-(4-fluorophenyl)-5-(10-fluoropyrido[3',2':4,5]pyrimido[1,6-a]indol-2-yl)-N-methyl-6-(N-methylmethylsulfonamido)benzofuran-3-carboxamide

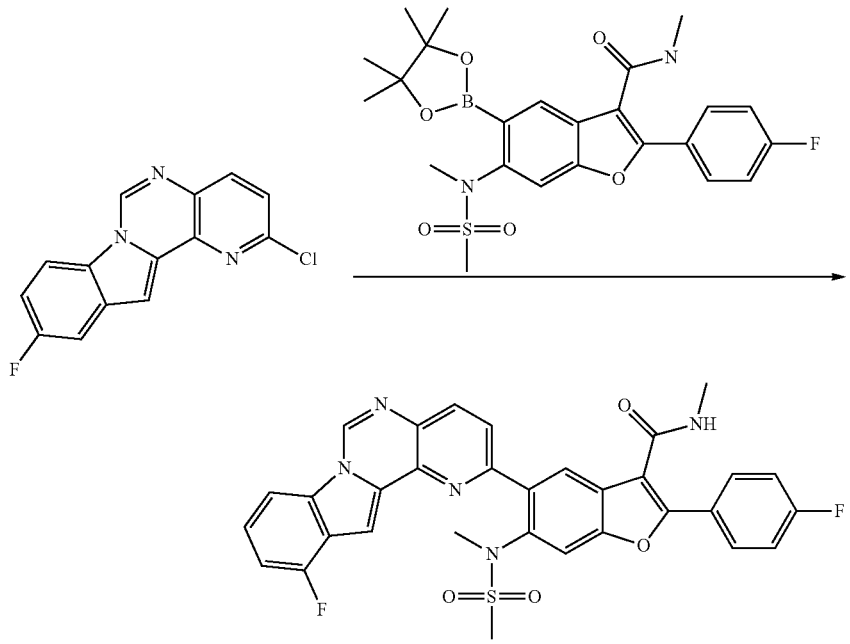

A mixture of 2-chloro-10-fluoropyrido[3',2':4,5]pyrimido[1,6-a]indole (50 mg, 0.184 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (102 mg, 0.203 mmol), $K_3PO_4 \cdot 3H_2O$ (146 mg, 0.552 mmol), $Pd_2(dba)_3$ (17 mg, 0.018 mmol) and X-Phos (18 mg, 0.037 mmol) in dioxane/$H_2O$ (2 mL/0.2 mL) was stirred at 80° C. for 2 hours under $N_2$ atmosphere. The mixture was then diluted with water (30 mL) and extracted with EtOAc (20 mL*3). The organic layer was washed with brine (30 mL), dried over $Na_2SO_4$ and concentrated. The residue was purified by prep-TLC (DCM:EA=1:1) to afford the desired product of 2-(4-fluorophenyl)-5-(10-fluoropyrido[3',2':4,5]pyrimido[1,6-a]indol-2-yl)-N-methyl-6-(N-methylmethylsulfonamido)benzofuran-3-carboxamide (40 mg, yield: 35.4%). $^1$H-NMR (CDCl$_3$, 400 MHz) δ 8.98 (s, 1H), 8.11 (d, J=8.4 Hz, 1H), 8.07 (s, 1H), 7.86~7.95 (m, 3H), 7.74 (d, J=8.4 Hz, 1H), 7.64 (s, 1H), 7.45 (dd, J=2.0, 9.2 Hz, 1H), 7.41 (s, 1H), 7.11~7.19 (m, 3H), 5.85 (d, J=3.2 Hz, 1H), 3.34 (s, 3H), 2.94 (d, J=4.4 Hz, 3H), 2.64 (s, 3H). MS (M+H)$^+$: 612.

Example 21

5-(10-fluoro-6-oxo-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide

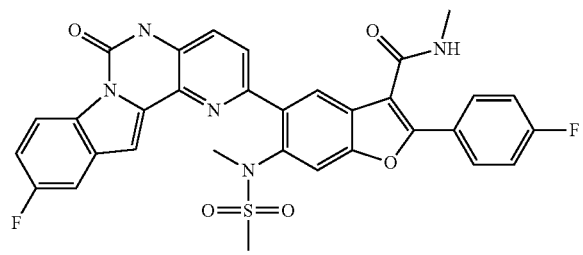 [SMILES: CNC(=O)c1c(-c2ccc(F)cc2)oc2cc(N(C)S(C)(=O)=O)c(-c3ccc4[nH]c(=O)n5c6ccc(F)cc6cc5c4n3)cc12]

Step 1—Synthesis of 2-chloro-10-fluoropyrido[3',2':4,5]pyrimido[1,6-a]indol-6(5H)-one

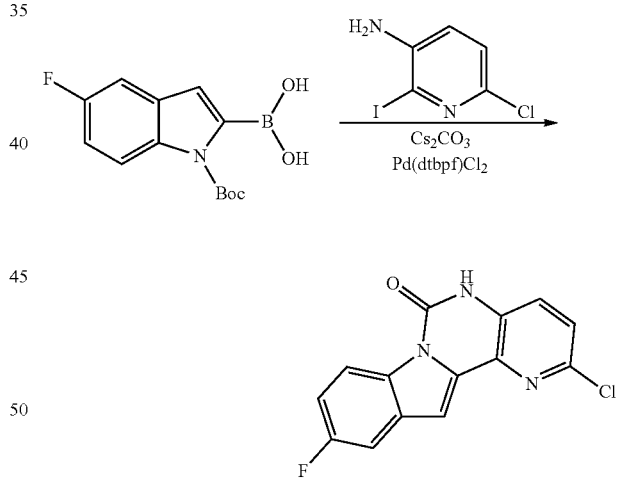

A mixture of (1-(tert-butoxycarbonyl)-5-fluoro-1H-indol-2-yl)boronic acid (100 mg, 0.358 mmol), 6-chloro-2-iodopyridin-3-amine (83 mg, 0.326 mmol), Pd(dtbpf)Cl$_2$ (21 mg, 0.033 mmol) and Cs$_2$CO$_3$ (212 mg, 0.652 mmol) in dioxane (2 mL) was stirred at 70° C. overnight. After concentrated, the residue was purified by column chromatography (PE:EA=10:1) to afford the desired product of 2-chloro-10-fluoropyrido[3',2':4,5]pyrimido[1,6-a]indol-6(5H)-one (60 mg, yield: 63.8%). $^1$H-NMR (DMSO-d$_6$, 400 MHz) δ 11.68 (br s, 1H), 8.53 (dd, J=4.4, 8.8 Hz, 1H), 7.56~7.66 (m, 2H), 7.53 (d, J=8.8 Hz, 1H), 7.38 (s, 1H), 7.27 (t, J=9.2 Hz, 1H). MS (M+H)$^+$: 288.

Step 2—Synthesis of 5-(10-fluoro-6-oxo-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide

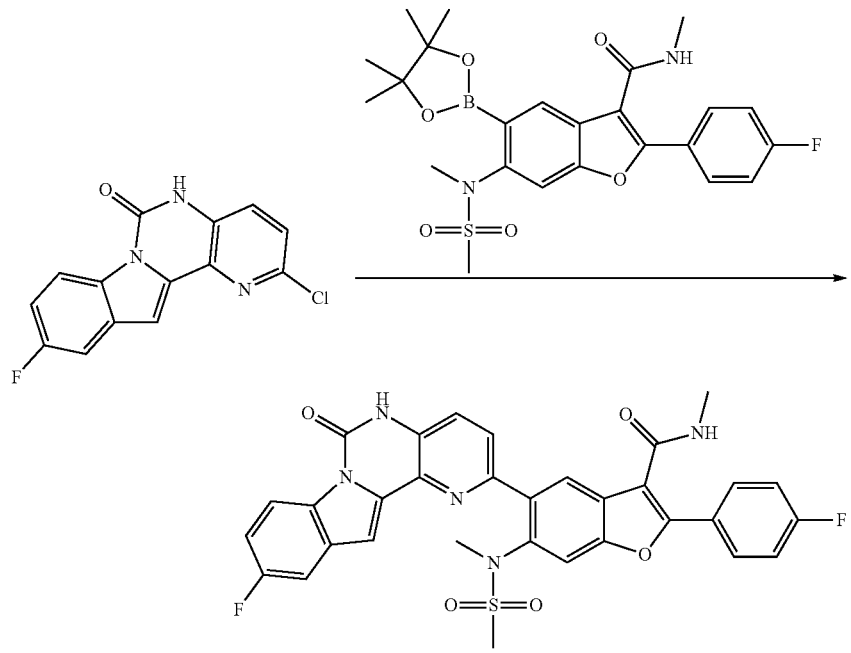

A mixture of 2-chloro-10-fluoropyrido[3',2':4,5]pyrimido[1,6-a]indol-6(5H)-one (57 mg, 0.199 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (100 mg, 0.199 mmol), K$_3$PO$_4$·3H$_2$O (159 mg, 0.597 mmol), Pd$_2$(dba)$_3$ (9 mg, 0.010 mmol) and X-Phos (10 mg, 0.020 mmol) in dioxane/H$_2$O (2 mL/0.2 mL) was stirred at 80° C. for 2 hours under N$_2$ atmosphere. The mixture was then diluted with water (50 mL) and extracted with EtOAc (20 mL*3). The organic layer was washed with brine (50 mL), dried over Na$_2$SO$_4$ and concentrated. The residue was purified by column chromatography (DCM:CH$_3$OH=10:1) to afford the desired product of 5-(10-fluoro-6-oxo-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide (60 mg, yield: 48.0%). $^1$H-NMR (DMSO-d$_6$, 400 MHz) δ 11.75 (br s, 1H), 8.66 (br s, 2H), 8.12 (d, J=18.0 Hz, 3H), 7.95 (br s, 1H), 7.80 (br s, 2H), 7.69 (d, J=8.4 Hz, 1H), 7.50 (br s, 3H), 7.35 (br s, 1H), 3.29~3.38 (m, 3H), 3.00 (br s, 3H), 2.90 (br s, 3H). MS (M+H)$^+$: 628.

Example 22

Example 22, depicted in the table below, was prepared in accordance with the method described in Example 21.

| Compound ID | Structure | NMR | MS (M + H)$^+$ |
|---|---|---|---|
| 22 | 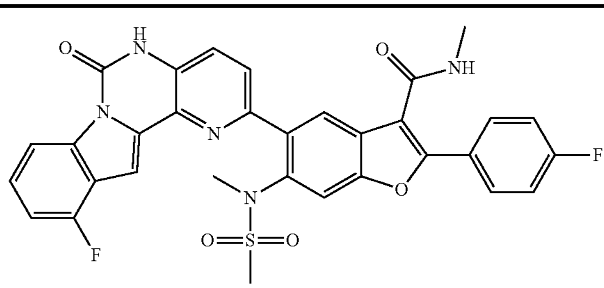 | $^1$H-NMR (CDCl$_3$, 400 MHz) δ 8.58 (d, J = 4.40 Hz, 1H), 8.46 (d, J = 8.00 Hz, 1H), 8.01~8.05 (m, 3H), 7.88 (s, 1H), 7.68~7.72 (m, 2H), 7.37~7.45 (m, 4H), 7.18~7.23 (m, 1H), 3.34 (s, 3H), 2.92 (s, 3H), 2.83 (d, J = 4.40 Hz, 3H). | 628 |

Example 23

5-(11-fluoro-6-((methylsulfonyl)methyl)pyrido[3',2':4,5]pyrimido[1,6-a]indol-2-yl)-2-(4-fluorophenyl)-N-methyl-6-(N-methylmethylsulfonamido)benzofuran-3-carboxamide

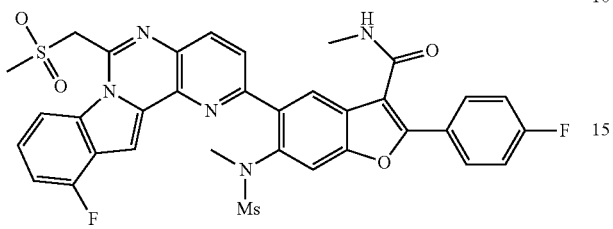

Step 1—Synthesis of 2-chloro-6-(chloromethyl)-11-fluoropyrido[3',2':4,5]pyrimido[1,6-a]indole

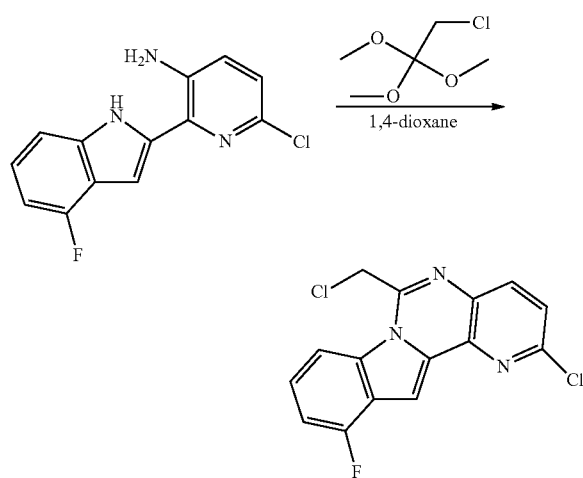

To a screw cap vial was added the reactant 6-chloro-2-(4-fluoro-1H-indol-2-yl)pyridin-3-amine (1 g, 3.8 mmol) and 2-chloro-1,1,1-trimethoxyethane (3 mg, 19 mmol), then 1,4-dioxane (10 mL) and 4.0 M HCl/1,4-dioxane (0.5 mL). The vial was capped and heated to 60° C. and stirred for 4 hours. The reaction mixture was evaporated in vacuo to remove the volatiles. The resulting residue in DCM:PE=(1:1) was stirred and filtered, the cake was dried to provide the yellow solid 2-chloro-6-(chloromethyl)-11-fluoropyrido[3',2':4,5]pyrimido[1,6-a]indole (1 g, yield: 81%). $^1$H-NMR (DMSO-$d_6$, 400 MHz) δ 8.18 (d, J=8.4 Hz, 1H), 8.05 (d, J=8.8 Hz, 1H), 7.70 (d, J=8.8 Hz, 1H), 7.61 (s, 1H), 7.50~7.56 (m, 1H), 7.33 (t, J=8.4 Hz, 1H), 5.39 (s, 2H). MS (M+H)$^+$: 320.

Step 2—Synthesis of 2-chloro-11-fluoro-6-((methylsulfonyl)methyl)pyrido[3',2':4,5]pyrimido[1,6-a]indole

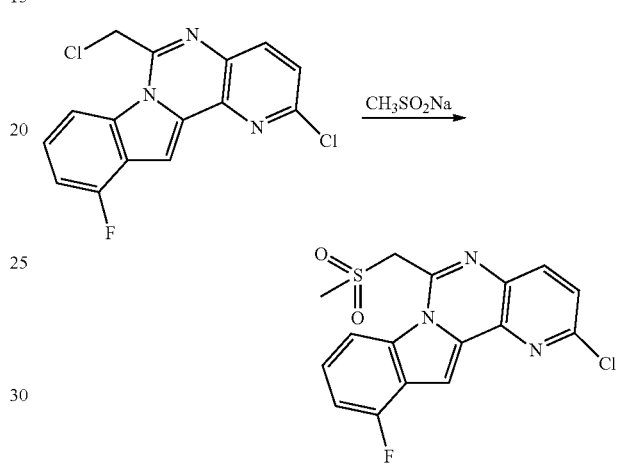

A solution of 2-chloro-6-(chloromethyl)-11-fluoropyrido[3',2':4,5]pyrimido[1,6-a]indole (200 mg, 0.6 mmol), CH$_3$SO$_2$Na (127 mg, 1.2 mmol) and K$_2$HPO$_4$ (326 mg, 187 mmol) in DMF (5 mL) was stirred at RT for 1.5 h. Then the mixture was poured into water and after filtration, the cake was dried to give compound 2-chloro-11-fluoro-6-((methylsulfonyl)methyl)pyrido[3',2':4,5]pyrimido[1,6-a]indole (180 mg, yield: 79%). $^1$H-NMR (DMSO-$d_6$, 400 MHz) δ 8.19 (d, J=8.4 Hz, 1H), 8.12 (d, J=8.8 Hz, 1H), 7.71 (d, J=8.4 Hz, 1H), 7.62 (s, 1H), 7.48~7.54 (m, 1H), 7.33 (t, J=8.0 Hz, 1H), 5.52 (s, 2H), 3.34 (s, 3H). MS (M+H)$^+$: 364.

Step 3—Synthesis of 5-(11-fluoro-6-((methylsulfonyl)methyl)pyrido[3',2':4,5]pyrimido[1,6-a]indol-2-yl)-2-(4-fluorophenyl)-N-methyl-6-(N-methylmethylsulfonamido)benzofuran-3-carboxamide

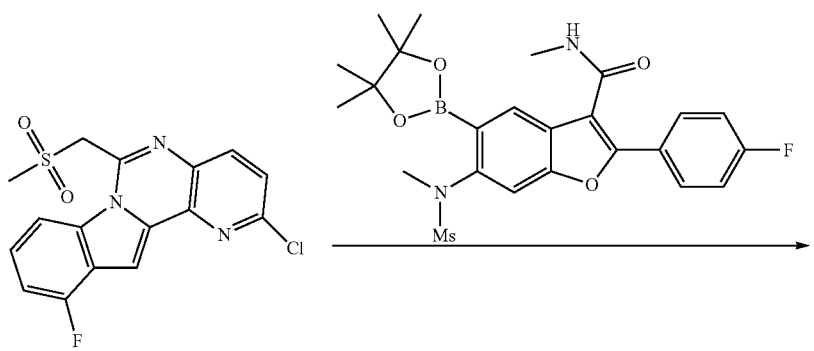

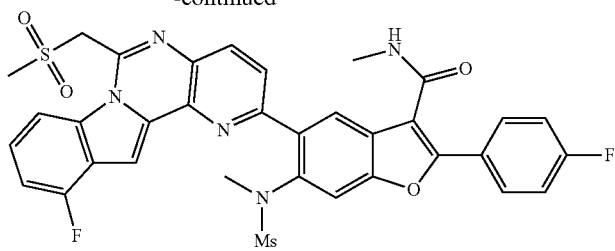

To a solution of 2-chloro-11-fluoro-6-((methylsulfonyl)methyl)pyrido[3',2':4,5]pyrimido[1,6-a]indole (130 mg, 0.36 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (150 mg, 0.3 mmol) and $K_2CO_3$ (83 mg, 0.6 mmol) in 1,4-dioxane (6 mL) and $H_2O$ (6 drops) were added $Pd_2(dba)_3$ (10 mg) and X-Phos (10 mg) under nitrogen atmosphere. The reaction mixture was heated at 100° C. for 3 h, concentrated in vacuo to remove 1,4-dioxane and purified by prep-HPLC to give the product of 5-(11-fluoro-6-((methylsulfonyl)methyl)pyrido[3',2':4,5]pyrimido[1,6-a]indol-2-yl)-2-(4-fluorophenyl)-N-methyl-6-(N-methylmethylsulfonamido)benzofuran-3-carboxamide (80 mg, yield: 31%). $^1$H-NMR (DMSO-$d_6$, 400 MHz) δ 8.57 (d, J=4.4 Hz, 1H), 8.23 (d, J=8.4 Hz, 1H), 8.10~8.14 (m, 2H), 7.99~8.02 (m, 2H), 7.93 (s, 1H), 7.89 (d, J=8.4 Hz, 1H), 7.62 (s, 1H), 7.46~7.52 (m, 1H), 7.40 (t, J=8.8 Hz, 2H), 7.32 (t, J=8.0 Hz, 1H), 5.56 (s, 2H), 3.38 (s, 3H), 3.33 (s, 3H), 2.94 (s, 3H), 2.81 (d, J=4.4 Hz, 3H). MS (M+H)$^+$: 704.

Example 24

Example 24, depicted in the table below, was prepared in accordance with the methods described in Example 23.

| Example | Structure | MS (M + H)$^+$ |
|---|---|---|
| 24 | 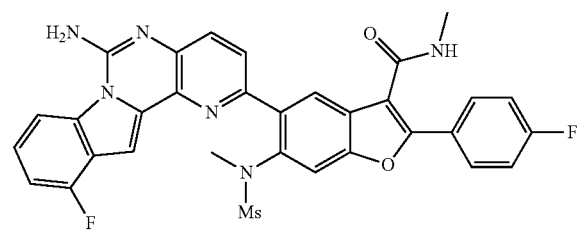 [SMILES: CNC(=O)c1c(-c2ccc(F)cc2)oc2cc(N(C)S(C)(=O)=O)c(-c3ccc4nc(N)n5c6cccc(F)c6cc5c4n3)cc12] | 704 |

Example 25

5-(6-amino-11-fluoropyrido[3',2':4,5]pyrimido[1,6-a]indol-2-yl)-2-(4-fluorophenyl)-N-methyl-6-(N-methylmethylsulfonamido)benzofuran-3-carboxamide Step 1—Synthesis of 2-chloro-11-fluoropyrido[3',2':4,5]pyrimido[1,6-a]indol-6-amine

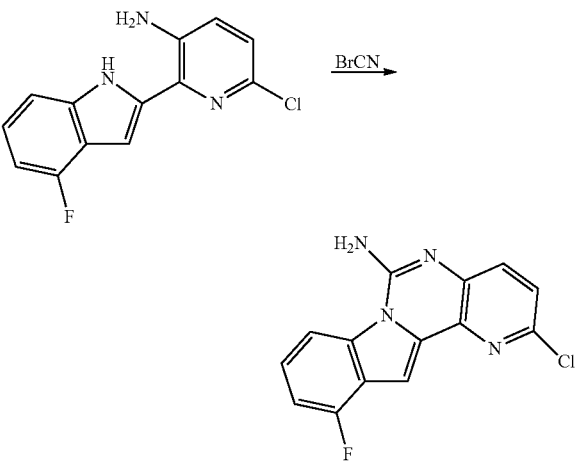

To a mixture of 6-chloro-2-(4-fluoro-1H-indol-2-yl)pyridin-3-amine (500 mg, 1.19 mmol) and BrCN (303 mg, 2.87 mmol) in $CH_3OH$ (5 mL) in seal tube was stirred at 100° C. for 10 hours. The reaction mixture was extracted with EtOAc, washed with brine, dried over $Na_2SO_4$, filtered and concentrated in vacuo. The residue was purified by column chromatography (PE:EA=3:1) to give the product of 2-chloro-11-fluoropyrido[3',2':4,5]pyrimido[1,6-a]indol-6-amine (300 mg, yield: 55%). $^1$H-NMR (CDCl$_3$, 400 MHz) δ 11.1 (s, 2H), 8.36 (d, J=8.4 Hz, 1H), 7.63 (d, J=8.0 Hz, 1H), 7.53 (d, J=8.4 Hz, 1H), 7.37~42 (m, 2H), 7.22. (d, J=8.4 Hz, 1H). MS (M+H)$^+$: 287.

Step 2—Synthesis of 5-(6-amino-11-fluoropyrido[3',2':4,5]pyrimido[1,6-a]indol-2-yl)-2-(4-fluorophenyl)-N-methyl-6-(N-methylmethylsulfonamido)benzofuran-3-carboxamide

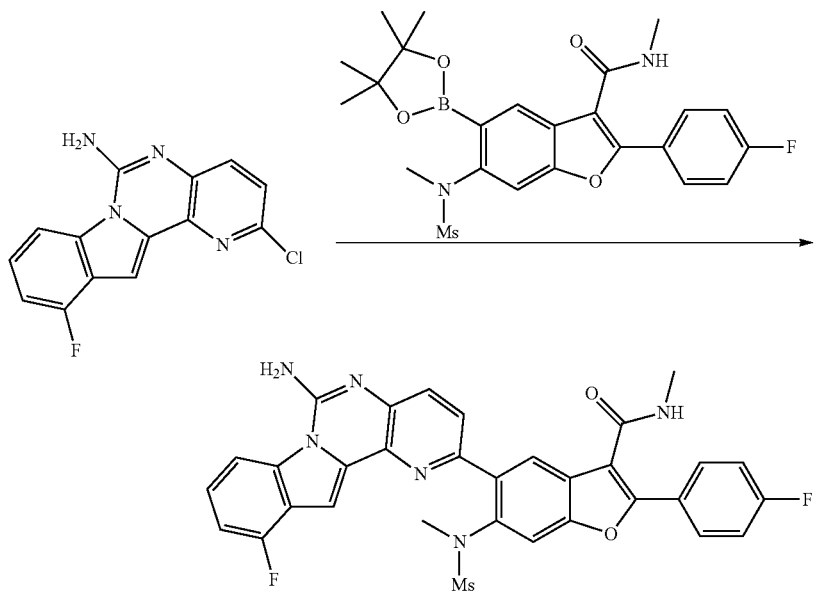

To a mixture of 2-chloro-11-fluoropyrido[3',2':4,5]pyrimido[1,6-a]indol-6-amine (100 mg, 0.383 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (211 mg, 0.421 mmol) and $K_3PO_4 \cdot 3H_2O$ (203 mg, 0.766 mmol) in 1,4-dioxane (3 mL) was added Pd(dtbpf)Cl$_2$ (10 mg) under N$_2$. The reaction mixture was stirred at 100° C. for 5 hours and concentrated in vacuo to remove 1,4-dioxane. The reaction mixture was extracted with EtOAc, washed with brine, dried over Na$_2$SO$_4$, filtered and concentrated in vacuo. The residue was purified by prep-HPLC to give the product of 5-(6-amino-11-fluoropyrido[3',2':4,5]pyrimido[1,6-a]indol-2-yl)-2-(4-fluorophenyl)-N-methyl-6-(N-methylmethylsulfonamido)benzofuran-3-carboxamide (20 mg, yield: 8%). $^1$H-NMR (CDCl$_3$, 400 MHz) δ 8.29 (s, 1H), 8.06 (s, 1H), 7.82~7.85 (m, 2H), 7.5 (s, 1H), 7.46 (s, 1H), 7.40 (d, J=8.0 Hz, 1H), 7.21~7.29 (m, 2H), 7.05 (t, J=8.8 Hz, 2H), 6.88~6.99 (m, 2H), 3.27 (s, 3H), 2.92 (d, J=4.8 Hz, 3H), 2.89 (s, 3H). MS (M+H)$^+$: 627.

Examples 26
(R or S)-5-(11-fluoro-6-methyl-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide and 27 (S or R)-5-(11-fluoro-6-methyl-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide

26

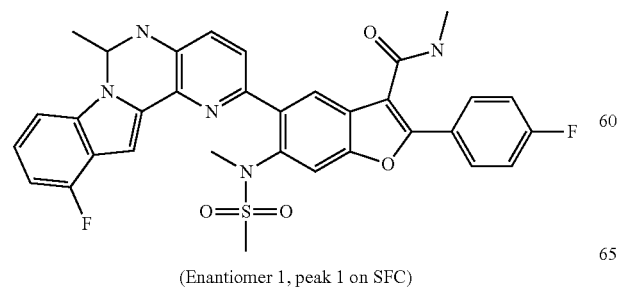

(Enantiomer 1, peak 1 on SFC)

-continued

27

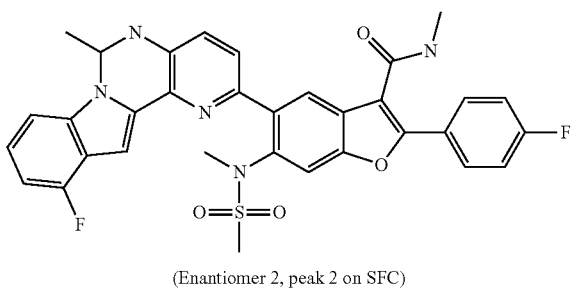

(Enantiomer 2, peak 2 on SFC)

Step 1—Synthesis of 2-chloro-11-fluoro-6-methyl-5,6-dihydropyrido[3',2':4,5]pyrimido[1,6-a]indole

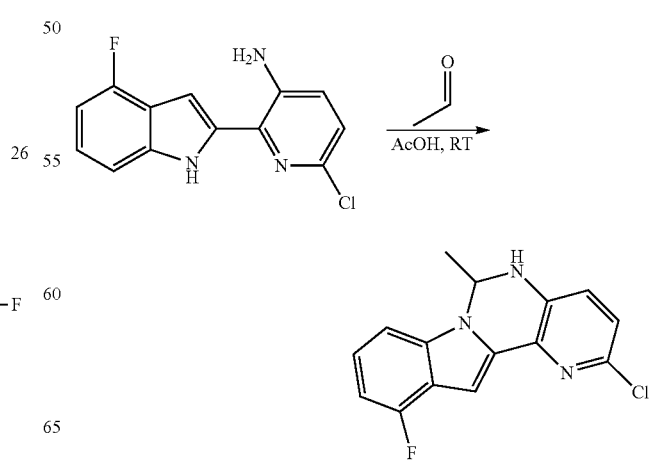

To a mixture of compound 6-chloro-2-(4-fluoro-1H-indol-2-yl)pyridin-3-amine (400 mg, 1.53 mmol) in AcOH (10 mL) was added acetaldehyde (672 mg, 15.25 mmol) in portions at 0° C. and then the mixture was stirred at room temperature for 2 hours. Then saturated NaHCO₃ (a.q.) was added into this reaction solution until pH=8~9 and extracted with EtOAc. The combined organic phase was washed with brine, dried over sodium sulfate and concentrated to afford 2-chloro-11-fluoro-6-methyl-5,6-dihydropyrido[3',2':4,5]pyrimido[1,6-a]indole (300 mg, yield: 68%) through the column chromatography (PE:EA=5:1). $^1$H-NMR (Methanol-d₄, 400 MHz) δ 7.09~7.21 (m, 5H), 6.74~6.79 (m, 1H), 6.20~6.07 (m, 1H), 1.40 (d, J=6.0 Hz, 3H). MS (M+H)$^+$: 288.

Step 2—Synthesis of (R or S)-5-(11-fluoro-6-methyl-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide and (S or R)-5-(11-fluoro-6-methyl-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide (Compound 26 and Compound 27)

A mixture of compound 2-chloro-11-fluoro-6-methyl-5,6-dihydropyrido[3',2':4,5]pyrimido[1,6-a]indole (120 mg, 0.417 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (251 mg, 0.499 mmol), sodium carbonate (88 mg, 0.830 mmol), Pd₂(dba)₃ (20 mg) and X-Phos (20 mg) in 1,4-dioxane/water (3/0.3 mL) was stirred at 70° C. for 16 hours under nitrogen atmosphere. After filtered through Celite and concentrated, the residue was suspended in water. After extracted with EtOAc, the combined organic phase was washed with brine, dried over sodium sulfate and concentrated. The residue was purified by prep-HPLC and SFC to give two single enantiomers.

Compound 26 (enantiomer 1, peak 1 on SFC, OD-H_5_5_40_2,35ML, HPLC_RT=8.505 min) (50 mg, yield: 19%). $^1$H-NMR (CDCl₃, 400 MHz) δ 7.96~7.99 (m, 3H), 7.66 (s, 1H), 7.35 (d, J=8.4 Hz, 1H), 7.11~7.22 (m, 5H), 7.05 (d, J=8.0 Hz, 1H), 6.77~6.82 (m, 1H), 5.98 (br s, 2H), 4.52 (br s, 1H), 3.42 (s, 3H), 3.00 (d, J=4.8 Hz, 3H), 2.66 (s, 3H), 1.53~1.59 (m, 3H). MS (M+H)$^+$: 628

Compound 27 (enantiomer 2, peak 2 on SFC, OD-H_5_5_40_2,35ML, HPLC_RT=9.254 min) (50 mg, yield: 19%). $^1$H-NMR (CDCl₃, 400 MHz) δ 7.96~7.99 (m, 3H), 7.66 (s, 1H), 7.35 (d, J=8.4 Hz, 1H), 7.11~7.22 (m, 5H), 7.05 (d, J=8.0 Hz, 1H), 6.77~6.82 (m, 1H), 5.98 (br s, 2H), 4.52 (br s, 1H), 3.42 (s, 3H), 3.00 (d, J=4.8 Hz, 3H), 2.66 (s, 3H), 1.53~1.59 (m, 3H). MS (M+H)$^+$: 628.

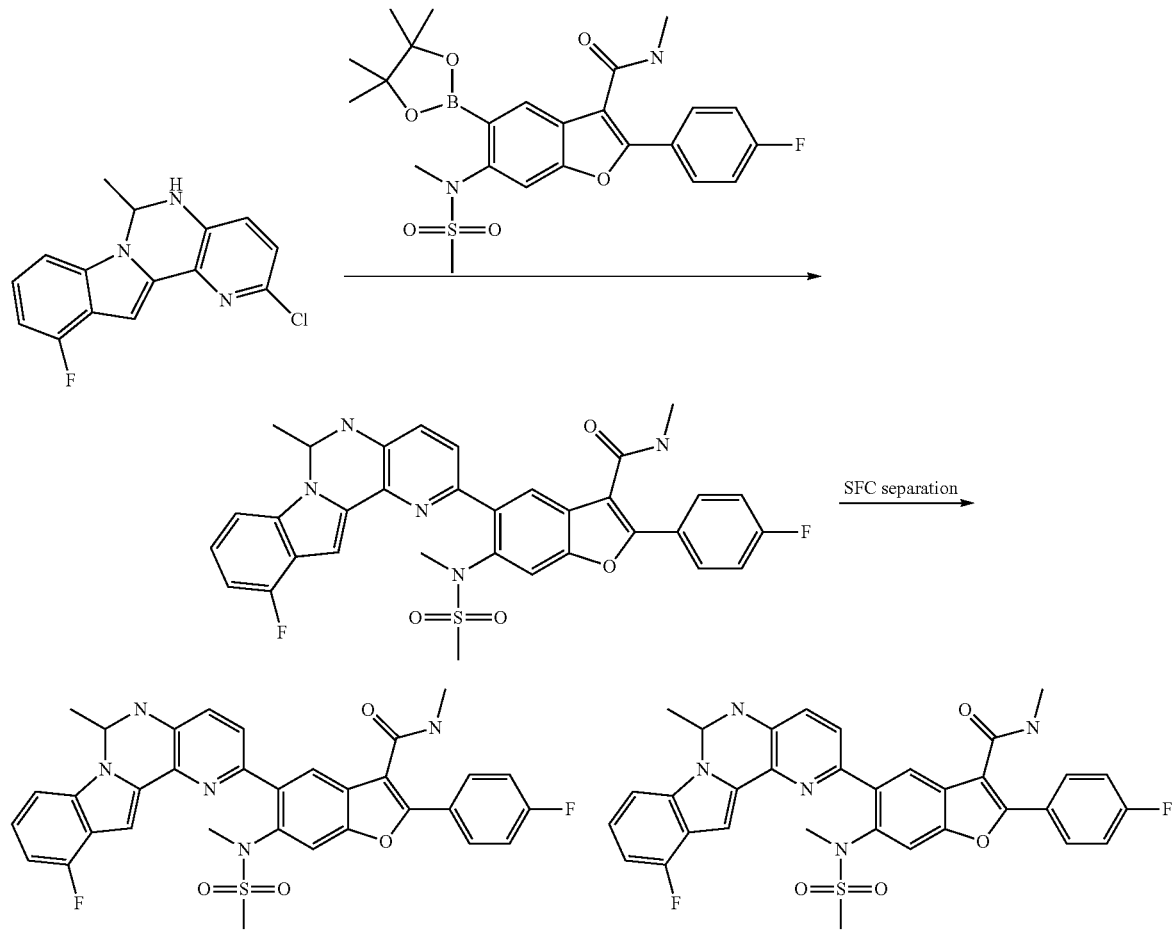

26 (Enantiomer 1, peak 1 on SFC)    27 (Enantiomer 2, peak 2 on SFC)

Example 28

5-(11-fluoro-6-((3-fluoroazetidin-1-yl)methyl)pyrido[3',2':4,5]pyrimido[1,6-a]indol-2-yl)-N-methyl-6-(N-methylmethylsulfonamido)-2-(6-methylpyridin-3-yl)benzofuran-3-carboxamide

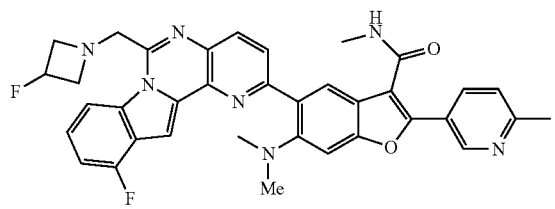 [SMILES: CNC(=O)c1c(-c2ccc(C)nc2)oc2cc(N(C)C)c(-c3ccc4nc(CN5CC(F)C5)n5c6cccc(F)c6cc5c4n3)cc12]

Step 1—Synthesis of 2-chloro-6-(chloromethyl)-11-fluoropyrido[3',2':4,5]pyrimido[1,6-a]indole

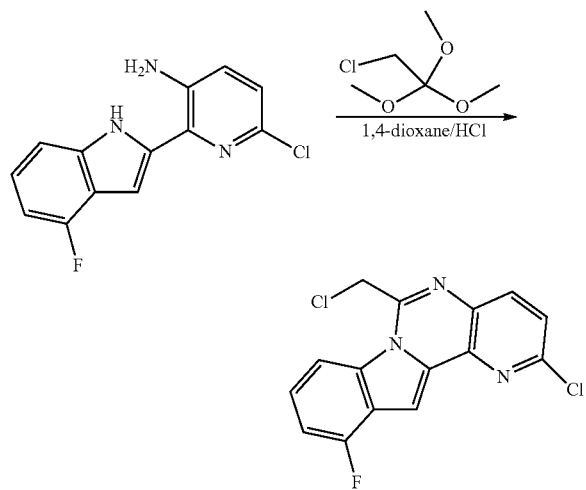

To a screw cap vial was added 6-chloro-2-(4-fluoro-1H-indol-2-yl)pyridin-3-amine (1 g, 3.8 mmol) and 2-chloro-1,1,1-trimethoxyethane (2.9 g, 19 mmol), and then 1,4-dioxane (10 mL) and 4.0 M HCl in 1,4-dioxane (0.5 mL) were also added. The vial was capped and heated to 60° C. and stirred for 4 hours. The reaction mixture was evaporated in vacuo to remove the volatiles. The resulting residue was suspended in DCM:PE (1:1), stirred and filtered, the cake was dried to provide 2-chloro-6-(chloromethyl)-11-fluoropyrido[3',2':4,5]pyrimido[1,6-a]indole as yellow solid (1 g, yield: 81%). $^1$H-NMR (DMSO-$d_6$, 400 MHz) δ 8.18 (d, J=8.4 Hz, 1H), 8.05 (d, J=8.8 Hz, 1H), 7.70 (d, J=8.8 Hz, 1H), 7.61 (s, 1H), 7.50~7.56 (m, 1H), 7.33 (t, J=8.4 Hz, 1H), 5.39 (s, 2H).

Step 2—Synthesis of 2-chloro-11-fluoro-6-((3-fluoroazetidin-1-yl)methyl)pyrido[3',2':4,5]pyrimido[1,6-a]indole

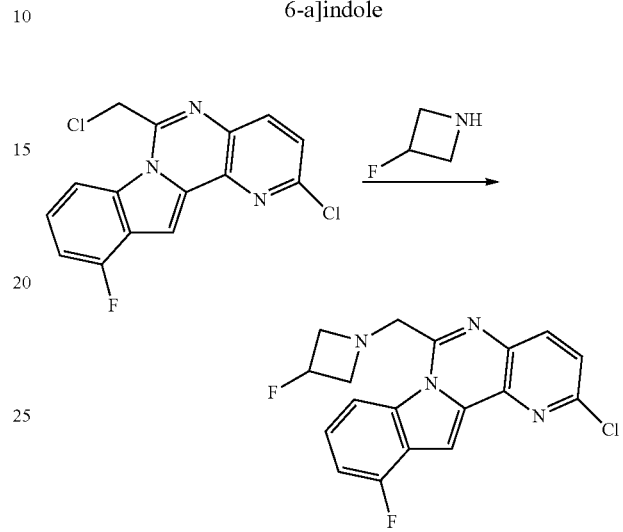

A mixture of compound 2-chloro-6-(chloromethyl)-11-fluoropyrido[3',2':4,5]pyrimido[1,6-a]indole (100 mg, 0.3 mmol), 3-fluoroazetidine (47 mg, 0.6 mmol) and $K_2CO_3$ (86 mg, 0.6 mmol) in DMF (3 mL) was stirred at RT for 5 h. Then the mixture was poured into water and filtered, the insoluble solid was dried to give crude product. After the crude product was suspended in DCM, stirred for 10 minutes and filtered, precipitate was collected and dried to afford 2-chloro-11-fluoro-6-((3-fluoroazetidin-1-yl)methyl)pyrido[3',2':4,5]pyrimido[1,6-a]indole (90 mg, yield: 80%). $^1$H-NMR (DMSO-$d_6$, 400 MHz) δ 8.20 (d, J=8.0 Hz, 1H), 7.98 (d, J=8.8 Hz, 1H), 7.21 (d, J=8.0 Hz, 1H), 7.59 (s, 1H), 7.51 (d, J=6.8 Hz, 1H), 7.33 (t, J=8.8 Hz, 1H), 5.17~5.32 (m, 1H), 4.42 (s, 2H), 3.81~3.85 (m, 2H), 3.31~3.35 (m, 2H). MS (M+H)$^+$: 359.

Step 3—Synthesis of 5-(11-fluoro-6-((3-fluoroazetidin-1-yl)methyl)pyrido[3',2':4,5]pyrimido[1,6-a]indol-2-yl)-N-methyl-6-(N-methylmethylsulfonamido)-2-(6-methylpyridin-3-yl)benzofuran-3-carboxamide

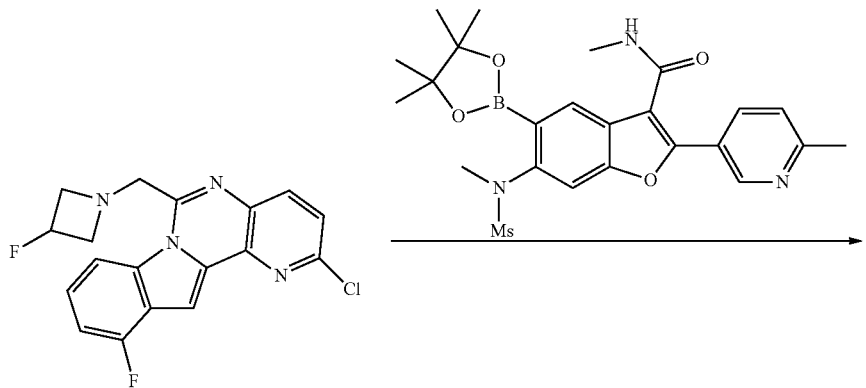

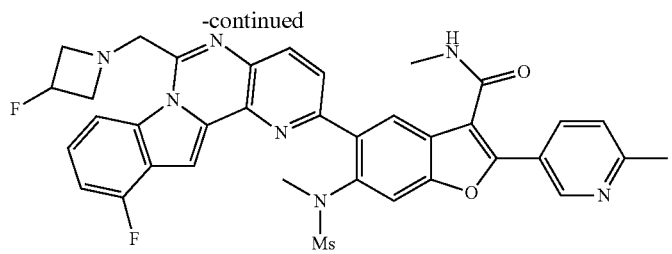

To a mixture of compound 2-chloro-11-fluoro-6-((3-fluoroazetidin-1-yl)methyl)pyrido[3',2':4,5]pyrimido[1,6-a]indole (86 mg, 0.24 mmol), N-methyl-6-(N-methylmethylsulfonamido)-2-(6-methylpyridin-3-yl)-5-(4,4,5,5-tetramethyl-1,3,2-dioxaborolan-2-yl)benzofuran-3-carboxamide (prepared using similar method described in Example 1, 100 mg, 0.2 mmol) and K₂CO₃ (55 mg, 0.4 mmol) in 1,4-dioxane (3 mL) and H₂O (0.3 mL) were added Pd₂(dba)₃ (10 mg) and X-Phos (10 mg) under nitrogen atmosphere. The reaction mixture was heated at 100° C. for 5 h, concentrated in vacuo to remove 1,4-dioxane and purified by prep-HPLC to give the product of 5-(11-fluoro-6-((3-fluoroazetidin-1-yl)methyl)pyrido[3',2':4,5]pyrimido[1,6-a]indol-2-yl)-N-methyl-6-(N-methylmethylsulfonamido)-2-(6-methylpyridin-3-yl)benzofuran-3-carboxamide (40 mg, yield: 28%). ¹H-NMR (CDCl₃, 400 MHz) δ 9.05 (s, 1H), 8.24 (dd, J=8.4 Hz, 2.4 Hz, 1H), 8.18 (d, J=8.4 Hz, 1H), 8.11 (s, 1H), 7.77~7.83 (m, 2H), 7.73 (s, 2H), 7.38~7.43 (m, 1H), 7.32 (d, J=8.0 Hz, 1H), 7.17 (t, J=8.4 Hz, 1H), 6.00 (br s, 1H), 5.22~5.39 (m, 1H), 4.45 (s, 2H), 4.04~4.11 (m, 2H), 3.54~3.64 (m, 2H), 3.43 (s, 3H), 3.02 (d, J=4.8 Hz, 3H), 2.70 (s, 3H), 2.66 (s, 3H). MS (M+H)⁺: 696.

Examples 29-37

Example 29~37, depicted in the table below, were prepared in accordance with the method described in Example 28.

| Example | Structure | NMR | MS (M + H)⁺ |
|---|---|---|---|
| 29 | 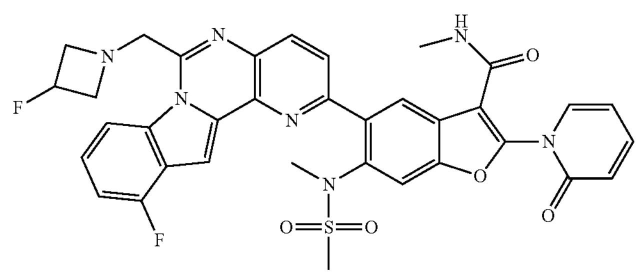 [SMILES: CNC(=O)c1c(-n2ccccc2=O)oc2cc(N(C)S(C)(=O)=O)c(-c3ccc4nc(CN5CC(F)C5)n5c6cccc(F)c6cc5c4n3)cc12] | ¹H-NMR (CDCl₃, 400 MHz) δ 8.25 (s, 1H), 8.14 (d, J = 8.4 Hz, 1H), 7.67~7.80 (m, 5H), 7.37~7.40 (m, 3H), 7.14~7.24 (m, 1H), 6.73 (d, J = 9.6 Hz, 1H), 6.44 (t, J = 6.4 Hz, 1H), 5.19~5.36 (m, 1H), 4.43 (s, 2H), 4.02~4.07 (m, 2H), 3.54~3.61 (m, 2H), 3.41 (s, 3H), 2.89 (d, J = 4.8 Hz, 3H), 2.58 (s, 3H). | 698 |
| 30 | 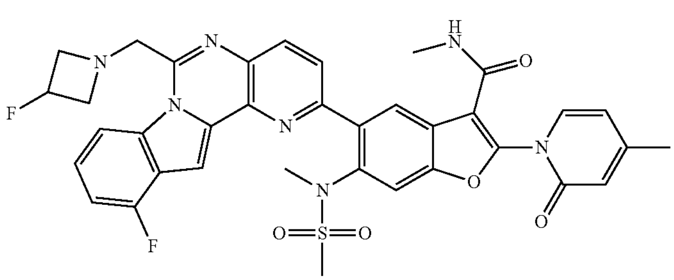 [SMILES: CNC(=O)c1c(-n2ccc(C)cc2=O)oc2cc(N(C)S(C)(=O)=O)c(-c3ccc4nc(CN5CC(F)C5)n5c6cccc(F)c6cc5c4n3)cc12] | ¹H-NMR (CDCl₃, 400 MHz) δ 8.28 (s, 1H), 8.18 (d, J = 8.0 Hz, 1H), 7.87 (br s, 1H), 7.80 (dd, J = 15.2, 8.8 Hz, 2 H), 7.69 (d, J = 3.2 Hz, 2H), 7.44~7.38 (m, 1H), 7.31 (d, J = 8.0 Hz, 1H), 7.17 (t, J = 8.4 Hz, 1H), 6.55 (s, 1H), 6.31 (d, J = 6.4 Hz, 1H), 5.23~5.39 (m, 1H), 4.46 (s, 2H), 4.05~4.12 (m, 2H), 3.57~3.64 (m, 2H), 6.55 (s, 3H), 2.92 (d, J = 4.8 Hz, 3H), 2.60 (s, 3H), 2.34 (s, 3H). | 712 |
| 31 | 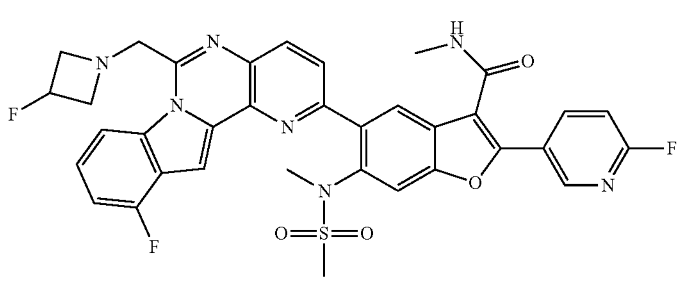 [SMILES: CNC(=O)c1c(-c2ccc(F)nc2)oc2cc(N(C)S(C)(=O)=O)c(-c3ccc4nc(CN5CC(F)C5)n5c6cccc(F)c6cc5c4n3)cc12] | ¹H-NMR (CDCl₃, 400 MHz) δ 8.85 (s, 1H), 8.56 (t, J = 6.8 Hz, 1H), 8.16 (d, J = 8.0 Hz, 1H), 8.05 (s, 1H), 7.76~7.81 (m, 2H), 7.71 (s, 2H), 7.41 (s, 1H), 7.15 (s, 1H), 7.05~7.08 (m, 1H), 6.23 (d, J = 3.6 Hz, 1H), 5.22~5.38 (m, 1H), 4.43 (s, 2H), 4.02~4.09 (m, 2H), 3.56~3.63 (m, 2H), 3.40 (s, 3H), 3.05 (d, J = 4.4 Hz, 3H), 2.72 (s, 3H). | 700 |

| Example | Structure | NMR | MS (M + H)+ |
|---|---|---|---|
| 32 | 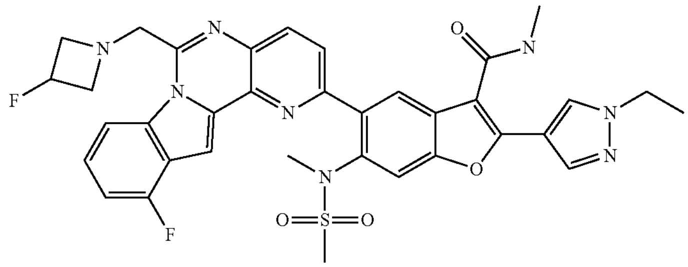 | ¹H-NMR (CDCl₃, 400 MHz) δ 8.52 (s, 1H), 8.18 (d, J = 8.8 Hz, 1H), 8.15 (s, 1H), 7.98 (s, 1H), 7.80 (t, J = 8.4 Hz, 2H), 7.75 (s, 1H), 7.66 (s, 1H), 7.38~7.43 (m, 1H), 7.16 (t, J = 8.8 Hz, 1H), 6.11 (br s, 1H), 5.23~5.37 (m, 1H), 4.45 (s, 2H), 4.24~4.30 (q, J = 7.2 Hz, 2H), 4.05~4.08 (m, 2H), 3.55~3.63 (m, 2H), 3.41 (s, 3H), 3.06 (d, J = 4.8 Hz, 3H), 2.74 (s, 3H), 1.51 (t, J = 7.2 Hz, 3H). | 699 |
| 33 | 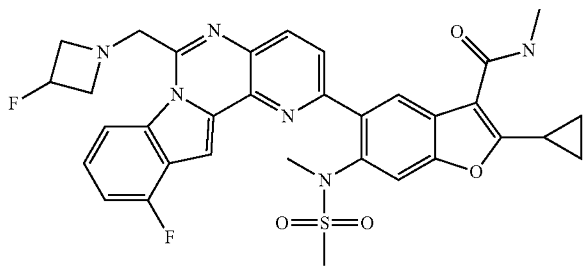 [SMILES: CNC(=O)c1c(C2CC2)oc2cc(N(C)S(C)(=O)=O)c(-c3ccc4nc(CN5CC(F)C5)n5c6cccc(F)c6cc5c4n3)cc12] | ¹H-NMR (CDCl₃, 400 MHz) δ 8.14 (d, J = 8.4 Hz, 1H), 7.96 (s, 1H), 7.74~7.78 (m, 2H), 7.70 (s, 1H), 7.52 (s, 1H), 7.35~7.41 (m, 1H), 7.14 (t, J = 8.8 Hz, 1H), 6.11 (br s, 1H), 5.21~5.36 (m, 1H), 4.43 (s, 2H), 4.01~4.10 (m, 2H), 3.60~3.62 (m, 1H), 3.52~3.57 (m, 2H), 3.38 (s, 3H), 3.04 (d, J = 4.8 Hz, 3H), 2.79~2.85 (m, 1H), 2.66 (s, 3H), 1.18~1.27 (m, 4H). | 645 |
| 34 | 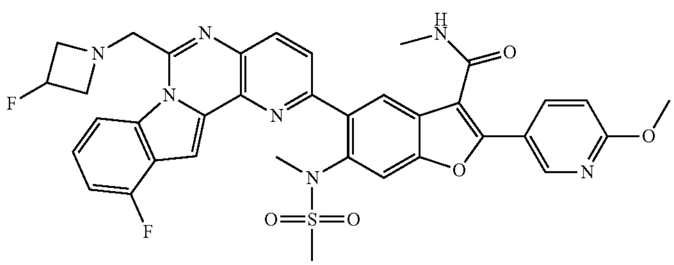 [SMILES: CNC(=O)c1c(-c2ccc(OC)nc2)oc2cc(N(C)S(C)(=O)=O)c(-c3ccc4nc(CN5CC(F)C5)n5c6cccc(F)c6cc5c4n3)cc12] | ¹H-NMR (DMSO-d₆, 400 MHz) δ 8.79 (d, J = 1.6 Hz, 1H), 8.56 (d, J = 4.4 Hz, 1H), 8.20~8.30 (m, 2H), 8.13 (s, 1H), 7.95~8.04 (m, 2H), 7.89 (d, J = 8.4 Hz, 1H), 7.60 (s, 1H), 7.44~7.54 (m, 1H), 7.32 (t, J = 8.8 Hz, 1H), 7.04 (d, J = 8.8 Hz, 1H), 5.09~5.41 (m, 1H), 4.46 (s, 2H), 3.95 (s, 3H), 3.81~3.91 (m, 2H), 3.44~3.62 (m, 5H), 2.95 (s, 3H), 2.84 (d, J = 4.4 Hz, 3H). | 712 |
| 35 | 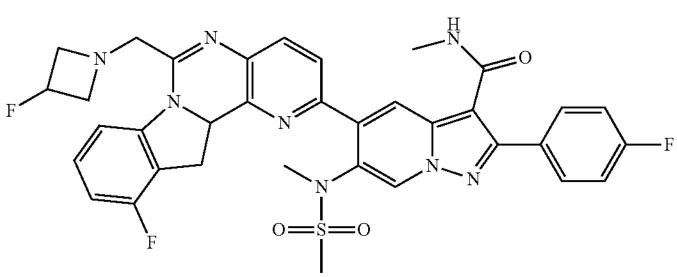 [SMILES: CNC(=O)c1c(-c2ccc(F)cc2)nn2cc(N(C)S(C)(=O)=O)c(-c3ccc4c(n3)C3Cc5c(F)cccc5N3C(CN3CC(F)C3)=N4)cc12] | ¹H-NMR (CDCl₃, 400 MHz) δ 8.69 (s, 1H), 8.62 (s, 1H), 8.20 (d, J = 8.4 Hz, 1H), 7.82~7.84 (m, 2H), 7.63~7.78 (m, 3H), 7.38~7.45 (m, 1H), 7.22~7.26 (m, 2H), 7.18 (t, J = 8.8 Hz, 1H), 5.59 (d, J = 4.4 Hz, 1H), 5.24~5.38 (m, 1H), 4.47 (s, 2H), 4.05~4.17 (m, 2H), 3.48~3.69 (m, 5H), 2.87 (d, J = 4.8 Hz, 3H), 2.63 (s, 3H). | 699 |
| 36 | 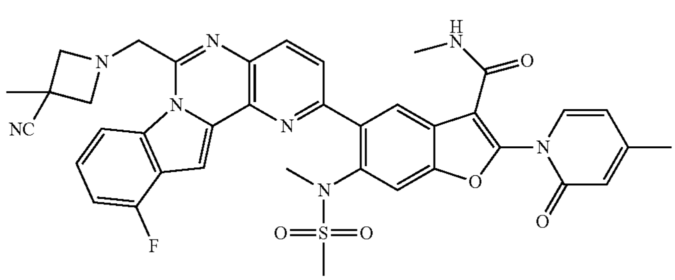 | ¹H-NMR (CDCl₃, 400 MHz) δ 8.21 (s, 1H), 8.08 (d, J = 4.4 Hz, 1H), 7.80 (d, J = 4.4 Hz, 1H), 7.69~7.73 (m, 2H), 7.62 (d, J = 3.6 Hz, 2H), 7.28~7.40 (m, 1H), 7.23 (d, J = 6.8 Hz, 1H), 7.10 (t, J = 8.8 Hz, 1H), 6.48 (s, 1H), 6.24 (d, J = 7.2 Hz, 1H), 4.35 (s, 2H), 3.87 (d, J = 7.2 Hz, 2H), 3.60 (d, J = 7.2 Hz, 2H), 3.37 (s, 3H), 2.85 (d, J = 4.8 Hz, 3H), 2.54 (s, 3H), 2.27 (s, 3H), 1.70 (s, 3H). | 733 |

| Example | Structure | NMR | MS (M + H)+ |
|---|---|---|---|
| 37 | 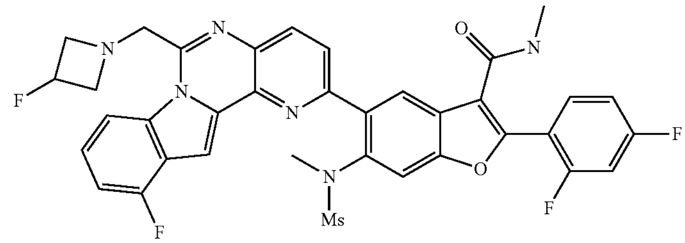 [SMILES: CNC(=O)c1c(-c2ccc(F)cc2F)oc2cc(N(C)S(C)(=O)=O)c(-c3ccc4nc(CN5CC(F)C5)n5c6cccc(F)c6cc5c4n3)cc12] | ¹H-NMR (CDCl₃, 400 MHz) δ 8.13~8.23 (m, 2H), 7.80 (t, J = 9.2 Hz, 3H), 7.72 (s, 2H), 7.37~7.43 (m, 1H), 7.16 (t, J = 8.8 Hz, 1H), 7.08 (t, J = 8.0 Hz, 1H), 7.02 (t, J = 9.2 Hz, 1H), 5.82 (d, J = 4.0 Hz, 1H), 5.23~5.38 (m, 1H), 4.46 (br s., 2H), 4.03~4.14 (m, 2H), 3.55~3.65 (m, 2H), 3.43 (s, 3H), 2.97 (d, J = 4.8 Hz, 3H), 2.67 (s, 3H). | 717 |

Example 38

5-(11-fluoro-6-((3-fluoroazetidin-1-yl)methyl)pyrido[3',2':4,5]pyrimido[1,6-a]indol-2-yl)-2-(4-fluorophenyl)-N-methyl-6-(N-methylmethylsulfonamido)furo[2,3-b]pyridine-3-carboxamide

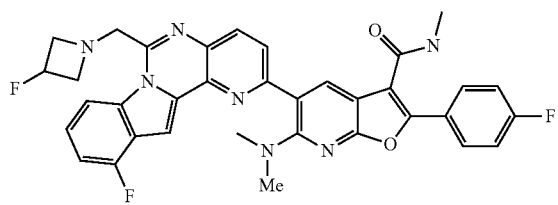 [SMILES: CNC(=O)c1c(-c2ccc(F)cc2)oc2nc(N(C)C)c(-c3ccc4nc(CN5CC(F)C5)n5c6cccc(F)c6cc5c4n3)cc12]

Step 1—Synthesis of (2-(4-fluorophenyl)-3-(methylcarbamoyl)-6-(N-methylmethylsulfonamido)furo[2,3-b]pyridin-5-yl)boronic acid

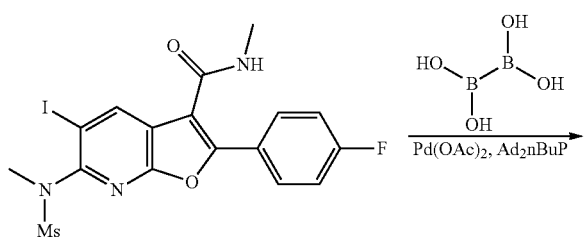

To a degassed solution of 2-(4-fluorophenyl)-5-iodo-N-methyl-6-(N-methylmethylsulfonamido)furo[2,3-b]pyridine-3-carboxamide (3 g, 6 mmol), tetrahydroxydiboron (1.08 g, 1.2 mmol) and KOAc (1.8 g, 1.8 mmol) in EtOH (60 mL) was added Pd(OAc)₂ (50 mg) and Ad₂nBuP (50 mg) under nitrogen atmosphere. The reaction mixture was stirred at 80° C. for 5 h, and then concentrated in vacuo to remove EtOH. The residue was purified by column chromatography (EA:DCM=1:1~DCM:MeOH=5:1) to afford the desired product of (2-(4-fluorophenyl)-3-(methylcarbamoyl)-6-(N-methylmethylsulfonamido)furo[2,3-b]pyridin-5-yl)boronic acid (1 g, yield: 40%). ¹H-NMR (DMSO-d₆, 400 MHz) δ 8.53 (d, J=4.4 Hz, 1H), 8.24 (s, 1H), 8.00~8.04 (m, 3H), 7.40 (t, J=8.8 Hz, 2H), 4.08 (br s, 1H), 3.17 (s, 3H), 3.06 (s, 3H), 2.85 (d, J=4.8 Hz, 3H). MS (M+H)+: 422.

Step 2—Synthesis of 5-(11-fluoro-6-((3-fluoroazetidin-1-yl)methyl)pyrido[3',2':4,5]pyrimido[1,6-a]indol-2-yl)-2-(4-fluorophenyl)-N-methyl-6-(N-methylmethylsulfonamido)furo[2,3-b]pyridine-3-carboxamide

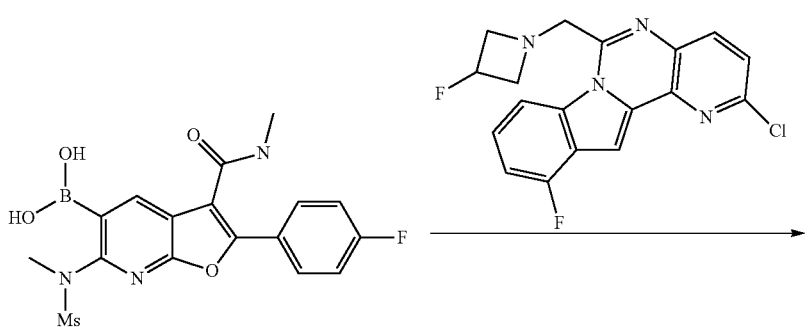

-continued

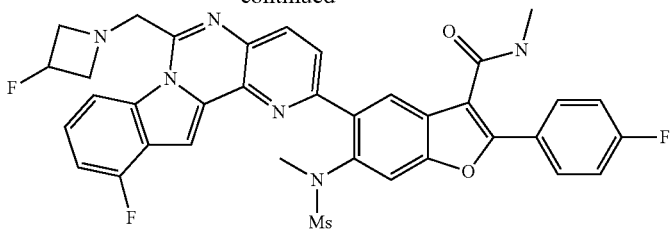

To a mixture of (2-(4-fluorophenyl)-3-(methylcarbamoyl)-6-(N-methylmethylsulfonamido)furo[2,3-b]pyridin-5-yl)boronic acid (70 mg, 0.14 mmol), 2-chloro-11-fluoro-6-((3-fluoroazetidin-1-yl)methyl)pyrido[3',2':4,5]pyrimido[1,6-a]indole (60 mg, 0.17 mmol) and Cs$_2$CO$_3$ (91 mg, 0.30 mmol) in 1,4-dioxane (2 mL) was added Pd(dtbpf)Cl$_2$ (10 mg) under N$_2$. The mixture was stirred at 100° C. for 3 hours. After concentrated, the residue was purified by prep-HPLC to afford the product of 5-(11-fluoro-6-((3-fluoroazetidin-1-yl)methyl)pyrido[3',2':4,5]pyrimido[1,6-a]indol-2-yl)-2-(4-fluorophenyl)-N-methyl-6-(N-methylmethylsulfonamido)furo[2,3-b]pyridine-3-carboxamide (15 mg, yield: 15%). $^1$H NMR (CDCl$_3$, 400 MHz) δ 8.73 (s, 1H), 8.15~8.21 (m, 1H), 8.01~8.08 (m, 3H), 7.79 (s, 2H), 7.37~7.42 (m, 1H), 7.23~7.25 (m, 1H), 7.15 (t, J=8.8 Hz, 1H), 5.97~6.03 (m, 1H), 5.23~5.38 (m, 1H), 4.47 (br s., 2H), 4.10 (br s, 2H), 3.74 (s, 1H), 3.57~3.66 (m, 2H), 3.28 (s, 3H), 3.25 (s, 3H), 3.04 (d, J=5.2 Hz, 3H). MS (M+H)$^+$: 700.

Examples 39 and 40

39

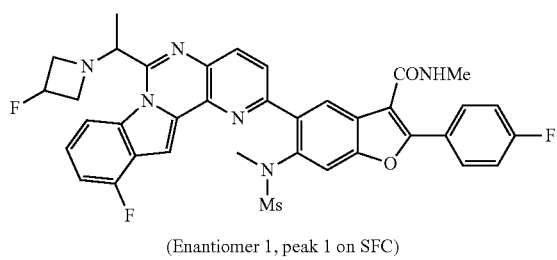

(Enantiomer 1, peak 1 on SFC)

40

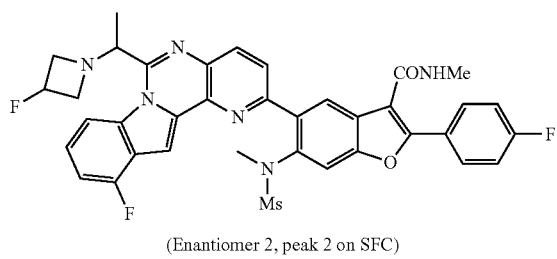

(Enantiomer 2, peak 2 on SFC)

Step 1—Synthesis of 2-chloro-N-(6-chloro-2-(4-fluoro-1H-indol-2-yl)pyridin-3-yl)propanamide

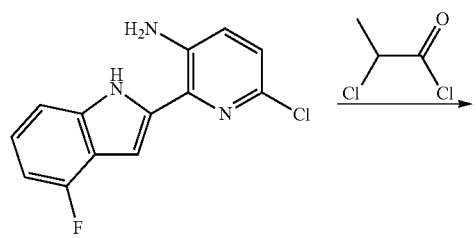

-continued

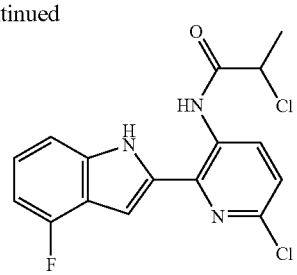

To a solution of compound 6-chloro-2-(4-fluoro-1H-indol-2-yl)pyridin-3-amine (50 mg, 0.19 mmol), DIPEA (0.2 mL) in Pyridine (1.0 mL) was added 2-chloropropanoyl chloride (0.05 mL) dropwise at 0° C. under nitrogen. For 1 hour later, the mixture was dilute with H$_2$O, extracted with EtOAc and the combined organic phase was washed with brine, dried over Na$_2$SO$_4$ and concentrated in vacuo to give the crude product of 2-chloro-N-(6-chloro-2-(4-fluoro-1H-indol-2-yl)pyridin-3-yl)propanamide (60 mg, yield: 90%). $^1$H-NMR (400 MHz, CDCl$_3$) δ 11.84 (s, 1H), 10.34 (s, 1H), 7.93 (d, J=8.0 Hz, 1H), 7.49 (d, J=8.8 Hz, 1H), 7.35 (d, J=8.4 Hz, 1H), 7.22 (s, 1H), 7.12 (d, J=5.6 Hz, 1H), 6.78 (t, J=7.6 Hz, 1H), 4.83~4.88 (m, 1H), 1.65 (d, J=6.4 Hz, 3H). MS (M+H)$^+$: 352/354.

Step 2—Synthesis of 2-chloro-6-(1-chloroethyl)-11-fluoropyrido[3',2':4,5]pyrimido[1,6-a]indole

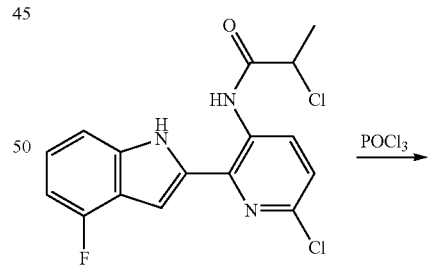

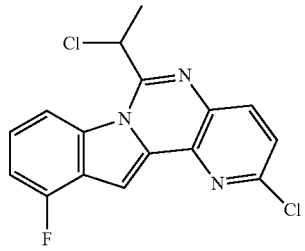

A solution of 2-chloro-N-(6-chloro-2-(4-fluoro-1H-indol-2-yl)pyridin-3-yl)propanamide (70 mg, 0.19 mmol) in POCl₃ (1.5 mL) was heated at 70° C. for 5 hours under nitrogen. The solution was concentrated and it was extracted with EtOAc. The residue was washed with NaHCO₃ (a.q.) to pH=7. The crude product of 2-chloro-6-(1-chloroethyl)-11-fluoropyrido[3',2':4,5]pyrimido[1,6-a]indole (25 mg, yield: 38%) was used to next step. ¹H-NMR (CDCl₃, 400 MHz) δ 7.96 (d, J=8.0 Hz, 2H), 7.81 (s, 1H), 7.40 (d, J=8.0 Hz, 2H), 7.13 (t, J=8.8 Hz, 1H), 5.64~5.69 (m, 1H), 2.11 (d, J=6.4 Hz, 3H). MS (M+H)⁺: 334/336.

Step 3—Synthesis of 2-chloro-11-fluoro-6-(1-(3-fluoroazetidin-1-yl)ethyl)pyrido[3',2':4,5]pyrimido[1,6-a]indole

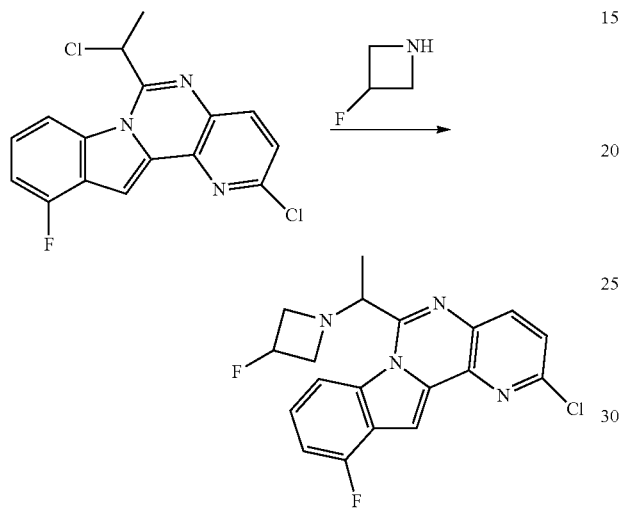

A solution of 2-chloro-6-(1-chloroethyl)-11-fluoropyrido[3',2':4,5]pyrimido[1,6-a]indole (300 mg, 0.89 mmol) in DMF (24 mL) was added 3-fluoroazetidine (85 mg, 1.13 mmol) and K₂CO₃ (162 mg, 1.17 mmol) under nitrogen. The mixture was put into a pre-heated oil-bath at 90° C. and it was stirred for 8 hours. The mixture was cooled to 25° C. and it was concentrated and it was extracted with EtOAc, then the combined organic phase was washed with brine, dried over Na₂SO₄ and concentrated in vacuo. The yellow solid was purified by column chromatography (PE:EA=3:1) to obtain the product of 2-chloro-11-fluoro-6-(1-(3-fluoro-azetidin-1-yl)ethyl)pyrido[3',2':4,5]pyrimido[1,6-a]indole (200 mg, yield: 62%). ¹H-NMR (CDCl₃, 400 MHz) δ 8.01 (d, J=8.0 Hz, 1H), 7.79 (s, 1H), 7.62 (s, 1H), 7.37 (t, J=8.4 Hz, 2H), 7.12 (t, J=8.0 Hz, 1H), 5.13~5.27 (m, 1H), 4.51 (s, 1H), 3.87 (s, 1H), 3.41~3.47 (m, 1H), 3.19~3.26 (m, 1H), 1.58 (d, J=6.4 Hz, 4H). MS (M+H)⁺: 373.

Step 4—Synthesis of (R or S)-5-(11-fluoro-6-(1-(3-fluoroazetidin-1-yl)ethyl)pyrido[3',2':4,5]pyrimido[1,6-a]indol-2-yl)-2-(4-fluorophenyl)-N-methyl-6-(N-methylmethylsulfonamido)benzofuran-3-carboxamide and (S or R)-5-(11-fluoro-6-(1-(3-fluoroazetidin-1-yl)ethyl)pyrido[3',2':4,5]pyrimido[1,6-a]indol-2-yl)-2-(4-fluorophenyl)-N-methyl-6-(N-methylmethylsulfonamido)benzofuran-3-carboxamide (Compound 39 and Compound 40)

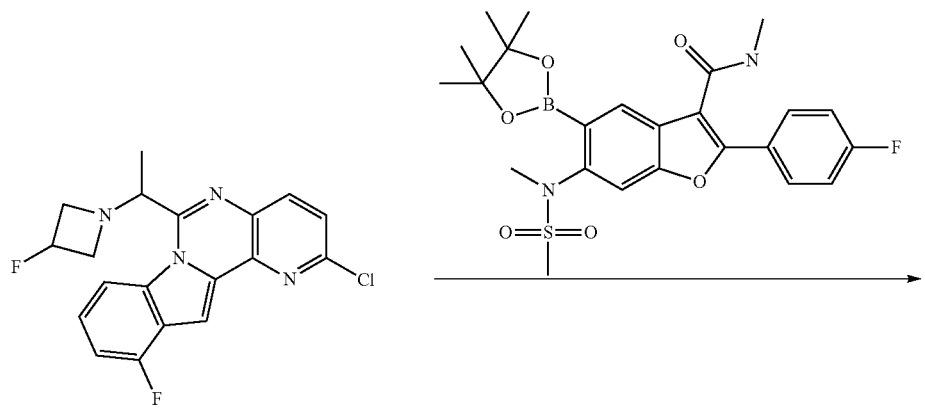

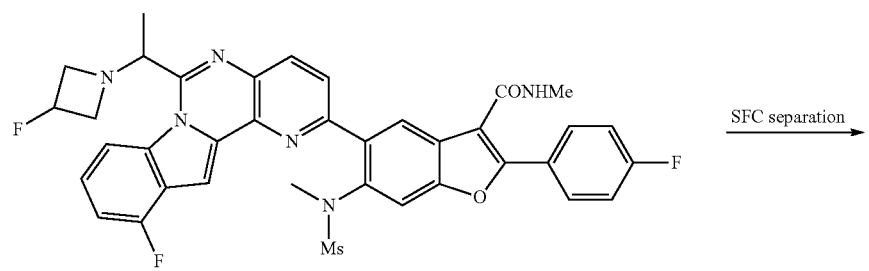

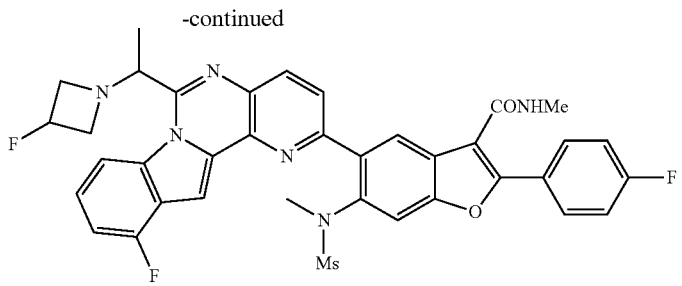

39 (Enantiomer 1, peak 1 on SFC)

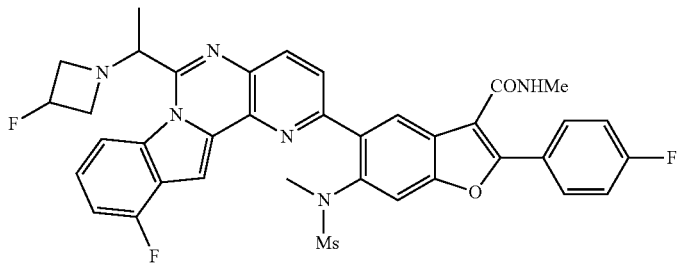

40 (Enantiomer 2, peak 2 on SFC)

To a solution of compound 2-chloro-11-fluoro-6-(1-(3-fluoroazetidin-1-yl)ethyl)pyrido[3',2':4,5]pyrimido[1,6-a]indole (20 mg, 0.05 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (50 mg, 0.10 mmol) and K$_2$CO$_3$ (18 mg, 0.13 mmol) in 1,4-dioxane (0.8 mL) and water (0.05 mL) was added X-Phos and Pd$_2$(dba)$_3$ (20 mg) under nitrogen. The mixture was heated at 100° C. for 3 hours and filtered through the Celite pad. The filtrate was extracted with EtOAc, then the combined organic phase was washed with brine, dried over Na$_2$SO$_4$ and concentrated, the residue was purified by prep-HPLC and SFC to give two single enantiomers.

Compound 39 (enantiomer 1, peak 1 on SFC, OJ_H_B3_5_40_25ML, HPLC_RT=5.977 min) (30 mg, yield: 42%). $^1$H-NMR (CDCl$_3$, 400 MHz) δ 8.17 (d, J=8.0 Hz, 1H), 8.08 (s, 1H), 7.90~7.94 (m, 2H), 7.65~7.72 (m, 4H), 7.30~7.45 (m, 1H), 7.09~7.16 (m, 3H), 5.83 (d, J=4.4 Hz, 1H), 5.16~5.31 (m, 1H), 4.54 (d, J=5.6 Hz, 1H), 3.91~4.03 (m, 2H), 3.15~3.60 (m, 5H), 2.94 (d, J=4.8 Hz, 3H), 2.65 (s, 3H), 1.62 (d, J=6.4 Hz, 3H). MS (M+H)$^+$: 713.

Compound 40 (enantiomer 2, peak 2 on SFC, OJ_H_B3_5_40_25ML, HPLC_RT=6.501 min) (30 mg, yield: 42%). $^1$H-NMR (CDCl$_3$, 400 MHz) δ 8.17 (d, J=8.0 Hz, 1H), 8.08 (s, 1H), 7.90~7.94 (m, 2H), 7.65~7.72 (m, 4H), 7.30~7.45 (m, 1H), 7.09~7.16 (m, 3H), 5.83 (d, J=4.4 Hz, 1H), 5.16~5.31 (m, 1H), 4.54 (d, J=5.6 Hz, 1H), 3.91~4.03 (m, 2H), 3.15~3.60 (m, 5H), 2.94 (d, J=4.8 Hz, 3H), 2.65 (s, 3H), 1.62 (d, J=6.4 Hz, 3H). MS (M+H)$^+$: 713.

Example 41

2-(4-fluorophenyl)-5-(indolo[1,2-c]quinazolin-2-yl)-N-methyl-6-(N-methylmethylsulfonamido)benzofuran-3-carboxamide

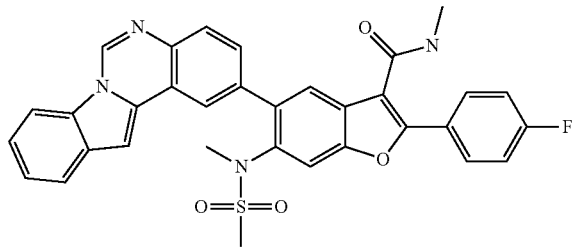 [SMILES: CNC(=O)c1c(-c2ccc(F)cc2)oc2cc(N(C)S(C)(=O)=O)c(-c3ccc4ncn5c6ccccc6cc5c4c3)cc12]

Step 1—Synthesis of 2-bromoindolo[1,2-c]quinazoline

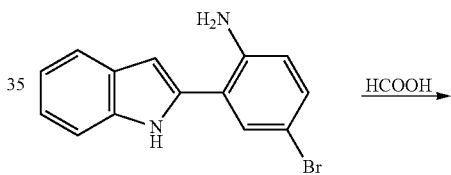

HCOOH

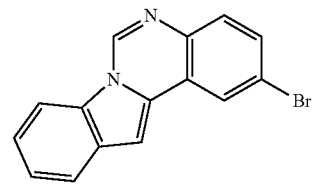

A solution of 4-bromo-2-(1H-indol-2-yl)aniline (prepared using similar method described in Example 1, 1 g, 3.48 mmol) in formic acid (10 mL) was stirred at 90° C. for 1 h. The reaction mixture was cooled to RT and poured into crushed ice and filtered. The cake was washed with water and purified by column chromatography (PE:EtOAc=8:1) to give 2-bromoindolo[1,2-c]quinazoline (490 mg, yield: 47%). $^1$H-NMR (CDCl$_3$, 400 MHz) δ 8.95 (s, 1H), 8.11 (s, 1H), 8.11~7.90 (m, 1H), 7.78~7.76 (m, 1H), 7.61~7.53 (m, 2H), 7.40~7.34 (m, 2H), 7.07 (s, 1H). MS (M+H)$^+$: 297/299.

Step 2—Synthesis of 2-(4-fluorophenyl)-5-(indolo[1,2-c]quinazolin-2-yl)-N-methyl-6-(N-methylmethylsulfonamido)benzofuran-3-carboxamide

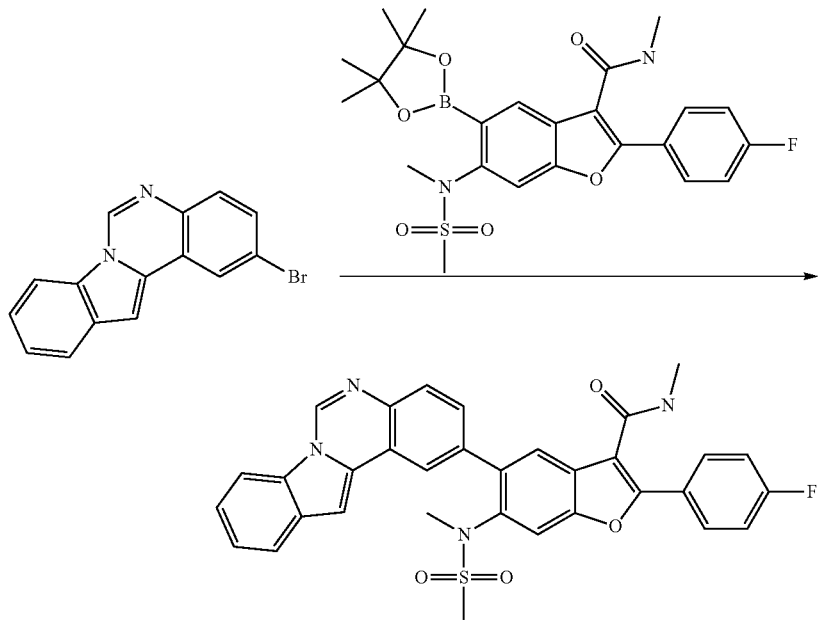

To a degassed solution of 2-bromoindolo[1,2-c]quinazoline (68 mg, 0.24 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamiden (100 mg, 0.20 mmol) in DMF (3.0 mL) were added Pd(dppf)Cl$_2$ and K$_3$PO$_4$ (106 mg, 0.40 mmol) under N$_2$. The mixture was heated at 90° C. for 3 h. The reaction mixture was cooled to RT and filtered. The filtrate was extracted with EtOAc, then the combined organic phase was washed with brine, dried over Na$_2$SO$_4$ and concentrated, the residue was purified by prep-TLC to give 2-(4-fluorophenyl)-5-(indolo[1,2-c]quinazolin-2-yl)-N-methyl-6-(N-methylmethylsulfonamido)benzofuran-3-carboxamide (80 mg, yield: 68%). $^1$H-NMR (CDCl$_3$, 400 MHz) δ 9.30 (s, 1H), 8.20 (s, 1H), 7.87 (t, J=3.2 Hz, 1H), 7.90~7.87 (m, 4H), 7.79 (d, J=8.0 Hz, 1H), 7.59 (d, J=8.0 Hz, 2H), 7.44~7.43 (m, 2H), 7.16~7.14 (m, 2H), 5.78 (s, 1H), 3.07 (s, 3H), 2.94 (d, J=4.8 Hz, 3H), 2.72 (s, 3H). MS (M+H)$^+$: 593.

Example 42

2-(4-fluorophenyl)-N-methyl-6-(N-methylmethylsulfonamido)-5-(5-(methylsulfonyl)-5,6-dihydroindolo[1,2-c]quinazolin-2-yl)benzofuran-3-carboxamide

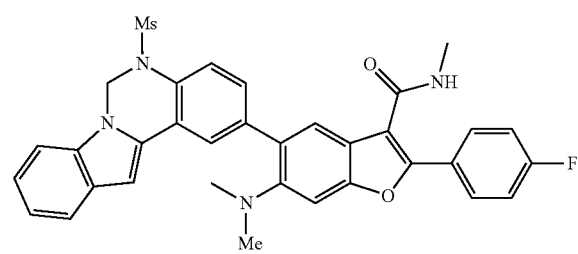 [SMILES: CNC(=O)c1c(-c2ccc(F)cc2)oc2cc(N(C)C)c(-c3ccc4c(c3)-c3cc5ccccc5n3CN4S(C)(=O)=O)cc12]

Step 1—Synthesis of 2-bromo-5,6-dihydroindolo[1,2-c]quinazoline

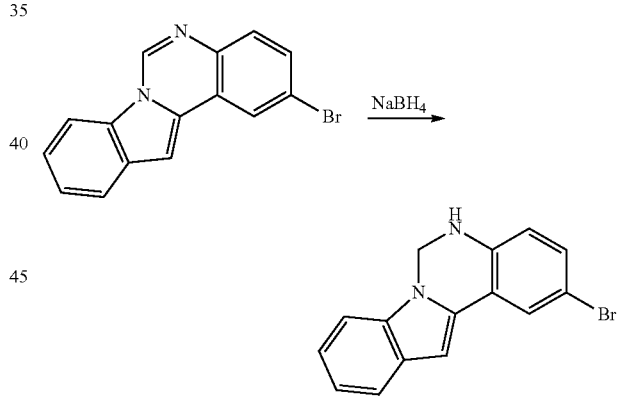

To a degassed solution of 2-bromoindolo[1,2-c]quinazoline (800 mg, 2.69 mmol) in CH$_3$OH (5 mL) was added NaBH$_4$ (1.0 g, 26 mmol). The mixture was refluxed for 5 h under N$_2$. The reaction mixture was cooled to RT and the solution was removed by evaporation in vacuo. The reaction mixture was dissolved in EtOAc and washed with H$_2$O, brine, dried over Na$_2$SO$_4$. After concentrated, the residue was purified by column chromatography (PE:EtOAc=8:1) to give 2-bromo-5,6-dihydroindolo[1,2-c]quinazoline (450 mg, yield: 56%). $^1$H-NMR (CDCl$_3$, 400 MHz) δ 7.70 (d, J=4.0 Hz, 1H), 7.57 (d, J=8.0 Hz, 1H), 7.16~7.12 (m, 2H), 7.08~7.04 (m, 1H), 6.73 (s, 1H), 6.62 (d, J=8.0 Hz, 2H), 5.31 (d, J=2.40 Hz, 2H), 4.31 (s, 1H). MS (M+H)$^+$: 299/301.

Step 2—Synthesis of 2-bromo-5-(methylsulfonyl)-5,6-dihydroindolo[1,2-c]quinazoline

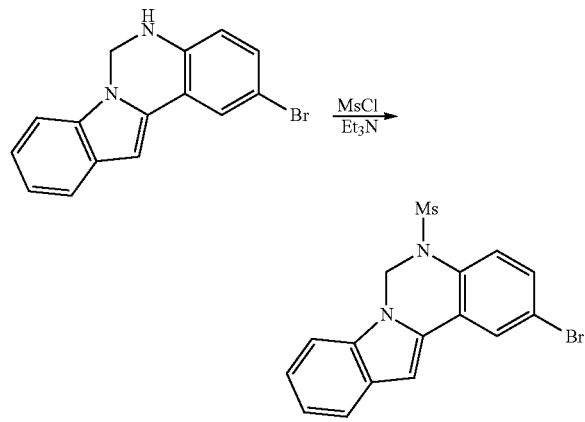

To a solution of 2-bromo-5,6-dihydroindolo[1,2-c]quinazoline (150 mg, 0.50 mmol) in $CH_2Cl_2$ (3 mL) was added triethylamine (120 mg, 1.0 mmol) dropwise at 0~5° C. with stirring. Then MsCl (130 mg, 1 mmol) was added dropwise at 5° C. After stirred for 2 h at RT under $N_2$, the reaction mixture was washed with $H_2O$, brine, dried over $Na_2SO_4$. After concentrated, the residue was purified by column chromatography (PE:EtOAc=8:1) to give 2-bromo-5-(methylsulfonyl)-5,6-dihydroindolo[1,2-c]quinazoline (100 mg, yield: 53%). $^1$H-NMR (CDCl$_3$, 400 MHz) δ 7.88 (s, 1H), 7.87~7.61 (m, 1H), 7.51 (d, J=8.0 Hz, 1H), 7.42~7.36 (m, 2H), 7.26~7.14 (m, 1H), 7.13~7.10 (m, 1H), 6.88 (s, 1H), 5.70 (s, 2H), 3.09 (s, 3H). MS (M+H)$^+$: 377/379.

Step 3—Synthesis of 2-(4-fluorophenyl)-N-methyl-6-(N-methylmethylsulfonamido)-5-(5-(methylsulfonyl)-5,6-dihydroindolo[1,2-c]quinazolin-2-yl)benzofuran-3-carboxamide

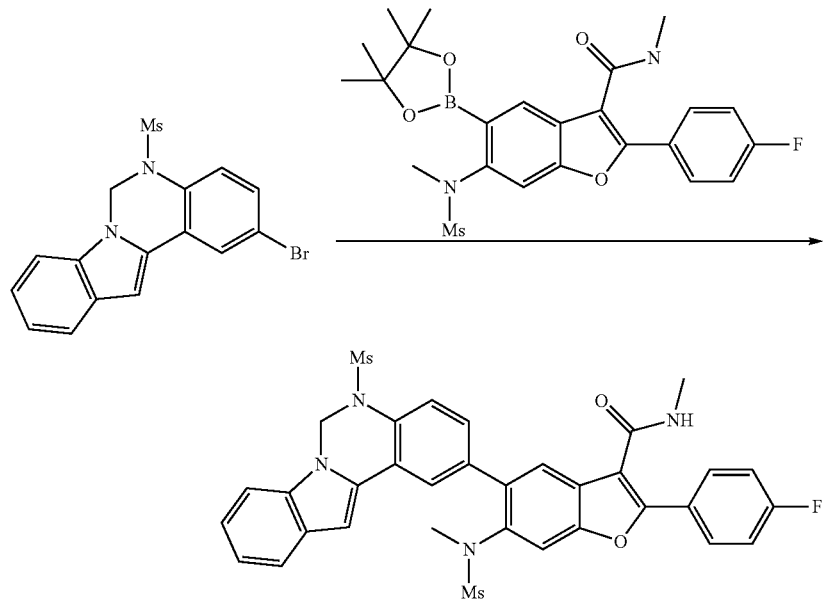

To a degassed solution of 2-bromo-5-(methylsulfonyl)-5,6-dihydroindolo[1,2-c]quinazoline (100 mg, 0.26 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (120 mg, 0.24 mmol) in DMF (3.0 mL) were added Pd(dppf)Cl$_2$ (10 mg) and K$_3$PO$_4$ (160 mg, 0.61 mmol) under $N_2$. The mixture was heated to 90° C. for 3 h. The reaction mixture was cooled to RT and filtered. The filtrate diluted with water, extracted with EtOAc, dried over Na$_2$SO$_4$ and concentrated. The residue was purified by prep-HPLC to give 2-(4-fluorophenyl)-N-methyl-6-(N-methylmethylsulfonamido)-5-(5-(methylsulfonyl)-5,6-dihydroindolo[1,2-c]quinazolin-2-yl)benzofuran-3-carboxamide (48 mg, yield: 30%). $^1$H-NMR (CDCl$_3$, 400 MHz) δ 8.00 (s, 1H), 8.00~7.90 (m, 3H), 7.79 (d, J=8.0 Hz, 1H), 7.67~7.65 (m, 1H), 7.62 (s, 1H), 7.46~7.42 (m, 2H), 7.32~7.28 (m, 1H), 7.24~7.15 (m, 3H), 6.99 (s, 1H), 5.88 (d, J=4.8 Hz, 1H), 5.85 (s, 2H), 3.15 (s, 3H), 2.99 (d, J=4.8 Hz, 3H), 2.32 (s, 3H). MS (M+H)$^+$: 673.

Example 44

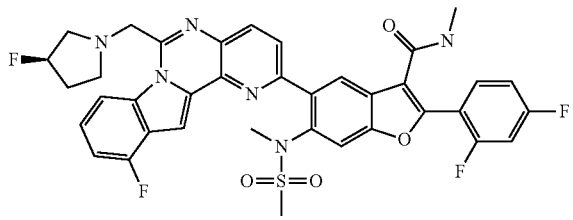 [SMILES: CNC(=O)c1c(-c2ccc(F)cc2F)oc2cc(N(C)S(C)(=O)=O)c(-c3ccc4nc(CN5CC[C@@H](F)C5)n5c6cccc(F)c6cc5c4n3)cc12]

Step 1—Synthesis of 5-(5-amino-6-(4-fluoro-1H-indol-2-yl)pyridin-2-yl)-2-(2,4-difluorophenyl)-N-methyl-6-(N-methylmethylsulfonamido)benzofuran-3-carboxamide

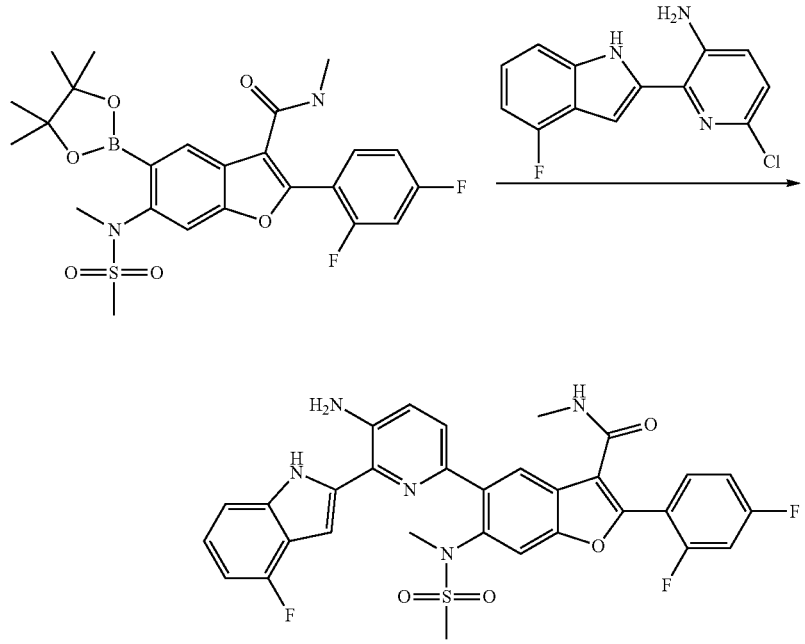 [SMILES: CNC(=O)c1c(-c2ccc(F)cc2F)oc2cc(N(C)S(C)(=O)=O)c(B3OC(C)(C)C(C)(C)O3)cc12 ; Nc1ccc(Cl)nc1-c1cc2c(F)cccc2[nH]1 ; CNC(=O)c1c(-c2ccc(F)cc2F)oc2cc(N(C)S(C)(=O)=O)c(-c3ccc(N)c(-c4cc5c(F)cccc5[nH]4)n3)cc12]

To a solution of 2-(2,4-difluorophenyl)-N-methyl-6-(N-methylmethyl sulfonamido)-5-(4,4,5,5-tetramethyl-1,3,2-dioxaborolan-2-yl)benzofuran-3-carboxamide (2.38 g, 4.59 mmol), 6-chloro-2-(4-fluoro-1H-indol-2-yl)pyridin-3-amine (1.0 g, 0.74 mmol) and $K_3PO_4 \cdot 3H_2O$ (2.03 g, 7.64 mmol) in IPA (15 mL) was added $Pd(OAc)_2/Cy_3P$ (100 mg/100 mg) under nitrogen. The mixture was heated at 90° C. for 8 hours and filtered through the celite pad. The filtrate was washed with EtOAc and obtained 5-(5-amino-6-(4-fluoro-1H-indol-2-yl)pyridin-2-yl)-2-(2,4-difluorophenyl)-N-methyl-6-(N-methylmethylsulfonamido)benzofuran-3-carboxamide (1.65 g, yield: 70%) without further purification. $^1$H-NMR (DMSO-$d_6$, 400 MHz) δ 11.47 (s, 1H), 8.32 (d, J=4.3 Hz, 1H), 8.05 (s, 1H), 7.98 (s, 1H), 7.85~7.87 (m, 1H), 7.42~7.50 (m, 2H), 7.32 (d, J=8.2 Hz, 3H), 7.13 (s, 1H), 7.06 (d, J=5.5 Hz, 1H), 6.73~6.77 (m, 1H), 5.66 (s, 2H), 3.17 (s, 3H), 2.98 (s, 3H), 2.75 (d, J=4.0 Hz, 3H). MS (M+H)$^+$: 620.

Step 2—Synthesis of 5-(6-(chloromethyl)-11-fluoropyrido[3',2':4,5]pyrimido[1,6-a]indol-2-yl)-2-(2,4-difluorophenyl)-N-methyl-6-(N-methylmethylsulfonamido)benzofuran-3-carboxamide

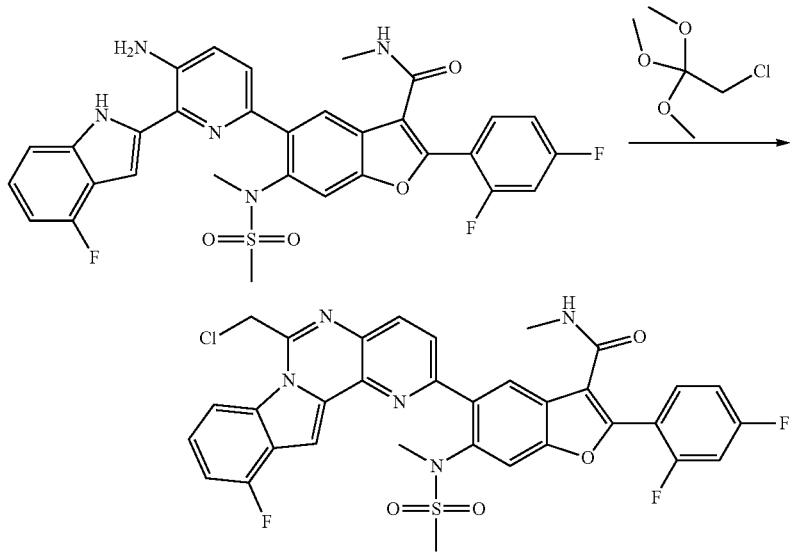

To a solution of 5-(5-amino-6-(4-fluoro-1H-indol-2-yl)pyridin-2-yl)-2-(2,4-difluorophenyl)-N-methyl-6-(N-methylmethylsulfonamido)benzofuran-3-carboxamide (500 mg, 0.80 mmol) in HOAc (9 mL) was added 2-chloro-1,1,1-trimethoxyethane (2.5 mL) at RT under nitrogen. The mixture was stirred at 70° C. overnight and then it was filtered. The insoluble solid was washed with water and collected to obtained crude 5-(6-(chloromethyl)-11-fluoropyrido[3',2':4,5]pyrimido[1,6-a]indol-2-yl)-2-(2,4-difluorophenyl)-N-methyl-6-(N-methylmethylsulfonamido)benzofuran-3-carboxamide (450 mg, yield: 82.5%) without further purification. $^1$H-NMR (CDCl$_3$, 400 MHz) δ 8.13~8.20 (m, 2H), 8.14 (d, J=8.4 Hz, 1H), 7.70~7.94 (m, 4H), 7.45~7.46 (m, 1H), 7.19~7.21 (m, 1H), 7.01~7.07 (m, 2H), 5.76 (s, 1H), 5.18 (s, 2H), 3.42 (s, 3H), 2.96 (d, J=4.4 Hz, 3H), 2.68 (s, 3H). MS (M+H)$^+$: 678/680.

Step 3—Synthesis of (R)-2-(2,4-difluorophenyl)-5-(11-fluoro-6-((3-fluoropyrrolidin-1-yl)methyl)pyrido[3',2':4,5]pyrimido[1,6-a]indol-2-yl)-N-methyl-6-(N-methylmethyl sulfonamido)benzofuran-3-carboxamide

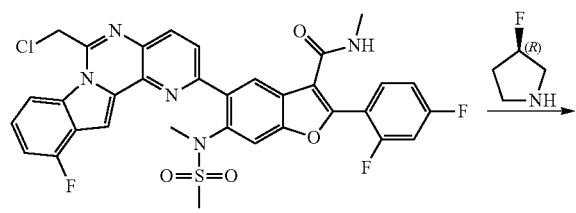

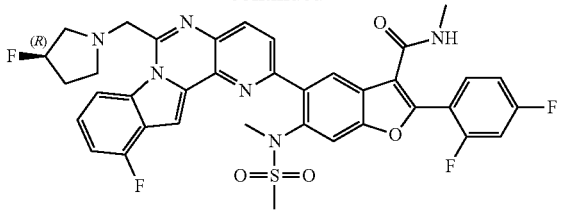

To a solution of 5-(6-(chloromethyl)-11-fluoropyrido[3',2':4,5]pyrimido[1,6-a]indol-2-yl)-2-(2,4-difluorophenyl)-N-methyl-6-(N-methylmethylsulfonamido)benzofuran-3-carboxamide (100 mg, 0.148 mmol) and (R)-3-fluoropyrrolidine (30 mg, 0.336 mmol) in DMF (2 mL) was added Et$_3$N (0.1 mL) under nitrogen. The mixture was stirred at 60° C. for 2 hours. After concentrated, the resulting residue was suspended in water and extracted with EtOAc, then the combined organic phase was washed with brine, dried over Na$_2$SO$_4$ and concentrated in vacuo and the residue was purified by the prep-HPLC to give (R)-2-(2,4-difluorophenyl)-5-(11-fluoro-6-((3-fluoropyrrolidin-1-yl)methyl)pyrido[3',2':4,5]pyrimido[1,6-a]indol-2-yl)-N-methyl-6-(N-methylmethylsulfonamido)benzofuran-3-carboxamide (45 mg, yield: 42%). $^1$H-NMR (CDCl$_3$, 400 MHz) δ 8.18 (s, 1H), 8.15 (d, J=8.8 Hz, 1H), 7.91 (d, J=8.4 Hz, 1H), 7.75~7.78 (m, 2H), 7.71 (s, 2H), 7.38 (d, J=5.6 Hz, 1H), 7.14~7.16 (m, 1H), 7.02~7.07 (m, 1H), 6.99~7.01 (m, 1H), 5.76 (br s, 1H), 5.19~5.33 (m, 1H), 4.36~4.47 (m, 2H), 3.42 (s, 3H), 3.10~3.22 (m, 3H), 2.94~2.97 (m, 4H), 2.65 (s, 3H), 2.16~2.25 (m, 2H). MS (M+H)$^+$: 731.

Examples 45-48

Examples 45-48, depicted in the table below, were prepared in accordance with the method described in Example 44.

| Example | Structure | NMR | MS (M + H)$^+$ |
|---|---|---|---|
| 45 | 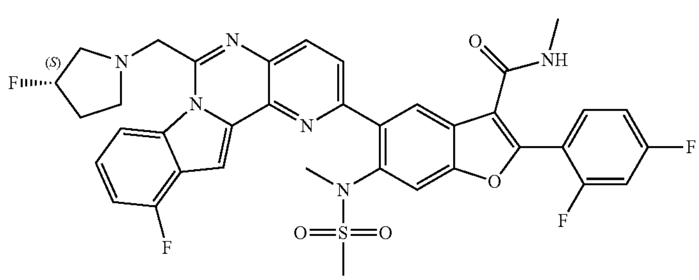 | $^1$H-NMR (CDCl$_3$, 400 MHz) δ 8.19 (s, 1H), 8.15 (d, J = 8.8 Hz, 1H), 7.92 (d, J = 8.4 Hz, 1H), 7.77~7.79 (m, 2H), 7.72 (s, 2H), 7.41 (d, J = 6.0 Hz, 1H), 7.14~7.16 (m, 1H), 7.01~7.06 (m, 2H), 5.87 (s, 1H), 5.22~5.36 (m, 1H), 4.39-4.50 (m, 2H), 3.44 (s, 3H), 3.12~3.25 (m, 3H), 2.97~2.99 (m, 4H), 2.67 (s, 3H), 2.15~2.24 (m, 2H). | 731 |
| 46 | 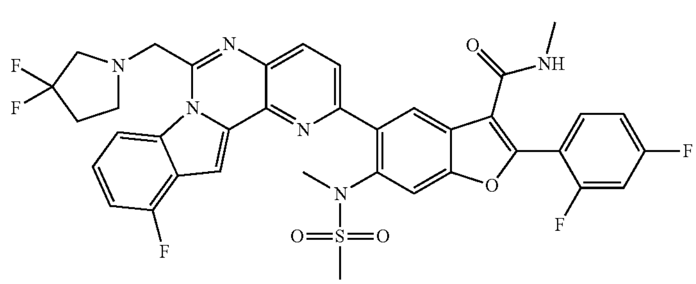 [SMILES: CNC(=O)c1c(-c2ccc(F)cc2F)oc2cc(N(C)S(C)(=O)=O)c(-c3ccc4nc(CN5CCC(F)(F)C5)n5c6cccc(F)c6cc5c4n3)cc12] | $^1$H-NMR (CDCl$_3$, 400 MHz) δ 8.14 (s, 1H), 8.09 (d, J = 8.0 Hz, 1H), 7.78 (d, J = 8.8 Hz, 1H), 7.72 (d, J = 8.4 Hz, 2H), 7.66 (d, J = 4.8 Hz, 2H), 7.34 (d, J = 5.6 Hz, 1H), 7.12 (d, J = 8.4 Hz, 1H), 7.02 (s, 1H), 6.95 (s, 1H), 5.72 (d, J = 4.4 Hz, 1H), 4.34 (s, 2H), 3.37 (s, 3H), 3.30 (t, J = 13.2 Hz, 2H), 3.08 (t, J = 4.8 Hz, 2H), 2.91 (d, J = 4.8 Hz, 3H), 2.62 (s, 3H), 2.29~2.34 (m, 2H). | 749 |

| Example | Structure | NMR | MS (M + H)+ |
|---|---|---|---|
| 47 | 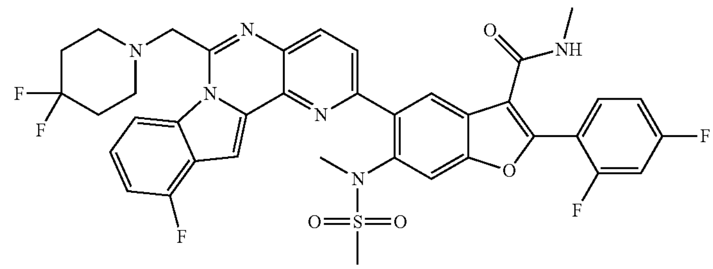 [SMILES: CNC(=O)c1c(-c2ccc(F)cc2F)oc2cc(N(C)S(C)(=O)=O)c(-c3ccc4nc(CN5CCC(F)(F)CC5)n5c6cccc(F)c6cc5c4n3)cc12] | ¹H-NMR (CDCl₃, 400 MHz) δ 8.13 (s, 1H), 8.07 (d, J = 8.4 Hz, 1H), 7.80 (d, J = 8.8 Hz, 1H), 7.71 (d, J = 8.0 Hz, 2H), 7.65 (d, J = 4.8 Hz, 2H), 7.32 (d, J = 5.6 Hz, 1H), 7.10 (d, J = 8.4 Hz, 1H), 7.01 (s, 1H), 6.94 (s, 1H), 5.73 (d, J = 3.6 Hz, 1H), 4.20 (s, 2H), 3.37 (s, 3H), 2.90 (d, J = 13.2 Hz, 3H), 2.86 (br s, 4H), 2.64 (s, 3H), 1.97~2.04 (m, 4H). | 763 |
| 48 | 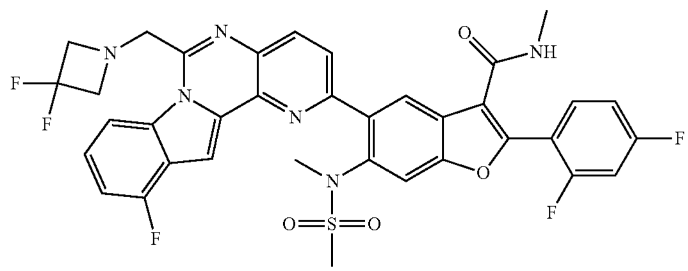 [SMILES: CNC(=O)c1c(-c2ccc(F)cc2F)oc2cc(N(C)S(C)(=O)=O)c(-c3ccc4nc(CN5CC(F)(F)C5)n5c6cccc(F)c6cc5c4n3)cc12] | ¹H-NMR (CDCl₃, 400 MHz) δ 8.14 (s, 1H), 8.10 (d, J = 8.4 Hz, 1H), 7.71~7.76 (m, 3H), 7.66 (d, J = 4.0 Hz, 2H), 7.31~7.34 (m, 1H), 7.09-7.11 (m, 1H), 7.03~7.05 (m, 1H), 6.93~6.96 (m, 1H), 5.68 (br s, 1H), 4.47 (s, 2H), 3.96~3.98 (m, 4H), 3.37 (s, 3H), 2.91 (d, J = 4.8 Hz, 3H), 2.61 (s, 3H). | 735 |

Example 49 diethyl ((11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indol-6-yl)methyl)phosphonate

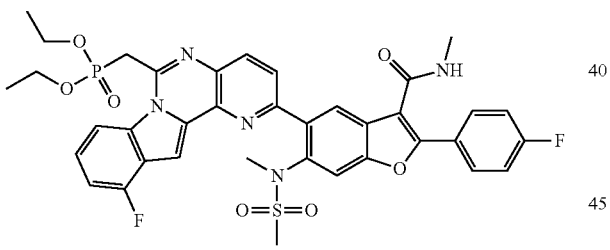

Step 1—Synthesis of diethyl ((11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indol-6-yl)methyl)phosphonate

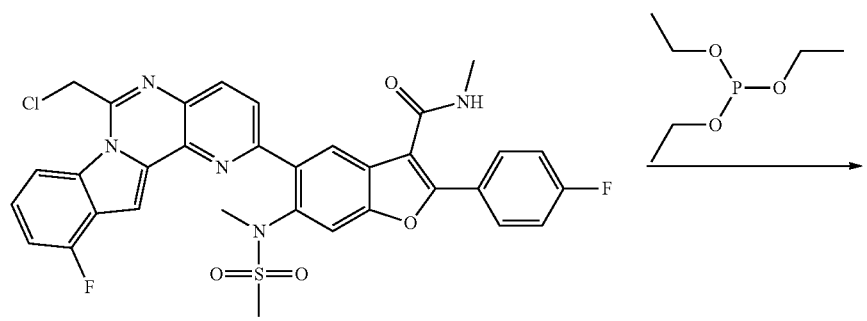

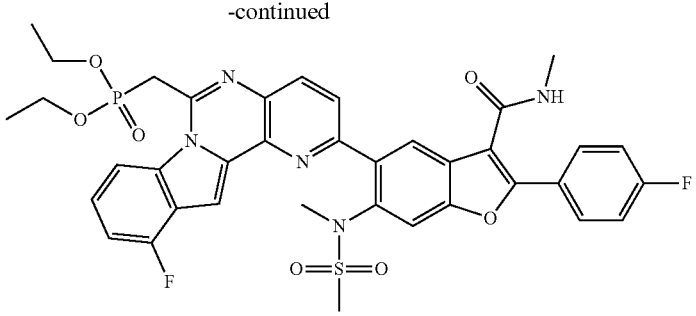

A solution of 5-(6-(chloromethyl)-11-fluoropyrido[3',2': 4,5]pyrimido[1,6-a]indol-2-yl)-2-(2,4-difluorophenyl)-N-methyl-6-(N-methylmethylsulfonamido)benzofuran-3-carboxamide (100 mg, 0.15 mmol) in P(OC$_2$H$_5$)$_3$ (1 mL) was stirred at 80° C. for 30 minutes, and then heated to 140° C. for 3 h, the resultant mixture was purified by prep-HPLC (neutral) to afford diethyl ((11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indol-6-yl)methyl)phosphonate (20 mg, 17.4% yield) as yellow solid. $^1$H-NMR (CDCl$_3$, 400 MHz) δ 8.06 (s, 2H), 7.89~7.95 (m, 3H), 7.72 (d, J=8.4 Hz, 1H), 7.63~7.65 (m, 2H), 7.35 (br s, 1H), 7.00~7.16 (m, 3H), 5.65 (br s, 1H), 4.21 (q, J=7.2 Hz, 4H), 4.11 (s, 2H), 3.36 (s, 3H), 2.95 (d, J=4.8 Hz, 3H), 2.63 (s, 3H), 1.22 (t, J=7.2 Hz, 6H). MS (M+H)$^+$: 762.

Example 50

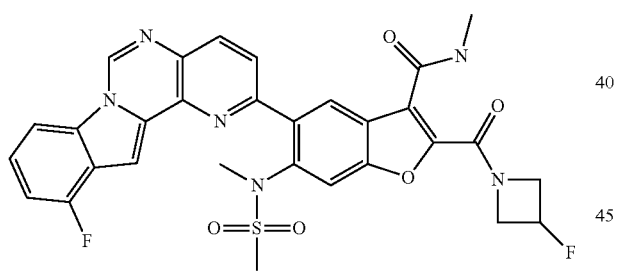

Step 1—Synthesis of methyl 5-bromo-3-(methylcarbamoyl)-6-(N-methylmethylsulfonamido)benzofuran-2-carboxylate

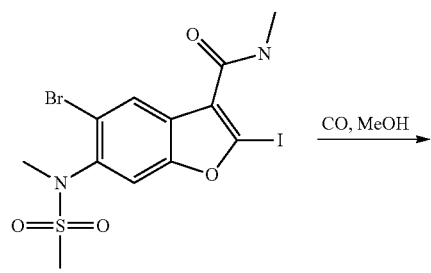

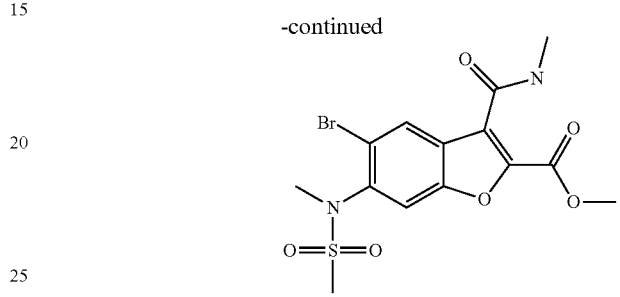

To a solution of 5-bromo-2-iodo-N-methyl-6-(N-methylmethylsulfonamido)benzofuran-3-carboxamide (4.0 g, 8.21 mmol) in MeOH (10 mL) and DMSO (35 mL) was added Pd(PPh$_3$)$_2$Cl$_2$ under N$_2$. The suspension was degassed under vacuum and purged with CO 4 times. The mixture was stirred under CO (50 Psi) at 50° C. for 16 h. Then 30 mL MeOH was added to the mixture, the resulting solid was filtered to give the crude product of methyl 5-bromo-3-(methylcarbamoyl)-6-(N-methylmethylsulfonamido)benzofuran-2-carboxylate (2.90 g, yield: 84%). $^1$H-NMR (CDCl$_3$, 400 MHz) δ 9.39 (br s, 1H), 8.94 (s, 1H), 7.74 (s, 1H), 4.08 (s, 3H), 3.34 (s, 3H), 3.08 (s, 3H), 3.04 (d, J=4.8 Hz, 3H). MS (M+H)$^+$: 419/421.

Step 2—Synthesis of methyl 3-(methylcarbamoyl)-6-(N-methylmethylsulfonamido)-5-(4,4,5,5-tetramethyl-1,3,2-dioxaborolan-2-yl)benzofuran-2-carboxylate

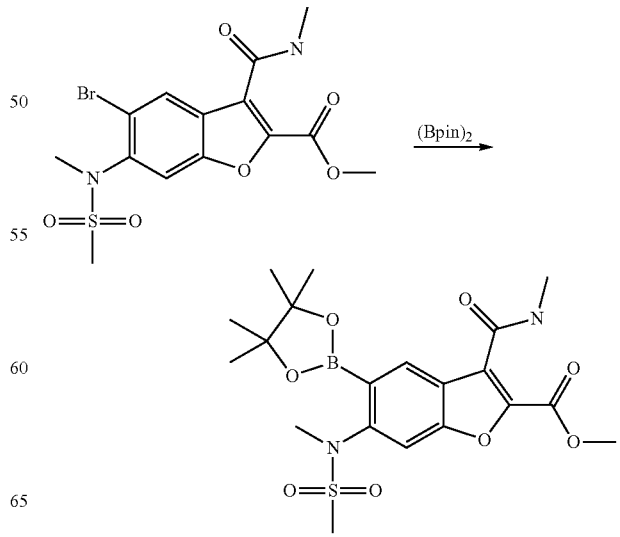

To a mixture of methyl 5-bromo-3-(methylcarbamoyl)-6-(N-methylmethylsulfonamido)benzofuran-2-carboxylate (1.0 g, 2.39 mmol), bis(pinacolato)diboron (908 mg, 3.58 mmol), CH₃COOK (702 mg, 7.16 mmol) in 1,4-dioxane was added Pd(dtbpf)Cl₂ under N₂. The mixture was stirred at 90° C. for 1.5 h and then it was concentrated in vacuo. The residue was purified by column chromatography (PE:EA=5:1-DCM:MeOH=100:1) to give the product of methyl 3-(methylcarbamoyl)-6-(N-methylmethylsulfonamido)-5-(4,4,5,5-tetramethyl-1,3,2-dioxaborolan-2-yl)benzofuran-2-carboxylate (700 mg, yield: 64%). ¹H-NMR (CDCl₃, 400 MHz) δ 9.30 (br s, 1H), 9.06 (s, 1H), 7.62 (s, 1H), 4.07 (s, 3H), 3.35 (s, 3H), 3.05 (d, J=4.8 Hz, 3H), 2.96 (s, 3H), 1.35 (s, 12H). MS (M+H)⁺: 467.

Step 3—Synthesis of 2-(3,3-difluoroazetidine-1-carbonyl)-5-(11-fluoropyrido[3',2':4,5]pyrimido[1,6-a]indol-2-yl)-N-methyl-6-(N-methylmethylsulfonamido)benzofuran-3-carboxamide

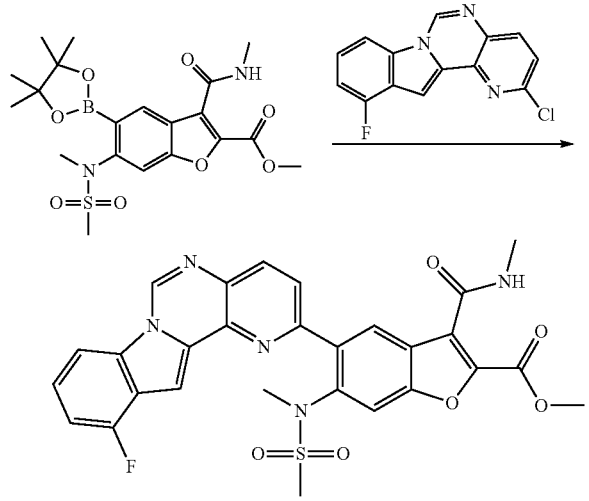

To a mixture of methyl 3-(methylcarbamoyl)-6-(N-methylmethylsulfonamido)-5-(4,4,5,5-tetramethyl-1,3,2-dioxaborolan-2-yl)benzofuran-2-carboxylate (1.48 g, 2.44 mmol), 2-chloro-11-fluoropyrido[3',2':4,5]pyrimido[1,6-a]indole (995 mg, 3.67 mmol) and K₃PO₄·3H₂O (1.95 g, 7.33 mmol) in 1,4-dioxane (20 mL), were added Pd₂(dba)₃ (150 mg) and X-Phos (150 mg) under N₂ protection. After stirred at 80° C. for 3 h, the mixture was concentrated in vacuo, and then the residue was purified by column chromatography (DCM:MeOH=100:1) to give the product of methyl 5-(11-fluoropyrido[3',2':4,5]pyrimido[1,6-a]indol-2-yl)-3-(methylcarbamoyl)-6-(N-methylmethylsulfonamido)benzofuran-2-carboxylate (450 mg, yield: 32%). ¹H-NMR (CDCl₃, 400 MHz) δ 9.41 (br s, 1H), 9.06 (s, 1H), 8.90 (s, 1H), 8.18 (d, J=8.2 Hz, 1H), 7.74~7.84 (m, 3H), 7.54 (s, 1H), 7.37~7.47 (m, 1H), 7.16 (t, J=8.8 Hz, 1H), 4.11 (s, 3H), 3.44 (s, 3H), 3.05 (d, J=4.8 Hz, 3H), 2.65 (s, 3H). MS (M+H)⁺: 576.

Step 4—Synthesis of 5-(11-fluoropyrido[3',2':4,5]pyrimido[1,6-a]indol-2-yl)-3-(methylcarbamoyl)-6-(N-methylmethylsulfonamido)benzofuran-2-carboxylic acid

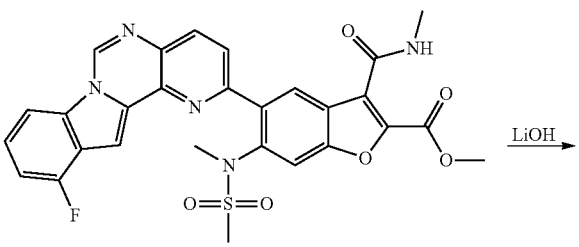

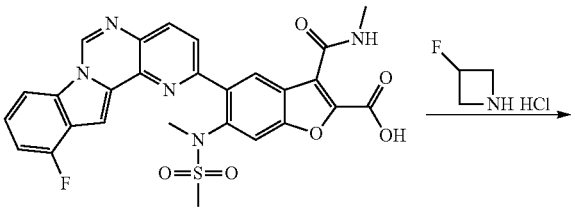

To a suspension of methyl 5-(11-fluoropyrido[3',2':4,5]pyrimido[1,6-a]indol-2-yl)-3-(methylcarbamoyl)-6-(N-methylmethylsulfonamido)benzofuran-2-carboxylate (450 mg, 0.78 mmol) in MeOH/H₂O (5 mL/1 mL) was added LiOH·H₂O (98 mg, 2.35 mmol). The reaction mixture was stirred at room temperature overnight. Then the mixture was acidified by HCl (aq. 1M) and extracted with EtOAc. The organic layer was washed with brine, dried over Na₂SO₄ and concentrated to give the product of 5-(11-fluoropyrido[3',2':4,5]pyrimido[1,6-a]indol-2-yl)-3-(methylcarbamoyl)-6-(N-methylmethylsulfonamido)benzofuran-2-carboxylic acid. It was used for the next step without further purification.

Step 5—Synthesis of 2-(3-fluoroazetidine-1-carbonyl)-5-(11-fluoropyrido[3',2':4,5]pyrimido[1,6-a]indol-2-yl)-N-methyl-6-(N-methylmethylsulfonamido)benzofuran-3-carboxamide -continued

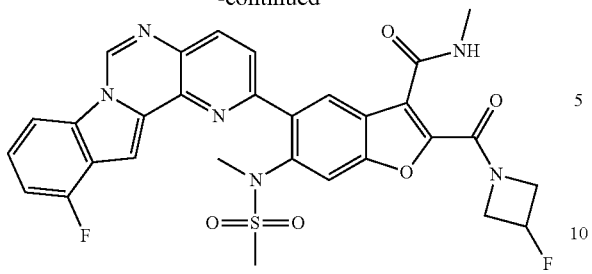

A mixture of 5-(11-fluoropyrido[3',2':4,5]pyrimido[1,6-a]indol-2-yl)-3-(methylcarbamoyl)-6-(N-methylmethylsulfonamido)benzofuran-2-carboxylic acid (50 mg, 0.09 mmol), 3-fluoroazetidine hydrochloride (30 mg, 0.27 mmol), HATU (170 mg, 0.45 mmol) and Et$_3$N (54 mg, 0.54 mmol) in THF (2 mL) was stirred at room temperature overnight. Then the reaction mixture was concentrated in vacuo, and the residue was purified by prep-TLC (DCM:EA=1:1) to give the product of 2-(3-fluoroazetidine-1-carbonyl)-5-(11-fluoropyrido[3',2':4,5]pyrimido[1,6-a]indol-2-yl)-N-methyl-6-(N-methylmethylsulfonamido)benzofuran-3-carboxamide (15 mg, yield: 27%). $^1$H-NMR (CDCl$_3$, 400 MHz) δ 10.35 (br s, 1H), 9.06 (s, 1H), 8.92 (s, 1H), 8.17 (d, J=8.4 Hz, 1H), 7.79 (d, J=8.4 Hz, 2H), 7.73 (s, 1H), 7.52 (s, 1H), 7.37~7.46 (m, 1H), 7.16 (t, J=8.8 Hz, 1H), 5.36~5.62 (m, 1H), 4.97~5.12 (m, 1H), 4.81~4.96 (m, 1H), 4.50~4.65 (m, 1H), 4.30~4.48 (m, 1H), 3.44 (s, 3H), 3.00 (d, J=4.8 Hz, 3H), 2.60 (s, 3H). MS (M+H)$^+$: 619.

Examples 51 and 52

Examples 51 and 52, depicted in the table below, were prepared in accordance with the method described in Examples 50.

Example 53

2-(2-ethylthiazol-5-yl)-5-(11-fluoropyrido[3',2':4,5]pyrimido[1,6-a]indol-2-yl)-N-methyl-6-(N-methylmethylsulfonamido)benzofuran-3-carboxamide

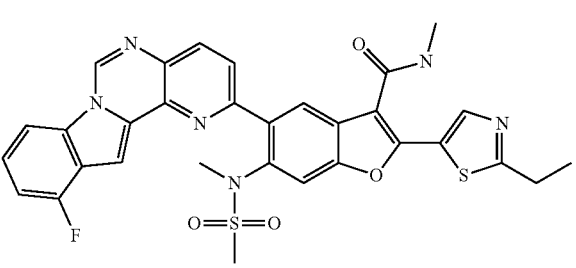

Step 1—Synthesis of 5-bromo-2-(2-ethylthiazol-5-yl)-N-methyl-6-(N-methylmethylsulfonamido)benzofuran-3-carboxamide

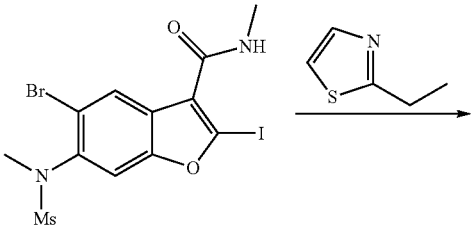

| Example | Structure | NMR | MS (M + H)$^+$ |
|---|---|---|---|
| 51 | 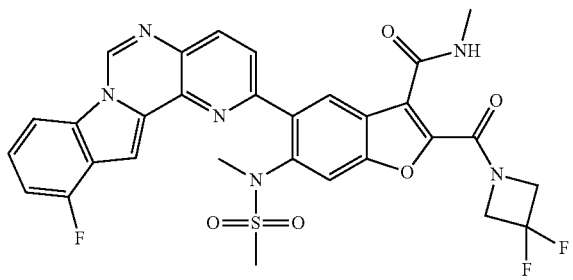 [SMILES: CNC(=O)c1c(C(=O)N2CC(F)(F)C2)oc2cc(N(C)S(C)(=O)=O)c(-c3ccc4ncn5c6cccc(F)c6cc5c4n3)cc12] | $^1$H-NMR (CDCl$_3$, 400 MHz) δ 10.18 (d, J = 4.4 Hz, 1H), 9.07 (s, 1H), 8.93 (s, 1H), 8.19 (d, J = 8.2 Hz, 1H), 7.80 (d, J = 8.2 Hz, 2H), 7.74 (s, 1H), 7.53 (s, 1H), 7.39~7.47 (m, 1H), 7.17 (t, J = 8.8 Hz, 1H), 5.09 (t, J = 11.6 Hz, 2H), 4.62 (t, J = 11.6 Hz, 2H), 3.43 (s, 3H), 3.01 (d, J = 4.4 Hz, 3H), 2.61 (s, 3H). | 637 |
| 52 | 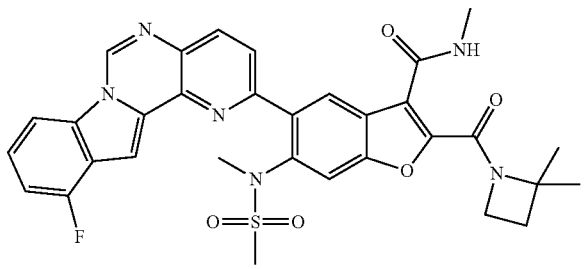 [SMILES: CNC(=O)c1c(C(=O)N2CCC2(C)C)oc2cc(N(C)S(C)(=O)=O)c(-c3ccc4ncn5c6cccc(F)c6cc5c4n3)cc12] | $^1$H-NMR (CDCl$_3$, 400 MHz) δ 10.62 (br s, 1H), 9.06 (s, 1H), 8.91 (s, 1H), 8.17 (d, J = 8.4 Hz, 1H), 7.72~7.83 (m, 2H), 7.71 (s, 1H), 7.53 (s, 1H), 7.40~7.43 (m, 1H), 7.14~7.18 (m, 1H), 4.69 (t, J = 8.0 Hz, 2H),, 3.45 (s, 3H), 3.00 (d, J = 4.8 Hz, 3H), 2.59 (s, 3H), 2.25 (t, J = 8.0 Hz, 2H), 1.72 (s, 6H). | 629 |

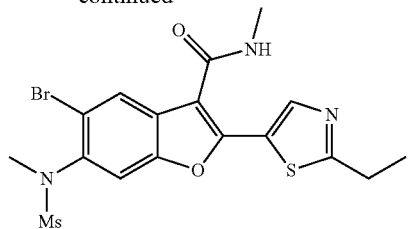

To a degassed solution of 5-bromo-2-iodo-N-methyl-6-(N-methylmethyl sulfonamido)benzofuran-3-carboxamide (100 mg, 0.2 mmol), 2-ethylthiazole (46 mg, 0.4 mmol) and Na$_2$CO$_3$ (44 mg, 0.2 mmol) in DMF (2 mL) was added Pd(OAc)$_2$ (10 mg) under N$_2$, and the mixture was stirred at 80° C. for 12 h. After the solvent was removed, the residue was purified by column chromatography (DCM:EtOAc=5:1) to give the product of 5-bromo-2-(2-ethylthiazol-5-yl)-N-methyl-6-(N-methylmethylsulfonamido)benzofuran-3-carboxamide (40 mg, yield: 41%). $^1$H-NMR (CDCl$_3$, 400 MHz) δ 8.40 (s, 1H), 8.01 (s, 1H), 7.67~7.72 (m, 1H), 6.01 (d, J=3.6 Hz, 1H), 3.34 (s, 3H), 3.11 (s, 3H), 3.09 (d, J=4.8 Hz, 3H), 3.08 (q, J=7.6 Hz, 2H), 1.46 (t, J=7.6 Hz, 3H). MS (M+H)$^+$: 472/474.

Step 2—Synthesis of 2-(2-ethylthiazol-5-yl)-N-methyl-6-(N-methylmethylsulfonamido)-5-(4,4,5,5-tetramethyl-1,3,2-dioxaborolan-2-yl)benzofuran-3-carboxamide

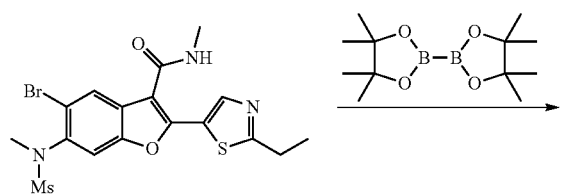

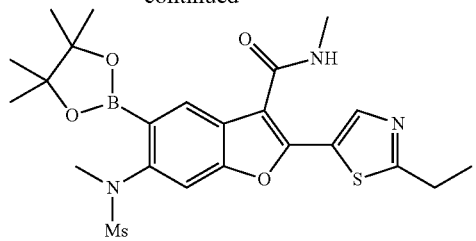

To a degassed solution of 5-bromo-2-(2-ethylthiazol-5-yl)-N-methyl-6-(N-methylmethylsulfonamido)benzofuran-3-carboxamide (50 mg, 0.1 mmol), KOAc (34 mg, 0.3 mmol) and dis(pinacolato)diboron (134 mg, 0.5 mmol) in 1,4-dioxane (2 mL) and H$_2$O (0.1 mL) was added Pd(dppf)Cl$_2$ (6 mg) under N$_2$, and the mixture was stirred at 130° C. for 3 hours. After the solvent was removed, the residue was purified by prep-TLC (DCM:EtOAc=2:1) to give the product of 2-(2-ethylthiazol-5-yl)-N-methyl-6-(N-methylmethylsulfonamido)-5-(4,4,5,5-tetramethyl-1,3,2-dioxaborolan-2-yl)benzofuran-3-carboxamide (30 mg, yield: 50%). $^1$H-NMR (CDCl$_3$, 400 MHz) δ 8.40 (s, 1H), 8.08 (s, 1H), 7.54~7.57 (m, 1H), 6.38 (d, J=3.6 Hz, 1H), 3.36 (s, 3H), 3.04~3.10 (m, 5H), 2.95 (s, 3H), 1.43 (t, J=7.6 Hz, 3H), 1.37 (s, 12H). MS (M+H)$^+$: 520.

Step 3—Synthesis of 2-(2-ethylthiazol-5-yl)-5-(11-fluoropyrido[3',2':4,5]pyrimido[1,6-a]indol-2-yl)-N-methyl-6-(N-methylmethylsulfonamido)benzofuran-3-carboxamide

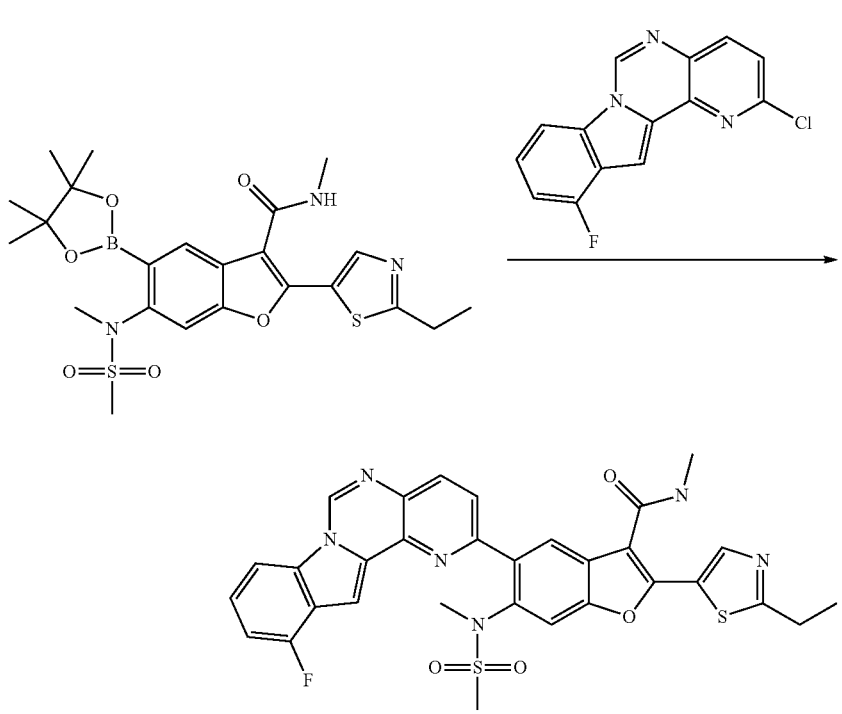

To a degassed solution of 2-(2-ethylthiazol-5-yl)-N-methyl-6-(N-methylmethyl sulfonamido)-5-(4,4,5,5-tetramethyl-1,3,2-dioxaborolan-2-yl)benzofuran-3-carboxamide (50 mg, 0.09 mmol), 2-chloro-11-fluoropyrido[3',2':4,5]pyrimido[1,6-a]indole (29 mg, 0.1 mmol) and Cs₂CO₃ (63 mg, 0.2 mmol) in dioxane (1 mL) was added Pd(dtbpf)Cl₂ (7 mg) under N₂. The mixture was stirred at 80° C. for 12 h. After the solvent was removed, the residue was purified by prep-HPLC to give the product of 2-(2-ethylthiazol-5-yl)-5-(11-fluoropyrido[3',2':4,5]pyrimido[1,6-a]indol-2-yl)-N-methyl-6-(N-methylmethylsulfonamido)benzofuran-3-carboxamide (25 mg, yield: 41%). ¹H-NMR (CDCl₃, 400 MHz) δ 9.05 (s, 1H), 8.46 (s, 1H), 8.18 (d, J=8.8 Hz, 1H), 8.02 (s, 1H), 7.78~7.81 (m, 2H), 7.69 (s, 1H), 7.58 (s, 1H), 7.42 (d, J=5.2 Hz, 1H), 7.14~7.19 (m, 1H), 6.15 (br s, 1H), 3.40 (s, 3H), 3.00~3.12 (m, 5H), 2.76 (s, 3H), 1.44 (t, J=7.6 Hz, 3H). MS (M+H)⁺: 629.

Example 54 and 54'

54

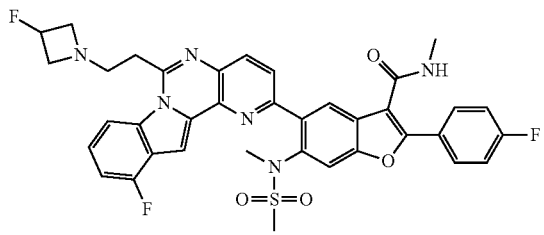

54'

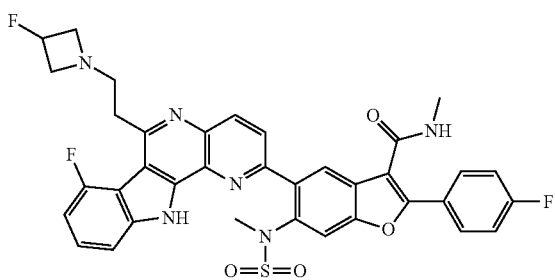

Step 1—Synthesis of 3-chloro-N-(6-chloro-2-(4-fluoro-1H-indol-2-yl)pyridin-3-yl)propanamide

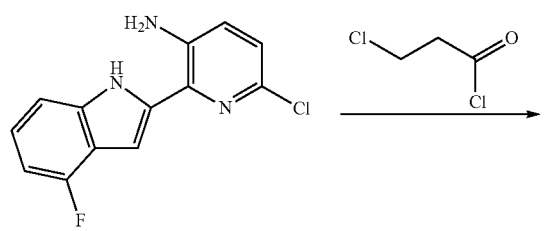

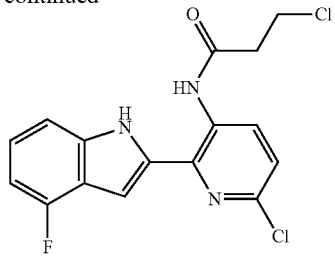

To a solution of 6-chloro-2-(4-fluoro-1H-indol-2-yl)pyridin-3-amine (2.5 g, 9.55 mmol) and NaOAc (250 mg, 3.15 mmol) in AcOH/THF (25 mL/25 mL) was added 3-chloropropanoyl chloride (2.0 g, 17.2 mmol) dropwise under N₂. The mixture was stirred at 20° C. for 10 hours, and then it was diluted with H₂O and extracted with EtOAc. The combined organic phase was washed with Na₂CO₃ (a.q), brine and dried over Na₂SO₄. The crude product was purified by column (PE:EA=8:1 then 4:1) to give the product of 3-chloro-N-(6-chloro-2-(4-fluoro-1H-indol-2-yl)pyridin-3-yl)propanamide (2 g, yield: 60%). ¹H-NMR (DMSO-d₆, 400 MHz) δ 11.82 (s, 1H), 10.13 (s, 1H), 7.95 (d, J=8.0 Hz, 1H), 7.47 (d, J=8.0 Hz, 1H), 7.34 (d, J=8.0 Hz, 1H), 7.23 (s, 1H), 7.05~7.13 (m, 1H), 6.72~6.80 (m, 1H), 3.91 (t, J=4.4 Hz, 2H), 2.96 (t, J=4.4 Hz, 2H). MS (M+H)⁺: 352/354.

Step 2—Synthesis of 2-chloro-6-(2-chloroethyl)-11-fluoropyrido[3',2':4,5]pyrimido[1,6-a]indole and 2-chloro-6-(2-chloroethyl)-7-fluoro-11H-indolo[3,2-c][1,5]naphthyridine

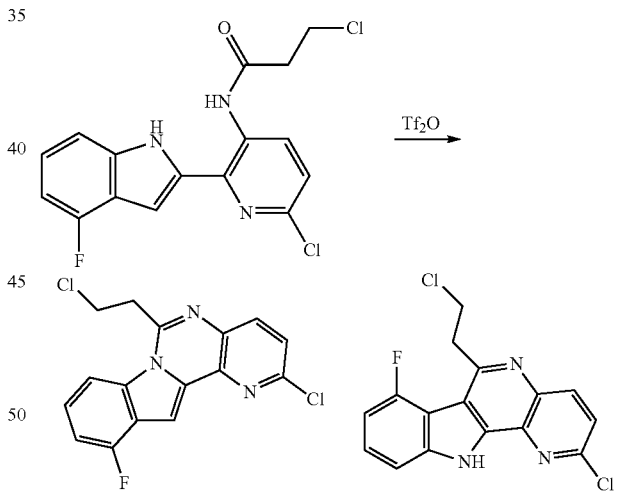

To a solution of OPPh₃ (46 mg, 0.17 mmol) in DCM (2.5 mL) was added Tf₂O (360 mg, 1.28 mmol) at 0° C. dropwise under N₂. Then a solution of 3-chloro-N-(6-chloro-2-(4-fluoro-1H-indol-2-yl)pyridin-3-yl)propanamide (200 mg, 0.56 mmol) in DCM (2.5 mL) was added and the mixture stirred at 20° C. for 3 hours. After diluted with H₂O and extracted with DCM, the combined organic phase was washed with brine, dried over Na₂SO₄ and concentrated. After purified prep-TLC (PE:EA=3:1), a mixture of 2-chloro-6-(2-chloroethyl)-11-fluoropyrido[3',2':4,5]pyrimido[1,6-a]indole and 2-chloro-6-(2-chloroethyl)-7-fluoro-11H-indolo[3,2-c][1,5]naphthyridine (~2:3, 130 mg, yield: 70%) was obtained.

Step 3—Synthesis of 2-chloro-11-fluoro-6-(2-(3-fluoroazetidin-1-yl)ethyl)pyrido[3',2':4,5]-pyrimido[1,6-a]indole and 2-chloro-7-fluoro-6-(2-(3-fluoroazetidin-1-yl)ethyl)-11H-indolo[3,2-c][1,5]naphthyridine

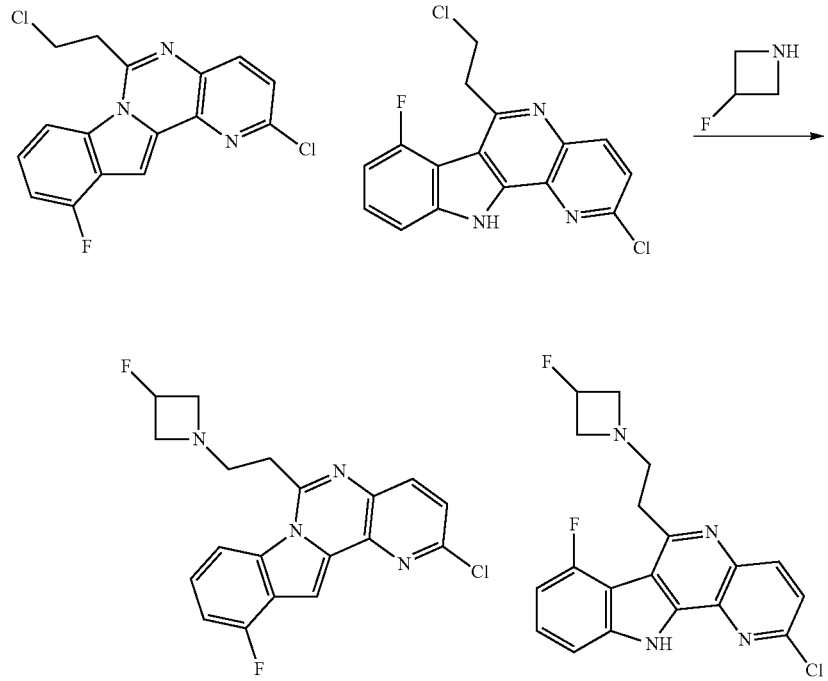 [SMILES: Fc1cccc2c1cc1c3nc(Cl)ccc3nc(CCCl)n21 ; Fc1cccc2[nH]c3c4nc(Cl)ccc4nc(CCCl)c3c12 ; FC1CNC1 ; Fc1cccc2c1cc1c3nc(Cl)ccc3nc(CCN3CC(F)C3)n21 ; Fc1cccc2[nH]c3c4nc(Cl)ccc4nc(CCN4CC(F)C4)c3c12]

To a solution of Et$_3$N (0.2 mL), 2-chloro-6-(2-chloroethyl)-11-fluoropyrido[3',2':4,5]pyrimido[1,6-a]indole and 2-chloro-6-(2-chloroethyl)-7-fluoro-11H-indolo[3,2-c][1,5]naphthyridine (~2:3, 50 mg, 0.15 mmol) in DMF (1 mL) was added 3-fluoroazetidine (30 mg, 0.18 mmol) under N$_2$. And then the mixture was put into a pre-heated oil-bath at 70° C. and stirred for 2 hours. The mixture was concentrated and extracted with EtOAc. The combined organic phase was washed with brine, dried over Na$_2$SO$_4$ and concentrated. The crude product was purified by column (DCM:EA=1:1) to give a mixture of 2-chloro-11-fluoro-6-(2-(3-fluoroazetidin-1-yl)ethyl)pyrido[3',2':4,5]pyrimido[1,6-a]indole and 2-chloro-7-fluoro-6-(2-(3-fluoroazetidin-1-yl)ethyl)-11H-indolo[3,2-c][1,5]naphthyridine (~2:3, 30 mg, yield: 65%).

Step 4—Synthesis of 5-(11-fluoro-6-(2-(3-fluoroazetidin-1-yl)ethyl)pyrido[3',2':4,5]pyrimido[1,6-a]indol-2-yl)-2-(4-fluorophenyl)-N-methyl-6-(N-methylmethylsulfonamido)benzofuran-3-carboxamide and 5-(7-fluoro-6-(2-(3-fluoroazetidin-1-yl)ethyl)-11H-indolo[3,2-c][1,5]naphthyridin-2-yl)-2-(4-fluorophenyl)-N-methyl-6-(N-methylmethylsulfonamido)benzofuran-3-carboxamide (Compound 53 and Compound 53')

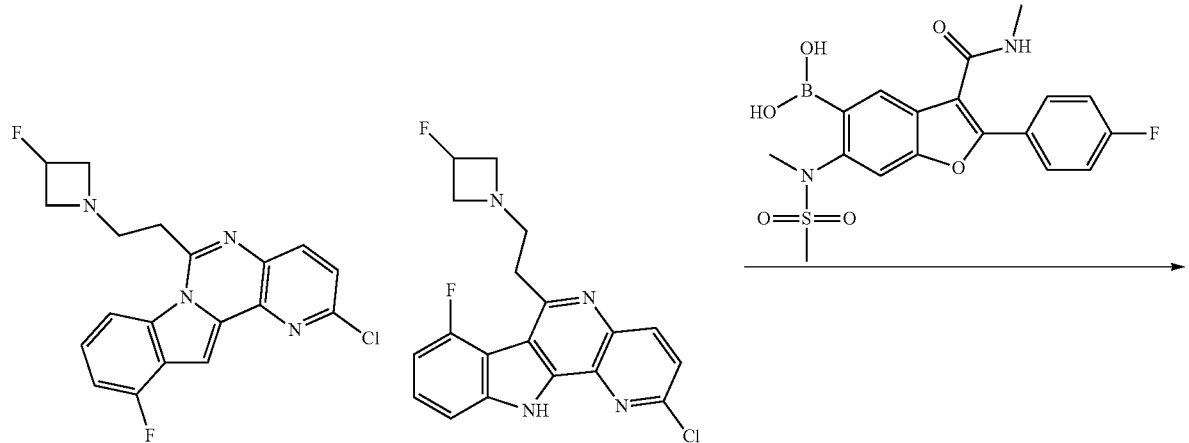

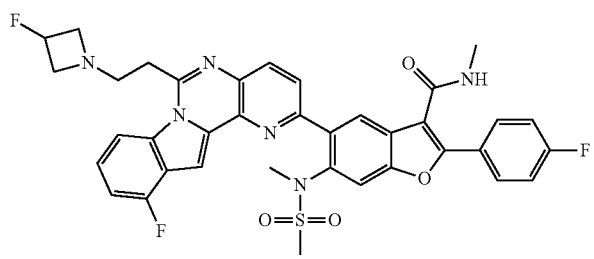

54

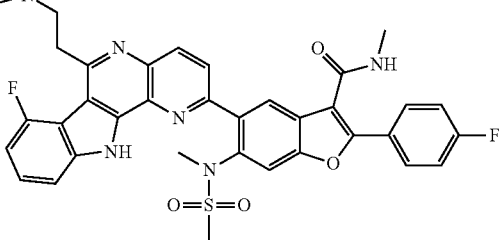

54'

To a solution of 2-chloro-11-fluoro-6-(2-(3-fluoroazetidin-1-yl)ethyl)pyrido[3',2':4,5]pyrimido[1,6-a]indole and 2-chloro-7-fluoro-6-(2-(3-fluoroazetidin-1-yl)ethyl)-11H-indolo[3,2-c][1,5]naphthyridine (~2:3, 20 mg, 0.07 mmol), 2-(4-fluorophenyl)-3-(methylcarbamoyl)-6-(N-methylmethylsulfonamido)benzofuran-5-ylboronic acid (50 mg, 0.13 mmol) and $K_2CO_3$ (18 mg, 0.13 mmol) in dioxane/$H_2O$ (0.5 mL/0.01 mL) was added $Pd_2(dba)_3$ (5 mg) and X-Phos (5 mg) under $N_2$. The mixture was put into a pre-heated oil-bath at 110° C. and stirred for 6 hours. The mixture was concentrated and extracted with EtOAc. The combined organic phase was washed with brine, dried over $Na_2SO_4$ and concentrated. The crude product was purified by prep-HPLC to give two isomers.

Compound 54 (15 mg, yield: 22%). $^1$H-NMR (CDCl$_3$, 400 MHz) δ 8.06 (s, 1H), 8.03 (d, J=8.0 Hz, 1H), 7.89~7.91 (m, 2H), 7.85 (d, J=8.4 Hz, 1H), 7.70 (d, J=8.4 Hz, 1H), 7.63~7.65 (m, 2H), 7.28~7.35 (m, 1H), 7.13~7.18 (m, 3H), 5.85 (d, J=8.0 Hz, 1H), 5.00~5.23 (m, 1H), 3.77~3.80 (m, 2H), 3.44~3.48 (m, 2H), 3.36 (s, 3H), 3.22~3.28 (m, 4H), 2.94 (d, J=4.8 Hz, 3H), 2.59 (s, 3H). MS (M+H)$^+$: 713.

Compound 54' (30 mg, yield: 42%). $^1$H-NMR (CDCl$_3$, 400 MHz) δ 10.98 (s, 1H), 8.46 (d, J=8.8 Hz, 1H), 8.27 (s, 1H), 7.89~7.97 (m, 3H), 7.58 (s, 1H), 7.39~7.43 (m, 2H), 7.10~7.17 (m, 2H), 7.00~7.05 (m, 1H), 5.88 (s, 1H), 5.00~5.17 (m, 1H), 3.65~3.73 (m, 4H), 3.11~3.28 (m, 4H), 3.06 (s, 3H), 2.97 (d, J=8.8 Hz, 3H), 2.95 (s, 3H). MS (M+H)$^+$: 713.

Example 55

Alternative Synthesis for Example 10

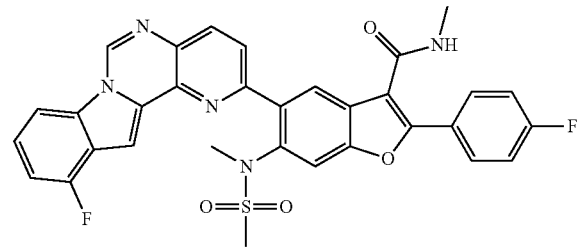 [SMILES: CNC(=O)c1c(-c2ccc(F)cc2)oc2cc(N(C)S(C)(=O)=O)c(-c3ccc4ncn5c6cccc(F)c6cc5c4n3)cc12]

Step 1—Synthesis of 6-chloro-2-(4-fluoro-1H-indol-2-yl)pyridin-3-amine

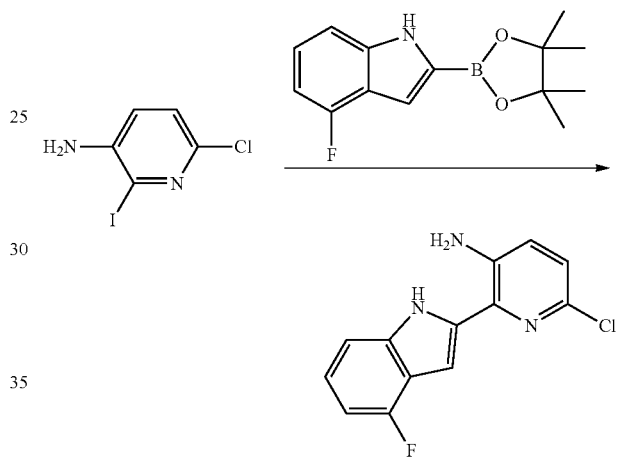

To a degassed solution of 6-chloro-2-iodopyridin-3-amine (468 mg, 1.8 mmol) and 4-fluoro-2-(4,4,5,5-tetramethyl-1,3,2-dioxaborolan-2-yl)-1H-indole (400 mg, 1.5 mmol) in 1,4-dioxane (6 mL) and water (200 μl) was added Cs$_2$CO$_3$ (998 mg, 3.1 mmol) and 1,1'-bis(di-tert-butylphosphino)ferrocene palladium chloride (100 mg, 0.15 mmol) under $N_2$ protection. The resulting mixture was heated to 70° C. and stirred at this temperature over night. The reaction was cooled, filtered through a pad of the celite and washed with ethyl acetate. The combined filtrate was evaporated in vacuo. The resulting residue was purified using column chromatography (eluted with 0-3% MeOH/DCM) to provide 6-chloro-2-(4-fluoro-1H-indol-2-yl)pyridin-3-amine (360 mg, yield: 90%). MS (M+H)$^+$: 262.

Steps 2—Synthesis of 2-chloro-11-fluoropyrido[3',2':4,5]pyrimido[1,6-a]indole

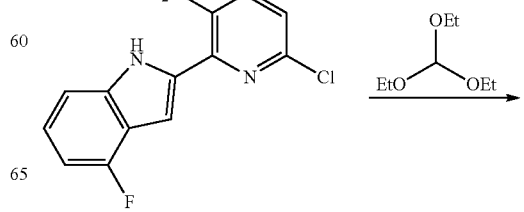

-continued

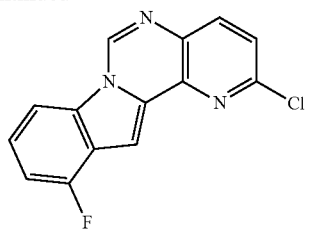

To a screw cap vial was added 6-chloro-2-(4-fluoro-1H-indol-2-yl)pyridin-3-amine (80 mg, 0.31 mmol), triethy orthoformate (453 mg, 3.1 mmol), 1,4-dioxane (3 ml) and 4.0 M HCl in 1,4-dioxane (0.76 ml). The vial was capped and heated to 50° C. and stirred for 3 hours. The reaction mixture was evaporated in vacuo to remove the volatiles. The residue was treated with NaHCO$_3$ and extracted with EtOAc. The organic layer was washed with brine, dried (Na$_2$SO$_4$), filtered and concentrated in vacuo to give the yellow solid without further purification and submitted for next step.

Step 3—Synthesis of 2-(4-fluorophenyl)-5-(11-fluoropyrido[3',2':4,5]pyrimido[1,6-a]indol-2-yl)-N-methyl-6-(N-methylmethylsulfonamido)benzofuran-3-carboxamide

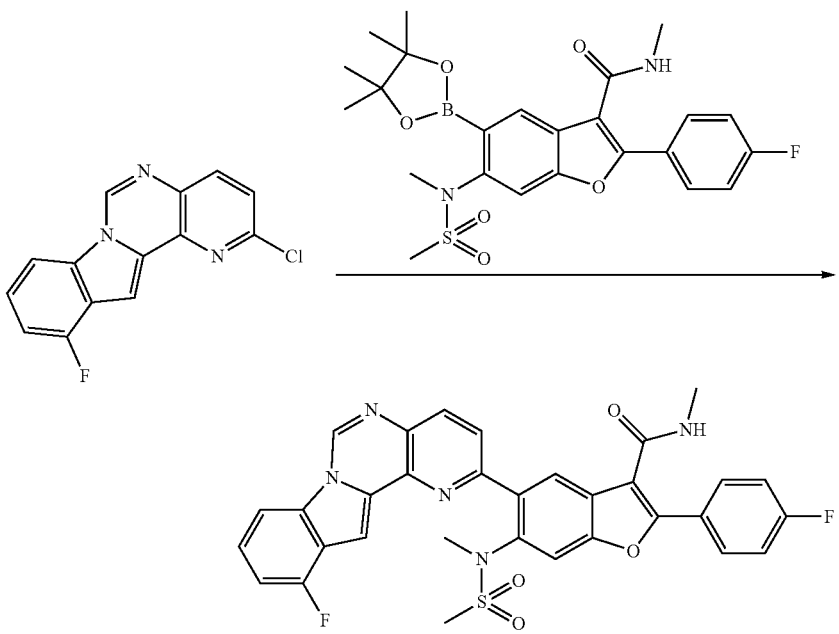

To a degassed solution of the above yellow solid and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (178 mg, 0.35 mmol) in 1,4-dioxane (2 mL) and water (100 µl) was added Cs$_2$CO$_3$ (287 mg, 0.88 mmol) and 1,1'-bis(di-tert-butylphosphino)ferrocene palladium chloride (20 mg, 0.03 mmol) under N$_2$ protection. The resulting mixture was heated to 70° C. and stirred at this temperature overnight. The reaction was cooled, filtered through a pad of the celite and washed with ethyl acetate. The combined filtrate was evaporated in vacuo. The resulting residue was purified using column chromatography (eluted with 4% MeOH/DCM) to provide 2-(4-fluorophenyl)-5-(11-fluoropyrido[3',2':4,5]pyrimido[1,6-a]indol-2-yl)-N-methyl-6-(N-methylmethylsulfonamido)benzofuran-3-carboxamide (60 mg) MS (M+H)$^+$: 612.

Example 55'

Example 55', depicted in the table below, were prepared in accordance with the methods described in Example 55.

| Compound ID | Structure | MS M + H)+ |
|---|---|---|
| 55' | 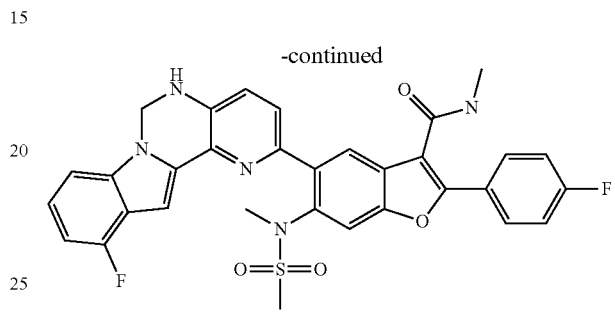 | 618 |

Example 56

5-(11-fluoro-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide Steps 1—Synthesis of 5-(11-fluoro-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide

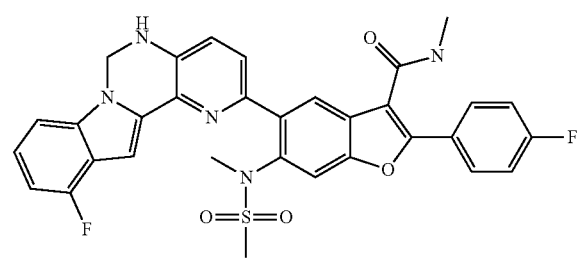 [SMILES: CNC(=O)c1c(-c2ccc(F)cc2)oc2cc(N(C)S(C)(=O)=O)c(-c3ccc4c(n3)-c3cc5c(F)cccc5n3CN4)cc12]

-continued

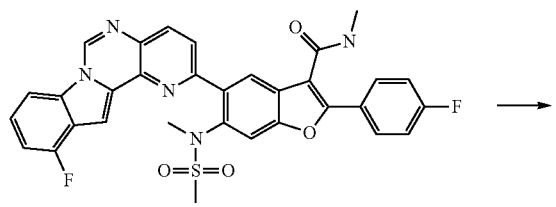

To a solution of 2-(4-fluorophenyl)-5-(11-fluoropyrido[3',2':4,5]pyrimido[1,6-a]indol-2-yl)-N-methyl-6-(N-methylmethylsulfonamido)benzofuran-3-carboxamide (compound 1, 12 mg, 0.02 mmol) in THF (1 ml) and MeOH (1 ml) was added NaBH$_4$ (7.42 mg, 0.2 mmol). The resulting mixture was stirred at RT for 20 min then treated with NH$_4$Cl and extracted with EtOAc. The organic layer was washed with brine, dried (Na$_2$SO$_4$), filtered and concentrated in vacuo. Preparative TLC gave 5-(11-fluoro-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide (9 mg, yield: 75%). MS (M+H)+: 614.

Examples 57 and 58

Examples 57 and 58, depicted in the table below, were prepared in accordance with the methods described above for Example 56.

| Example | Structure | MS M + H)+ |
|---|---|---|
| 57 | 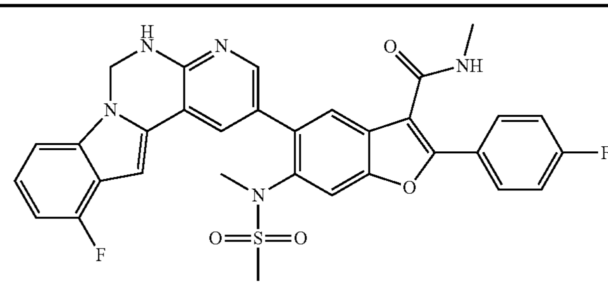 | 614 |

| Example | Structure | MS M + H)+ |
|---|---|---|
| 58 | 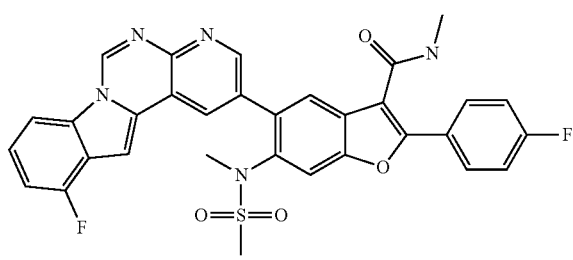 [SMILES: CNC(=O)c1c(-c2ccc(F)cc2)oc2cc(N(C)S(C)(=O)=O)c(-c3cnc4ncn5c6cccc(F)c6cc5c4c3)cc12] | 631 |

Example 59

2-(4-fluorophenyl)-5-(11-fluoropyrido[2',3':4,5]pyrimido[1,6-a]indol-2-yl)-N-methyl-6-(N-methylmethylsulfonamido)benzofuran-3-carboxamide

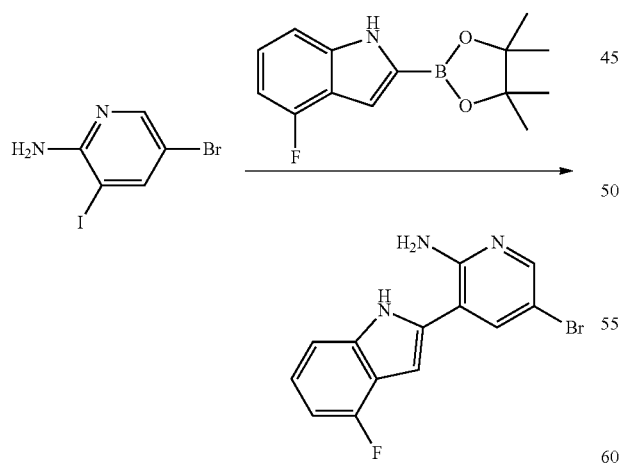

Step 1—Synthesis of 5-bromo-3-(4-fluoro-1H-indol-2-yl)pyridin-2-amine

To a degassed solution of 5-bromo-3-iodopyridin-2-amine (700 mg, 2.3 mmol) and 4-fluoro-2-(4,4,5,5-tetramethyl-1,3,2-dioxaborolan-2-yl)-1H-indole (261 mg, 2.6 mmol) in 1,4-dioxane (6 mL) and water (200 µl) was added Cs₂CO₃ (1.52 g, 4.7 mmol) and 1,1'-bis(di-tert-butylphosphino)ferrocene palladium chloride (153 mg, 0.23 mmol) under N₂ protection. The resulting mixture was heated to 70° C. and stirred at this temperature overnight. The reaction was cooled, filtered through a pad of the celite and washed with ethyl acetate. The combined filtrate was evaporated in vacuo. The resulting residue was purified using column chromatography (eluted with 0-1% MeOH/DCM) to provide 5-bromo-3-(4-fluoro-1H-indol-2-yl)pyridin-2-amine (500 mg, yield: 70%). MS (M+H)⁺: 308.

Step 2—Synthesis of 2-bromo-11-fluoropyrido[2',3':4,5]pyrimido[1,6-a]indole

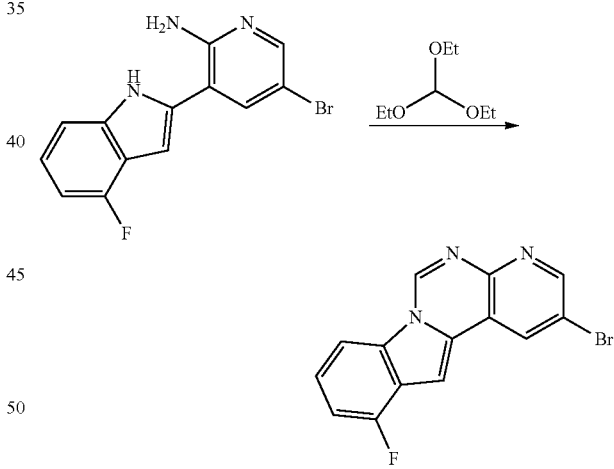

To a screw cap vial was added 5-bromo-3-(4-fluoro-1H-indol-2-yl)pyridin-2-amine (200 mg, 0.65 mmol), triethy orthoformate (968 mg, 6.5 mmol), 1,4-dioxane (3 ml) and 4.0 M HCl in 1,4-dioxane (0.49 ml). The vial was capped and heated to 70° C. and stirred for 2 hours. The reaction mixture was evaporated in vacuo to remove the volatiles. The residue was treated with NaHCO₃ and extracted with EtOAc. The organic layer was washed with brine, dried (Na₂SO₄), filtered and concentrated in vacuo to give the yellow solid without further purification and submitted for next step.

Step 3—Synthesis of 2-(4-fluorophenyl)-5-(11-fluoropyrido[2',3':4,5]pyrimido[1,6-a]indol-2-yl)-N-methyl-6-(N-methylmethylsulfonamido)benzofuran-3-carboxamide

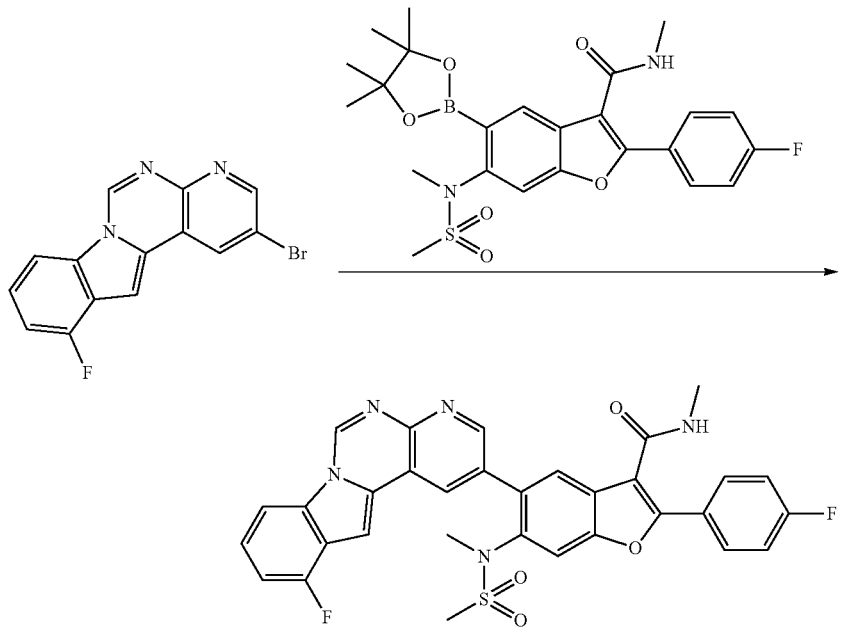

To a degassed solution of the above yellow solid and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (200 mg, 0.40 mmol) in 1,4-dioxane (3 mL) and water (100 μl) was added Cs$_2$CO$_3$ (259 mg, 0.80 mmol) and 1,1'-bis(di-tert-butylphosphino)ferrocene palladium chloride (40 mg, 0.06 mmol) under N$_2$ protection. The resulting mixture was heated to 80° C. and stirred at this temperature overnight. The reaction was cooled, filtered through a pad of the celite and washed with ethyl acetate. The combined filtrate was evaporated in vacuo. The resulting residue was purified using column chromatography (eluted with 4% MeOH/DCM) to provide 2-(4-fluorophenyl)-5-(11-fluoropyrido[2',3':4,5]pyrimido[1,6-a]indol-2-yl)-N-methyl-6-(N-methylmethylsulfonamido)benzofuran-3-carboxamide (compound 5, 60 mg) MS (M+H)$^+$: 612.

Example 60

5-(11-fluoro-6-methylpyrido[3',2':4,5]pyrimido[1,6-a]indol-2-yl)-2-(4-fluorophenyl)-N-methyl-6-(N-methylmethylsulfonamido)benzofuran-3-carboxamide

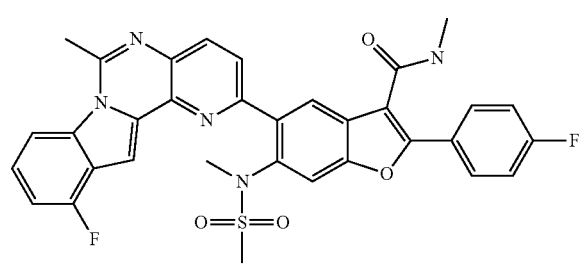 [SMILES: CNC(=O)c1c(-c2ccc(F)cc2)oc2cc(N(C)S(C)(=O)=O)c(-c3ccc4nc(C)n5c6cccc(F)c6cc5c4n3)cc12]

Step 1—Synthesis of 2-chloro-11-fluoro-6-methylpyrido[3',2':4,5]pyrimido[1,6-a]indole

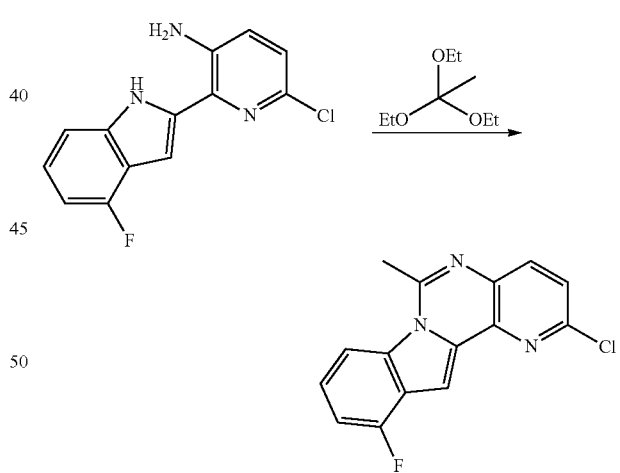

To a screw cap vial was added 6-chloro-2-(4-fluoro-1H-indol-2-yl)pyridin-3-amine (80 mg, 0.31 mmol), triethyl orthoacetate (496 mg, 3.1 mmol), 1,4-dioxane (2 ml) and 4.0M HCl in 1,4-dioxane (2 ml). The vial was capped and heated to 80° C. and stirred for 4 hours. The reaction mixture was evaporated in vacuo to remove the volatiles. The residue was treated with NaHCO$_3$ and extracted with EtOAc. The organic layer was washed with brine, dried (Na$_2$SO$_4$), filtered and concentrated in vacuo to give the yellow solid without further purification and submitted for next step.

Step 1—Synthesis of 5-(11-fluoro-6-methylpyrido[3',2':4,5]pyrimido[1,6-a]indol-2-yl)-2-(4-fluorophenyl)-N-methyl-6-(N-methylmethylsulfonamido)benzofuran-3-carboxamide

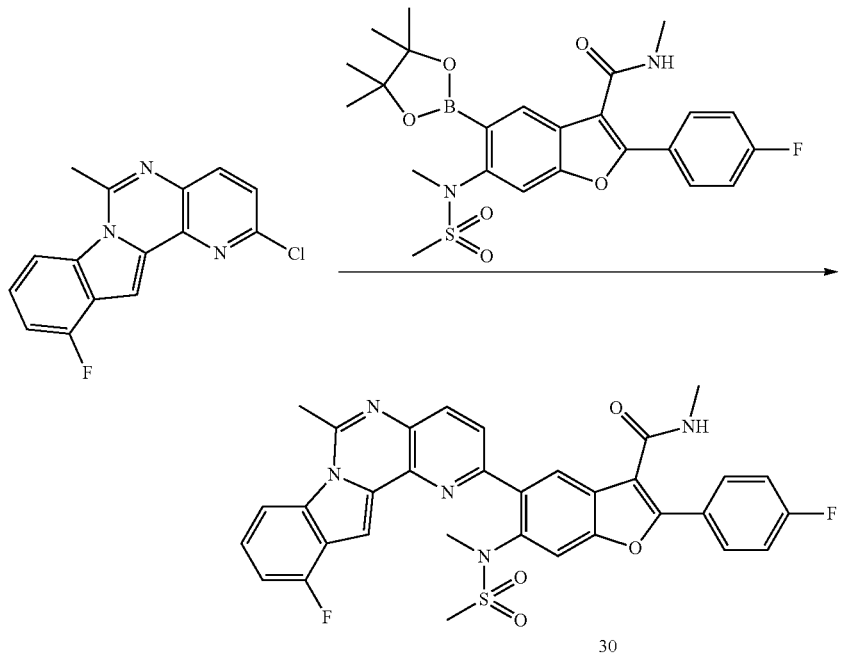

To a degassed solution of the above yellow solid and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (184 mg, 0.37 mmol) in 1,4-dioxane (3 mL) and water (200 μl) was added $Cs_2CO_3$ (298 mg, 0.91 mmol) and 1,1'-bis(di-tert-butylphosphino)ferrocene palladium chloride (20 mg, 0.03 mmol) under $N_2$ protection. The resulting mixture was heated to 70° C. and stirred at this temperature overnight. The reaction was cooled, filtered through a pad of the celite and washed with ethyl acetate. The combined filtrate was evaporated in vacuo. The residue was purified using column chromatography (eluted with 4% MeOH/DCM) to provide 5-(11-fluoro-6-methylpyrido[3',2':4,5]pyrimido[1,6-a]indol-2-yl)-2-(4-fluorophenyl)-N-methyl-6-(N-methylmethylsulfonamido)benzofuran-3-carboxamide (70 mg) MS (M+H)$^+$: 626.

Example 61

5-(11-fluoro-6-methyl-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide

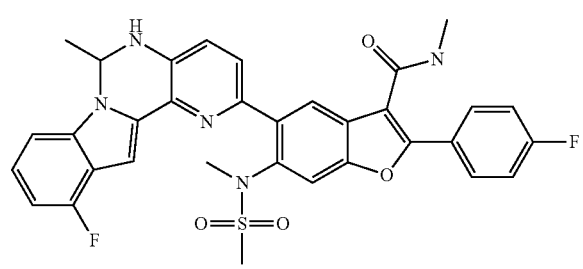

Step 1—Synthesis of 2-chloro-11-fluoro-6-methylpyrido[3',2':4,5]pyrimido[1,6-a]indole

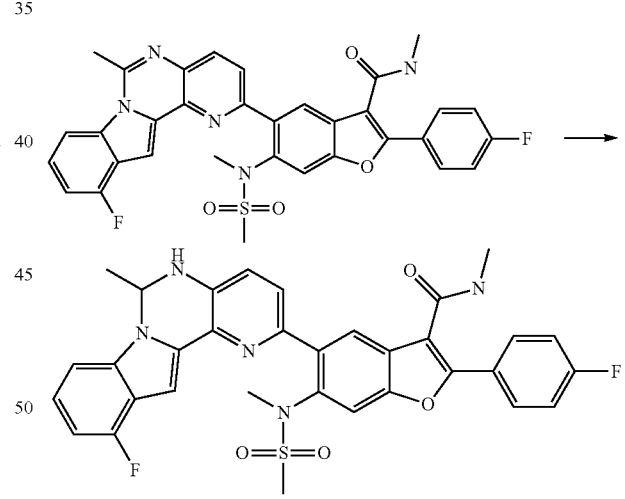

To a solution of 5-(11-fluoro-6-methylpyrido[3',2':4,5]pyrimido[1,6-a]indol-2-yl)-2-(4-fluorophenyl)-N-methyl-6-(N-methylmethylsulfonamido)benzofuran-3-carboxamide (Example 6, 12 mg, 0.02 mmol) in THF (1 ml) and MeOH (1 ml) was added $NaBH_4$ (7.26 mg, 0.2 mmol). The resulting mixture was stirred at RT for 2 hours then treated with $NH_4Cl$ and extracted with EtOAc. The organic layer was washed with brine, dried ($Na_2SO_4$), filtered and concentrated in vacuo. Preparative TLC gave 5-(11-fluoro-6-methyl-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide (10 mg, yield: 83%). MS (M+H)$^+$: 628.

Example 62

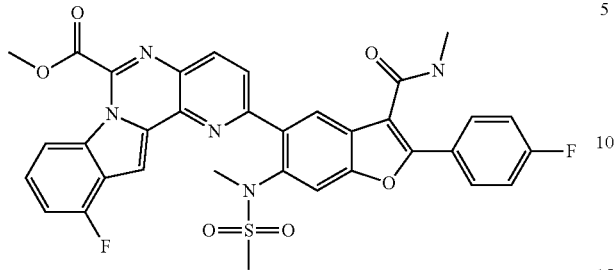

Step 1—Synthesis of methyl 2-chloro-11-fluoro-pyrido[3',2':4,5]pyrimido[1,6-a]indole-6-carboxylate

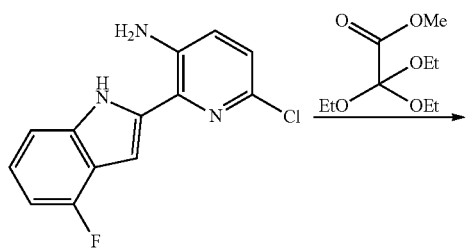

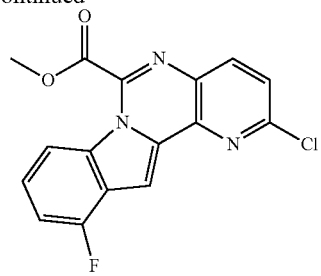

To a screw cap vial was added 6-chloro-2-(4-fluoro-1H-indol-2-yl)pyridin-3-amine (180 mg, 0.69 mmol), methyl 2,2,2-trimethoxyacetate (339 mg, 2.1 mmol), 1,4-dioxane (2 ml) and 4.0 M HCl in 1,4-dioxane (2 ml). The vial was capped and heated to 90° C. and stirred for 3 hours. The reaction mixture was evaporated in vacuo to remove the volatiles. The residue was treated with NaHCO$_3$ and extracted with EtOAc. The organic layer was washed with brine, dried (Na$_2$SO$_4$), filtered and concentrated in vacuo. The resulting residue was purified using column chromatography (eluted with 0-2% MeOH/DCM) to provide methyl 2-chloro-11-fluoropyrido[3',2':4,5]pyrimido[1,6-a]indole-6-carboxylate (150 mg, yield: 66%). MS (M+H)$^+$: 330.

Step 2—Synthesis of methyl 11-fluoro-2-(2-(4-fluorophenyl)-3-(methylcarbamoyl)-6-(N-methylmethyl-sulfonamido)benzofuran-5-yl)pyrido[3',2':4,5]py-rimido[1,6-a]indole-6-carboxylate

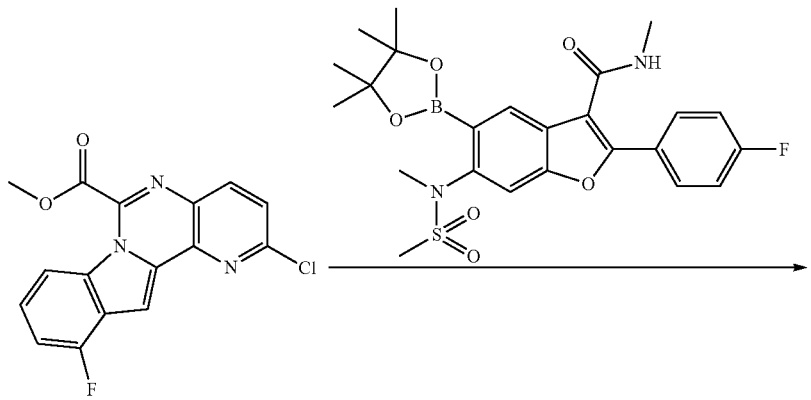

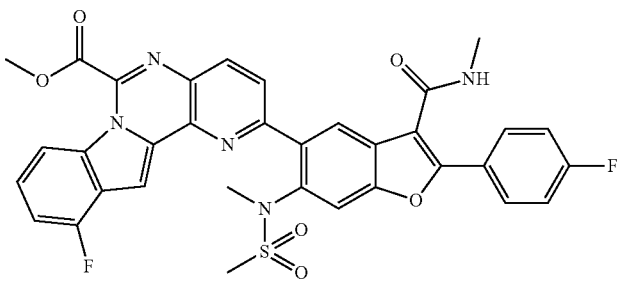

123

To a degassed solution of methyl 2-chloro-11-fluoropyrido[3',2':4,5]pyrimido[1,6-a]indole-6-carboxylate (150 mg, 0.46 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (343 mg, 0.68 mmol) in 1,4-dioxane (3 mL) and water (200 µl) was added $Cs_2CO_3$ (296 mg, 0.91 mmol) and 1,1'-bis(di-tert-butylphosphino)ferrocene palladium chloride (30 mg, 0.05 mmol) under $N_2$ protection. The resulting mixture was heated to 80° C. and stirred at this temperature overnight. The reaction was cooled, filtered through a pad of the celite and washed with ethyl acetate. The combined filtrate was evaporated in vacuo. The residue was purified using preparative TLC (eluted with 30% EtOAc/DCM) to provide methyl 11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indole-6-carboxylate (compound 8, 120 mg, yield: 40%). MS (M+H)+: 669.

Example 63

Example 63, depicted in the table below, were prepared in accordance with the methods described above for Example 62.

| Compound ID | Structure | MS M + H+ |
|---|---|---|
| 63 | 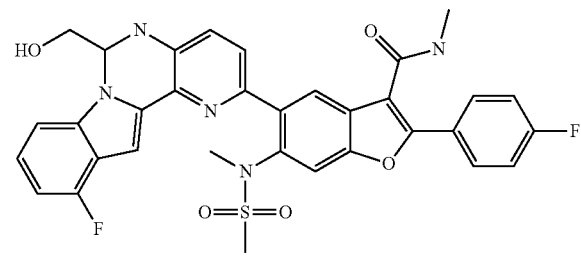 [SMILES: CNC(=O)c1c(-c2ccc(F)cc2)oc2cc(N(C)S(C)(=O)=O)c(-c3ccc4c(n3)-c3cc5c(F)cccc5n3C(CO)N4)cc12] | 683 |

Example 64

5-(11-fluoro-6-(hydroxymethyl)-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide

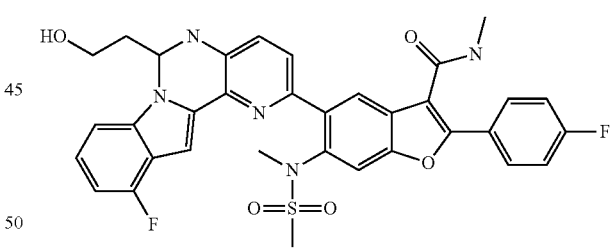

Step 1—Synthesis of 5-(11-fluoro-6-(hydroxymethyl)-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide

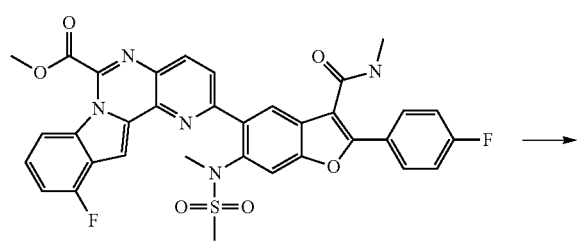

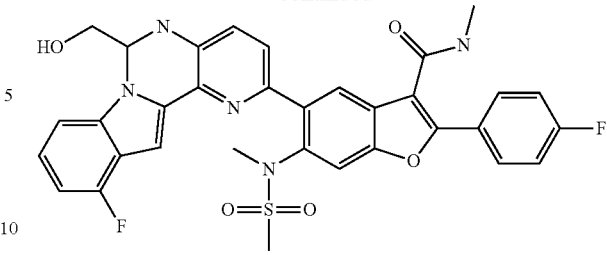 [SMILES: CNC(=O)c1c(-c2ccc(F)cc2)oc2cc(N(C)S(C)(=O)=O)c(-c3ccc4c(n3)-c3cc5c(F)cccc5n3C(CCO)N4)cc12]

To a solution of methyl 11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indole-6-carboxylate (12 mg, 0.02 mmol) in THF (2 ml) at 0° C. was added 1.0 M DIBAL-H in toluene (179 µl, 0.18 mmol) and stirred at 0° C. for 2 hours. Preparative TLC provided 5-(11-fluoro-6-(hydroxymethyl)-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide (6 mg, yield: 52%). MS (M+H)+: 644.

Example 65

5-(11-fluoro-6-(2-hydroxyethyl)-5,6-dihydropyrido[3',2':4,5]pyrimido[1,6-a]indol-2-yl)-2-(4-fluorophenyl)-N-methyl-6-(N-methylmethyl sulfonamido)benzofuran-3-carboxamide

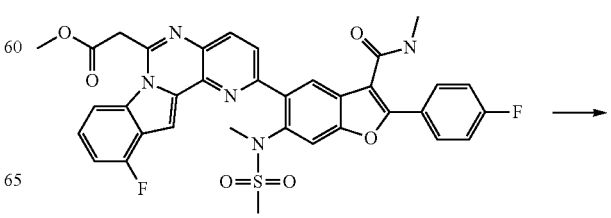

Step 1—Synthesis of 5-(11-fluoro-6-(hydroxymethyl)-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide -continued

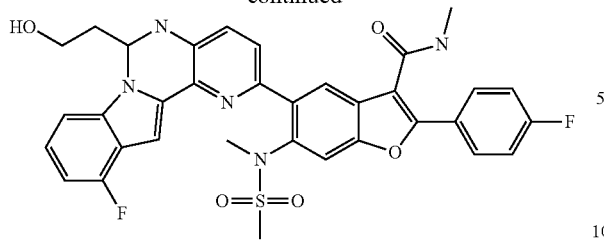

To a solution of methyl 2-(11-fluoro-2-(2-(4-fluorophenyl)-3-(methylcarbamoyl)-6-(N-methylmethylsulfonamido)benzo furan-5-yl)pyrido[3',2':4,5]pyrimido[1,6-a]indol-6-yl)acetate (compound 9, 40 mg, 0.06 mmol) in THF (2 ml) was added NaBH$_4$ (12 mg, 0.29 mmol) and stirred at 40° C. for 2 hours. Preparative TLC provided 5-(11-fluoro-6-(2-hydroxyethyl)-5,6-dihydropyrido[3',2':4,5]pyrimido[1,6-a]indol-2-yl)-2-(4-fluorophenyl)-N-methyl-6-(N-methylmethyl sulfonamido)benzofuran-3-carboxamide (25 mg, yield: 65%). MS (M+H)$^+$: 658.

Example 66

5-(11-fluoro-6,6-dimethyl-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide

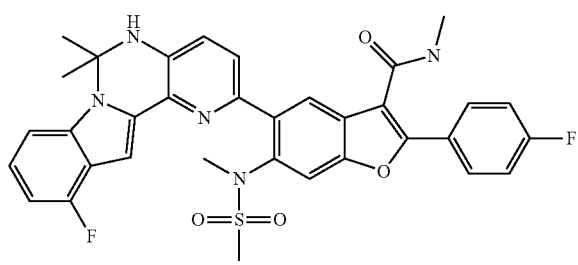 [SMILES: CNC(=O)c1c(-c2ccc(F)cc2)oc2cc(N(C)S(C)(=O)=O)c(-c3ccc4c(n3)-c3cc5c(F)cccc5n3C(C)(C)N4)cc12]

Step 1—Synthesis of 2-chloro-11-fluoro-6,6-dimethyl-5,6-dihydropyrido[3',2':4,5]pyrimido[1,6-a]indole

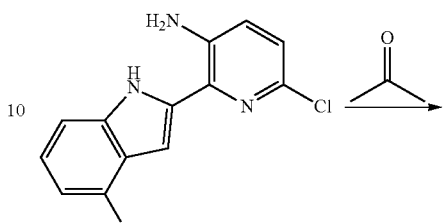

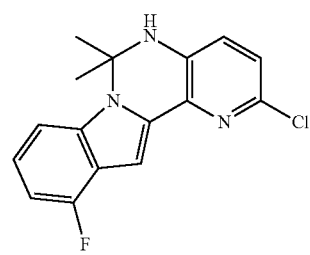

To a screw cap vial was added 6-chloro-2-(4-fluoro-1H-indol-2-yl)pyridin-3-amine (130 mg, 0.50 mmol), acetone (577 mg, 9.9 mmol), 1,4-dioxane (3 ml) and 4.0 M HCl in 1,4-dioxane (0.80 ml). The vial was capped and heated to 90° C. and stirred for 3 hours. The reaction mixture was evaporated in vacuo to remove the volatiles. The residue was treated with NaHCO$_3$ and extracted with EtOAc. The organic layer was washed with brine, dried (Na$_2$SO$_4$), filtered and concentrated in vacuo. The resulting residue was purified using column chromatography (eluted with 0-10% EtOAc/DCM) to provide 2-chloro-11-fluoro-6,6-dimethyl-5,6-dihydropyrido[3',2':4,5]pyrimido[1,6-a]indole (100 mg, yield: 67%). MS (M+H)$^+$: 302.

Step 2—Synthesis of 5-(11-fluoro-6,6-dimethyl-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide

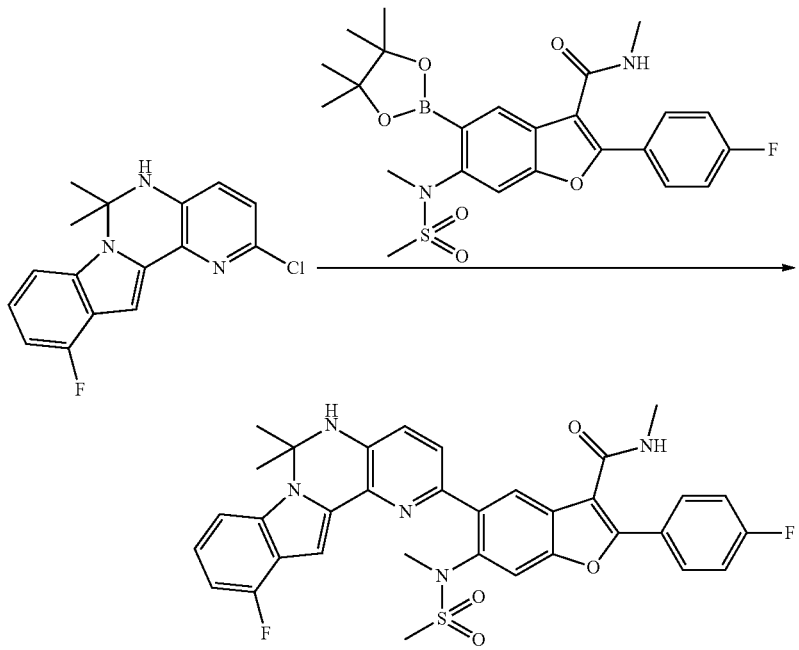

To a degassed solution of 2-chloro-11-fluoro-6,6-dimethyl-5,6-dihydropyrido[3',2':4,5]pyrimido[1,6-a]indole (60 mg, 0.20 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (130 mg, 0.26 mmol) in 1,4-dioxane (2 mL) and water (200 μl) was added $Cs_2CO_3$ (130 mg, 0.40 mmol) and 1,1'-bis(di-tert-butylphosphino)ferrocene palladium chloride (40 mg, 0.06 mmol) under $N_2$ protection. The resulting mixture was heated to 90° C. and stirred at this temperature overnight. The reaction was cooled, filtered through a pad of the celite and washed with ethyl acetate. The combined filtrate was evaporated in vacuo. Preparative TLC provided 5-(11-fluoro-6,6-dimethyl-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide (95 mg, yield: 74%). MS (M+H)+: 642.

Example 67

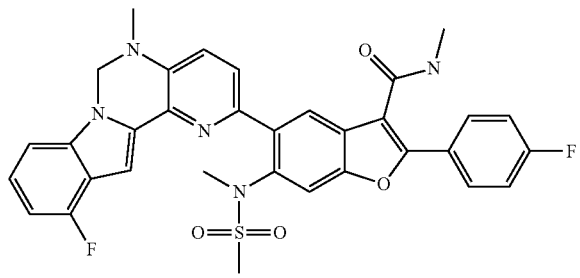 [SMILES: CNC(=O)c1c(-c2ccc(F)cc2)oc2cc(N(C)S(C)(=O)=O)c(-c3ccc4c(n3)-c3cc5c(F)cccc5n3CN4C)cc12]

Step 1—Synthesis of 2-chloro-11-fluoro-5,6-dihydropyrido[3',2':4,5]pyrimido[1,6-a]indole

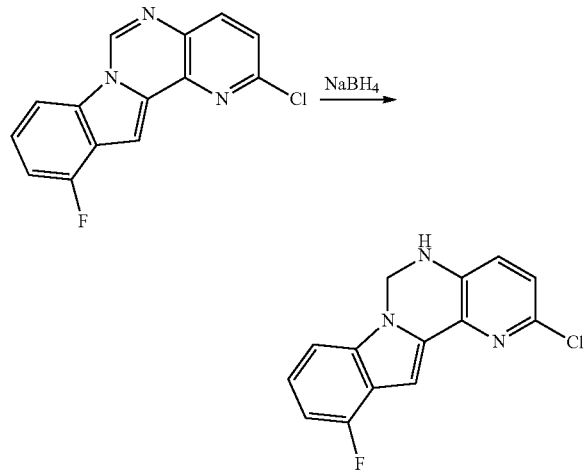

To a solution of 2-chloro-11-fluoropyrido[3',2':4,5]pyrimido[1,6-a]indole (50 mg, 0.18 mmol) in THF (1 ml) and MeOH (1 ml) was added $NaBH_4$ (14 mg, 0.37 mmol). The resulting mixture was stirred at RT for 3 hours then treated with $NH_4Cl$ and extracted with EtOAc. The organic layer was washed with brine, dried ($Na_2SO_4$), filtered and concentrated in vacuo. Preparative TLC gave 2-chloro-11-fluoro-5,6-dihydropyrido[3',2':4,5]pyrimido[1,6-a]indole (50 mg, yield: 99%). MS (M+H)+: 274.

Step 2—Synthesis of 2-chloro-11-fluoro-5-methyl-5,6-dihydropyrido[3',2':4,5]pyrimido[1,6-a]indole

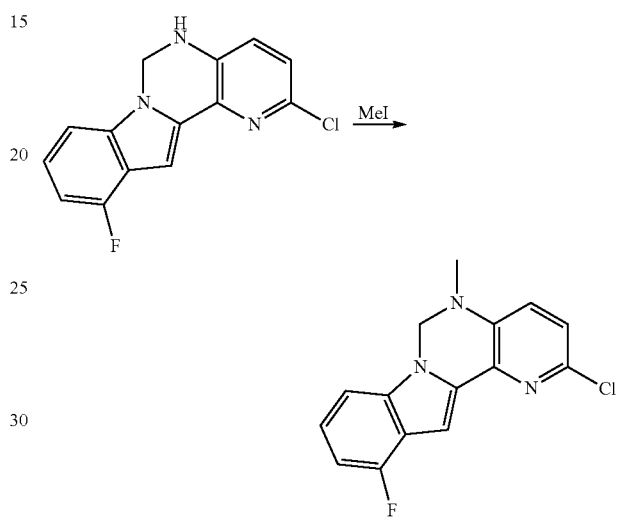

To a solution of 2-chloro-11-fluoro-5,6-dihydropyrido[3',2':4,5]pyrimido[1,6-a]indole (50 mg, 0.18 mmol) in THF (2 ml) was added potassium tert-butoxide (62 mg, 0.55 mmol) and MeI (78 mg, 0.55 mmol). The resulting mixture was stirred at RT for 2 hours, quenched with water and extracted with EtOAc. The organic layer was washed with brine, dried ($Na_2SO_4$), filtered and concentrated in vacuo to afford 2-chloro-11-fluoro-5-methyl-5,6-dihydropyrido[3',2':4,5] pyrimido[1,6-a]indole (50 mg, yield: 95%). MS (M+H)+: 288.

Step 3—Synthesis of 5-(11-fluoro-5-methyl-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide

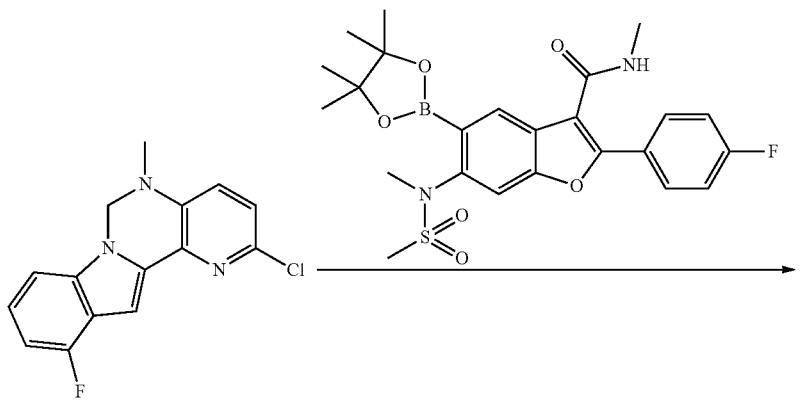

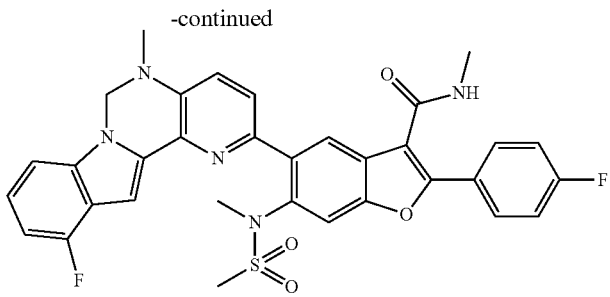

To a degassed solution of 2-chloro-11-fluoro-5-methyl-5,6-dihydropyrido[3',2':4,5]pyrimido[1,6-a]indole (40 mg, 0.14 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (91 mg, 0.18 mmol) in 1,4-dioxane (2 mL) and water (200 μl) was added $Cs_2CO_3$ (91 mg, 0.28 mmol) and 1,1'-bis(di-tert-butylphosphino)ferrocene palladium chloride (15 mg, 0.02 mmol) under $N_2$ protection. The resulting mixture was heated to 90° C. and stirred at this temperature overnight. The reaction was cooled, filtered through a pad of the celite and washed with ethyl acetate. The combined filtrate was evaporated in vacuo. Preparative TLC provided 5-(11-fluoro-5-methyl-5,6-dihydropyrido[3',2':4,5]pyrimido[1,6-a]indol-2-yl)-2-(4-fluorophenyl)-N-methyl-6-(N-methylmethylsulfonamido)benzofuran-3-carboxamide (20 mg, yield: 23%). MS (M+H)$^+$: 642.

Example 68

Example 68, depicted in the table below, were prepared in accordance with the methods described above for Example 67.

| Example | Structure | MS M + H)$^+$ |
|---|---|---|
| 68 | 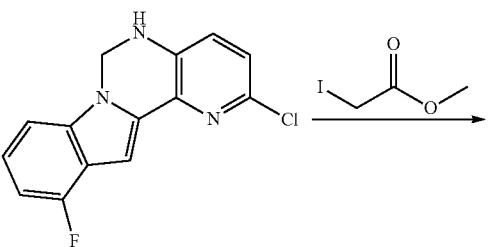 | 673 |

Example 69

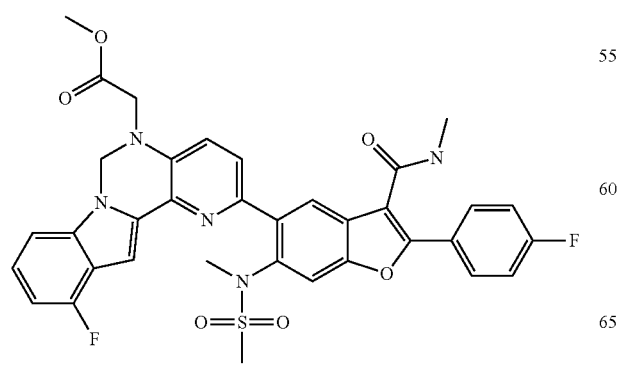

Step 1—Synthesis of methyl 2-(2-chloro-11-fluoropyrido[3',2':4,5]pyrimido[1,6-a]indol-5(6H)-yl)acetate

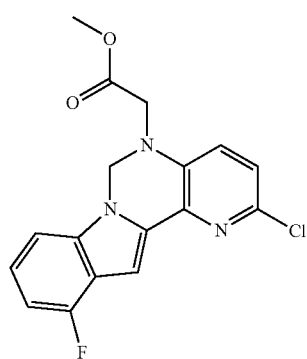

-continued

To a solution of 2-chloro-11-fluoro-5,6-dihydropyrido[3',2':4,5]pyrimido[1,6-a]indole (250 mg, 0.91 mmol) in THF (8 ml) was added 60% NaH (55 mg, 1.37 mmol) and methyl 2-iodoacetate (274 mg, 1.37 mmol). The resulting mixture was stirred at RT overnight, then treated with $H_2O$ and extracted with EtOAc. The organic layer was washed with brine, dried ($Na_2SO_4$), filtered and concentrated in vacuo. The resulting residue was purified using column chromatography (eluted with 0-20% EtOAc/DCM) to provide methyl 2-(2-chloro-11-fluoropyrido[3',2':4,5]pyrimido[1,6-a]indol-5(6H)-yl)acetate (200 mg, yield: 63%). MS (M+H)$^+$: 346.

Step 2—Synthesis of methyl 2-(11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indol-5(6H)-yl)acetate To a degassed solution of 2-(2-chloro-11-fluoropyrido[3',2':4,5]pyrimido[1,6-a]indol-5(6H)-yl)acetate (200 mg, 0.58 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (436 mg, 0.87 mmol) in 1,4-dioxane (8 mL) and water (300 μl) was added $Cs_2CO_3$ (377 mg, 1.16 mmol) and 1,1'-bis(di-tert-butylphosphino)ferrocene palladium chloride (45 mg, 0.12 mmol) under $N_2$ protection. The resulting mixture was heated to 80° C. and stirred at this temperature overnight. The reaction was cooled, filtered through a pad of the celite and washed with ethyl acetate. The combined filtrate was evaporated in vacuo. Preparative TLC (20% ethyl acetate in DCM) provided methyl 2-(11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indol-5(6H)-yl)acetate (130 mg, yield: 33%). MS (M+H)$^+$: 686.

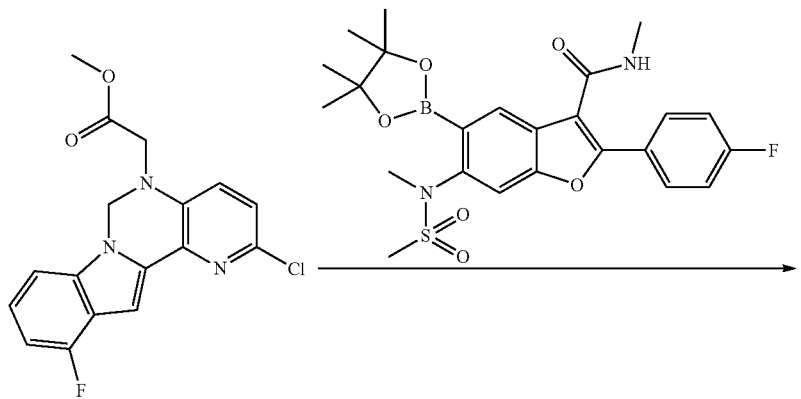

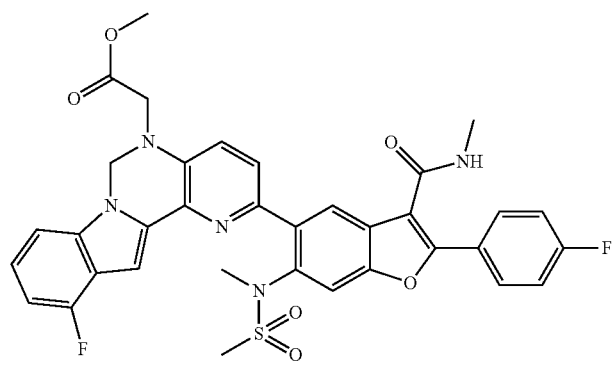

Example 70

2-(11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indol-5(6H)-yl)acetic acid

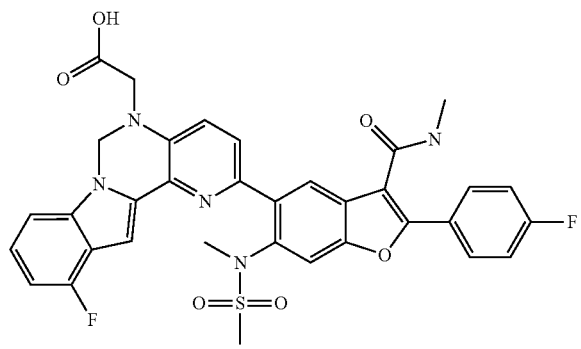 [SMILES: CNC(=O)c1c(-c2ccc(F)cc2)oc2cc(N(C)S(C)(=O)=O)c(-c3ccc4c(n3)-c3cc5c(F)cccc5n3CN4CC(=O)O)cc12]

Step 1—Synthesis of 2-(11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indol-5(6H)-yl)acetic acid

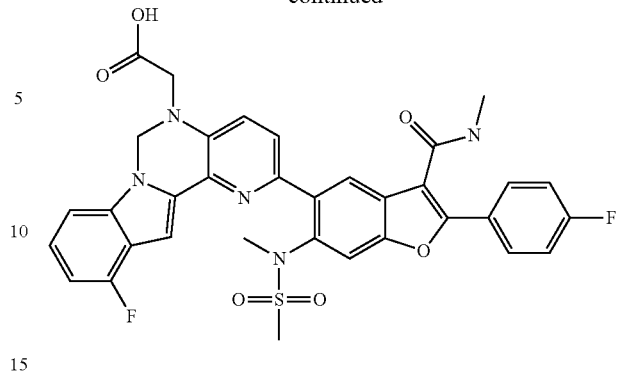

To a suspension of methyl 2-(11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indol-5(6H)-yl)acetate (80 mg, 0.12 mmol) in MeOH (8 mL) was added 1N NaOH solution (2 ml, 17.1 mmol). The resulting mixture was heated to 50° C., stirred at this temperature for 3 h and continued at RT overnight. To the reaction was added 1N HCl (2.5 ml), H$_2$O (10 ml) and stirred for 20 min. The precipitate was collected by the filtration. After washing with H$_2$O, air drying afforded 2-(11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indol-5(6H)-yl)acetic acid (77 mg, yield: 98%). MS (M+H)$^+$: 672.

Example 71 methyl 2-(11-fluoro-2-(2-(4-fluorophenyl)-3-(methylcarbamoyl)-6-(N-methylmethylsulfonamido)benzofuran-5-yl)-5,6-dihydropyrido[3',2':4,5]pyrimido[1,6-a]indol-6-yl)acetate

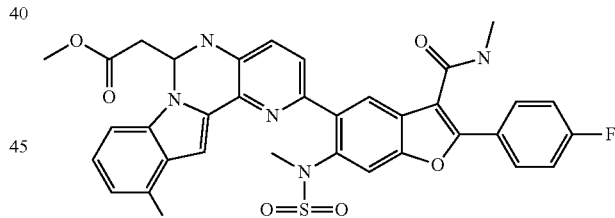

Step 1—Synthesis of 5-(5-amino-6-(4-fluoro-1H-indol-2-yl)pyridin-2-yl)-2-(4-fluorophenyl)-N-methyl-6-(N-methylmethylsulfonamido)benzofuran-3-carboxamide

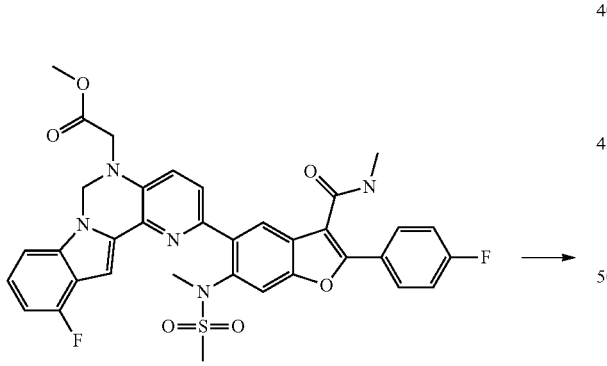

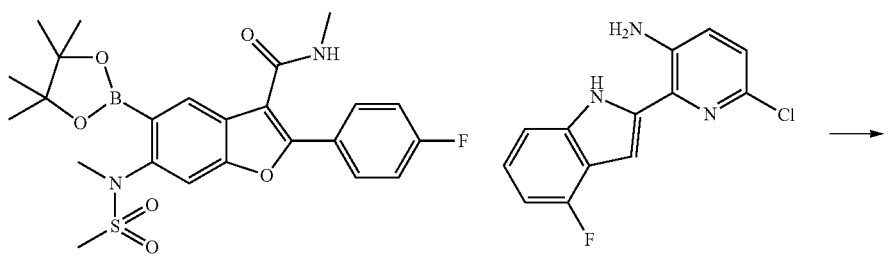

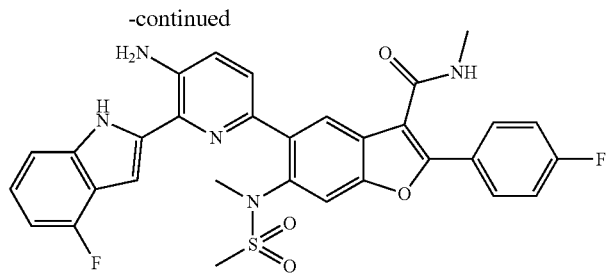

To a degassed solution of 6-chloro-2-(4-fluoro-1H-indol-2-yl)pyridin-3-amine (660 mg, 2.52 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (1647 mg, 3.28 mmol) in 1,4-dioxane (10 mL) and water (200 μl) was added Cs$_2$CO$_3$ (2465 mg, 7.57 mmol) and 1,1'-bis(di-tert-butylphosphino) ferrocene palladium dichloride (160 mg, 0.25 mmol) under N$_2$ protection. The resulting mixture was heated to 90° C. and stirred at this temperature overnight. The reaction was cooled, filtered through a pad of the celite and washed with ethyl acetate. The combined filtrate was evaporated in vacuo. The resulting residue was purified using column chromatography (eluted with 0-30% EtOAc/DCM) to provide 5-(5-amino-6-(4-fluoro-1H-indol-2-yl)pyridin-2-yl)-2-(4-fluorophenyl)-N-methyl-6-(N-methylmethyl sulfonamido)benzofuran-3-carboxamide (1010 mg, yield: 66%). MS (M+H)$^+$: 602.

Step 2—Synthesis of methyl 2-(11-fluoro-2-(2-(4-fluorophenyl)-3-(methylcarbamoyl)-6-(N-methylmethylsulfonamido)benzofuran-5-yl)-5,6-dihydropyrido[3',2':4,5]pyrimido[1,6-a]indol-6-yl)acetate To a solution of 5-(5-amino-6-(4-fluoro-1H-indol-2-yl)pyridin-2-yl)-2-(4-fluorophenyl)-N-methyl-6-(N-methylmethylsulfonamido)benzofuran-3-carboxamide (100 mg, 0.17 mmol) and methyl 3,3-dimethoxypropanoate (32 mg, 0.22 mmol) in 1,4-dioxane (2 mL) was added 4.0 M HCl (46 μl, 0.16 mmol) in 1,4-dioxane under N$_2$ protection. The resulting mixture was heated to 95° C. and stirred at this temperature for 1 h. The reaction was cooled and added Et$_3$N (300 μl). Preparative TLC gave methyl 2-(11-fluoro-2-(2-(4-fluorophenyl)-3-(methylcarbamoyl)-6-(N-methylmethylsulfonamido)benzofuran-5-yl)-5,6-dihydropyrido[3',2':4,5]pyrimido[1,6-a]indol-6-yl)acetate (100 mg, yield: 88%). MS (M+H)$^+$: 686.

Example 72

2-(11-fluoro-2-(2-(4-fluorophenyl)-3-(methylcarbamoyl)-6-(N-methylmethylsulfonamido)benzofuran-5-yl)-5,6-dihydropyrido[3',2':4,5]pyrimido[1,6-a]indol-6-yl)acetic acid

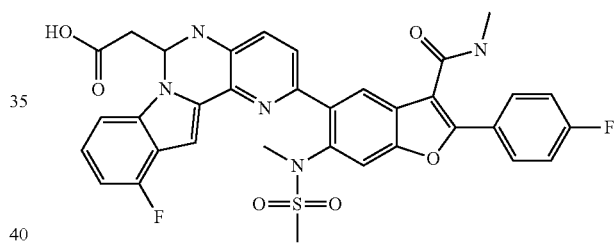

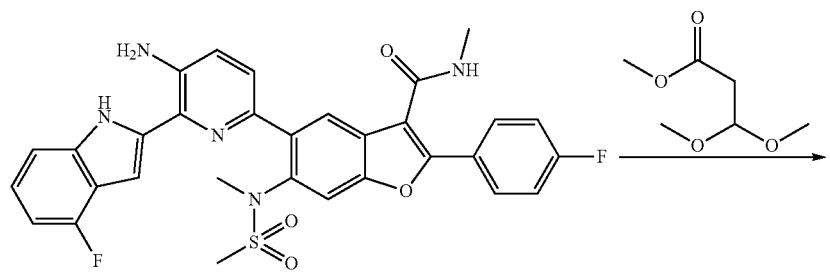

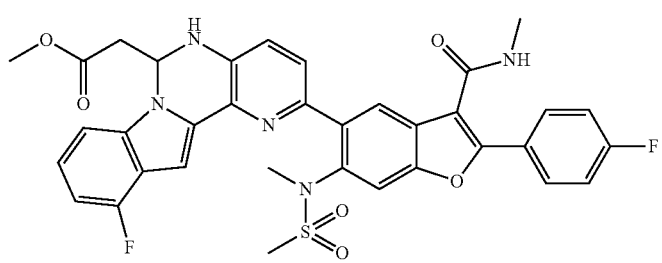

137

Step 1—Synthesis of 2-(11-fluoro-2-(2-(4-fluorophenyl)-3-(methylcarbamoyl)-6-(N-methylmethylsulfonamido)benzofuran-5-yl)-5,6-dihydropyrido[3',2':4,5]pyrimido[1,6-a]indol-6-yl)acetic acid

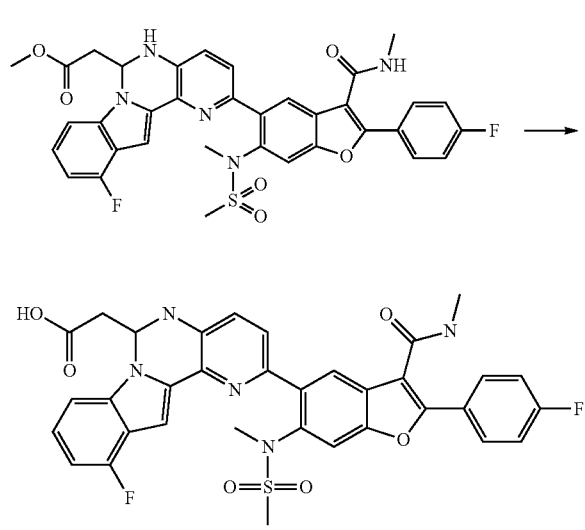 [SMILES: CNC(=O)c1c(-c2ccc(F)cc2)oc2cc(N(C)S(C)(=O)=O)c(-c3ccc4c(n3)-c3cc5c(F)cccc5n3C(CC(=O)OC)N4)cc12 ; CNC(=O)c1c(-c2ccc(F)cc2)oc2cc(N(C)S(C)(=O)=O)c(-c3ccc4c(n3)-c3cc5c(F)cccc5n3C(CC(=O)O)N4)cc12]

To a suspension of methyl methyl 2-(11-fluoro-2-(2-(4-fluorophenyl)-3-(methylcarbamoyl)-6-(N-methylmethylsulfonamido)benzofuran-5-yl)-5,6-dihydropyrido[3',2':4,5]pyrimido[1,6-a]indol-6-yl)acetate (60 mg, 0.08 mmol) in MeOH (2 mL) was added 1N NaOH solution (2 ml, 2.0 mmol). The resulting mixture was stirred at RT for 30 min, then added 1N HCl (2.3 ml) and H₂O (10 ml) and stirred for 20 min. The precipitate was collected by the filtration. After washed with H₂O, air drying afforded 2-(11-fluoro-2-(2-(4-fluorophenyl)-3-(methylcarbamoyl)-6-(N-methylmethylsulfonamido)benzofuran-5-yl)-5,6-dihydropyrido[3',2':4,5]pyrimido[1,6-a]indol-6-yl)acetic acid (45 mg, yield: 77%). MS (M+H)⁺: 672.

Example 73

5-(11'-fluoro-5'H-spiro[cyclobutane-1,6'-pyrido[3',2':4,5]pyrimido[1,6-a]indol]-2'-yl)-2-(4-fluorophenyl)-N-methyl-6-(N-methylmethylsulfonamido)benzofuran-3-carboxamide

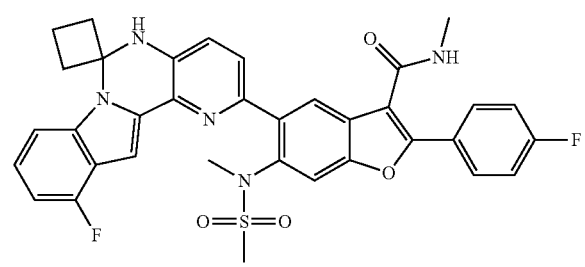 [SMILES: CNC(=O)c1c(-c2ccc(F)cc2)oc2cc(N(C)S(C)(=O)=O)c(-c3ccc4c(n3)-c3cc5c(F)cccc5n3C3(CCC3)N4)cc12]

138

Step 1—Synthesis of 5-(11'-fluoro-5'H-spiro[cyclobutane-1,6'-pyrido[3',2':4,5]pyrimido[1,6-a]indol]-2'-yl)-2-(4-fluorophenyl)-N-methyl-6-(N-methylmethylsulfonamido)benzofuran-3-carboxamide

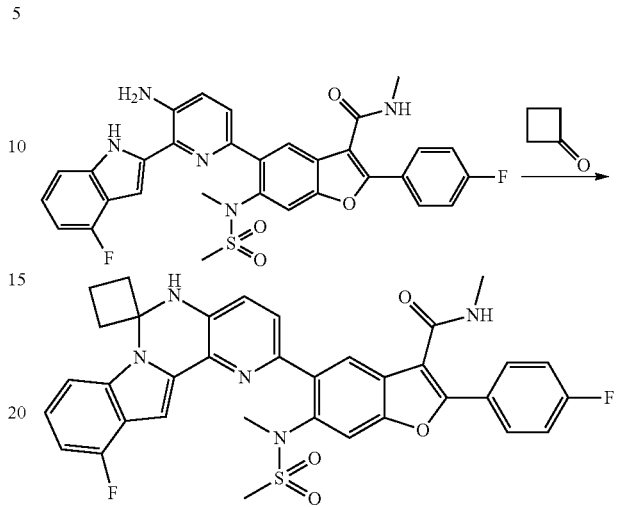

To a screw cap vial was added 5-(5-amino-6-(4-fluoro-1H-indol-2-yl)pyridin-2-yl)-2-(4-fluorophenyl)-N-methyl-6-(N-methylmethylsulfonamido)benzofuran-3-carboxamide (80 mg, 0.13 mmol), cyclobutanone (186 mg, 2.66 mmol) and 1,4-dioxane (2 ml) with 4.0 HCl in dioxane (300 µl). The vial was capped and heated to 80° C. and stirred for 2 hours. The reaction mixture was evaporated in vacuo to remove the volatiles. The residue was treated with NaHCO₃ and extracted with EtOAc. The organic layer was washed with brine, dried (Na₂SO₄), filtered and concentrated in vacuo. Preparative TLC (3% MeOH in DCM) gave 5-(11'-fluoro-5'H-spiro[cyclobutane-1,6'-pyrido[3',2':4,5]pyrimido[1,6-a]indol]-2'-yl)-2-(4-fluorophenyl)-N-methyl-6-(N-methylmethylsulfonamido)benzofuran-3-carboxamide (26 mg, yield: 30%). MS (M+H)⁺: 653.

Example 74

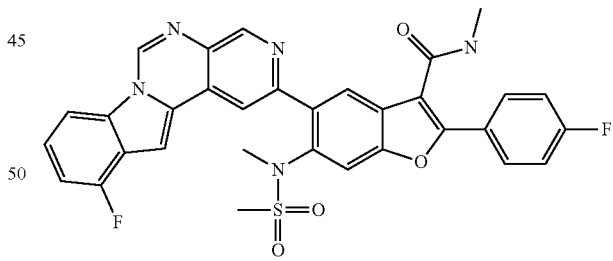

Step 1—Synthesis of 6-chloro-4-(4-fluoro-1H-indol-2-yl)pyridin-3-amine

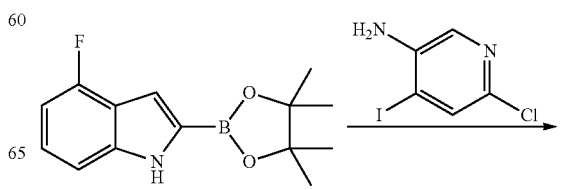

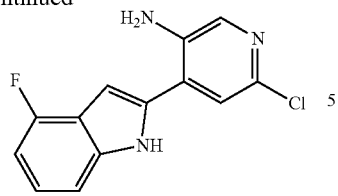

A mixture of boronic ester (8.5 g, 32.6 mmol), iodide (39.94 g, 39.1 mmol), cesium carbonate (21.85 g, 67.1 mmol) and Pd(dtbpf)Cl₂ (1.70 g, 2.6 mmol) in 1,4-dioxane (130 mL) and water (4.25 mL) was heated to 90° C. for 10 minutes under nitrogen atmosphere. It was then cooled, filtered off inorganic solids and concentrated. The residue was purified on silica gel eluting with 0-10% MeOH/DCM to give 7.2 g product in 85% yield.

Step 2—Synthesis of 2-chloro-11-fluoropyrido[3',4': 4,5]pyrimido[1,6-a]indole

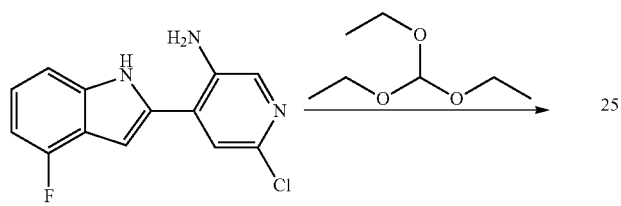

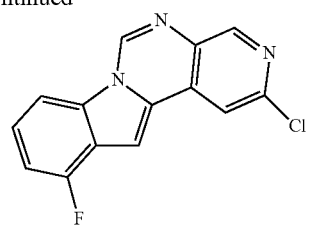

To a solution of diamine (5 g, 19.1 mmol) and triethoxymethane (12.7 mL, 76 mmol) in 1,4-dioxane (43 mL) was added 4 M HCl/1,4-dioxane (7.2 mL) and the slurry was heated to reflux at 90° C. for 20 minutes, forming a thick slurry which was then thinned. After cooling, the slurry was filtered and washed with dioxane to give 1.8 g solid with a minor impurity. The filtrate was concentrated, reslurried in methanol and filtered to give another 1.65 g pure product, in 66% total yield.

Step 3—Synthesis of 2-(4-fluorophenyl)-5-(11-fluoropyrido[3',4':4,5]pyrimido[1,6-a]indol-2-yl)-N-methyl-6-(N-methylmethylsulfonamido)benzofuran-3-carboxamide

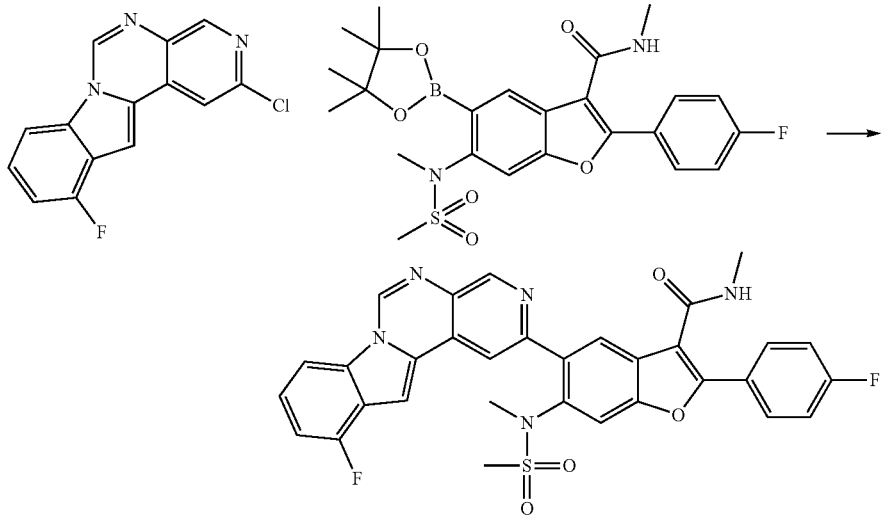

To a degassed solution of chloride (250 mg, 0.92 mmol), boronic ester (462 mg, 0.92 mmol) and Cs₂CO₃ (600 mg, 1.84 mmol) in 1,4-dioxane (5 mL) and H₂O (0.25 mL) was added 1,1'-bis(di-tert-butylphosphino)ferrocene palladium dichloride (60 mg, 0.092 mmol) under nitrogen atmosphere. The reaction mixture was stirred at 70° C. for 2.5 h, then cooled, filtered off inorganic solids and concentrated. The residue was purified on silica gel eluting with 0-100% EtOAc/hexane to give 221 mg product in 33% yield.

Example 75

Example 75, depicted in the table below, was prepared in accordance with the methods described above for Example 74.

| Example | Structure | MS M + H)+ |
|---|---|---|
| 75 | 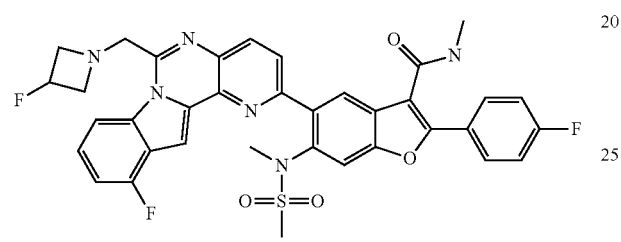 | 629 |

Example 76

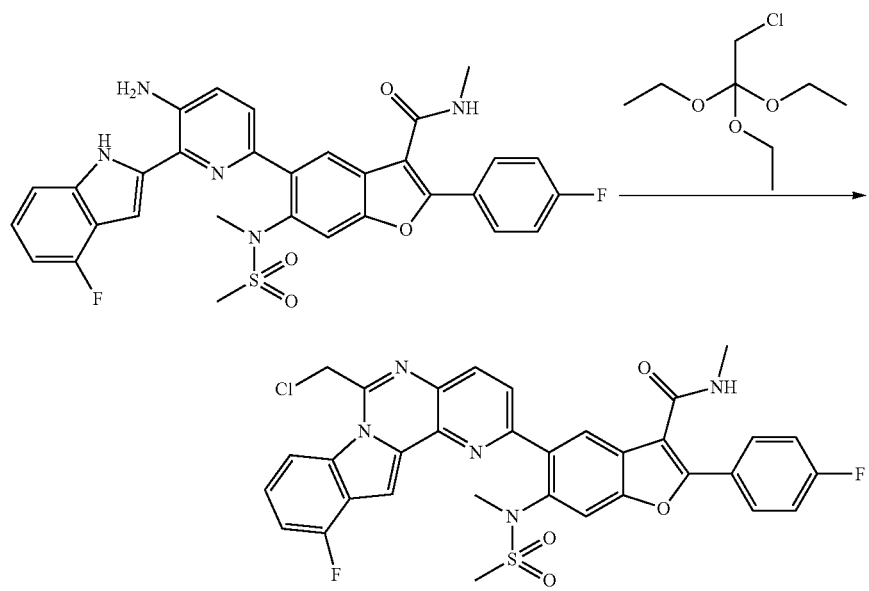

Step 1—5-(6-(chloromethyl)-11-fluoropyrido[3',2':4,5]pyrimido[1,6-a]indol-2-yl)-2-(4-fluorophenyl)-N-methyl-6-(N-methylmethylsulfonamido)benzofuran-3-carboxamide To a solution of 5-(5-amino-6-(4-fluoro-1H-indol-2-yl)pyridin-2-yl)-2-(4-fluorophenyl)-N-methyl-6-(N-methylethylsulfonamido)benzofuran-3-carboxamide (900 mg, 1.496 mmol) and 2-chloro-1,1,1-trimethoxyethane (1850 mg, 11.97 mmol) in 1,4-Dioxane (15 ml) was added TFA (1 ml, 12.98 mmol). The mixture was heated to 85° C. and stirred for 3 h. The mixture was concentrated in vacuo, then dissolved in 15 ml DCM. 5 ml Et$_3$N was added and then the mixture evaporated in vacuo. The resulting mixture was purified using column chromatography (eluted with 0-20% ethyl acetate/DCM) to provide 5-(6-(chloromethyl)-11-fluoropyrido[3',2':4,5]pyrimido[1,6-a]indol-2-yl)-2-(4-fluorophenyl)-N-methyl-6-(N-methylmethylsulfonamido)benzofuran-3-carboxamide (500 mg, yield: 51%). MS (M+H)+: 661.

Step 2—Synthesis of 5-(11-fluoro-6-((3-fluoroazetidin-1-yl)methyl)pyrido[3',2':4,5]pyrimido[1,6-a]indol-2-yl)-2-(4-fluorophenyl)-N-methyl-6-(N-methylmethylsulfonamido)benzofuran-3-carboxamide

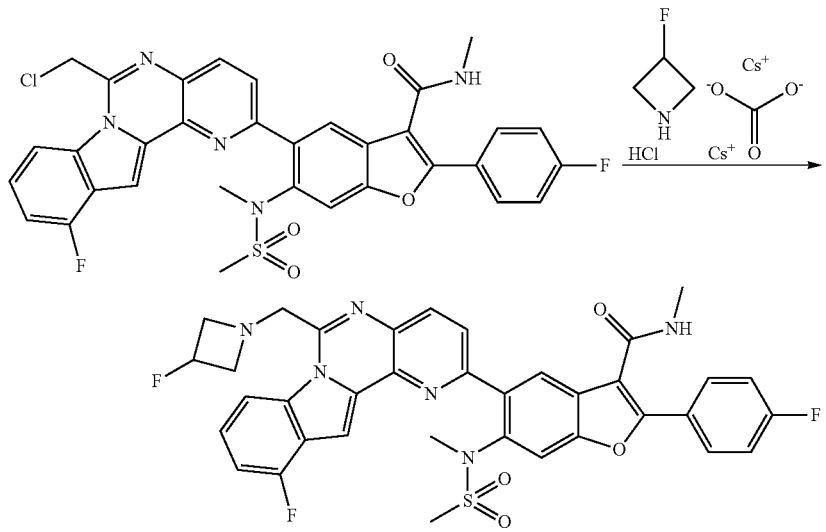

To a solution of the 5-(6-(chloromethyl)-11-fluoropyrido[3',2':4,5]pyrimido[1,6-a]indol-2-yl)-2-(4-fluorophenyl)-N-methyl-6-(N-methylmethyl sulfonamido)benzofuran-3-carboxamide (500 mg, 0.757 mmol) in DMF (8 ml) was added 3-fluoroazetidine hydrochloride (253 mg, 2.272 mmol) and Cs$_2$CO$_3$ (740 mg, 2.272 mmol). The resulting mixture was heated to 50° C. and stirred overnight. The mixture was cooled to RT. 20 ml H$_2$O was added and the resulting mixture stirred for 20 min. The filtration collected the solid. After washing with H$_2$O, air drying gave the yellow solid which was further purified by preparative TLC and gave 5-(11-fluoro-6-((3-fluoroazetidin-1-yl)methyl)pyrido[3',2':4,5]pyrimido[1,6-a]indol-2-yl)-2-(4-fluorophenyl)-N-methyl-6-(N-methylmethylsulfonamido)benzofuran-3-carboxamide (230 mg, yield: 44%). MS (M+H)$^+$: 699.

Step 3—3-fluoro-1-((11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indol-6-yl)methyl)azetidin-1-ium methanesulfonate

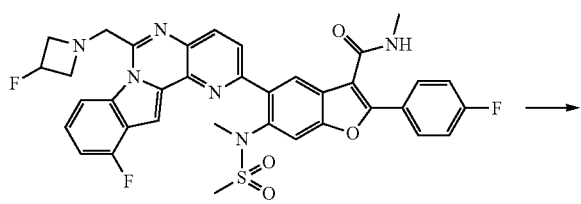

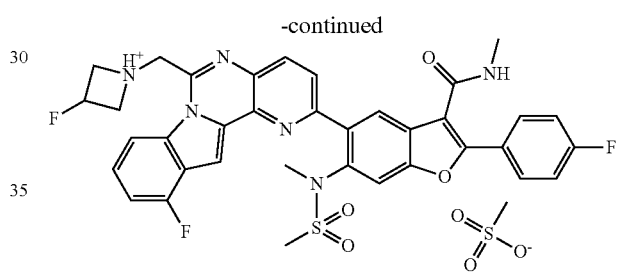

5-(11-fluoro-6-((3-fluoroazetidin-1-yl)methyl)pyrido[3',2':4,5]pyrimido[1,6-a]indol-2-yl)-2-(4-fluorophenyl)-N-methyl-6-(N-methylmethylsulfonamido)benzofuran-3-carboxamide (1.20 g, 1.717 mmol) and methanesulfonic acid (0.165 g, 1.717 mmol) were combined in MeOH (30 ml) and become a clear solution, followed by addition of Ethyl ether (40 ml). The solid was precipitated out. The filtration was collected as a yellow solid. After washed with additional ether, air drying gave 3-fluoro-1-((11-fluoro-2-(2-(4-fluorophenyl)-3-(methylcarbamoyl)-6-(N-methylmethylsulfonamido)benzofuran-5-yl)pyrido[3',2':4,5]pyrimido[1,6-a]indol-6-yl)methyl)azetidin-1-ium methanesulfonate (1.35 g, Yield: 99%).

The HCl salt and TsOH salt were prepared in the similar fashion.

Examples 77-151

Examples 77-151, depicted in the table below, were prepared in accordance with the methods described above for Example 73, 5-(11'-fluoro-5'H-spiro[cyclobutane-1,6'-pyrido[3',2':4,5]pyrimido[1,6-a]indol]-2'-yl)-2-(4-fluorophenyl)-N-methyl-6-(N-methylmethylsulfonamido)benzofuran-3-carboxamide.

| Compound ID | Structure | MS (M + H)+ |
|---|---|---|
| 77 | 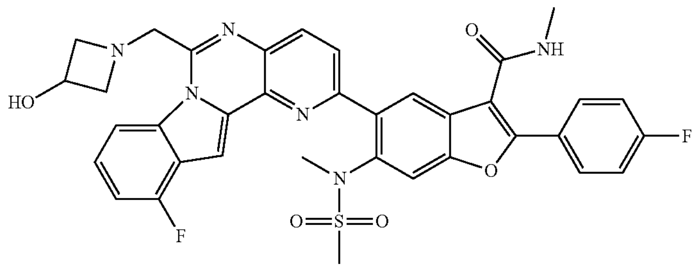 [SMILES: CNC(=O)c1c(-c2ccc(F)cc2)oc2cc(N(C)S(C)(=O)=O)c(-c3ccc4nc(CN5CC(O)C5)n5c6cccc(F)c6cc5c4n3)cc12] | 696 |
| 78 | 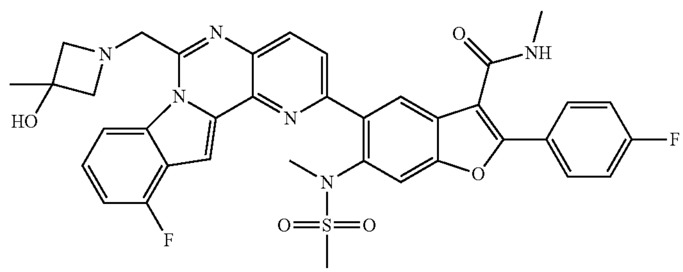 [SMILES: CNC(=O)c1c(-c2ccc(F)cc2)oc2cc(N(C)S(C)(=O)=O)c(-c3ccc4nc(CN5CC(C)(O)C5)n5c6cccc(F)c6cc5c4n3)cc12] | 710 |
| 79 | 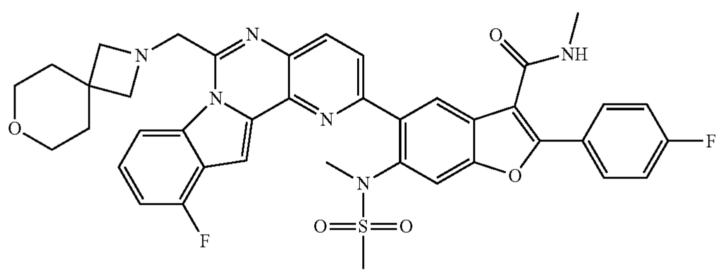 [SMILES: CNC(=O)c1c(-c2ccc(F)cc2)oc2cc(N(C)S(C)(=O)=O)c(-c3ccc4nc(CN5CC6(CCOCC6)C5)n5c6cccc(F)c6cc5c4n3)cc12] | 750 |
| 80 | 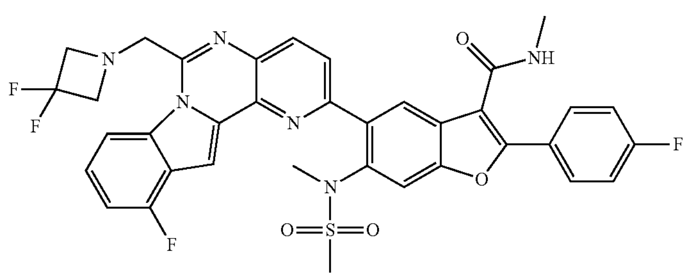 [SMILES: CNC(=O)c1c(-c2ccc(F)cc2)oc2cc(N(C)S(C)(=O)=O)c(-c3ccc4nc(CN5CC(F)(F)C5)n5c6cccc(F)c6cc5c4n3)cc12] | 717 |
| 81 | 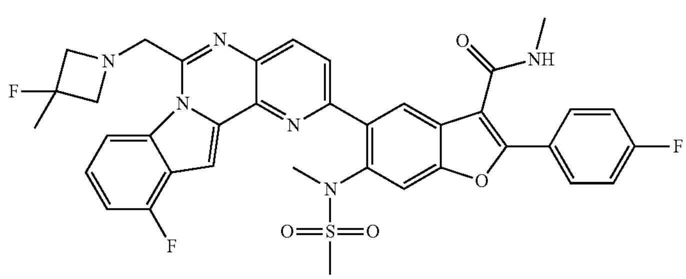 | 713 |

-continued
| Compound ID | Structure | MS (M + H)+ |
|---|---|---|
| 82 | 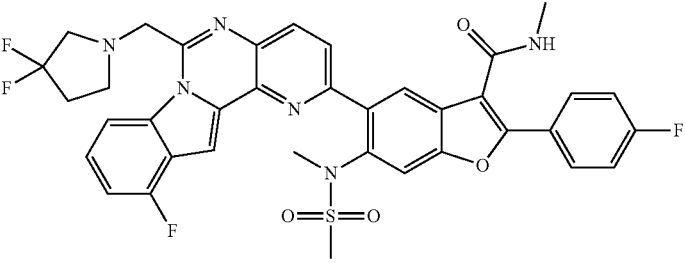 [SMILES: CNC(=O)c1c(-c2ccc(F)cc2)oc2cc(N(C)S(C)(=O)=O)c(-c3ccc4nc(CN5CCC(F)(F)C5)n5c6cccc(F)c6cc5c4n3)cc12] | 731 |
| 83 | 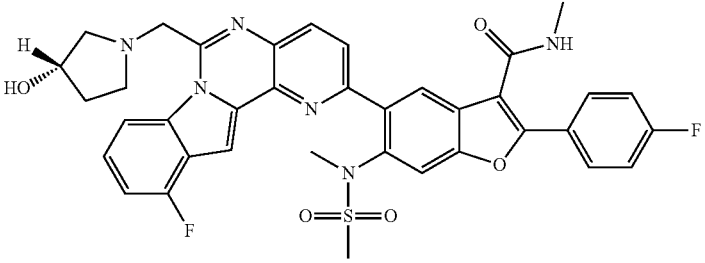 [SMILES: CNC(=O)c1c(-c2ccc(F)cc2)oc2cc(N(C)S(C)(=O)=O)c(-c3ccc4nc(CN5CC[C@H](O)C5)n5c6cccc(F)c6cc5c4n3)cc12] | 711 |
| 84 | 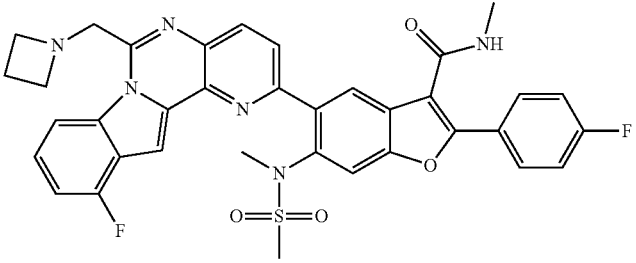 [SMILES: CNC(=O)c1c(-c2ccc(F)cc2)oc2cc(N(C)S(C)(=O)=O)c(-c3ccc4nc(CN5CCC5)n5c6cccc(F)c6cc5c4n3)cc12] | 681 |
| 85 | 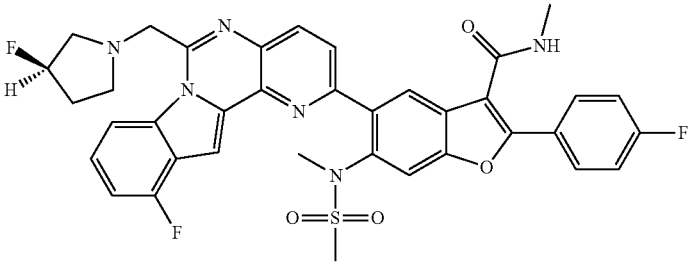 | 713 |
| 86 | 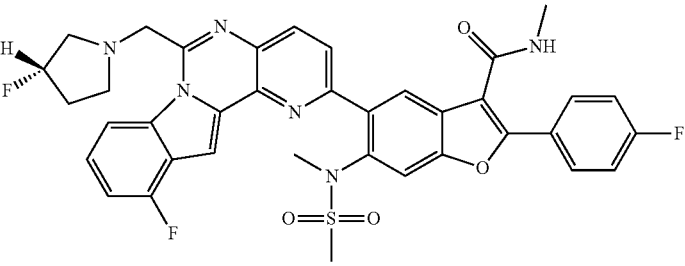 [SMILES: CNC(=O)c1c(-c2ccc(F)cc2)oc2cc(N(C)S(C)(=O)=O)c(-c3ccc4nc(CN5CC[C@@H](F)C5)n5c6cccc(F)c6cc5c4n3)cc12] | 713 |

-continued

| Compound ID | Structure | MS (M + H)+ |
|---|---|---|
| 87 | 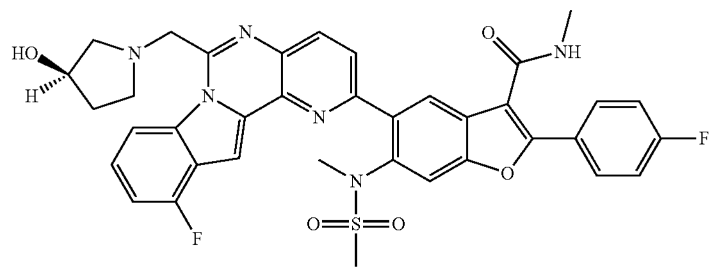 [SMILES: CNC(=O)c1c(-c2ccc(F)cc2)oc2cc(N(C)S(C)(=O)=O)c(-c3ccc4nc(CN5CC[C@@H](O)C5)n5c6cccc(F)c6cc5c4n3)cc12] | 711 |
| 88 | 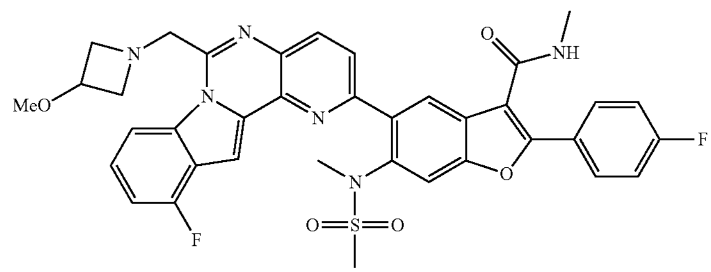 [SMILES: CNC(=O)c1c(-c2ccc(F)cc2)oc2cc(N(C)S(C)(=O)=O)c(-c3ccc4nc(CN5CC(OC)C5)n5c6cccc(F)c6cc5c4n3)cc12] | 710 |
| 89 | 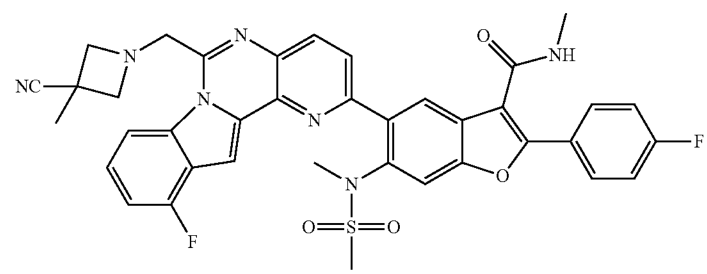 [SMILES: CNC(=O)c1c(-c2ccc(F)cc2)oc2cc(N(C)S(C)(=O)=O)c(-c3ccc4nc(CN5CC(C)(C#N)C5)n5c6cccc(F)c6cc5c4n3)cc12] | 719 |
| 90 | 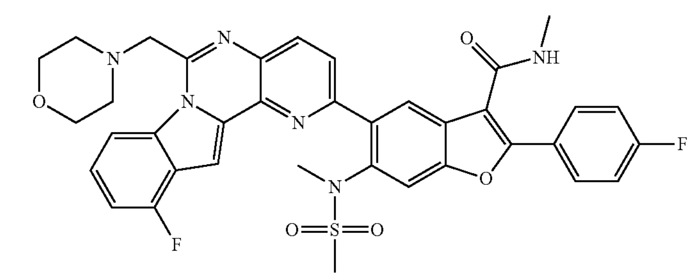 [SMILES: CNC(=O)c1c(-c2ccc(F)cc2)oc2cc(N(C)S(C)(=O)=O)c(-c3ccc4nc(CN5CCOCC5)n5c6cccc(F)c6cc5c4n3)cc12] | 710 |
| 91 | 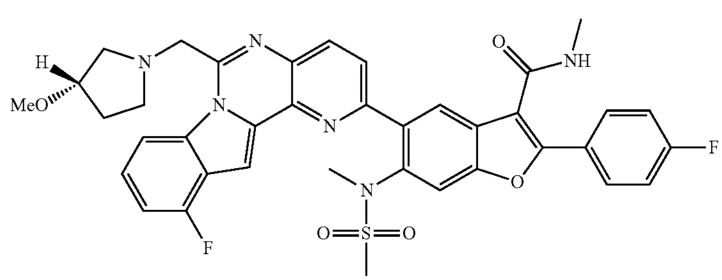 | 724 |

-continued
| Compound ID | Structure | MS (M + H)+ |
|---|---|---|
| 92 | 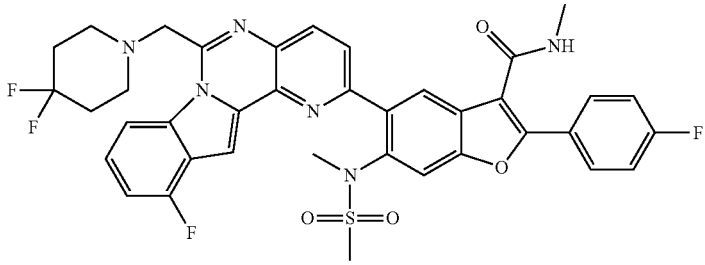 [SMILES: CNC(=O)c1c(-c2ccc(F)cc2)oc2cc(N(C)S(C)(=O)=O)c(-c3ccc4nc(CN5CCC(F)(F)CC5)n5c6cccc(F)c6cc5c4n3)cc12] | 744 |
| 93 | 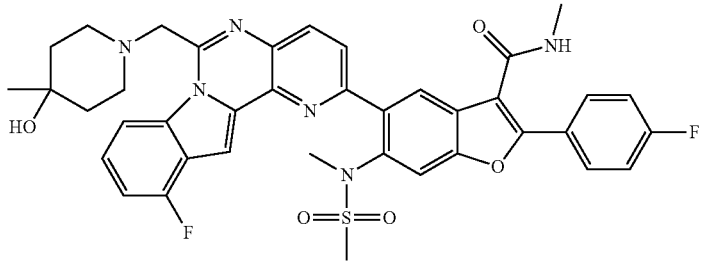 [SMILES: CNC(=O)c1c(-c2ccc(F)cc2)oc2cc(N(C)S(C)(=O)=O)c(-c3ccc4nc(CN5CCC(C)(O)CC5)n5c6cccc(F)c6cc5c4n3)cc12] | 738 |
| 94 | 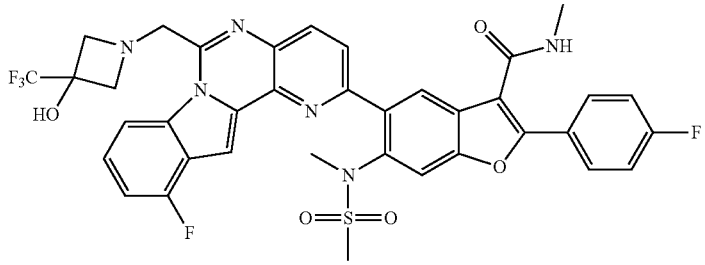 [SMILES: CNC(=O)c1c(-c2ccc(F)cc2)oc2cc(N(C)S(C)(=O)=O)c(-c3ccc4nc(CN5CC(O)(C(F)(F)F)C5)n5c6cccc(F)c6cc5c4n3)cc12] | 765 |
| 95 | 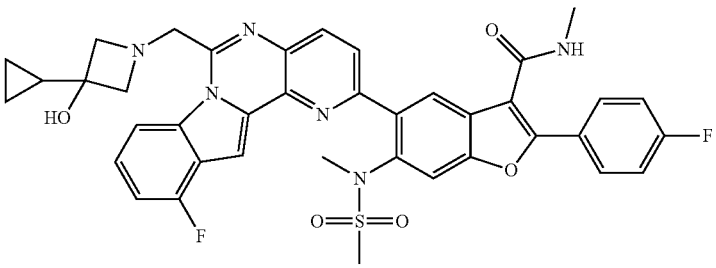 [SMILES: CNC(=O)c1c(-c2ccc(F)cc2)oc2cc(N(C)S(C)(=O)=O)c(-c3ccc4nc(CN5CC(O)(C6CC6)C5)n5c6cccc(F)c6cc5c4n3)cc12] | 737 |
| 96 | 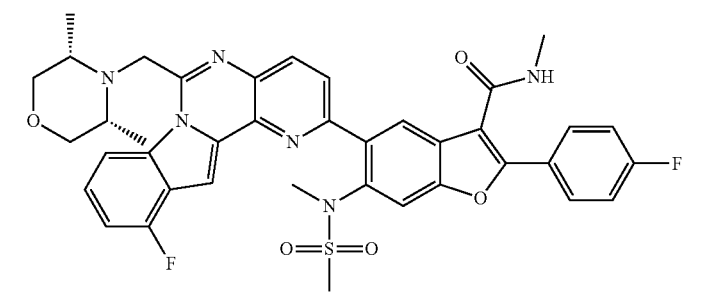 [SMILES: CNC(=O)c1c(-c2ccc(F)cc2)oc2cc(N(C)S(C)(=O)=O)c(-c3ccc4nc(CN5[C@H](C)COC[C@@H]5C)n5c6cccc(F)c6cc5c4n3)cc12] | 739 |

-continued
| Compound ID | Structure | MS (M + H)+ |
|---|---|---|
| 97 | 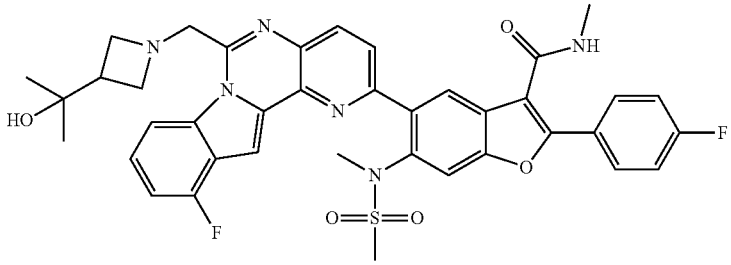 [SMILES: CNC(=O)c1c(-c2ccc(F)cc2)oc2cc(N(C)S(C)(=O)=O)c(-c3ccc4nc(CN5CC(C(C)(C)O)C5)n5c6cccc(F)c6cc5c4n3)cc12] | 739 |
| 98 | 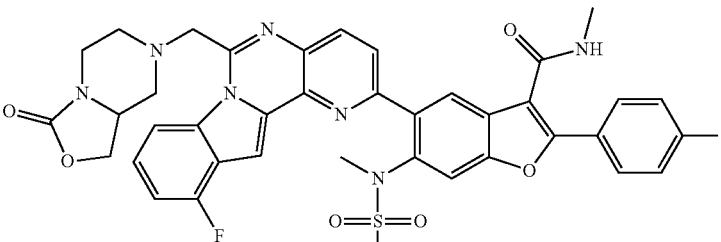 | 766 |
| 99 | 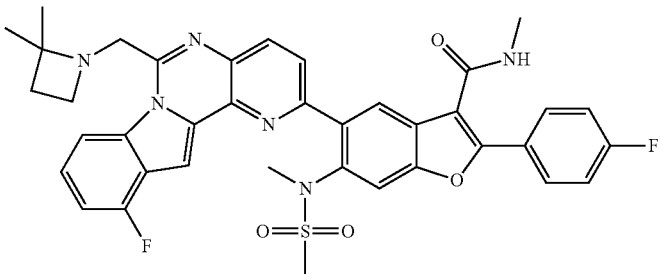 [SMILES: CNC(=O)c1c(-c2ccc(F)cc2)oc2cc(N(C)S(C)(=O)=O)c(-c3ccc4nc(CN5CCC5(C)C)n5c6cccc(F)c6cc5c4n3)cc12] | 709 |
| 100 | 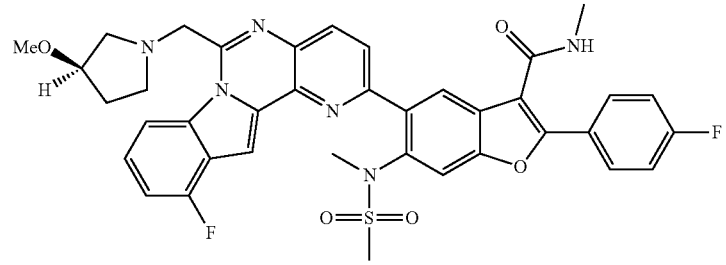 [SMILES: CNC(=O)c1c(-c2ccc(F)cc2)oc2cc(N(C)S(C)(=O)=O)c(-c3ccc4nc(CN5CC[C@@H](OC)C5)n5c6cccc(F)c6cc5c4n3)cc12] | 725 |
| 101 | 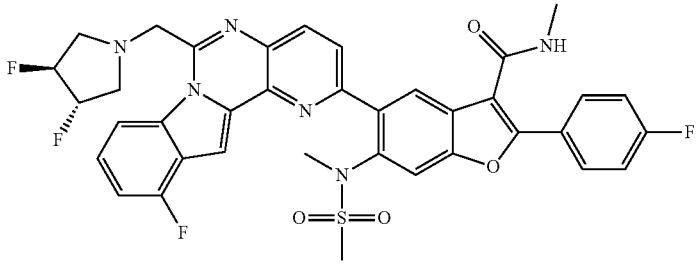 [SMILES: CNC(=O)c1c(-c2ccc(F)cc2)oc2cc(N(C)S(C)(=O)=O)c(-c3ccc4nc(CN5C[C@H](F)[C@@H](F)C5)n5c6cccc(F)c6cc5c4n3)cc12] | 731 |

-continued

| Compound ID | Structure | MS (M + H)+ |
| --- | --- | --- |
| 102 | 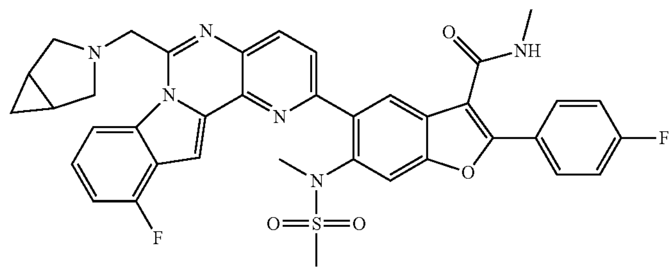 [SMILES: CNC(=O)c1c(-c2ccc(F)cc2)oc2cc(N(C)S(C)(=O)=O)c(-c3ccc4nc(CN5CC6CC6C5)n5c6cccc(F)c6cc5c4n3)cc12] | 707 |
| 103 | 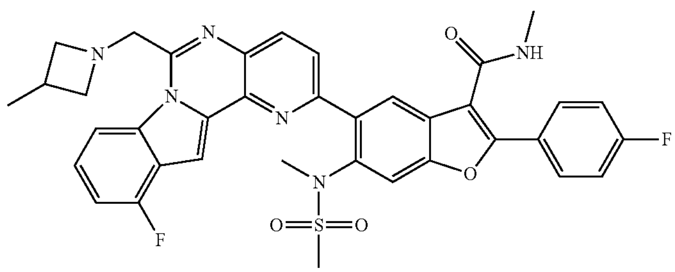 [SMILES: CNC(=O)c1c(-c2ccc(F)cc2)oc2cc(N(C)S(C)(=O)=O)c(-c3ccc4nc(CN5CC(C)C5)n5c6cccc(F)c6cc5c4n3)cc12] | 695 |
| 104 | 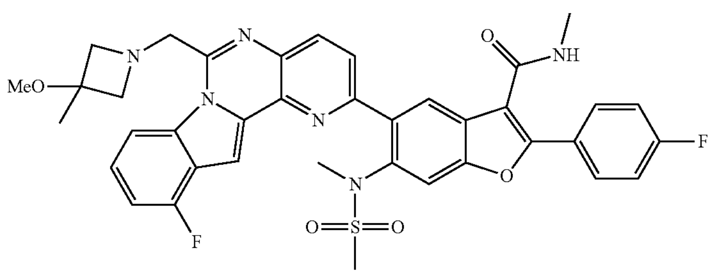 [SMILES: CNC(=O)c1c(-c2ccc(F)cc2)oc2cc(N(C)S(C)(=O)=O)c(-c3ccc4nc(CN5CC(C)(OC)C5)n5c6cccc(F)c6cc5c4n3)cc12] | 725 |
| 105 | 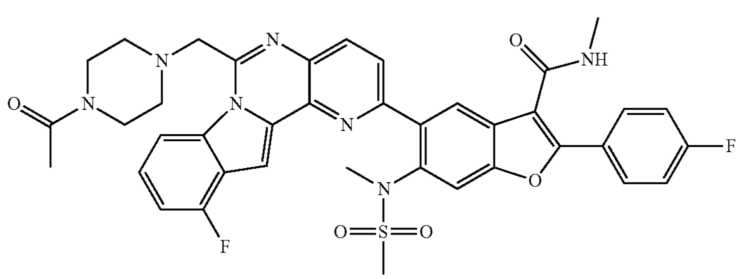 [SMILES: CNC(=O)c1c(-c2ccc(F)cc2)oc2cc(N(C)S(C)(=O)=O)c(-c3ccc4nc(CN5CCN(C(C)=O)CC5)n5c6cccc(F)c6cc5c4n3)cc12] | 752 |
| 106 | 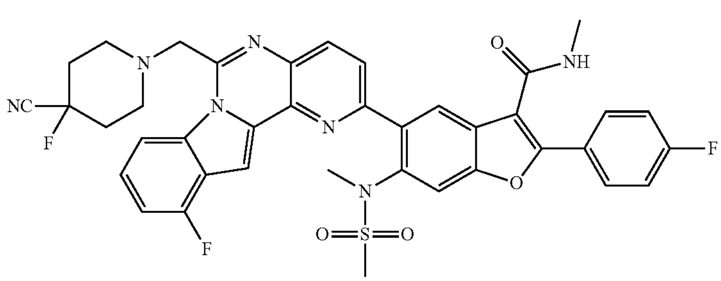 [SMILES: CNC(=O)c1c(-c2ccc(F)cc2)oc2cc(N(C)S(C)(=O)=O)c(-c3ccc4nc(CN5CCC(F)(C#N)CC5)n5c6cccc(F)c6cc5c4n3)cc12] | 752 |

-continued
| Compound ID | Structure | MS (M + H)+ |
|---|---|---|
| 107 | 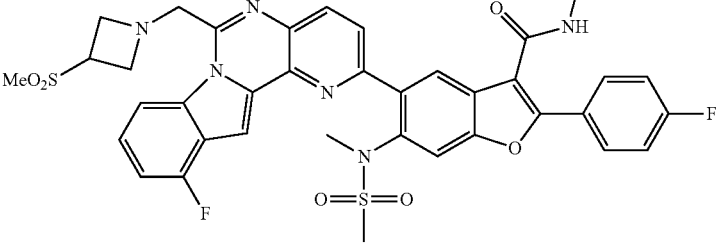 | 759 |
| 108 | 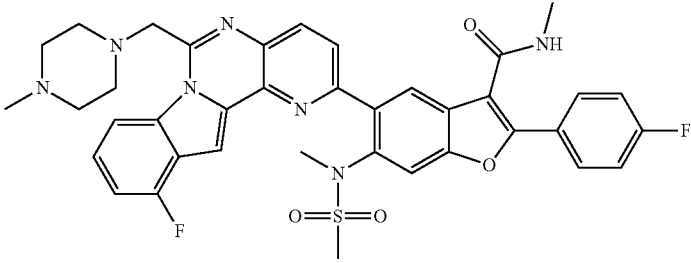 [SMILES: CNC(=O)c1c(-c2ccc(F)cc2)oc2cc(N(C)S(C)(=O)=O)c(-c3ccc4nc(CN5CCN(C)CC5)n5c6cccc(F)c6cc5c4n3)cc12] | 724 |
| 109 | 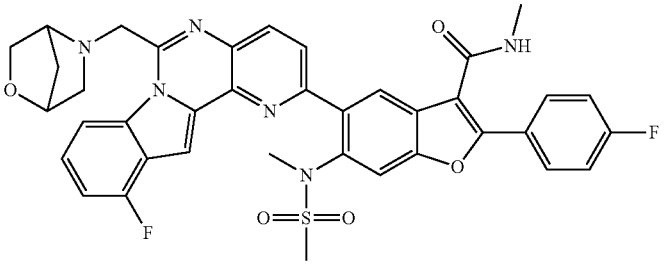 [SMILES: CNC(=O)c1c(-c2ccc(F)cc2)oc2cc(N(C)S(C)(=O)=O)c(-c3ccc4nc(CN5CC6CC5CO6)n5c6cccc(F)c6cc5c4n3)cc12] | 723 |
| 110 | 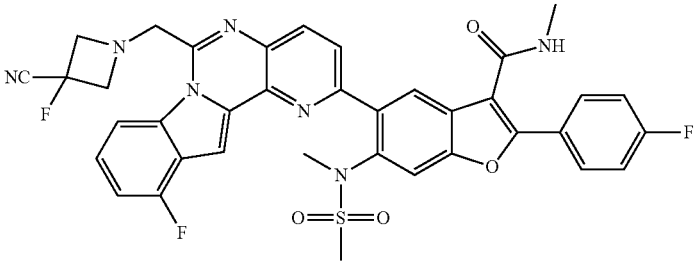 [SMILES: CNC(=O)c1c(-c2ccc(F)cc2)oc2cc(N(C)S(C)(=O)=O)c(-c3ccc4nc(CN5CC(F)(C#N)C5)n5c6cccc(F)c6cc5c4n3)cc12] | 724 |
| 111 | 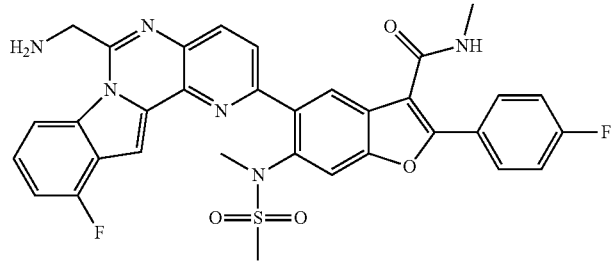 [SMILES: CNC(=O)c1c(-c2ccc(F)cc2)oc2cc(N(C)S(C)(=O)=O)c(-c3ccc4nc(CN)n5c6cccc(F)c6cc5c4n3)cc12] | 641 |

-continued

| Compound ID | Structure | MS (M + H)+ |
|---|---|---|
| 112 | 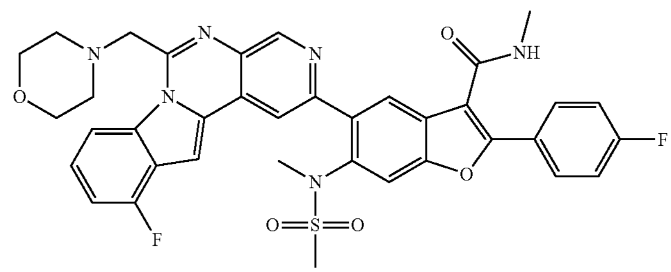 [SMILES: CNC(=O)c1c(-c2ccc(F)cc2)oc2cc(N(C)S(C)(=O)=O)c(-c3cc4c(cn3)nc(CN3CCOCC3)n3c5cccc(F)c5cc43)cc12] | 710 |
| 113 | 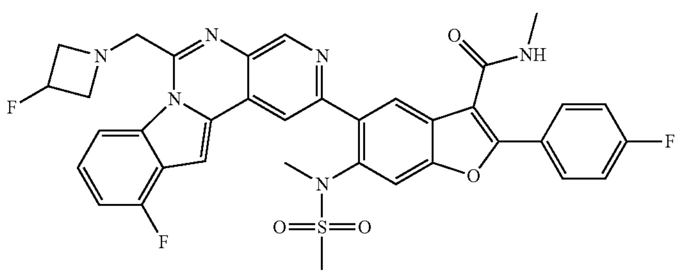 [SMILES: CNC(=O)c1c(-c2ccc(F)cc2)oc2cc(N(C)S(C)(=O)=O)c(-c3cc4c(cn3)nc(CN3CC(F)C3)n3c5cccc(F)c5cc43)cc12] | 699 |
| 114 | 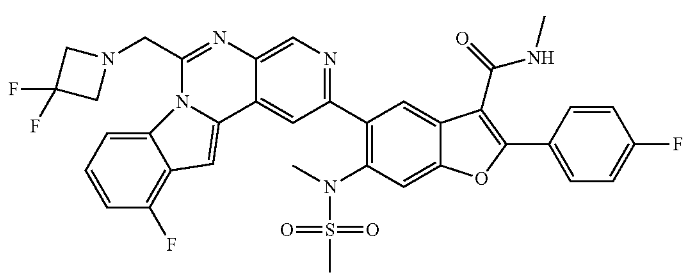 [SMILES: CNC(=O)c1c(-c2ccc(F)cc2)oc2cc(N(C)S(C)(=O)=O)c(-c3cc4c(cn3)nc(CN3CC(F)(F)C3)n3c5cccc(F)c5cc43)cc12] | 717 |
| 115 | 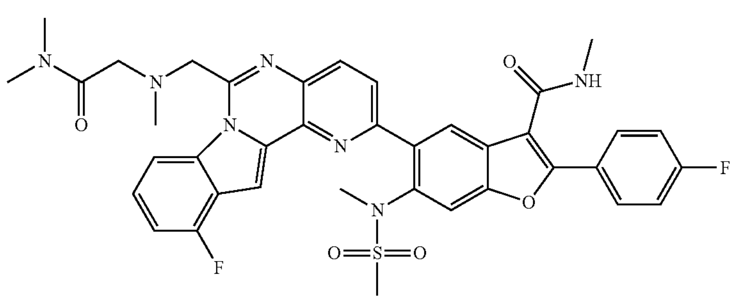 [SMILES: CNC(=O)c1c(-c2ccc(F)cc2)oc2cc(N(C)S(C)(=O)=O)c(-c3ccc4nc(CN(C)CC(=O)N(C)C)n5c6cccc(F)c6cc5c4n3)cc12] | 740 |
| 116 | 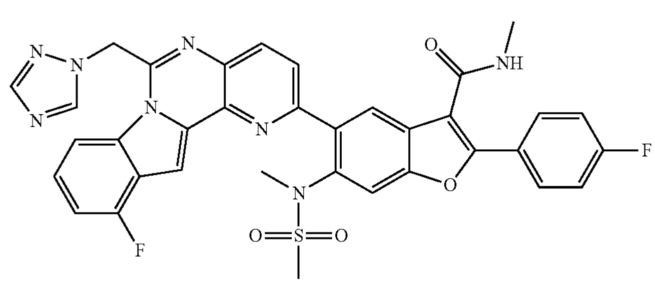 [SMILES: CNC(=O)c1c(-c2ccc(F)cc2)oc2cc(N(C)S(C)(=O)=O)c(-c3ccc4nc(Cn5cncn5)n5c6cccc(F)c6cc5c4n3)cc12] | 693 |

-continued

| Compound ID | Structure | MS (M + H)+ |
|---|---|---|
| 117 | 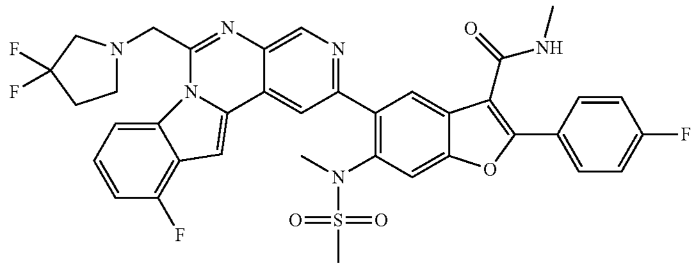 [SMILES: CNC(=O)c1c(-c2ccc(F)cc2)oc2cc(N(C)S(C)(=O)=O)c(-c3cc4c(cn3)nc(CN3CCC(F)(F)C3)n3c5cccc(F)c5cc43)cc12] | 731 |
| 118 | 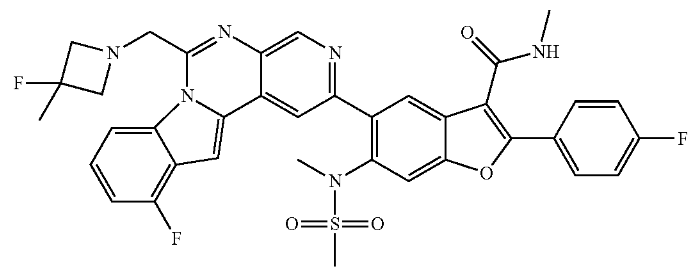 [SMILES: CNC(=O)c1c(-c2ccc(F)cc2)oc2cc(N(C)S(C)(=O)=O)c(-c3cc4c(cn3)nc(CN3CC(C)(F)C3)n3c5cccc(F)c5cc43)cc12] | 713 |
| 119 | 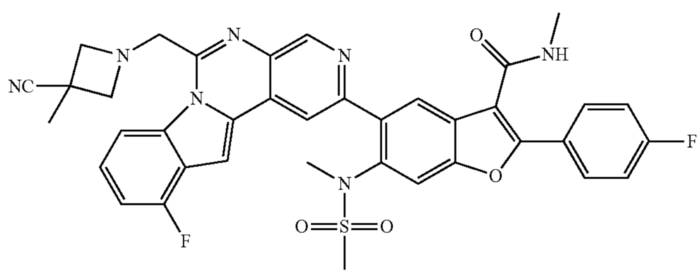 | 719 |
| 120 | 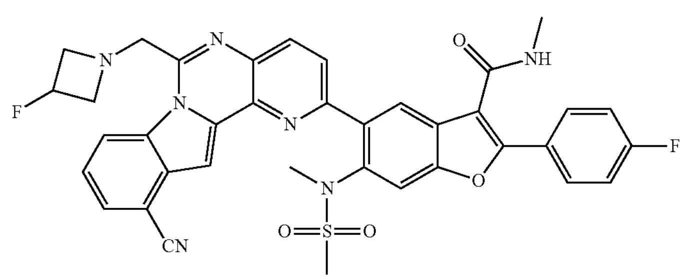 | 706 |
| 121 | 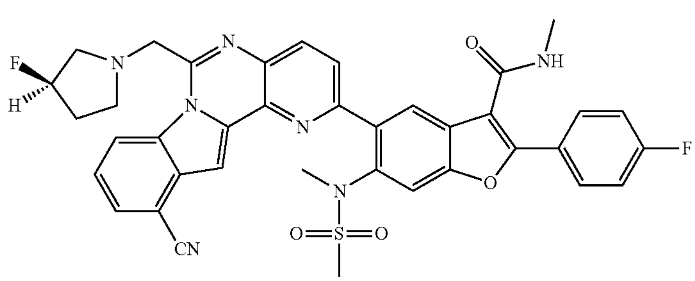 [SMILES: CNC(=O)c1c(-c2ccc(F)cc2)oc2cc(N(C)S(C)(=O)=O)c(-c3ccc4nc(CN5CC[C@@H](F)C5)n5c6cccc(C#N)c6cc5c4n3)cc12] | 720 |

| Compound ID | Structure | MS (M + H)+ |
|---|---|---|
| 122 | 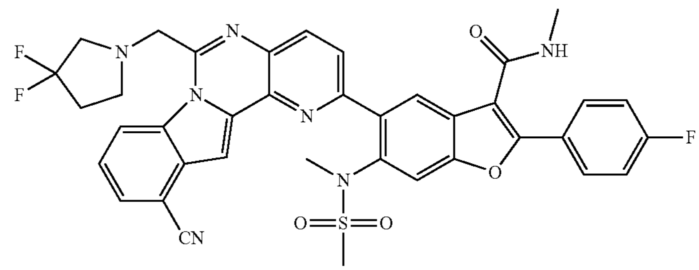 [SMILES: CNC(=O)c1c(-c2ccc(F)cc2)oc2cc(N(C)S(C)(=O)=O)c(-c3ccc4nc(CN5CCC(F)(F)C5)n5c6cccc(C#N)c6cc5c4n3)cc12] | 738 |
| 123 | 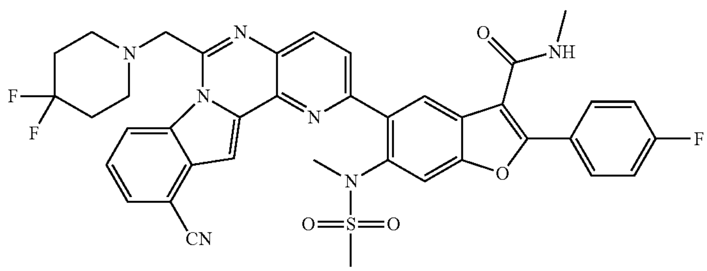 [SMILES: CNC(=O)c1c(-c2ccc(F)cc2)oc2cc(N(C)S(C)(=O)=O)c(-c3ccc4nc(CN5CCC(F)(F)CC5)n5c6cccc(C#N)c6cc5c4n3)cc12] | 752 |
| 124 | 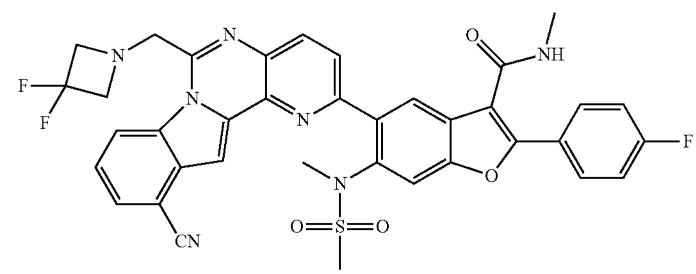 | 724 |
| 125 | 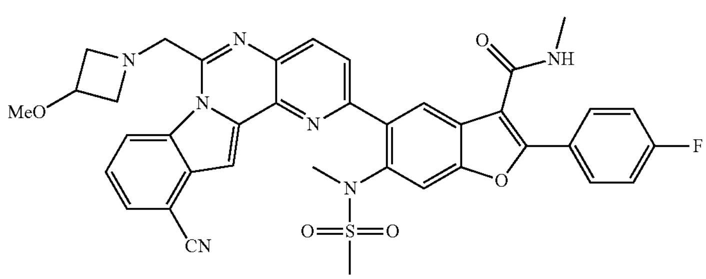 | 718 |
| 126 | 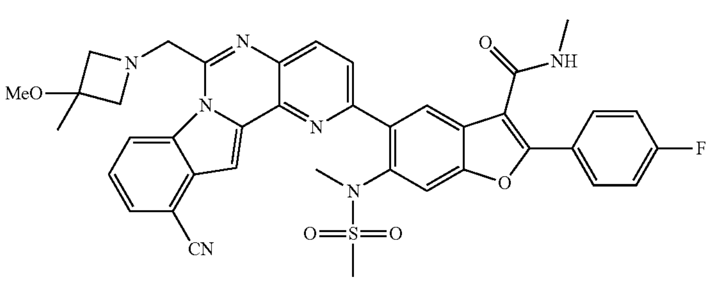 [SMILES: CNC(=O)c1c(-c2ccc(F)cc2)oc2cc(N(C)S(C)(=O)=O)c(-c3ccc4nc(CN5CC(C)(OC)C5)n5c6cccc(C#N)c6cc5c4n3)cc12] | 732 |

US 9,493,461 B2

165                                                         166
-continued

| Compound ID | Structure | MS (M + H)+ |
|---|---|---|
| 127 | 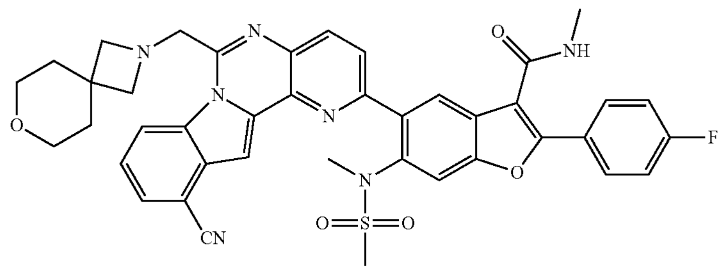 [SMILES: CNC(=O)c1c(-c2ccc(F)cc2)oc2cc(N(C)S(C)(=O)=O)c(-c3ccc4nc(CN5CC6(CCOCC6)C5)n5c6cccc(C#N)c6cc5c4n3)cc12] | 758 |
| 128 | 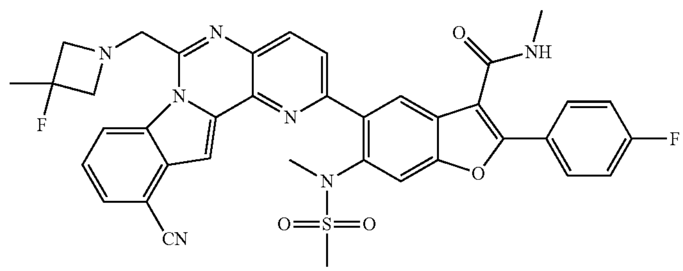 [SMILES: CNC(=O)c1c(-c2ccc(F)cc2)oc2cc(N(C)S(C)(=O)=O)c(-c3ccc4nc(CN5CC(C)(F)C5)n5c6cccc(C#N)c6cc5c4n3)cc12] | 720 |
| 129 | 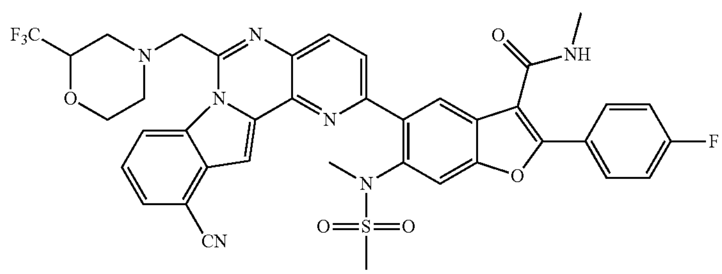 [SMILES: CNC(=O)c1c(-c2ccc(F)cc2)oc2cc(N(C)S(C)(=O)=O)c(-c3ccc4nc(CN5CCOC(C(F)(F)F)C5)n5c6cccc(C#N)c6cc5c4n3)cc12] | 786 |
| 130 | 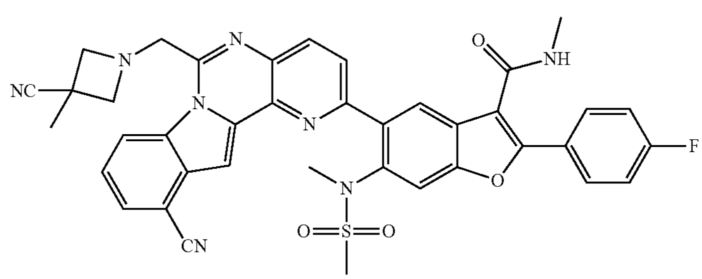 | 727 |
| 131 | 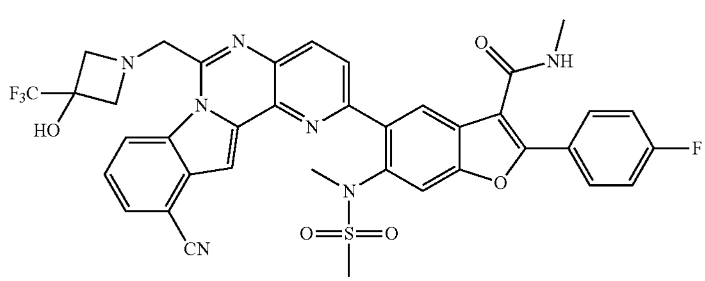 [SMILES: CNC(=O)c1c(-c2ccc(F)cc2)oc2cc(N(C)S(C)(=O)=O)c(-c3ccc4nc(CN5CC(O)(C(F)(F)F)C5)n5c6cccc(C#N)c6cc5c4n3)cc12] | 772 |

-continued
| Compound ID | Structure | MS (M + H)+ |
|---|---|---|
| 132 | 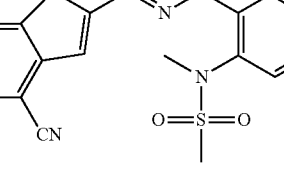 | 732 |
| 133 | 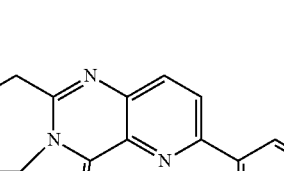 | 732 |
| 134 | 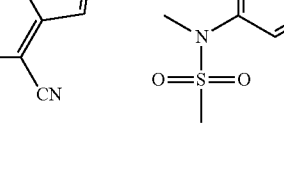 | 718 |
| 135 | 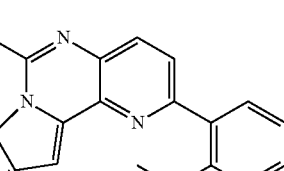 | 720 |
| 136 | 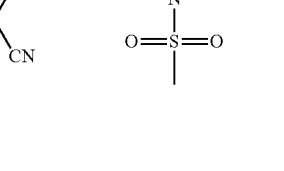 | 770 |

-continued

| Compound ID | Structure | MS (M + H)+ |
|---|---|---|
| 137 | 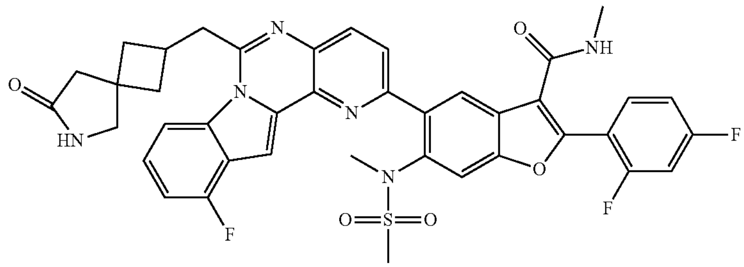 [SMILES: CNC(=O)c1c(-c2ccc(F)cc2F)oc2cc(N(C)S(C)(=O)=O)c(-c3ccc4nc(CC5CC6(CNC(=O)C6)C5)n5c6cccc(F)c6cc5c4n3)cc12] | 768 |
| 138 | 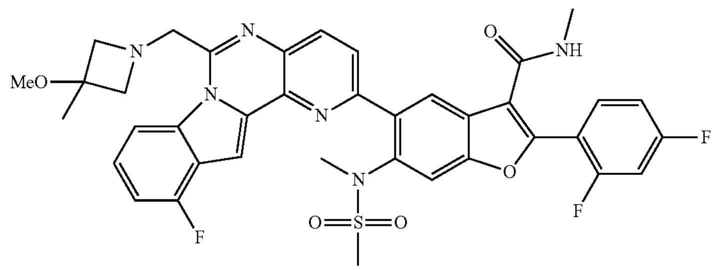 [SMILES: CNC(=O)c1c(-c2ccc(F)cc2F)oc2cc(N(C)S(C)(=O)=O)c(-c3ccc4nc(CN5CC(C)(OC)C5)n5c6cccc(F)c6cc5c4n3)cc12] | 743 |
| 139 | 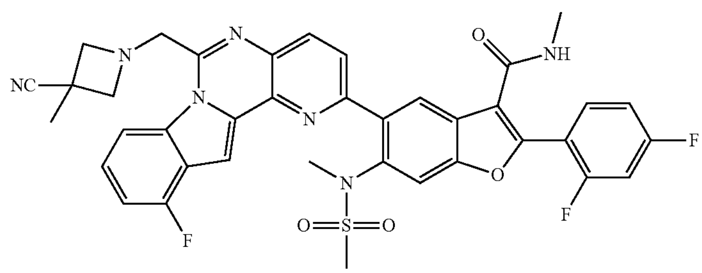 [SMILES: CNC(=O)c1c(-c2ccc(F)cc2F)oc2cc(N(C)S(C)(=O)=O)c(-c3ccc4nc(CN5CC(C)(C#N)C5)n5c6cccc(F)c6cc5c4n3)cc12] | 738 |
| 140 | 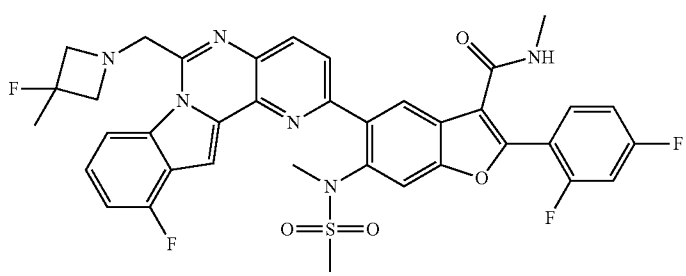 [SMILES: CNC(=O)c1c(-c2ccc(F)cc2F)oc2cc(N(C)S(C)(=O)=O)c(-c3ccc4nc(CN5CC(C)(F)C5)n5c6cccc(F)c6cc5c4n3)cc12] | 731 |
| 141 | 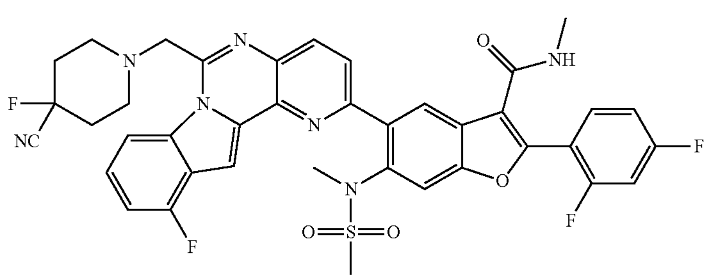 [SMILES: CNC(=O)c1c(-c2ccc(F)cc2F)oc2cc(N(C)S(C)(=O)=O)c(-c3ccc4nc(CN5CCC(F)(C#N)CC5)n5c6cccc(F)c6cc5c4n3)cc12] | 770 |

| Compound ID | Structure | MS (M + H)+ |
| --- | --- | --- |
| 142 | 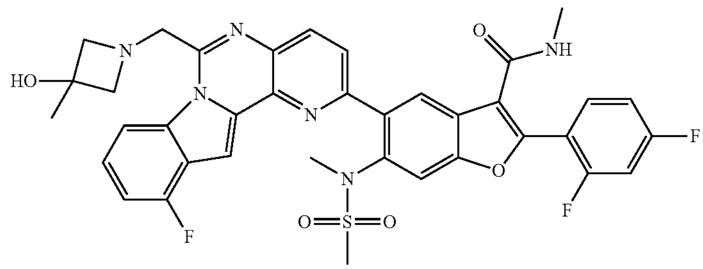 | 729 |
| 143 | 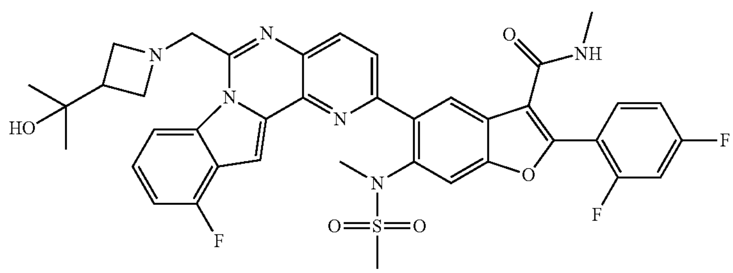 [SMILES: CNC(=O)c1c(-c2ccc(F)cc2F)oc2cc(N(C)S(C)(=O)=O)c(-c3ccc4nc(CN5CC(C(C)(C)O)C5)n5c6cccc(F)c6cc5c4n3)cc12] | 757 |
| 144 | 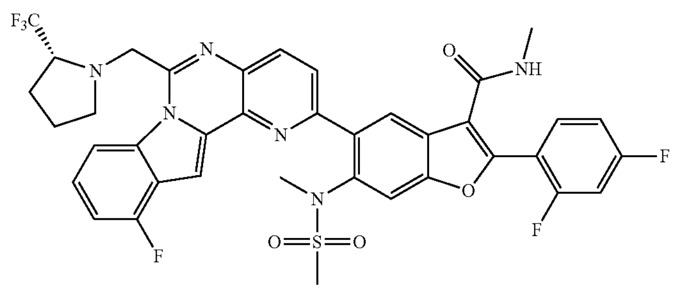 [SMILES: CNC(=O)c1c(-c2ccc(F)cc2F)oc2cc(N(C)S(C)(=O)=O)c(-c3ccc4nc(CN5CCC[C@@H]5C(F)(F)F)n5c6cccc(F)c6cc5c4n3)cc12] | 781 |
| 145 | 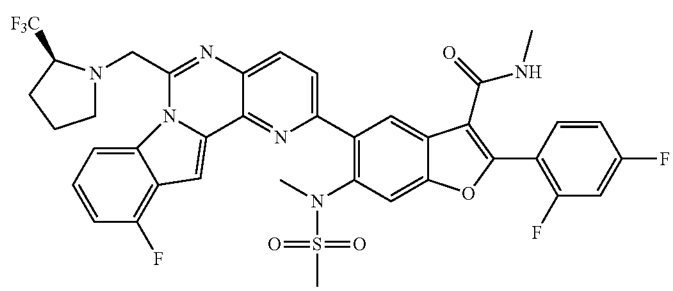 [SMILES: CNC(=O)c1c(-c2ccc(F)cc2F)oc2cc(N(C)S(C)(=O)=O)c(-c3ccc4nc(CN5CCC[C@H]5C(F)(F)F)n5c6cccc(F)c6cc5c4n3)cc12] | 781 |
| 146 | 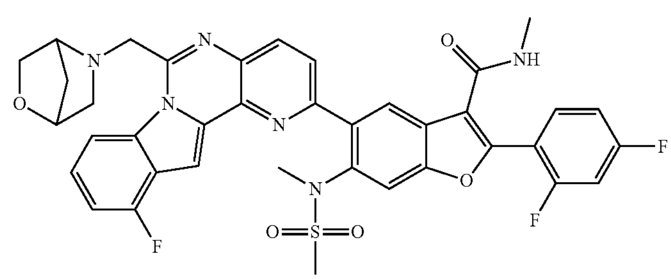 [SMILES: CNC(=O)c1c(-c2ccc(F)cc2F)oc2cc(N(C)S(C)(=O)=O)c(-c3ccc4nc(CN5CC6CC5CO6)n5c6cccc(F)c6cc5c4n3)cc12] | 741 |

| Compound ID | Structure | MS (M + H)+ |
| --- | --- | --- |
| 147 | 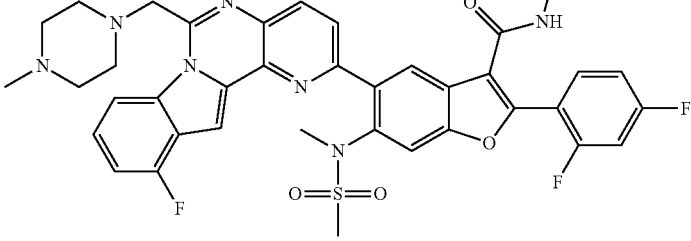 | 742 |
| 148 | 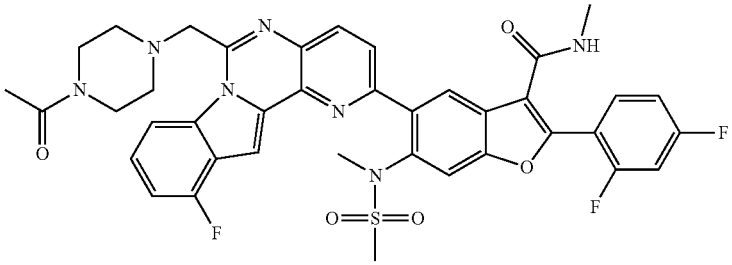 [SMILES: CNC(=O)c1c(-c2ccc(F)cc2F)oc2cc(N(C)S(C)(=O)=O)c(-c3ccc4nc(CN5CCN(C(C)=O)CC5)n5c6cccc(F)c6cc5c4n3)cc12] | 770 |
| 149 | 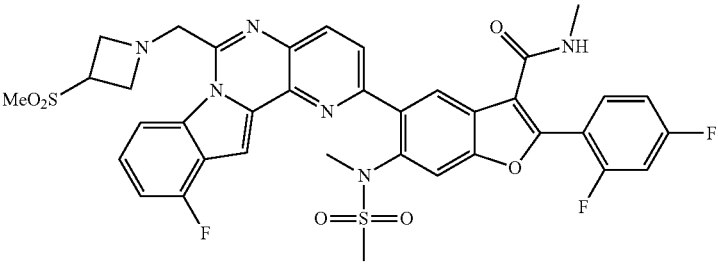 [SMILES: CNC(=O)c1c(-c2ccc(F)cc2F)oc2cc(N(C)S(C)(=O)=O)c(-c3ccc4nc(CN5CC(S(C)(=O)=O)C5)n5c6cccc(F)c6cc5c4n3)cc12] | 777 |
| 150 | 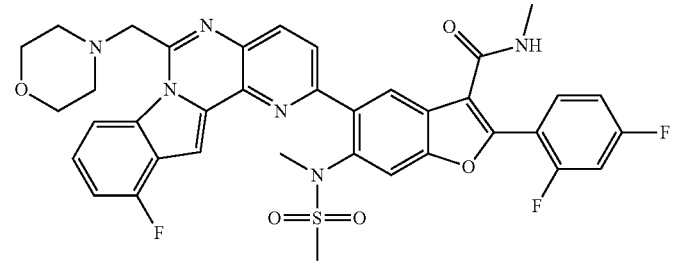 [SMILES: CNC(=O)c1c(-c2ccc(F)cc2F)oc2cc(N(C)S(C)(=O)=O)c(-c3ccc4nc(CN5CCOCC5)n5c6cccc(F)c6cc5c4n3)cc12] | 729 |
| 151 | 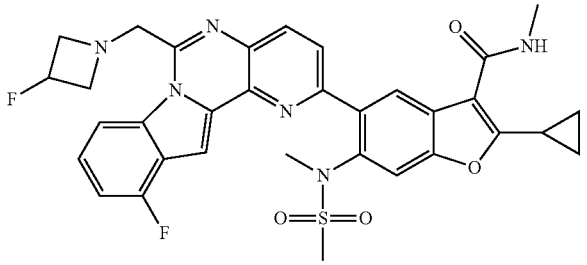 [SMILES: CNC(=O)c1c(C2CC2)oc2cc(N(C)S(C)(=O)=O)c(-c3ccc4nc(CN5CC(F)C5)n5c6cccc(F)c6cc5c4n3)cc12] | 645 |

Example 152

Measuring Compound Inhibitory Potency

Measurement of inhibition by compounds was performed using the HCV replicon system. Several different replicons encoding different HCV genotypes or mutations were used. In addition, potency measurements were made using different formats of the replicon assay, including different ways of measurements and different plating formats. See Jan M. Vrolijk et al., *A replicons-based bioassay for the measurement of interferons in patients with chronic hepatitis C*, 110

J. Virological Methods 201 (2003); Steven S. Carroll et al., *Inhibition of Hepatitis C Virus RNA Replication by 2'-Modified Nucleoside Analogs*, 278(14) J. Biological Chemistry 11979 (2003). However, the underlying principles are common to all of these determinations, and are outlined below.

Stable neomycin phosphotransferase encoding replicons-harboring cell lines were used, so all cell lines were maintained under G418 selection prior to the assay. Potency was determined using a cell ELISA assay with an antibody to the replicons encoded NS3/4a protease. See Caterina Trozzi et al., *In Vitro Selection and Characterization of Hepatitis C Virus Serine Protease Variants Resistant to an Active-Site Peptide Inhibitor*, 77(6) J. Virol. 3669 (2003). To initiate an assay, replicon cells were plated in the presence of a dilution series of test compound in the absence of G418. Typically, the assays were performed in a 96-well plate formate for manual operation, or a 384-well plate format for automated assay. Replicon cells and compound were incubated for 96 hours. At the end of the assay, cells were washed free of media and compound, and the cells were then lysed. RNA was quantified indirectly through detection of replicon-encoded NS3/4A protein levels, through an ELISA-based assay with an antibody specific for NS3/4A. $IC_{50}$ determinations were calculated as a percentage of a DMSO control by fitting the data to a four-parameter fit function and the data obtained is provided in the table below.

Data for selected compounds of the present invention was obtained for genotypes 1a and 1b using this method and is provided in the table below:

TABLE 1

| Compound No. | 1a $IC_{50}$ (nM) | 1b $IC_{50}$ (nM) |
| --- | --- | --- |
| 1 | 6.558 | 4.006 |
| 2 | 2.835 | 6.908 |
| 3 | 3.382 | 4.118 |
| 4 | 2.044 | 2.803 |
| 5 | 3.699 | 7.399 |
| 6 | 3.198 | 5.081 |
| 7 | 1.486 | 3.6 |
| 8 | 5.71 | 5.818 |
| 9 | 1.157 | 1.992 |
| 10 | 2.01 | 3.241 |
| 11 | 2.026 | 2.259 |
| 12 | 2.111 | 2.357 |
| 13 | 297.7 | 99.46 |
| 14 | 1.75 | 3.723 |
| 15 | 3.038 | 5.267 |
| 16 | 0.9543 | 2.223 |
| 17 | 1.269 | 1.779 |
| 18 | 1.06 | 1.858 |
| 19 | 2.792 | 5.642 |
| 20 | 1.591 | 3.332 |
| 21 | 7.606 | 8.736 |
| 22 | 4.342 | 3.417 |
| 23 | 1.848 | 2.977 |
| 24 | 2.729 | 1.902 |
| 25 | 245 | 144.8 |
| 28 | 15.22 | 5.375 |
| 29 | 2.206 | 3.632 |
| 30 | 2.414 | 2.322 |
| 31 | 2.951 | 4.693 |
| 32 | 18.64 | 8.23 |
| 33 | 2.347 | 2.548 |
| 34 | 2.433 | 4.661 |
| 35 | 2.251 | 4.536 |
| 36 | 2.49 | 3.209 |
| 37 | 5.261 | 7.262 |
| 38 | 6.379 | 14.7 |
| 39 | 6.367 | 6.076 |
| 40 | 3.914 | 4.421 |
| 41 | 2.091 | 2.57 |
| 42 | 17.25 | 13.09 |
| 44 | 3.223 | 3.453 |
| 45 | 4.433 | 4.292 |
| 46 | 7.756 | 11.35 |
| 47 | 9.666 | 11.18 |
| 48 | 2.82 | 3.045 |
| 49 | 2.781 | 4.876 |
| 50 | 18.14 | 19.77 |
| 51 | 39.07 | 31.99 |
| 52 | 259.6 | 120.3 |
| 53 | 7.793 | 6.367 |
| 54 | 2.142 | 4.862 |
| 54' | 4.165 | 4.242 |
| 55 | 1.547 | 2.008 |
| 56 | 5.262 | 5.318 |
| 57 | 2.664 | 3.113 |
| 58 | 1.683 | 2.761 |
| 59 | 1.995 | 2.156 |
| 60 | 2.778 | 2.773 |
| 61 | 2.604 | 3.013 |
| 62 | 8.669 | 12.16 |
| 63 | 1.551 | 2.758 |
| 64 | 11.81 | 11.84 |
| 65 | 2.521 | 2.415 |
| 66 | 5.955 | 9.231 |
| 67 | 1.563 | 2.72 |
| 69 | 9.692 | 6.038 |
| 70 | 35.22 | 26.77 |
| 71 | 2.985 | 3.44 |
| 72 | 22.78 | 15.62 |
| 74 | 1.213 | 3.074 |
| 75 | 1.033 | 2.777 |
| 76 | 4.134 | 3.778 |
| 77 | 5.259 | 5.611 |
| 78 | 2.798 | 3.343 |
| 79 | 2.37 | 3.986 |
| 80 | 2.646 | 2.461 |
| 81 | 3.239 | 3.279 |
| 82 | 2.742 | 2.45 |
| 83 | 1.329 | 1.307 |
| 84 | 1.345 | 1.955 |
| 85 | 1.76 | 2.34 |
| 86 | 1.99 | 2.66 |
| 87 | 1.285 | 1.256 |
| 88 | 4.092 | 4.218 |
| 89 | 3.406 | 3.452 |
| 90 | 3.619 | 3.659 |
| 91 | 3.584 | 6.545 |
| 92 | 14.63 | 23.69 |
| 93 | 4.189 | 7.775 |
| 94 | 4.325 | 6.976 |
| 95 | 4.554 | 9.116 |
| 96 | 7.764 | 11.18 |
| 97 | 2.978 | 3.488 |
| 98 | 4.793 | 4.164 |
| 99 | 3.317 | 5.763 |
| 100 | 2.599 | 4.464 |
| 101 | 3.129 | 4.235 |
| 102 | 7.026 | 11.81 |
| 103 | 2.047 | 5.274 |
| 104 | 2.307 | 5.227 |
| 105 | 2.598 | 3.792 |
| 106 | 7.245 | 8.199 |
| 107 | 3.329 | 3.035 |
| 108 | 6.081 | 8.478 |
| 109 | 8.104 | 11.22 |
| 110 | 4.044 | 5.511 |
| 111 | 4.147 | 7.789 |
| 112 | 2.023 | 3.454 |
| 115 | 2.186 | 4.929 |
| 116 | 1.875 | 1.696 |
| 117 | 3.493 | 5.014 |
| 118 | 2.675 | 4.236 |
| 119 | 1.738 | 3.588 |
| 120 | 1.671 | 2.007 |
| 121 | 2.949 | 3.249 |
| 122 | 2.435 | 3.465 |

TABLE 1-continued

| Compound No. | 1a IC$_{50}$ (nM) | 1b IC$_{50}$ (nM) |
|---|---|---|
| 123 | 6.906 | 5.797 |
| 124 | 1.886 | 1.757 |
| 125 | 2.316 | 3.211 |
| 126 | 2.244 | 2.719 |
| 127 | 1.5 | 2.567 |
| 128 | 2.299 | 2.981 |
| 129 | 5.68 | 6.951 |
| 130 | 1.219 | 1.387 |
| 131 | 4.089 | 4.229 |
| 132 | 2.827 | 3.503 |
| 133 | 2.981 | 3.561 |
| 134 | 2.6 | 2.016 |
| 135 | 2.707 | 3.656 |
| 136 | 6.602 | 10.55 |
| 137 | 6.67 | 5.041 |
| 138 | 4.332 | 4.594 |
| 139 | 2.789 | 3.157 |
| 140 | 2.951 | 4.314 |
| 141 | 5.48 | 5.986 |
| 142 | 3.051 | 2.849 |
| 143 | 5.17 | 6.206 |
| 144 | 13.31 | 14.63 |
| 145 | 19.98 | 12.15 |
| 146 | 3.375 | 3.384 |
| 147 | 3.481 | 3.989 |
| 148 | 2.519 | 3.175 |
| 149 | 3.385 | 2.493 |
| 151 | 2.662 | 3.426 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:
1. A compound having structural formula I:

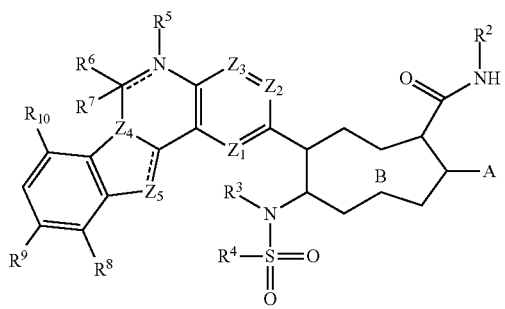

I or a pharmaceutically acceptable salt thereof,
wherein:
A is $C_3$-$C_6$ cycloalkyl,

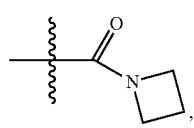

wherein the azetinidyl is substituted with 1 or 2 substituents selected from halo and $C_1$-$C_6$ alkyl;

or a 5-6 membered aromatic monocyclic ring with 0, 1, 2 or 3 heteroatom ring atoms independently selected from N and S, optionally substituted with 1 or 2 substituents independently selected from $C_1$-$C_6$ alkyl, $C_1$-$C_6$ alkoxy, $C_1$-$C_6$ haloalkyl, oxo, halo, and —O—$C_1$-$C_6$ haloalkyl;

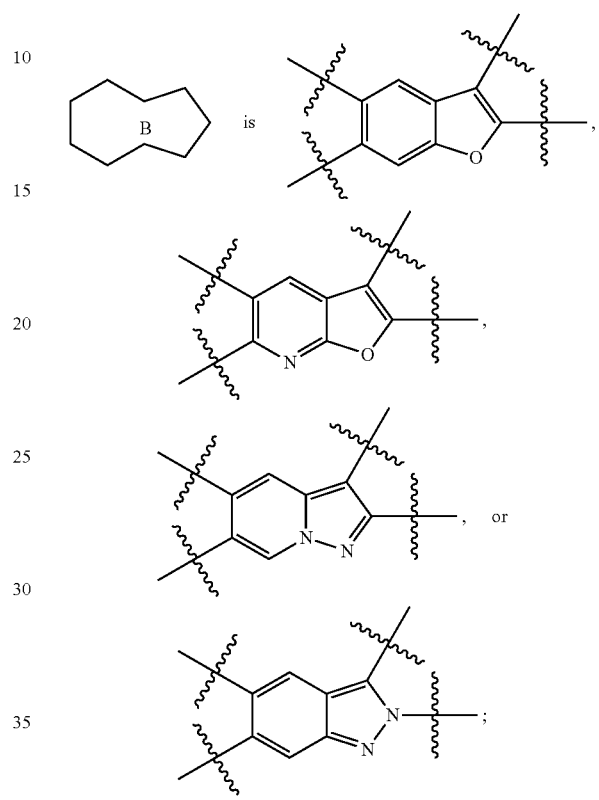

$Z_1$, $Z_2$, and $Z_3$ are independently CH or N wherein no more than one of $Z_1$, $Z_2$, and $Z_3$ is N;
$Z_4$ is N, $Z_5$ is CH, and the ===== attached to $Z_5$ is a double bond, or
$Z_4$ is CH, $Z_5$ is NH, and the ===== attached to $Z_5$ is a single bond;
$R^2$ is hydrogen, $C_1$-$C_6$ alkyl or —O—$C_1$-$C_6$ alkyl;
$R^3$ is hydrogen or $C_1$-$C_6$ alkyl;
$R^4$ is $C_1$-$C_6$ alkyl or —O—$C_1$-$C_6$ alkyl;
$R^5$ is hydrogen, $C_1$-$C_6$ alkyl, or —CH$_2$COOR$^a$, —SO$_2$CH$_3$;
$R^a$ is hydrogen or $C_1$-$C_6$ alkyl;
$R^6$ is hydrogen, $C_1$-$C_6$ alkyl, $C_1$-$C_6$ haloalkyl, $C_1$-$C_6$ hydroxyalkyl, alkyl-COOR$^a$, —CH$_2$SO$_2$CH$_3$, —CH$_2$NH$_2$, —CH$_2$N(CH$_3$)CH$_2$CON(CH$_3$)$_2$, —C$_0$-C$_6$ alkyl-(4- to 7-membered monocyclic heterocycloalkyl), alkyl-(6- to 9-membered bicyclic heterocycloalkyl), —CH$_2$-triazole, —CH$_7$PO(OCH$_2$CH$_3$)$_2$, or —NH$_2$;
wherein the 4- to 7-membered monocyclic heterocycloalkyl is optionally substituted with one or two substituents independently selected from oxo, F, $C_1$-$C_6$ alkyl, $C_1$-$C_6$ haloalkyl, $C_1$-$C_6$ hydroxyalkyl, $C_1$-$C_6$ alkoxy, —COCH$_3$, —OR$^a$, $C_3$-$C_6$ cycloalkyl, cyano and —SO$_2$CH$_3$;
$R^7$ is hydrogen or $C_1$-$C_6$ alkyl;
or $R^6$ and $R^7$ together form oxo or ether with the C to which they are attached form a $C_3$-$C_4$ cycloalkyl; and $R^8$ is hydrogen, halo, or cyano;
$R^9$ and $R^{10}$ are independently hydrogen or halo;
wherein when the ----- adjacent to $NR_5$ is a double bond, $R^5$ and $R^7$ are absent.

2. The compound of claim 1, wherein $R^2$ and $R^4$ are independently $C_1$-$C_6$ alkyl.

3. The compound of claim 2, wherein $R^2$, $R^3$ and $R^4$ are methyl.

4. The compound of claim 3, wherein two or three of $R^8$, $R^9$ and $R^{10}$ are hydrogen.

5. The compound of claim 4, wherein each halo is F.

6. The compound of claim 1, or a pharmaceutically acceptable salt thereof, having the formula:

(Ia)

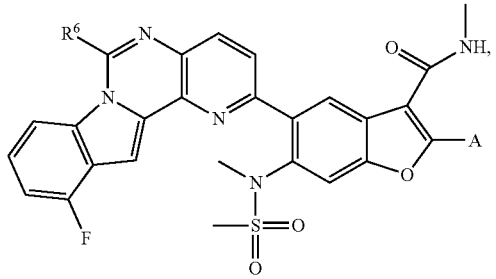

(Ib)

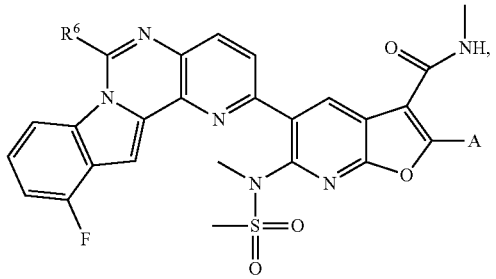

(Ic)

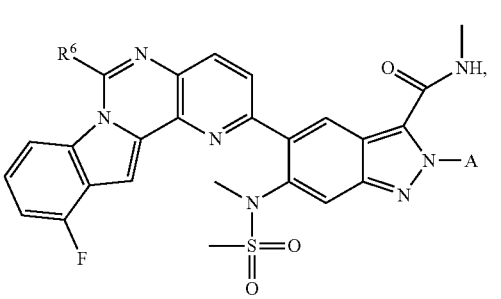

(Id)

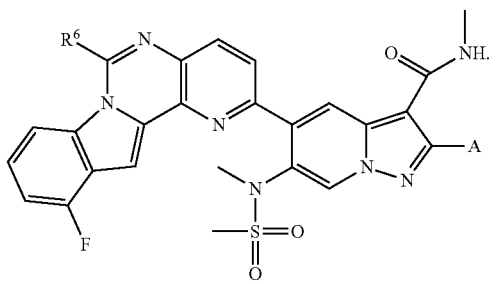

7. The compound of claim 4, wherein A is $C_3$-$C_6$ cycloalkyl, or a 5-6 membered aromatic monocyclic ring with 0, 1, 2 or 3 heteroatom ring atoms independently selected from N and S, optionally substituted with 1 or 2 substituents independently selected from $C_1$-$C_6$ alkyl, $C_1$-$C_6$ alkoxy, $C_1$-$C_6$ haloalkyl, oxo, halo, and —O—$C_1$-$C_6$ haloalkyl.

8. The compound of claim 7, wherein A is cyclopropyl,

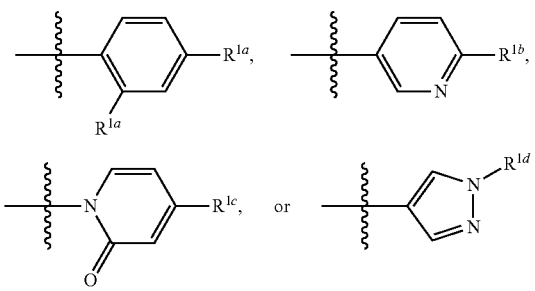

wherein each $R^{1a}$ is independently selected m o hydrogen, F, methyl, ethyl, and —OCHF$_2$; $R^{1b}$ is independently selected from hydrogen, F, methyl, ethyl, —CHF$_2$, —CF$_3$, —OCH$_3$, —OCHF$_2$, —OCH$_2$CF$_3$, and —OCHF$_2$; $R^{1c}$ is independently selected from hydrogen, and methyl; $R^{1d}$ is independently selected from hydrogen, methyl, and ethyl.

9. The compound of claim 8, wherein A is cyclopropyl,

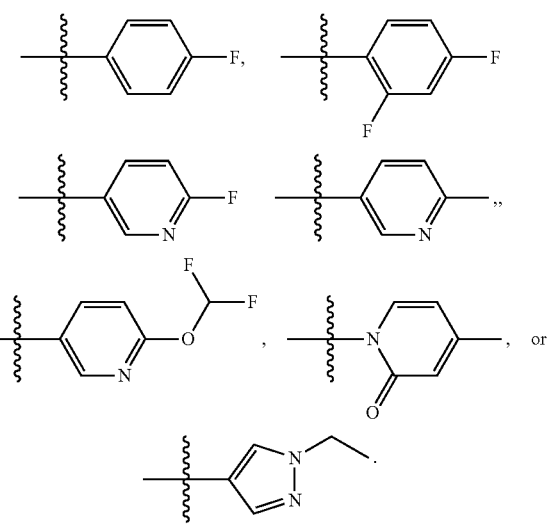

10. The compound of claim 4, wherein $R^b$ is hydrogen, —CH$_2$SO$_2$CH$_3$, —CH$_2$PO(OCH$_2$CH$_3$)$_2$,

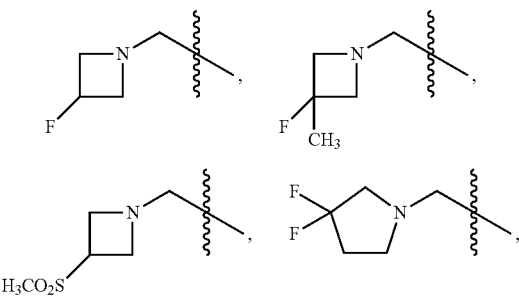

-continued
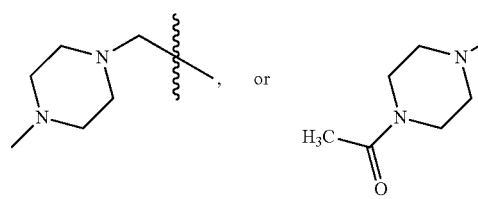
11. The compound of claim 4, wherein $R^6$ is
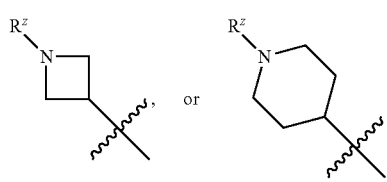
wherein $R^z$ is hydrogen, $C_1$-$C_6$ alkyl, $C_1$-$C_6$ haloalkyl, $C_1$-$C_6$ hydroxyalkyl, alkyl-COOH, or —$C_0$-$C_6$ alkyl-(3- to 7-membered monocyclic cycloalkyl).
12. The compound of claim 1 which is any one of
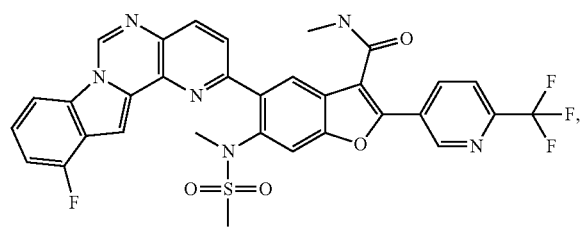
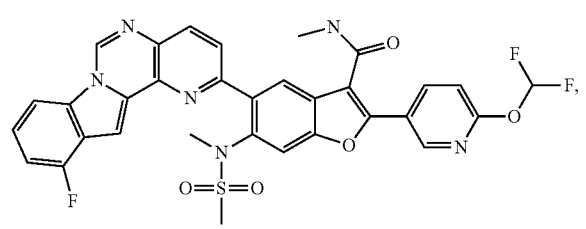
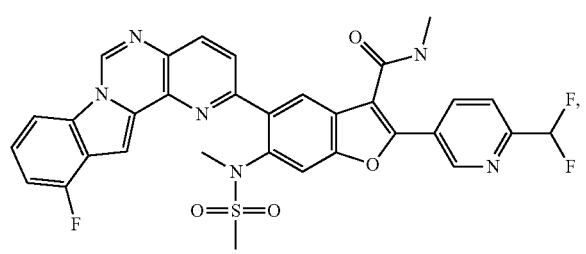
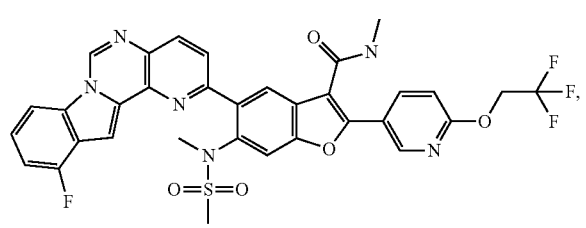
-continued
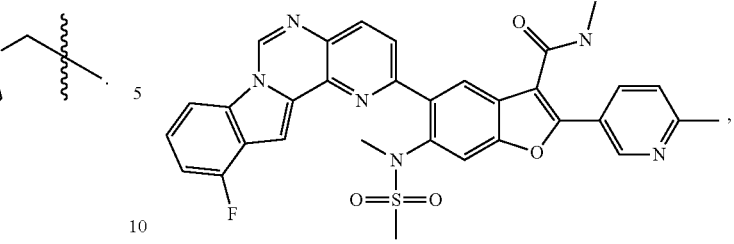
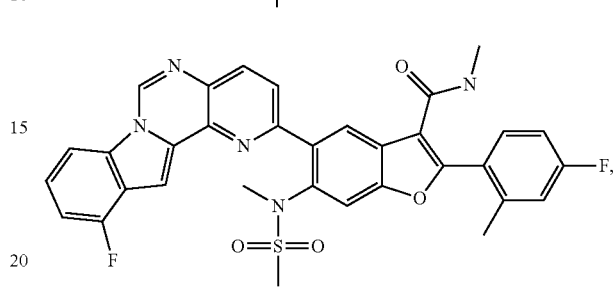
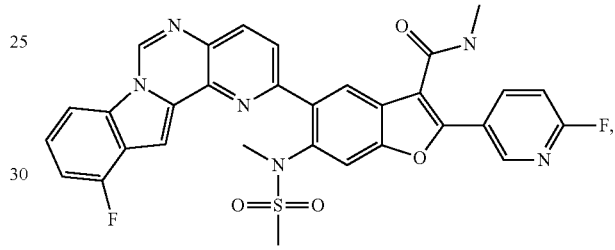
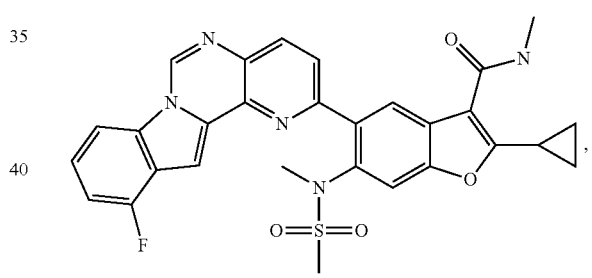
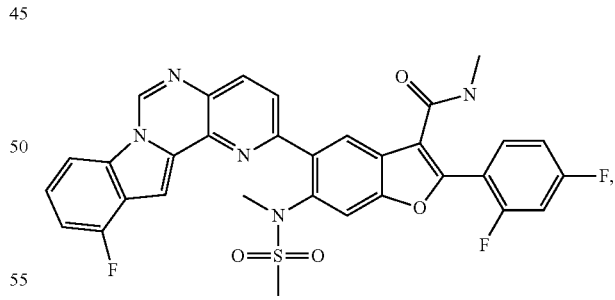
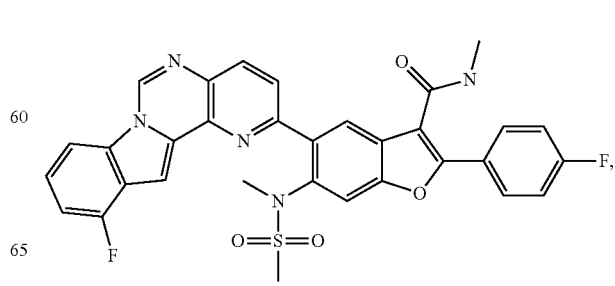

183
-continued
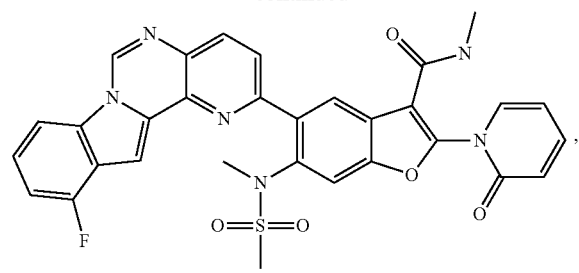
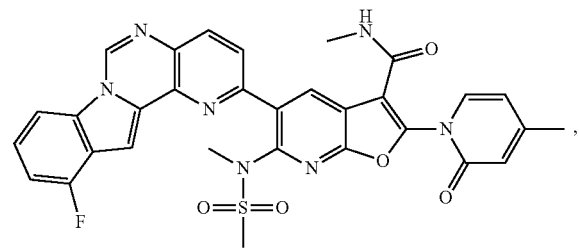
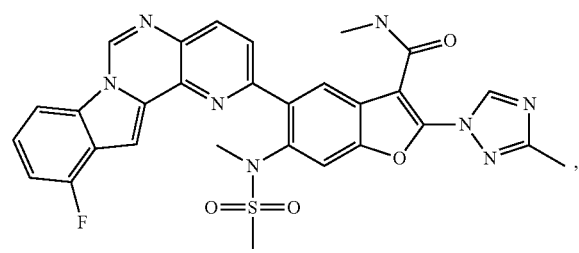
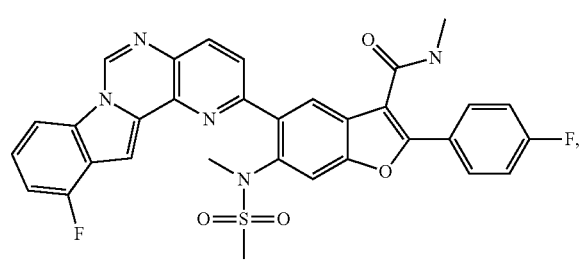
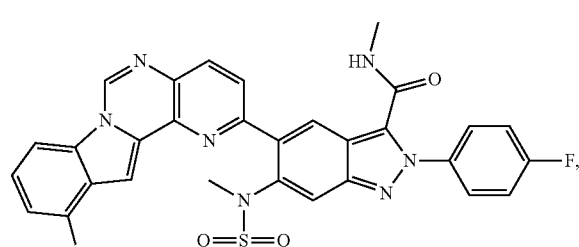
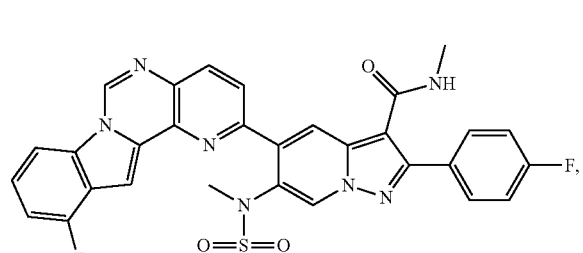
184
-continued
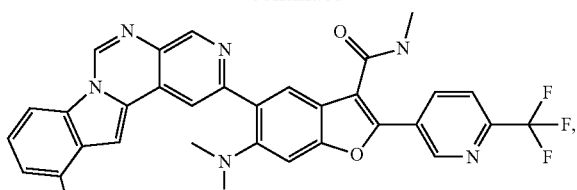
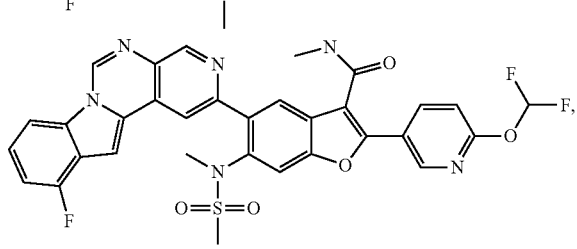
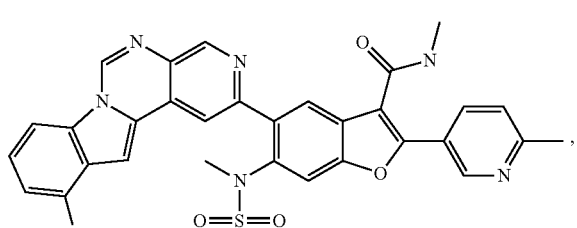
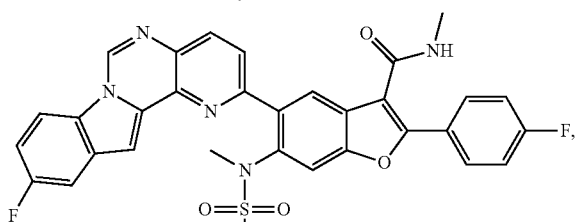
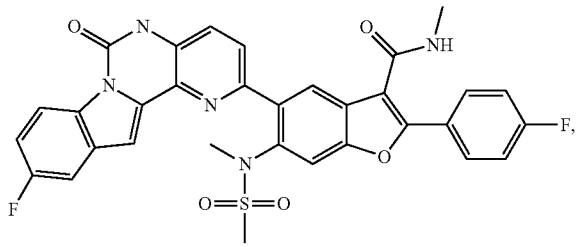
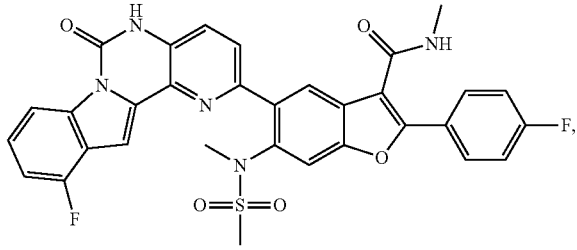
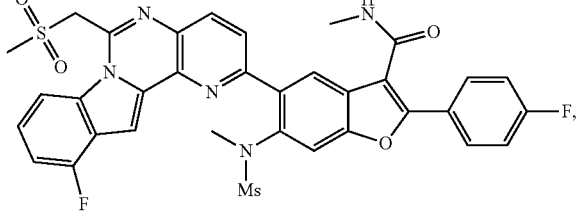

185
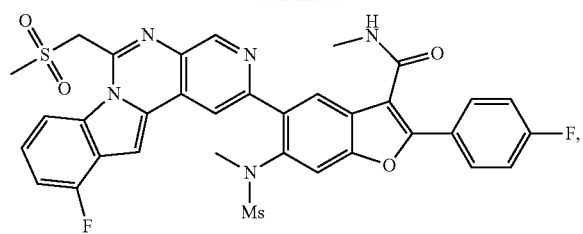
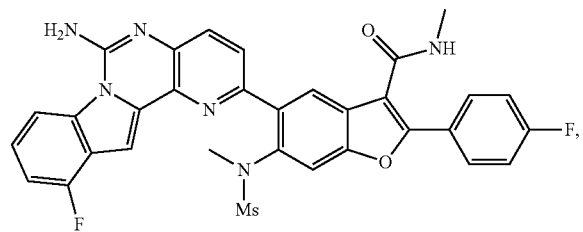
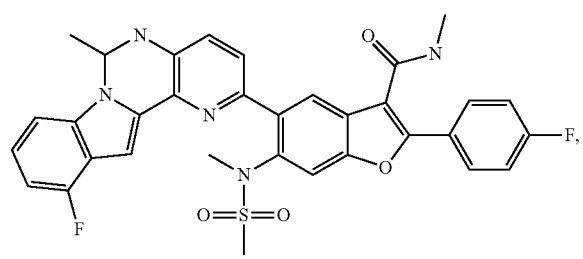
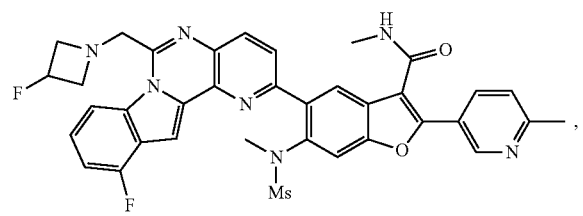
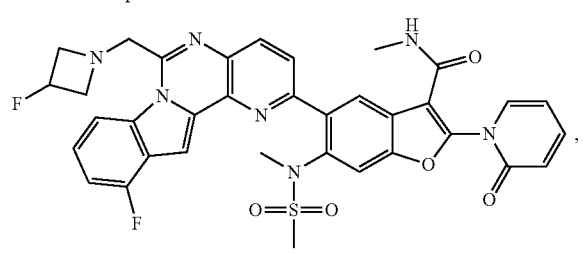
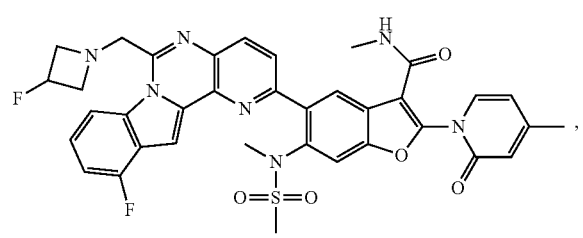
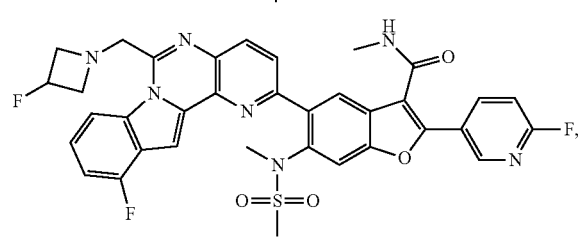
186
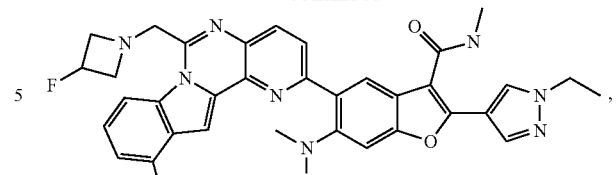
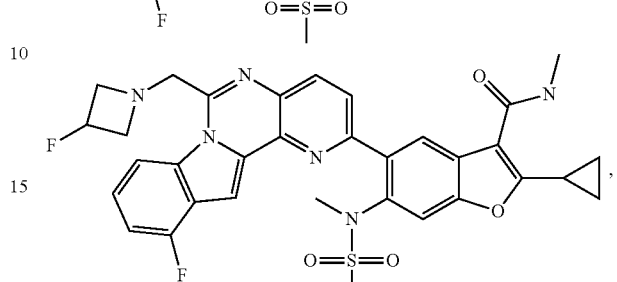
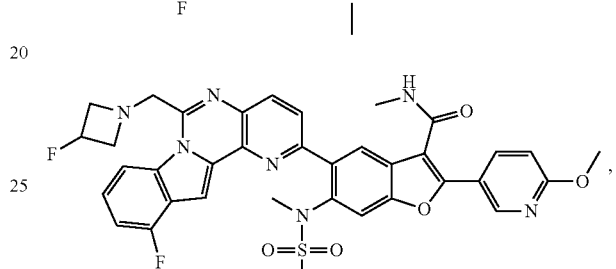
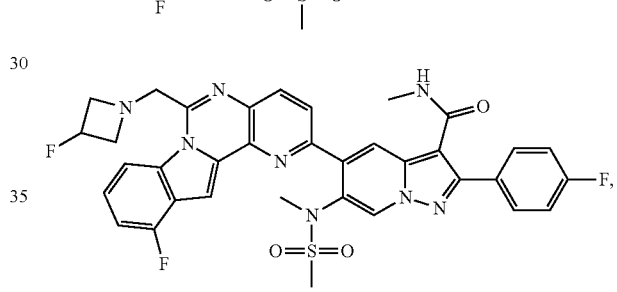
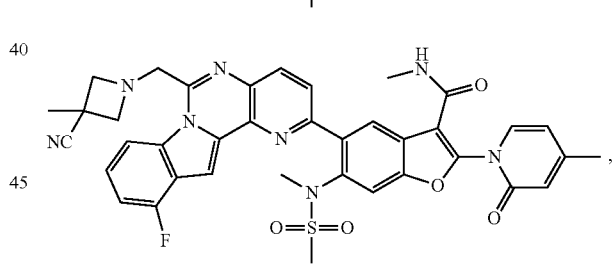
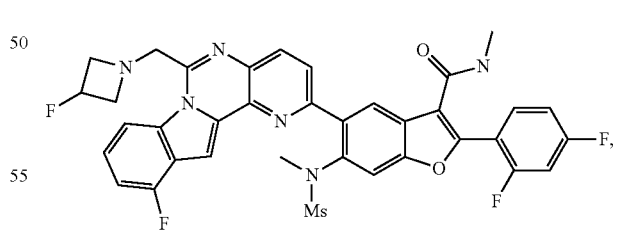
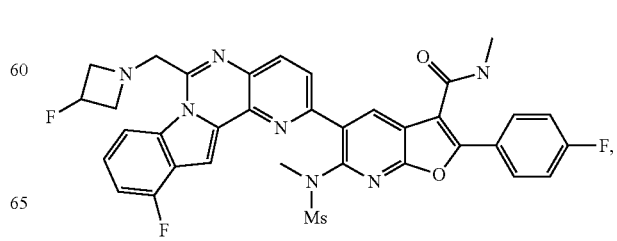

187
-continued
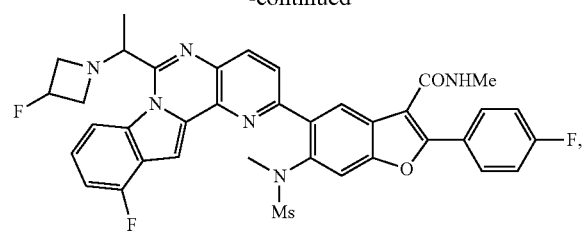
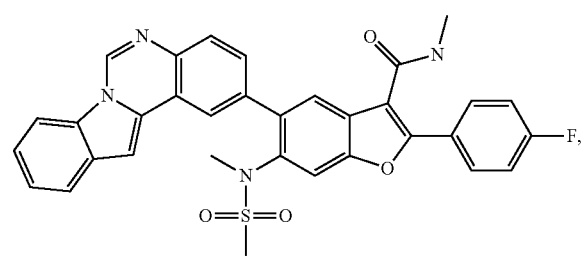
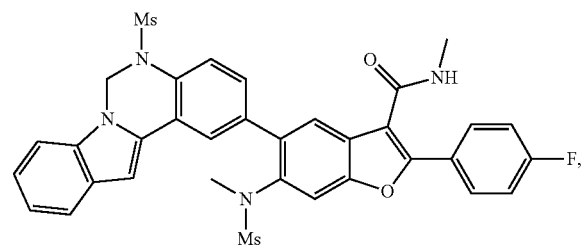
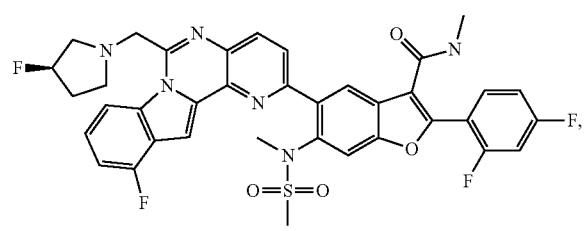
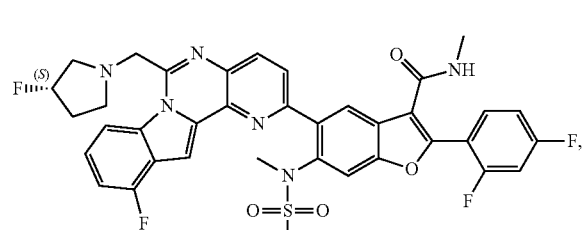
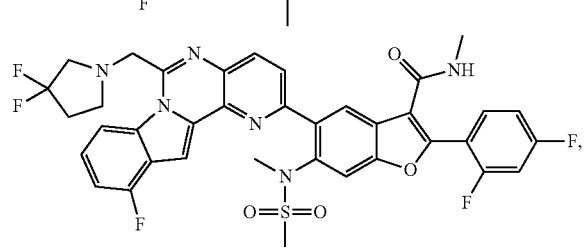
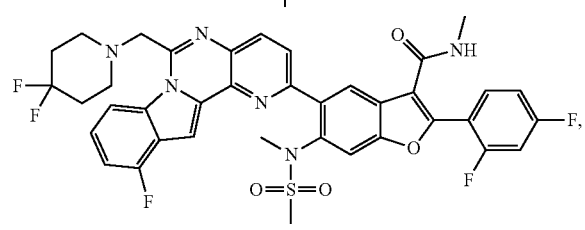
188
-continued
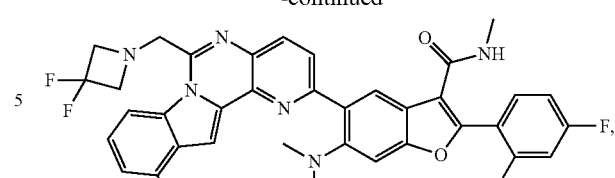
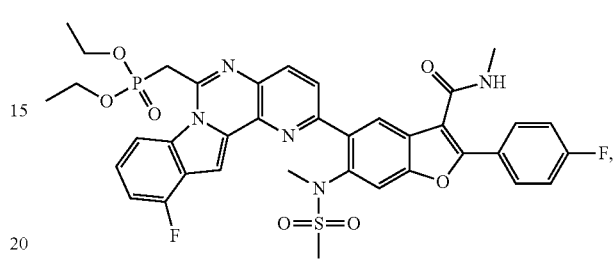
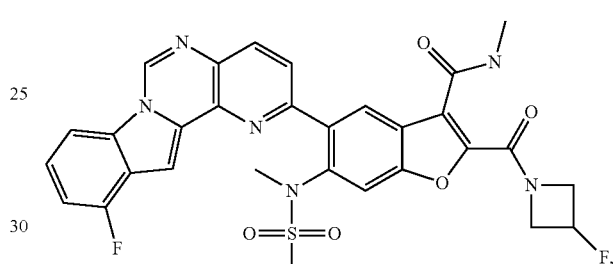
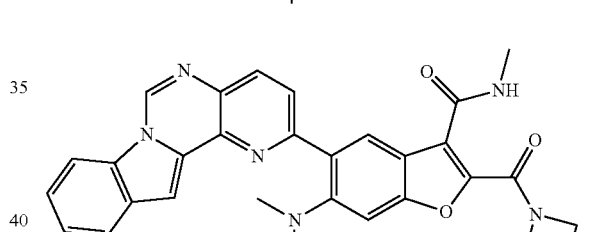
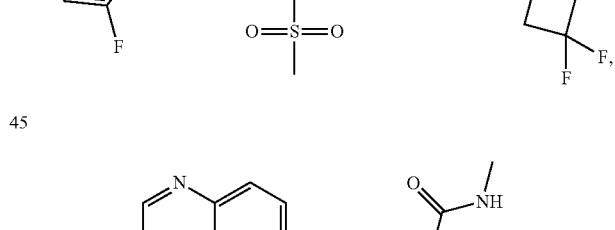
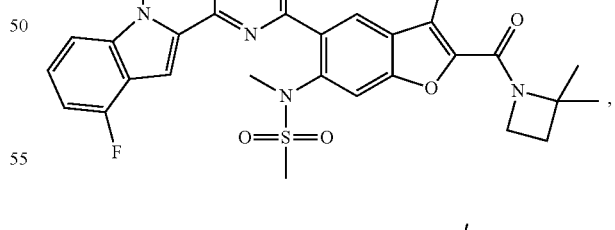
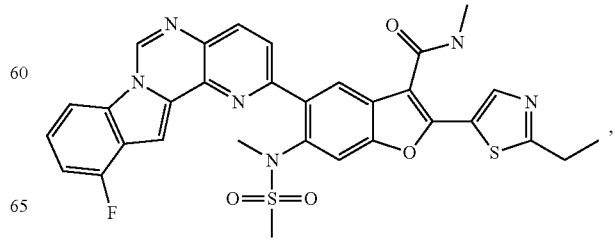

189
-continued
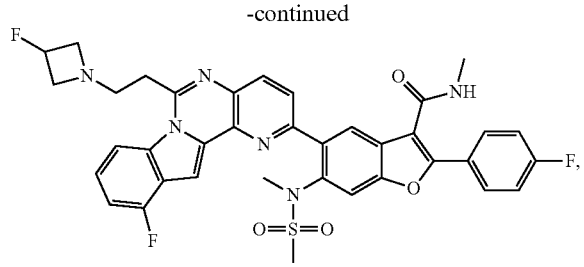
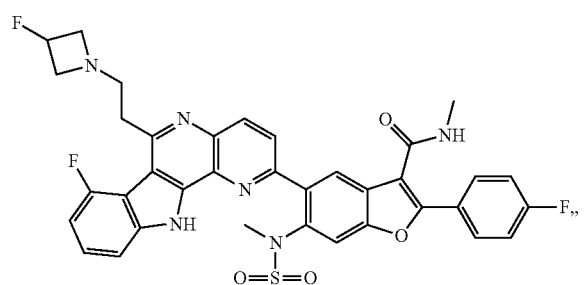
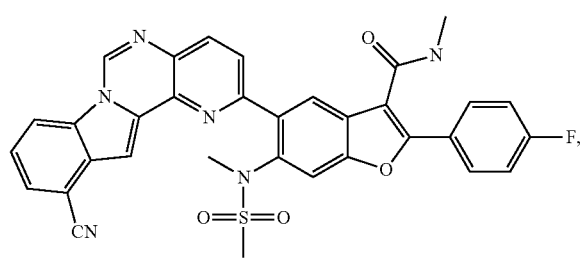
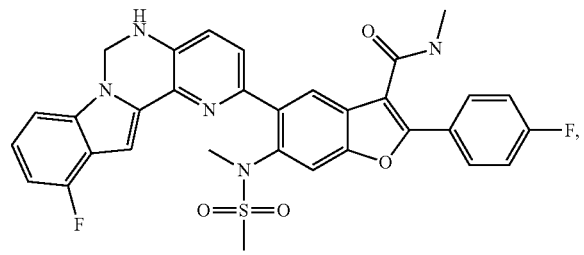
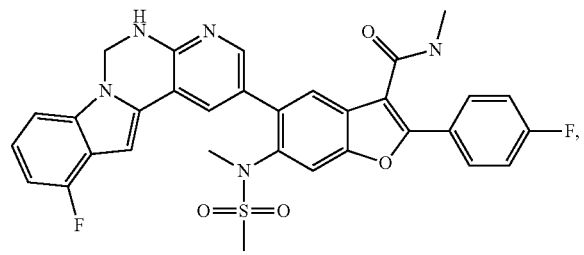
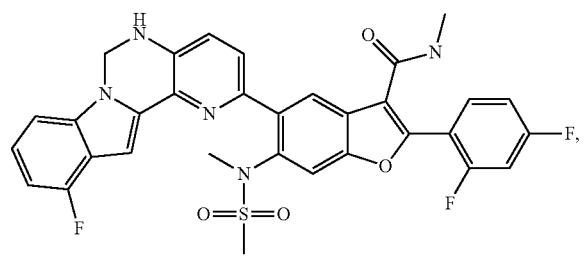
190
-continued
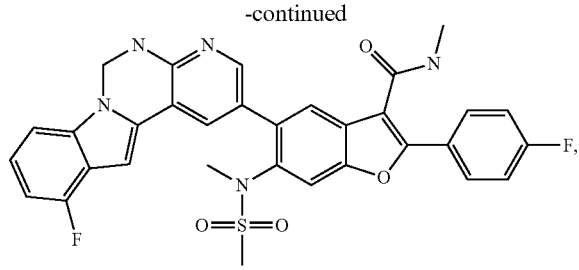
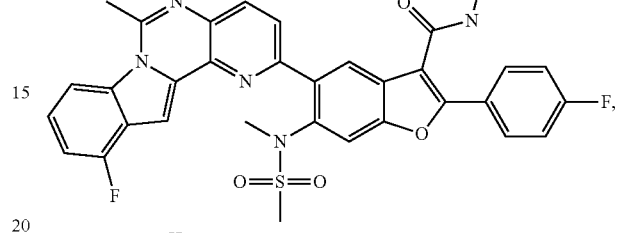
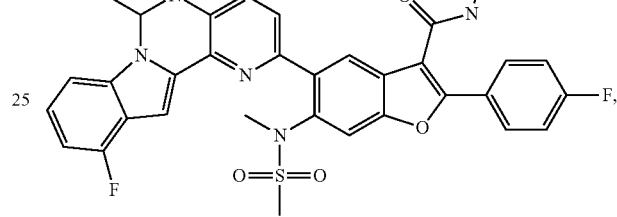
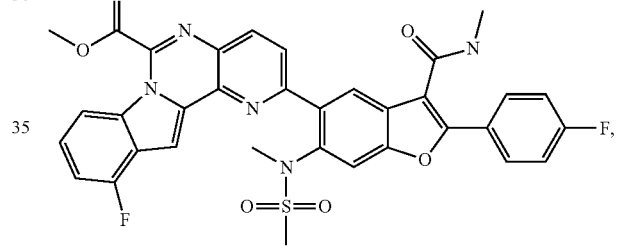
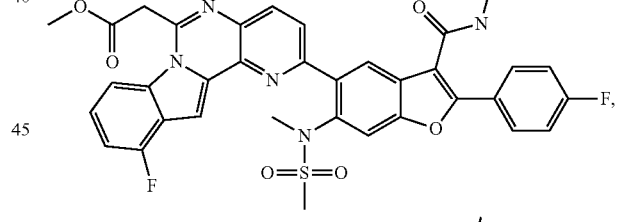
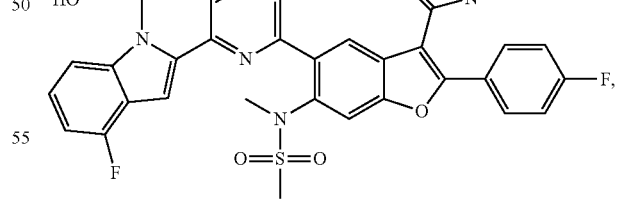
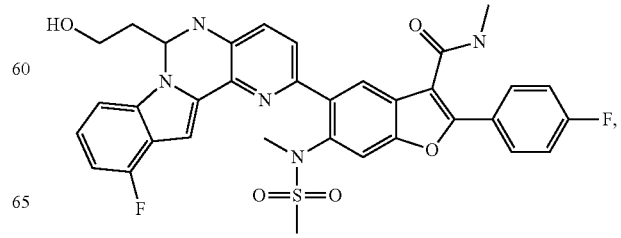

191
-continued
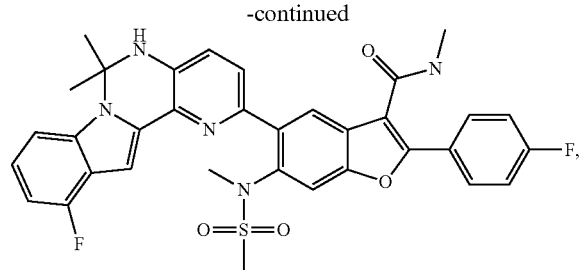
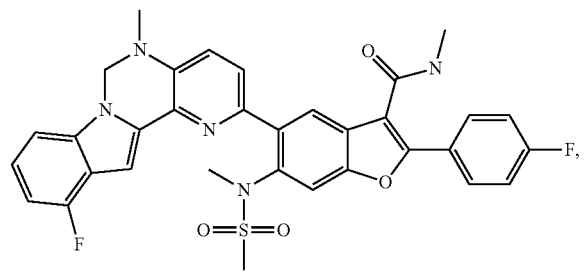
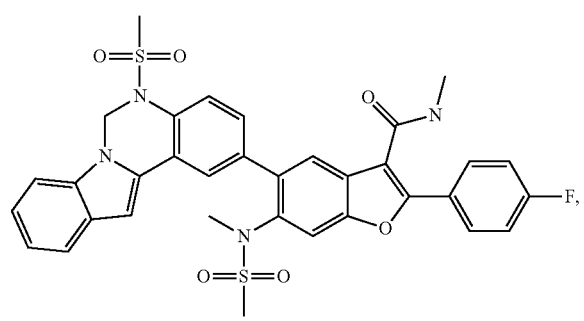
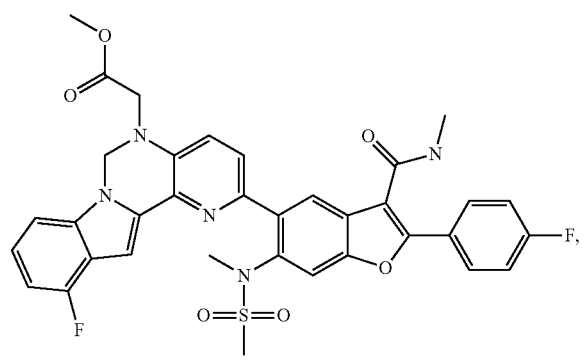
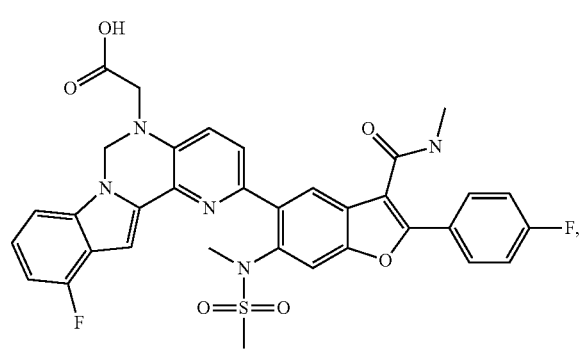
192
-continued
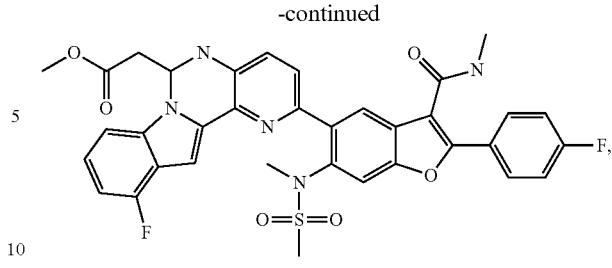
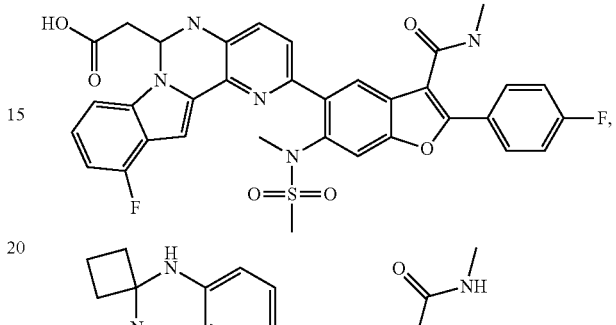
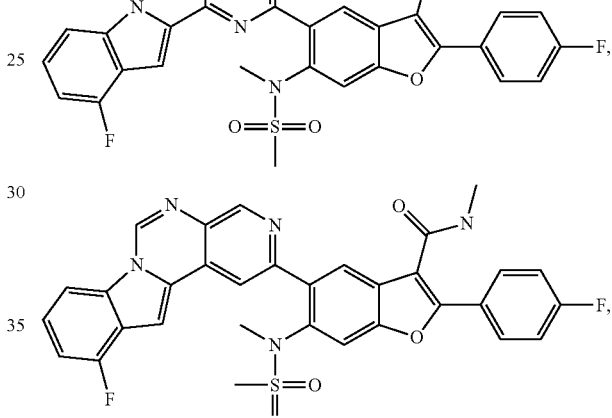
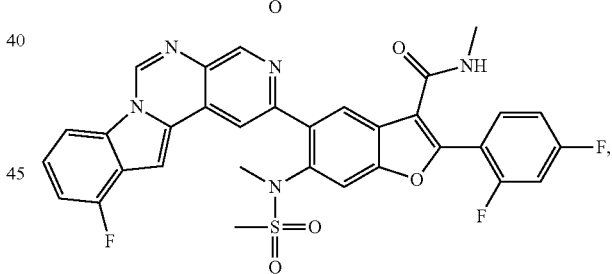
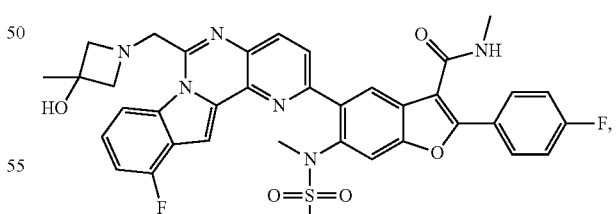
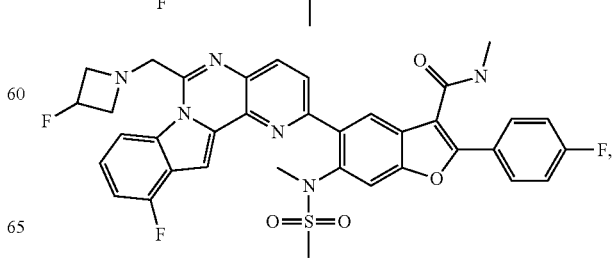

193
-continued
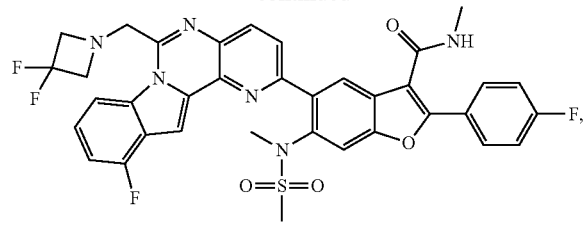
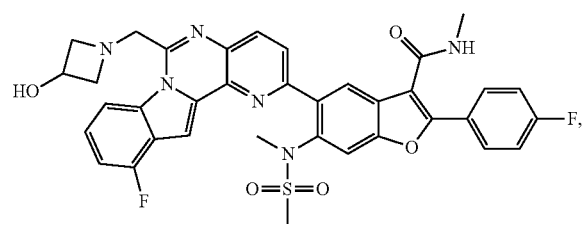
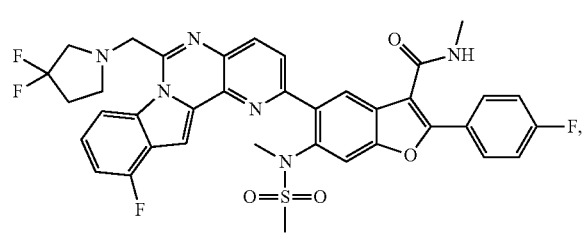
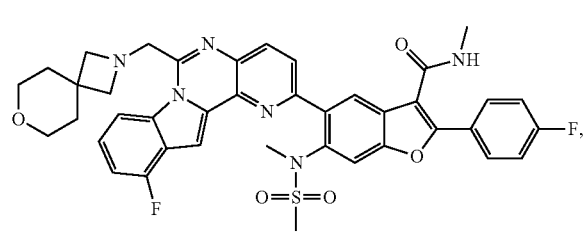
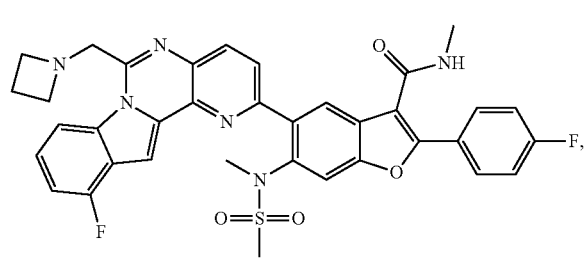
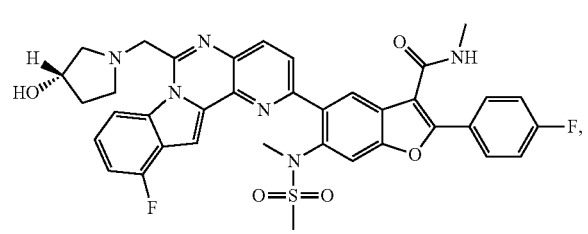
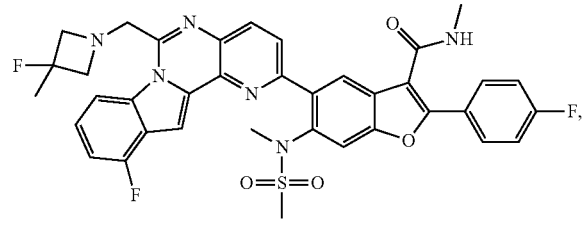
194
-continued
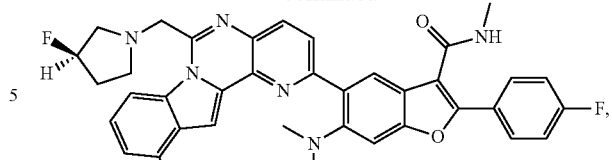
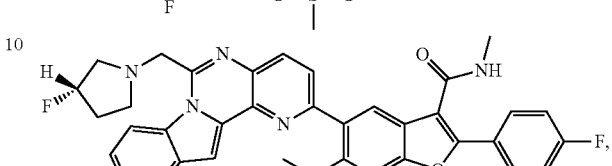
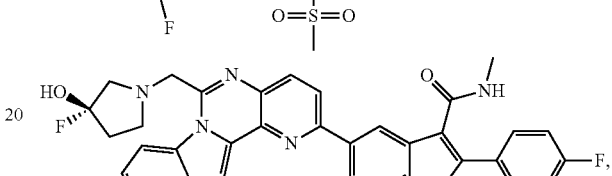
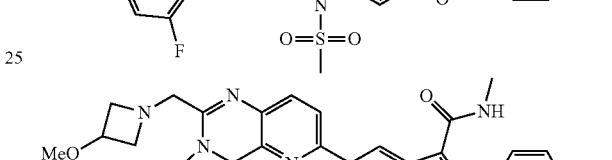
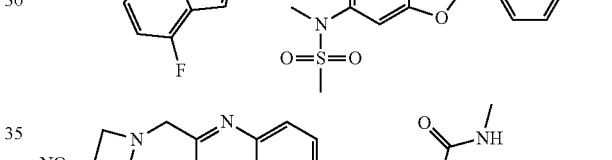
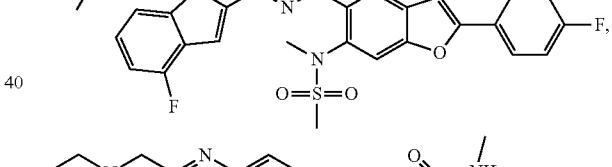
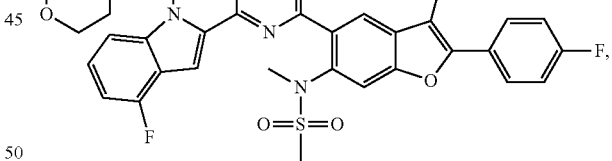
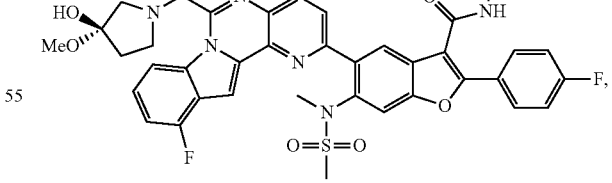
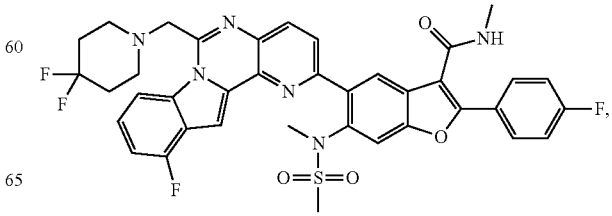

195
-continued
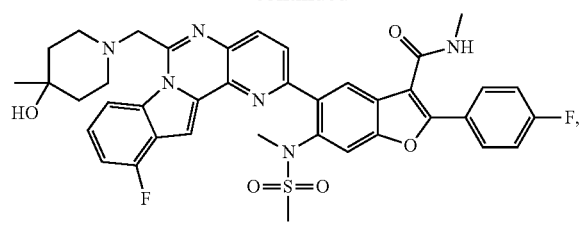
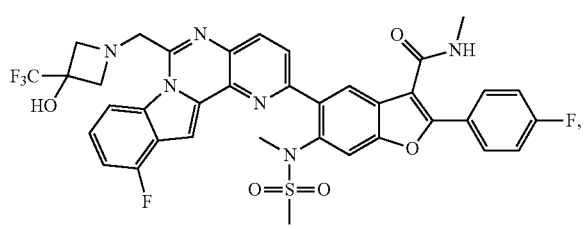
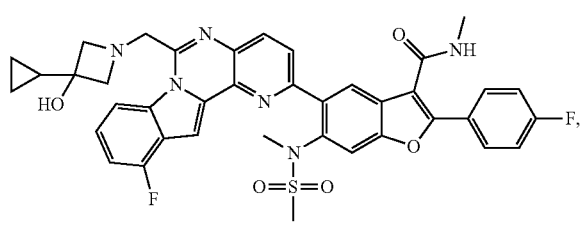
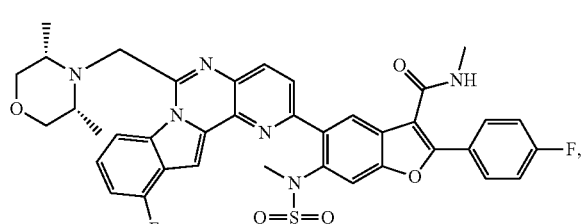
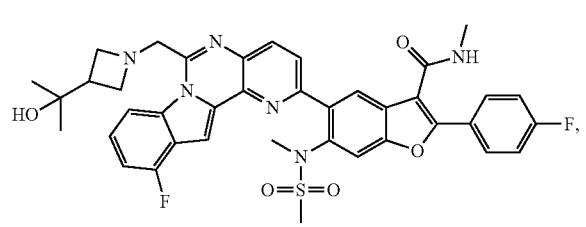
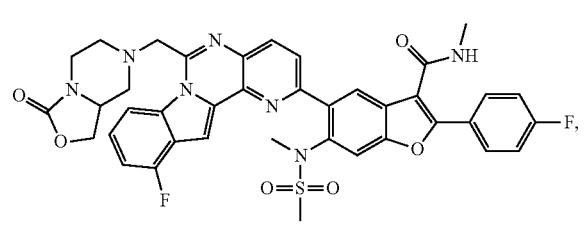
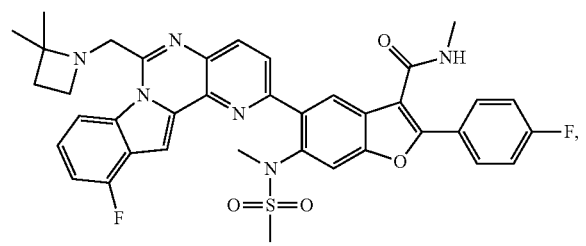
196
-continued
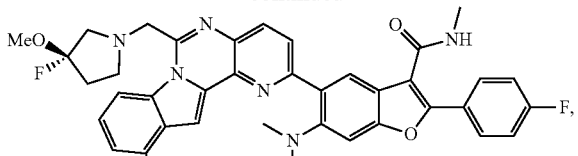
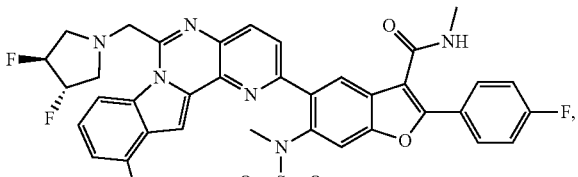
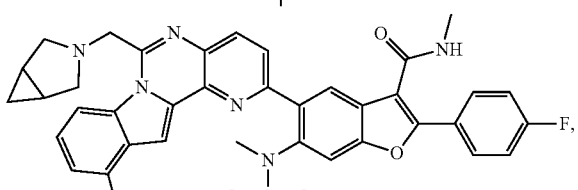
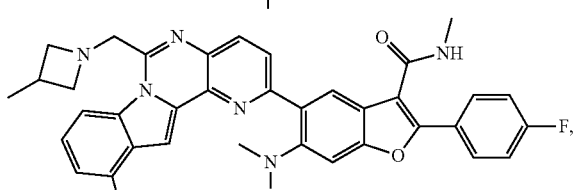
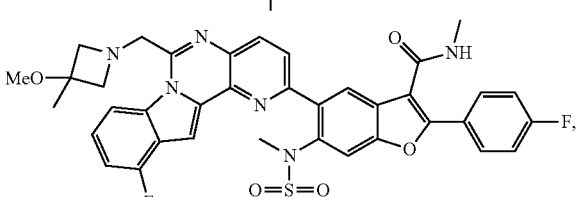
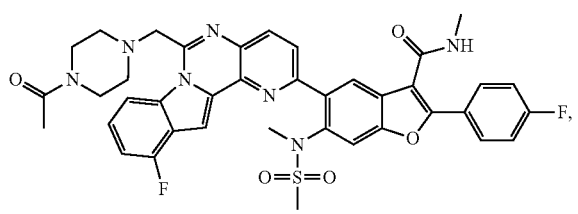
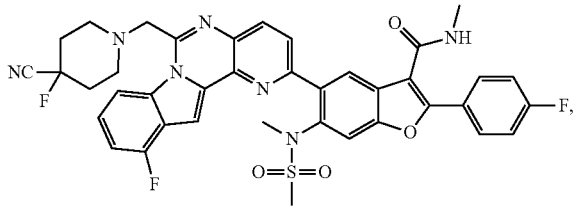
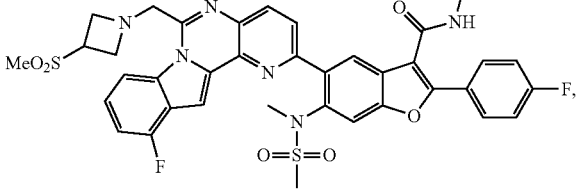

197
-continued
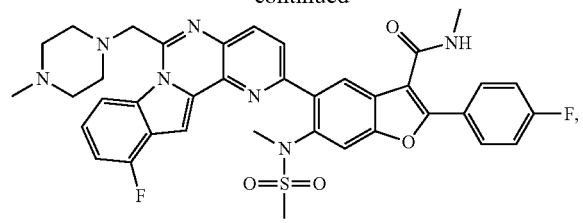
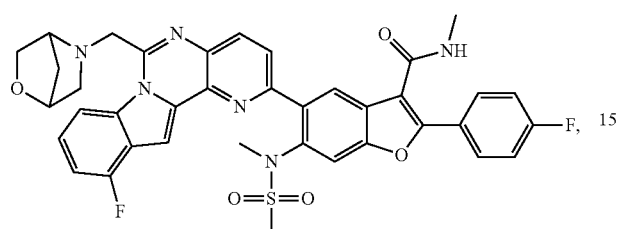
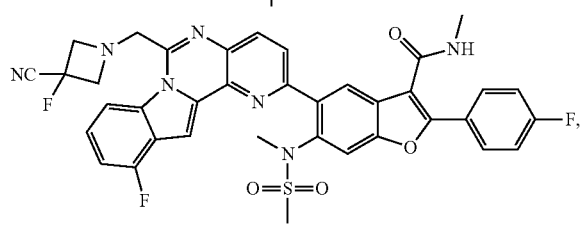
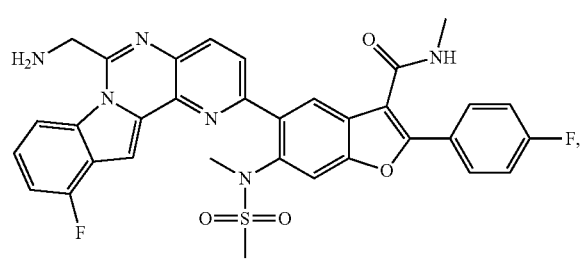
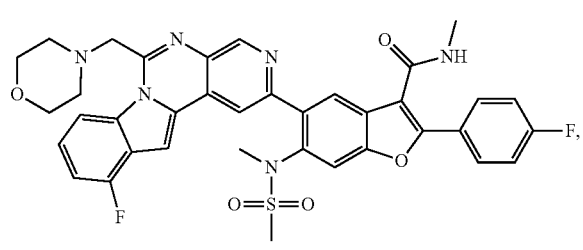
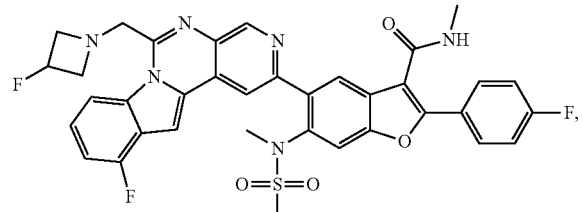
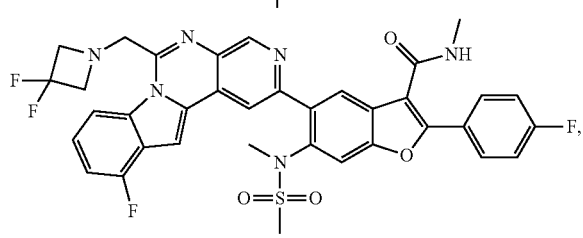
198
-continued
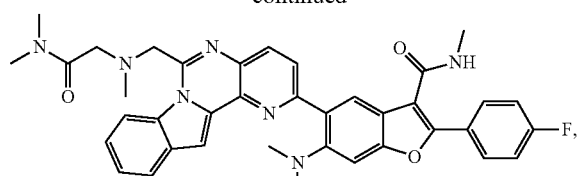
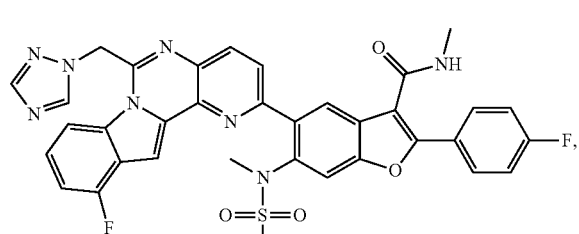
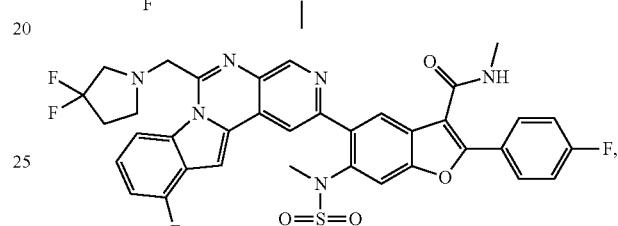
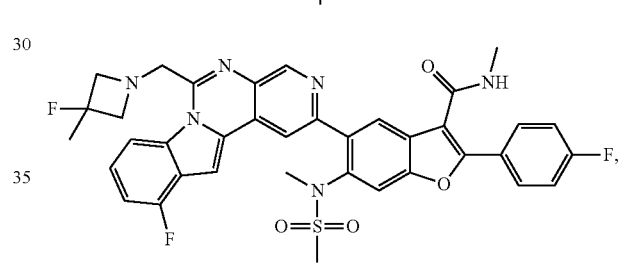
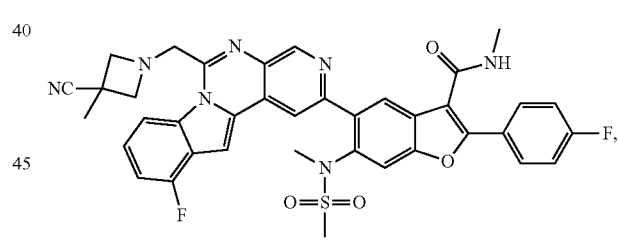
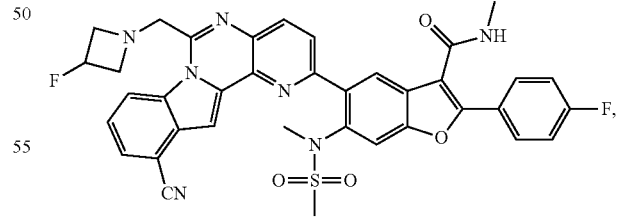
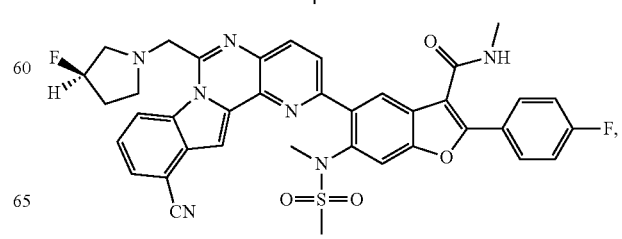

199
-continued
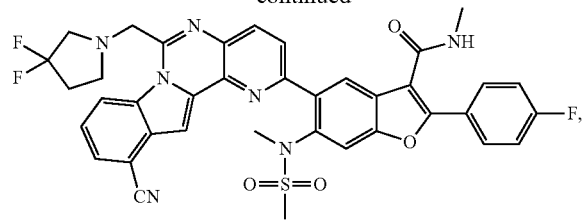
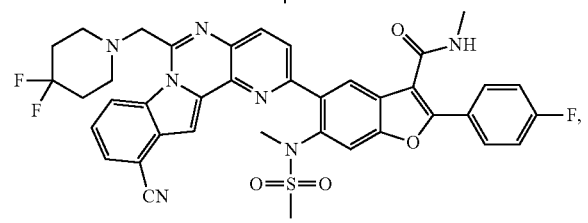
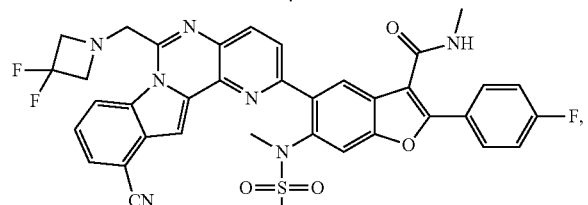
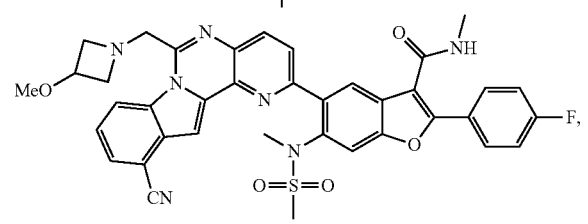
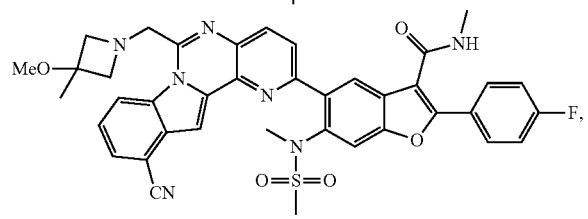
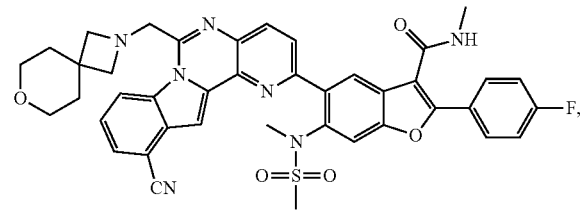
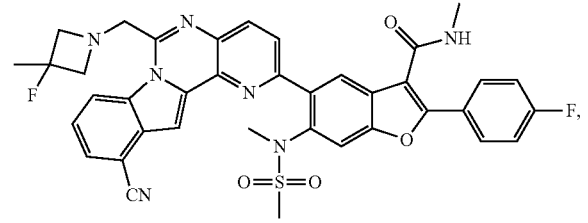
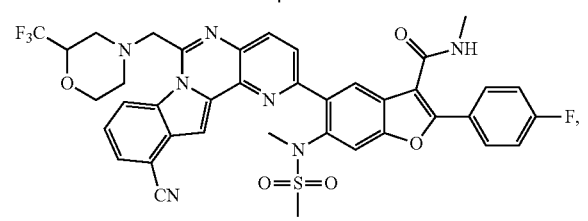
200
-continued
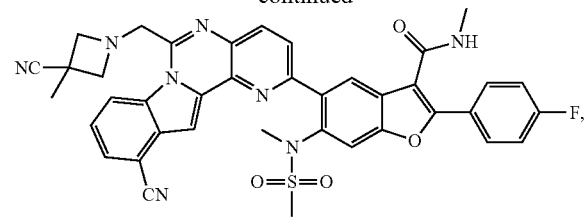
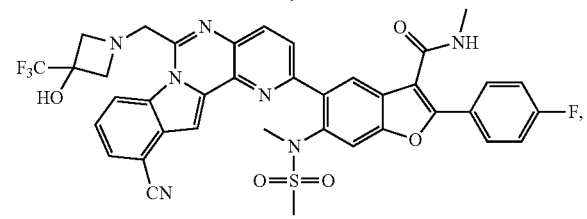
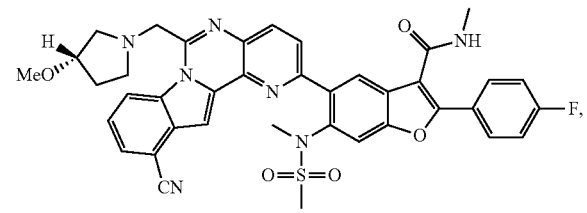
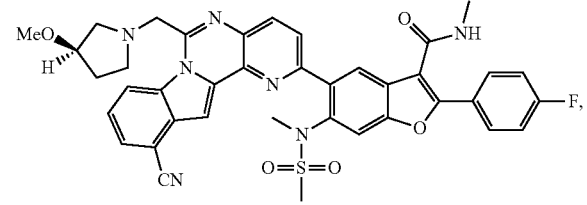
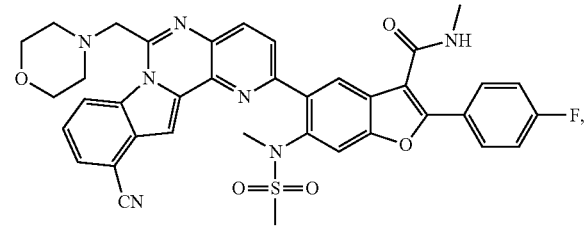
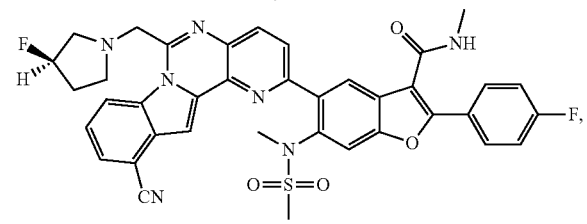
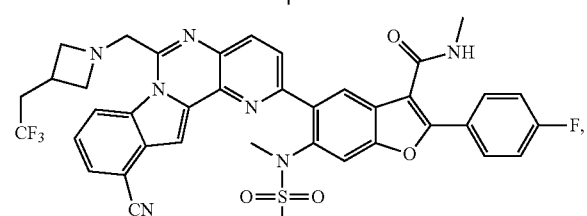
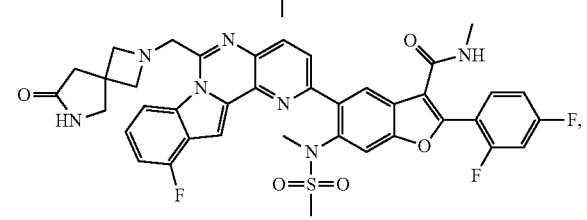

201
-continued

202
-continued or a pharmaceutically acceptable salt thereof.

13. The compound of claim 1 which is any one of
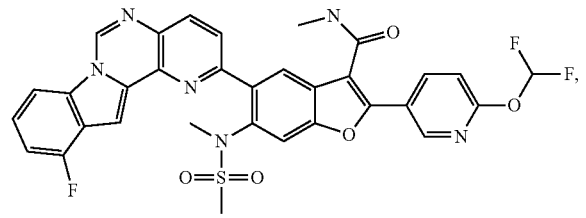
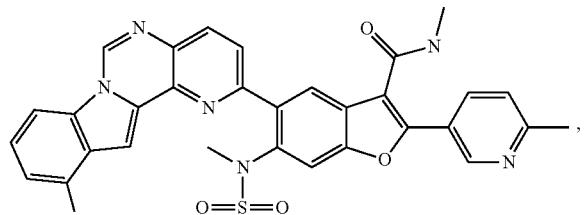
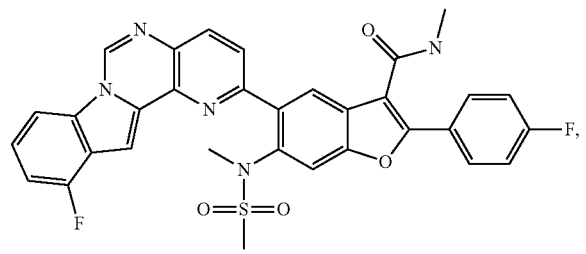
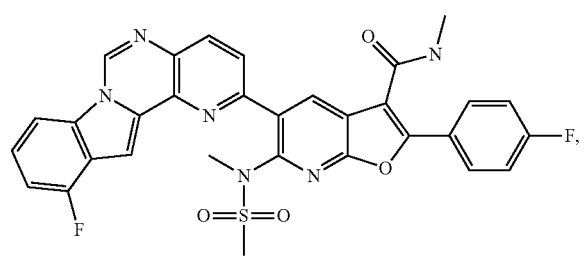
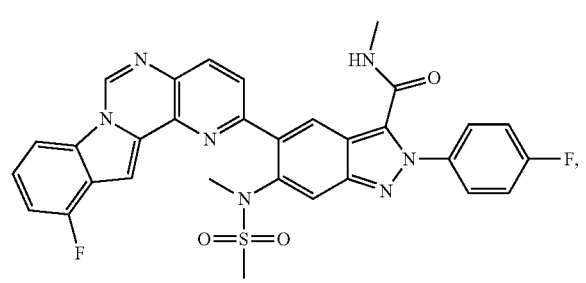
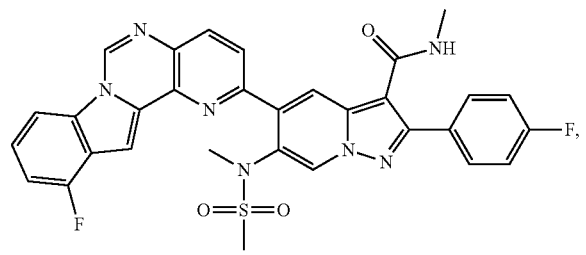
-continued
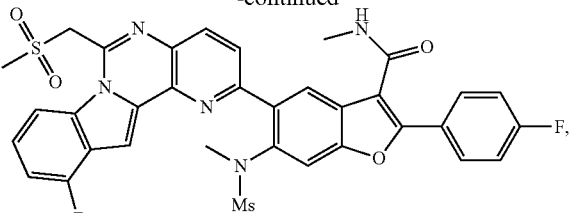
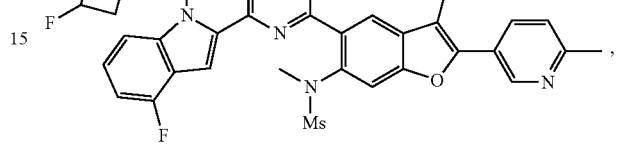
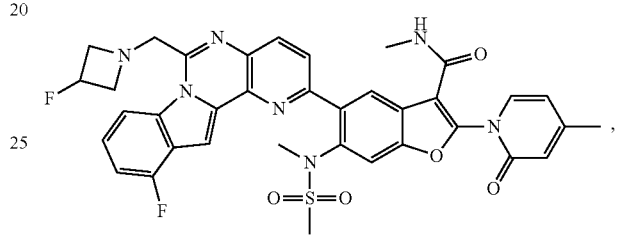
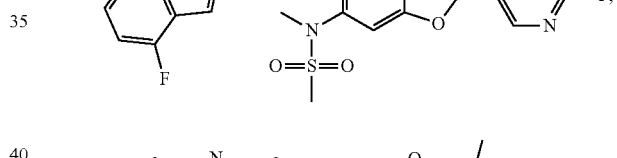
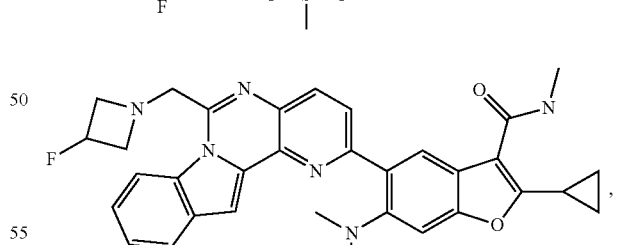
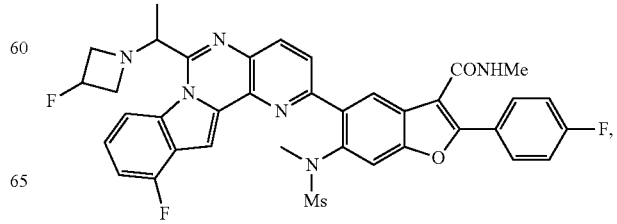

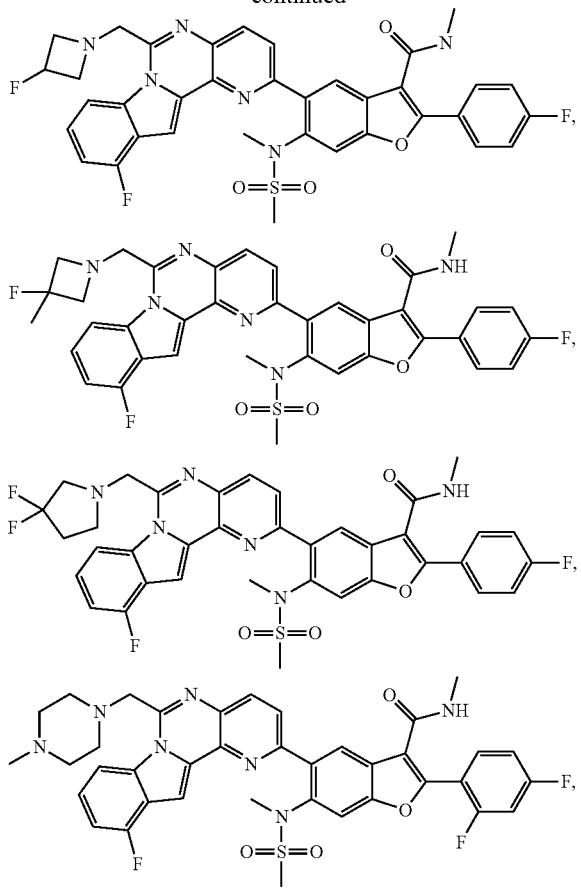

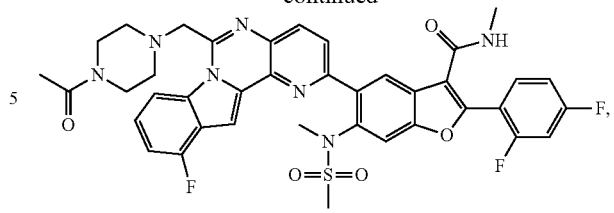

pharmaceutically acceptable salt thereof.

14. A pharmaceutical composition comprising (i) a pharmaceutically acceptable carrier and (ii) the compound of claim 1 or a pharmaceutically acceptable salt thereof, in an amount effective to treat HCV.

15. The pharmaceutical composition of claim 14, further comprising a second therapeutic agent selected from the group consisting of HCV antiviral agents, immunomodulators, and anti-infective agents.

16. The pharmaceutical composition of claim 15, wherein the second therapeutic agent is selected from the group consisting of HCV NS3 and NS3/4A protease inhibitors, HCV NS5A inhibitors and HCV NS5B polymerase inhibitors.

17. A method of treating a patient infected with HCV, the method comprising administering to the patient the compound of claim 1, or a pharmaceutically acceptable salt thereof, in an amount effective to treat infection by HCV in the patient.

18. The method of claim 17, further comprising administering to said patient an effective amount of at least one second therapeutic agent selected from the group consisting of HCV NS3 and NS3/4A protease inhibitors, HCV NS5A inhibitors and HCV NS5B polymerase inhibitors.

* * * * *